US011834720B2

(12) United States Patent
Huletsky et al.

(10) Patent No.: US 11,834,720 B2
(45) Date of Patent: *Dec. 5, 2023

(54) SEQUENCES FOR DETECTION AND IDENTIFICATION OF METHICILLIN-RESISTANT *STAPHYLOCOCCUS AUREUS* (MRSA) OF MREJ TYPES XI TO XX

(75) Inventors: Ann Huletsky, Québec (CA); Richard Giroux, Québec (CA)

(73) Assignee: GENEOHM SCIENCES, INC., San Diego, CA (US)

( * ) Notice: Subject to any disclaimer, the term of this patent is extended or adjusted under 35 U.S.C. 154(b) by 750 days.

This patent is subject to a terminal disclaimer.

(21) Appl. No.: 11/545,986

(22) Filed: Oct. 10, 2006

(65) Prior Publication Data

US 2008/0227087 A1     Sep. 18, 2008
US 2008/0227087 A1     Sep. 18, 2008

Related U.S. Application Data

(63) Continuation-in-part of application No. 11/248,438, filed on Oct. 11, 2005, now Pat. No. 7,838,221.

(51) Int. Cl.
*C12Q 1/689*     (2018.01)
(52) U.S. Cl.
CPC ....... *C12Q 1/689* (2013.01); *C12Q 2600/156* (2013.01)
(58) Field of Classification Search
CPC .................... C12Q 1/689; C12Q 2600/156
See application file for complete search history.

(56) References Cited

U.S. PATENT DOCUMENTS

| | | |
|---|---|---|
| 4,458,066 A | 7/1984 | Caruthers et al. |
| 4,683,195 A | 7/1987 | Mullis et al. |
| 4,683,202 A | 7/1987 | Mullis |
| 5,272,236 A | 12/1993 | Lai et al. |
| 5,437,978 A | 8/1995 | Ubukata et al. |
| 5,475,610 A | 12/1995 | Atwood et al. |
| 5,496,706 A | 3/1996 | Kuusela et al. |
| 5,538,871 A | 7/1996 | Nuovo et al. |
| 5,602,756 A | 2/1997 | Atwood et al. |
| 5,612,473 A | 3/1997 | Wu et al. |
| 5,702,895 A | 12/1997 | Matsunaga et al. |
| 5,776,712 A | 7/1998 | Kuusela et al. |
| 5,780,610 A | 7/1998 | Collins et al. |
| 5,783,638 A | 7/1998 | Lai et al. |
| 5,866,366 A | 2/1999 | Kallender |
| 5,994,066 A | 11/1999 | Bergeron et al. |
| 6,001,564 A | 12/1999 | Bergeron et al. |
| 6,083,587 A | 7/2000 | Smith et al. |
| 6,090,592 A | 7/2000 | Adams et al. |
| 6,117,635 A | 9/2000 | Nazarenko et al. |
| 6,117,986 A | 9/2000 | Nardone et al. |
| 6,156,507 A | 12/2000 | Hiramatsu et al. |
| 6,271,351 B1 | 8/2001 | Gawryl et al. |
| 6,380,370 B1 | 4/2002 | Doucette-Stamm et al. |
| 6,703,492 B1 * | 3/2004 | Kimmerly ............... A61P 37/04 536/23.1 |
| 7,108,974 B2 | 9/2006 | Ecker et al. |
| 7,205,111 B2 | 4/2007 | Christensen et al. |
| 7,226,739 B2 | 6/2007 | Ecker et al. |
| 7,255,992 B2 | 8/2007 | Ecker et al. |
| 7,399,590 B2 | 7/2008 | Piepenburg et al. |
| 7,435,561 B2 | 10/2008 | Piepenburg et al. |
| 7,449,289 B2 | 11/2008 | Huletsky et al. |
| 7,466,908 B1 | 12/2008 | Lem et al. |
| 7,666,588 B2 | 2/2010 | Ecker et al. |
| 7,666,592 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 7,838,221 B2 | 11/2010 | Huletsky et al. |
| 7,955,796 B2 | 6/2011 | Schrenzel et al. |
| 7,956,175 B2 | 6/2011 | Sampath et al. |
| 8,013,142 B2 | 9/2011 | Sampath et al. |
| 8,017,322 B2 | 9/2011 | Ecker et al. |
| 8,017,337 B2 | 9/2011 | Paitan |
| 8,017,358 B2 | 9/2011 | Ecker et al. |
| 8,017,743 B2 | 9/2011 | Ecker et al. |
| 8,034,588 B2 | 10/2011 | Bergeron et al. |
| 8,062,850 B2 | 11/2011 | Piepenburg et al. |
| 8,067,207 B2 | 11/2011 | Bergeron et al. |
| 8,071,309 B2 | 12/2011 | Ecker et al. |

(Continued)

FOREIGN PATENT DOCUMENTS

| | | |
|---|---|---|
| AU | 731850 | 4/2001 |
| AU | 775763 | 8/2004 |

(Continued)

OTHER PUBLICATIONS

Buck et al. (Biotechniques. Sep. 1999;27(3):528-36).*
Ito et al (Antimicrobial Agents and Chemotherapy(2001) vol. 45, p. 1323).*
Huletsky et al (J. Clin Microbiol (2004) vol. 42, p. 1875, May 4, 2004).*
NCBI blast 2 sequences (http://blast.ncbi.nlm.nih.gov/Blast.cgi , downloaded Aug. 13, 2013).*
Blast SEQ ID No. 18 (http://blast.ncbi.nlm.nih.gov/Blast.cgi, Feb. 13, 2015).*
(BLAST® >> Microbes >> RID-V9G669R4015 ,https://blast.ncbi. nlm.nih.gov/Blast.cgi, downloaded Oct. 3, 2018).*
WU (Clinical Microbiology and Infection (2010) vol. 16, pp. 245-254).*

(Continued)

*Primary Examiner* — Steven Pohnert
(74) *Attorney, Agent, or Firm* — Knobbe, Martens, Olson & Bear, LLP

(57) ABSTRACT

Described herein are novel SCCmec right extremity junction (MREJ) sequences for the detection and/or identification of methicillin-resistant *Staphylococcus aureus* (MRSA). Disclosed are methods and compositions based on DNA sequences for the specific detection of MREJ sequences designated types xi, xii, xiii, xiv, xv, xvi, xvii, xviii, xix, and xx for diagnostic purposes and/or epidemiological typing.

39 Claims, 22 Drawing Sheets

Specification includes a Sequence Listing.

(56) References Cited

U.S. PATENT DOCUMENTS

| | | |
|---|---|---|
| 8,084,207 B2 | 12/2011 | Sampath et al. |
| 8,097,416 B2 | 1/2012 | Hall et al. |
| 8,114,601 B2 | 2/2012 | Bergeron et al. |
| 8,163,895 B2 | 4/2012 | Sampath et al. |
| 8,182,992 B2 | 5/2012 | Sampath |
| 8,182,996 B2 | 5/2012 | Bergeron et al. |
| 8,187,812 B2 | 5/2012 | Zhang et al. |
| 8,187,814 B2 | 5/2012 | Ecker et al. |
| 8,214,154 B2 | 7/2012 | Ecker et al. |
| 8,242,254 B2 | 8/2012 | Sampath et al. |
| 8,265,848 B2 | 9/2012 | Ecker et al. |
| 8,268,565 B2 | 9/2012 | Ecker et al. |
| 8,288,523 B2 | 10/2012 | Sampath et al. |
| 8,323,898 B2 | 12/2012 | Niimi et al. |
| 8,362,228 B2 | 1/2013 | Paitan |
| 8,367,337 B2 | 2/2013 | Jay et al. |
| 8,394,945 B2 | 3/2013 | Sampath et al. |
| 8,426,137 B2 | 4/2013 | Bergeron et al. |
| 8,518,646 B2 | 8/2013 | Jean et al. |
| 9,777,335 B2 | 10/2017 | Huletsky et al. |
| 10,577,664 B2 | 3/2020 | Huletsky et al. |
| 10,801,074 B2 | 10/2020 | Huletsky et al. |
| 2002/0055101 A1 | 5/2002 | Bergeron et al. |
| 2002/0103338 A1 | 8/2002 | Choi |
| 2002/0106646 A1 | 8/2002 | Remacle et al. |
| 2003/0027135 A1 | 2/2003 | Ecker et al. |
| 2003/0049636 A1* | 3/2003 | Bergeron ............... C12Q 1/689 435/6.12 |
| 2003/0054436 A1 | 3/2003 | Kunsch et al. |
| 2003/0124556 A1 | 7/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0180733 A1 | 9/2003 | Bergeron et al. |
| 2003/0190605 A1 | 10/2003 | Ecker et al. |
| 2003/0198943 A1 | 10/2003 | Remacle et al. |
| 2004/0043037 A1* | 3/2004 | Kunsch .................. C07K 14/31 424/190.1 |
| 2004/0082002 A1 | 4/2004 | Choi |
| 2004/0110138 A1 | 6/2004 | Lem et al. |
| 2004/0110169 A1 | 6/2004 | Ecker et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121313 A1 | 6/2004 | Ecker et al. |
| 2004/0121314 A1 | 6/2004 | Ecker et al. |
| 2004/0121335 A1 | 6/2004 | Ecker et al. |
| 2004/0147734 A1* | 7/2004 | Doucette-Stamm ........................ A61K 31/7052 536/23.7 |
| 2004/0161770 A1 | 8/2004 | Ecker et al. |
| 2004/0180328 A1 | 9/2004 | Ecker et al. |
| 2004/0185437 A1 | 9/2004 | Hermet et al. |
| 2004/0185438 A1 | 9/2004 | Ecker |
| 2004/0185478 A1 | 9/2004 | Bergeron et al. |
| 2004/0202997 A1 | 10/2004 | Ecker et al. |
| 2004/0219517 A1 | 11/2004 | Ecker et al. |
| 2004/0241824 A1 | 12/2004 | Schrenzel et al. |
| 2004/0253583 A1 | 12/2004 | Ecker et al. |
| 2004/0253619 A1 | 12/2004 | Ecker et al. |
| 2005/0019893 A1 | 1/2005 | Huletsky et al. |
| 2005/0037408 A1 | 2/2005 | Christensen et al. |
| 2005/0059064 A1 | 3/2005 | Obst et al. |
| 2005/0112631 A1 | 5/2005 | Piepenburg et al. |
| 2005/0115903 A1 | 6/2005 | Hallier-Soulier et al. |
| 2006/0057613 A1 | 3/2006 | Ramakrishnan et al. |
| 2006/0105354 A1 | 4/2006 | Remacle et al. |
| 2006/0121520 A1 | 6/2006 | Ecker et al. |
| 2006/0205040 A1 | 9/2006 | Sampath |
| 2006/0240412 A1 | 10/2006 | Hall et al. |
| 2006/0252069 A1 | 11/2006 | Zhang et al. |
| 2006/0252078 A1 | 11/2006 | Huletsky et al. |
| 2006/0263810 A1 | 11/2006 | Bergeron et al. |
| 2006/0275749 A1 | 12/2006 | Sampath et al. |
| 2006/0275788 A1 | 12/2006 | Ecker et al. |
| 2006/0281112 A1 | 12/2006 | Remacle et al. |
| 2007/0009947 A1 | 1/2007 | Bergeron et al. |
| 2007/0037187 A1 | 2/2007 | Alexandre et al. |
| 2007/0048735 A1 | 3/2007 | Ecker et al. |
| 2007/0054296 A1 | 3/2007 | Piepenburg et al. |
| 2007/0082340 A1 | 4/2007 | Huletsky et al. |
| 2007/0099204 A1 | 5/2007 | Alexandre et al. |
| 2007/0105129 A1 | 5/2007 | Bergeron et al. |
| 2007/0218489 A1 | 9/2007 | Sampath et al. |
| 2007/0224614 A1 | 9/2007 | Sampath et al. |
| 2007/0238116 A1 | 10/2007 | Sampath et al. |
| 2007/0243544 A1 | 10/2007 | Sampath et al. |
| 2007/0248969 A1 | 10/2007 | Sampath et al. |
| 2007/0298423 A1 | 12/2007 | Remacle et al. |
| 2008/0038737 A1 | 2/2008 | Smith et al. |
| 2008/0057544 A1 | 3/2008 | Lem et al. |
| 2008/0085515 A1 | 4/2008 | Remacle et al. |
| 2008/0138808 A1 | 6/2008 | Hall et al. |
| 2008/0145847 A1 | 6/2008 | Hall et al. |
| 2008/0146455 A1 | 6/2008 | Hall et al. |
| 2008/0160512 A1 | 7/2008 | Ecker et al. |
| 2008/0220428 A1 | 9/2008 | Aichinger et al. |
| 2008/0233570 A1 | 9/2008 | Hall et al. |
| 2008/0311558 A1 | 12/2008 | Ecker et al. |
| 2009/0004643 A1 | 1/2009 | Ecker et al. |
| 2009/0035780 A1 | 2/2009 | McCarthy et al. |
| 2009/0047665 A1 | 2/2009 | Hall et al. |
| 2009/0047669 A1 | 2/2009 | Zhang et al. |
| 2009/0047671 A1 | 2/2009 | Bergeron et al. |
| 2009/0053702 A1 | 2/2009 | Bergeron et al. |
| 2009/0053703 A1 | 2/2009 | Bergeron et al. |
| 2009/0061446 A1 | 3/2009 | Niimi et al. |
| 2009/0068641 A1 | 3/2009 | Bergeron et al. |
| 2009/0081663 A1 | 3/2009 | Paitan |
| 2009/0111134 A1 | 4/2009 | Zhang et al. |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0181395 A1 | 7/2009 | Becker et al. |
| 2009/0182511 A1 | 7/2009 | Ecker et al. |
| 2009/0203013 A1 | 8/2009 | Jay et al. |
| 2009/0220937 A1 | 9/2009 | Sampath |
| 2009/0239224 A1 | 9/2009 | Ecker et al. |
| 2009/0280471 A1 | 11/2009 | Ecker et al. |
| 2010/0035232 A1 | 2/2010 | Ecker et al. |
| 2010/0035239 A1 | 2/2010 | Sampath et al. |
| 2010/0099860 A1 | 4/2010 | Remacle et al. |
| 2010/0129811 A1 | 5/2010 | Sampath et al. |
| 2010/0136515 A1 | 6/2010 | Sampath et al. |
| 2010/0145626 A1 | 6/2010 | Ecker et al. |
| 2010/0152432 A1 | 6/2010 | Wu et al. |
| 2010/0204266 A1 | 8/2010 | Ecker et al. |
| 2010/0267012 A1 | 10/2010 | Bergeron et al. |
| 2010/0304366 A1 | 12/2010 | Wu et al. |
| 2011/0091886 A1 | 4/2011 | Hirama et al. |
| 2011/0151452 A1 | 6/2011 | Jean et al. |
| 2012/0015349 A1 | 1/2012 | Sampath et al. |
| 2012/0015367 A1 | 1/2012 | Piepenburg et al. |
| 2012/0035071 A1 | 2/2012 | Bergeron et al. |
| 2012/0058487 A1 | 3/2012 | Bergeron et al. |
| 2012/0077684 A1 | 3/2012 | O'Hara |
| 2012/0107795 A1 | 5/2012 | Ecker et al. |
| 2012/0122086 A1 | 5/2012 | Ecker et al. |
| 2012/0122096 A1 | 5/2012 | Sampath et al. |
| 2012/0122097 A1 | 5/2012 | Sampath et al. |
| 2012/0122098 A1 | 5/2012 | Sampath et al. |
| 2012/0122099 A1 | 5/2012 | Sampath et al. |
| 2012/0122100 A1 | 5/2012 | Sampath et al. |
| 2012/0122101 A1 | 5/2012 | Sampath et al. |
| 2012/0122102 A1 | 5/2012 | Sampath et al. |
| 2012/0122103 A1 | 5/2012 | Sampath et al. |
| 2012/0142085 A1 | 6/2012 | Ecker et al. |
| 2012/0164625 A1 | 6/2012 | Ecker et al. |
| 2012/0171679 A1 | 7/2012 | Ecker et al. |
| 2012/0171692 A1 | 7/2012 | Sampath et al. |
| 2012/0208179 A1 | 8/2012 | Sampath et al. |
| 2013/0065774 A1 | 3/2013 | Zhang et al. |
| 2013/0266942 A1 | 10/2013 | Menard et al. |
| 2013/0338036 A1 | 12/2013 | Jean et al. |

(56) References Cited

U.S. PATENT DOCUMENTS

| | | |
|---|---|---|
| 2013/0338037 A1 | 12/2013 | Jean et al. |
| 2015/0232919 A1 | 8/2015 | Menard et al. |
| 2018/0208972 A1 | 7/2018 | Huletsky et al. |
| 2020/0109442 A1 | 4/2020 | Huletsky et al. |
| 2021/0230672 A1 | 7/2021 | Huletsky et al. |
| 2022/0170079 A1 | 6/2022 | Menard et al. |

FOREIGN PATENT DOCUMENTS

| | | |
|---|---|---|
| AU | 2008255266 | 1/2009 |
| AU | 2010202418 | 7/2010 |
| AU | 2012247038 | 11/2012 |
| CA | 2283458 | 3/2001 |
| CA | 2348042 A1 | 12/2002 |
| CA | 2448975 | 12/2002 |
| CN | 1505685 | 6/2004 |
| DE | 10051174 | 5/2002 |
| EP | 0 497 272 | 8/1992 |
| EP | 0 526 876 A1 | 2/1993 |
| EP | 0 527 628 | 2/1993 |
| EP | 0 543 942 | 6/1993 |
| EP | 0887424 | 12/1998 |
| EP | 1 136 566 A | 9/2001 |
| EP | 1 522 595 | 4/2005 |
| EP | 1 529 847 A | 5/2005 |
| EP | 1 541 696 A | 6/2005 |
| EP | 1 659 183 A | 5/2006 |
| EP | 1 788 095 A1 | 5/2007 |
| EP | 1 903 116 A1 | 3/2008 |
| EP | 1 997 886 A1 | 12/2008 |
| EP | 0 943 009 B1 | 6/2009 |
| EP | 1 397 510 B1 | 11/2009 |
| EP | 2 128 268 A1 | 12/2009 |
| EP | 2 150 625 A2 | 2/2010 |
| EP | 2 236 621 A1 | 10/2010 |
| EP | 2 253 712 A1 | 11/2010 |
| EP | 1 934 613 B1 | 1/2011 |
| EP | 2 302 074 | 3/2011 |
| EP | 2 311 992 | 4/2011 |
| EP | 2 322 649 | 5/2011 |
| EP | 2 322 655 A1 | 5/2011 |
| EP | 2 322 661 A1 | 5/2011 |
| EP | 2 322 663 A1 | 5/2011 |
| EP | 2 322 664 A1 | 5/2011 |
| EP | 2 322 666 A2 | 5/2011 |
| EP | 2 322 667 A2 | 5/2011 |
| EP | 2 322 668 A2 | 5/2011 |
| EP | 2 322 930 A2 | 5/2011 |
| EP | 2 325 643 A2 | 5/2011 |
| EP | 2 325 644 A2 | 5/2011 |
| EP | 2 325 645 A2 | 5/2011 |
| EP | 2 325 646 A2 | 5/2011 |
| EP | 2 325 647 A2 | 5/2011 |
| EP | 2 333 118 | 6/2011 |
| EP | 2 336 364 A1 | 6/2011 |
| EP | 2 336 365 A1 | 6/2011 |
| EP | 2 336 366 A2 | 6/2011 |
| EP | 2 339 033 A1 | 6/2011 |
| EP | 2 339 034 A1 | 6/2011 |
| EP | 2 345 746 A1 | 7/2011 |
| EP | 2 385 140 A1 | 11/2011 |
| EP | 2 064 332 B1 | 7/2012 |
| EP | 2 016 186 B1 | 1/2013 |
| EP | 1 929 049 B1 | 4/2013 |
| JP | H 0670771 | 3/1994 |
| JP | 11056371 | 3/1999 |
| JP | 2004-534537 | 11/2004 |
| JP | 2006271370 | 10/2006 |
| JP | 2010057495 | 3/2010 |
| KR | 20030003576 | 1/2003 |
| KR | 20050117281 | 12/2005 |
| MX | PA03007927 | 10/2004 |
| MY | 141881 A | 7/2010 |
| WO | WO 92/02638 | 8/1991 |
| WO | WO 92/05281 | 4/1992 |
| WO | WO 95/13395 | 5/1995 |
| WO | WO 1996/008582 | 3/1996 |
| WO | WO 1997/031125 | 8/1997 |
| WO | WO 1997/31125 | 8/1997 |
| WO | WO 1998/20157 | 5/1998 |
| WO | WO 1999/47706 | 9/1999 |
| WO | WO 2001/016292 | 3/2001 |
| WO | WO 01/23604 A2 | 4/2001 |
| WO | WO 2001/077372 | 10/2001 |
| WO | WO 2002/070664 | 9/2002 |
| WO | WO 2002/082086 | 10/2002 |
| WO | WO 02/099034 | 12/2002 |
| WO | WO 2004/052175 | 6/2004 |
| WO | WO 2004/053076 | 6/2004 |
| WO | WO 2004/053141 | 6/2004 |
| WO | WO 2004/053164 | 6/2004 |
| WO | WO 2004/055205 | 7/2004 |
| WO | WO 2004/060278 | 7/2004 |
| WO | WO 2005/014857 | 2/2005 |
| WO | WO 2005/024046 | 3/2005 |
| WO | WO 2005/094421 | 10/2005 |
| WO | WO 2005/098047 | 10/2005 |
| WO | WO 2005/100538 | 10/2005 |
| WO | WO 2006/028601 | 3/2006 |
| WO | WO 2006/053769 | 5/2006 |
| WO | WO 2006/053770 | 5/2006 |
| WO | WO 2006/071241 | 7/2006 |
| WO | WO 2006/094238 | 9/2006 |
| WO | WO 2006/111028 | 10/2006 |
| WO | WO 2006/116127 | 11/2006 |
| WO | WO 2006/135400 | 12/2006 |
| WO | WO 2007/023461 | 3/2007 |
| WO | WO 2007/086904 | 8/2007 |
| WO | WO 2007/096702 | 8/2007 |
| WO | WO 2007/100397 | 9/2007 |
| WO | WO 2007/130951 A2 | 11/2007 |
| WO | WO 2007/131995 | 11/2007 |
| WO | WO 2007/131999 | 11/2007 |
| WO | WO 2007/132001 | 11/2007 |
| WO | WO 2007/132002 | 11/2007 |
| WO | WO 2007/133732 | 11/2007 |
| WO | WO 2008/061376 | 5/2008 |
| WO | WO 2008/080620 | 7/2008 |
| WO | WO 2008/140612 | 11/2008 |
| WO | WO 2008/143627 | 11/2008 |
| WO | WO 2009/049007 | 4/2009 |
| WO | WO 2009/090310 | 7/2009 |
| WO | WO 2009/110473 | 9/2009 |
| WO | WO 2009/123667 | 10/2009 |
| WO | WO 2011/038197 | 3/2011 |

OTHER PUBLICATIONS

SEQ ID No. 45 (BLAST® >> Microbes >> RID-V9C1J132014, https://blast.ncbi.nlm.nih.gov/Blast.cgi, downloaded Oct. 3, 2018).*
Rychlik (Nucleic Acids Research (1990) vol. 18, pp. 6409-6412.*
Clustal alignment of clustalo-I20200716-132748-0378-29512231-p1m (https://www.ebi.ac.uk/Tools/services/web/toolresult.ebi?jobId=clustalo-I20200716-132748-0378-29512231-p1m, downloaded, Jul. 16, 2020).*
Further alignment c (BLAST®>> blastn suite-2sequences >> results for RID-H3DKFEYJ114, https://blast.ncbi.nlm.nih.gov/Blast.cgi, printed Jul. 17, 2020).*
U10927 (https://www.ncbi.nlm.nih.gov/nuccore/16579831?sat=34 &satkey=3325739, filed Jun. 13, 2002).*
Alignment 2 Clustal omega (Results for job clustalo-I20200716-155010-0333-57277635-p2m, downloaded Jul. 16, 2020 ).*
Alignment 5 (Results for job clustalo-I20200717-201612-0129-96637519-p2m, https://www.ebi.ac.uk/Tools/services/web/toolresult.ebi?jobId=clustalo-I20200717-201612-0129-96637519-p2m, downloaded Jul. 17, 2020).*
Al-Soud, et al. "Capacity of nine thermostable DNA Polymerases to mediate DNA amplification in the presence of PCR-Inhibiting samples." *Appl. Environ. Microbiol.* 64(10): 3748-3753 (1998).
Al-Soud, et al. "Effects of amplification facilitators on diagnostic PCR in the presence of blood, feces, and meat." *J. Clin. Microbiol.* 38(12): 4463-4470 (2002).

(56) References Cited

OTHER PUBLICATIONS

Arnheim, et al. "Polymerase Chain Reaction." C&EN. 36-47 (1990).
Archer and Niemeyer, "Origin and Evolution of DNA Associated with Resistance to Methicillin in Staphylococci." Trends in Microbiology. 2(10):343-347 (1994).
Archer, et al. "Dissemination among Staphylococci of DNA Sequences Associated with Methicillin Resistance." Antimicrobial Agents and Chemotherapy. 38(3):447-54 (1994).
Baba et al., "Genome and Virulence Determinants of High Virulence Community-acquired MRSA." Lancet, England, May 25, 2002; vol. 359, No. 9320; pp. 1819-1827.
Barberis-Maino. IS431, a staphylococcai insertion sequence-like element related to IS26 from *Proteus vulgaris*. Gene. 59:107-13 (1983).
Barringer, et al. "Blunt-end and single strand ligations by *Escherichia coli* ligase: influence on an in vitro amplification scheme." Gene. 89:117-122 (1990).
Berger-Bachi, et al. Insertional Inactivation of Staphylococcal Methicillin Resistance by Tn551. Journal of Bacteriology. 154(1):479-87 (1983).
Chakrabarti et al. "Novel Sulfoxides Facilitate GC-Rich Template Amplification." Biotechniques. 32: 866-874 (2002).
Database EMBL 'Online! May 14, 2001; retrieved from EBI, Database Accession No. AB037671, XP002238391.
Database EMBL 'Online! Jan. 7, 2000; retrieved from EBI Database Accession No. AB014433; XP002238392.
De Lencastre et al. Methicillin-Resistant *Staphylococcus aureus* disease in a Portuguese Hospital: Characterization of clonal Types by a Combination of DNA Typing Methods. Eur. *J. Clin. Microbiol. Infect. Dis.* 13: 64-73 (1994).
Deplano et al. "In Vivo deletion of the methicillin resistance mec region from the chromosome of I *Staphylococcus aureus* strains." *J. Antimicrob. Chemotherapy*, 46-617-619 (2000).
Derbise et al. "Mapping the Regions Carrying the Three Contiguous Antibiotic Resistance Genes aadE, sat4, and aphA-3 in the Genomes of Staphylococci." Antimicrobial Agents and Chemotherapy. 41(5): 1024-32 (1997).
Dubin et al., "Physical Mapping of the mec Region of an American Methicillin-Resistant *Staphylococcus aureus* Strain." Antimicrobial Agents and Chemotherapy. 35(8):1661-65 (1991).
Egholm et al. "PNA hybridizes to complementary oligoncleotides obeying the Watson-Crick hydrogen-bonding rules." Nature. 365: 566-568 (1993).
Elghanian et al. "Selective Colorimetric Detection of Polynucleotides Based on the Distance-Dependent Optical Properties of Gold Nanoparticles." (1997) Science 277:1078-1081.
Flores et al. "A rapid, inexpensive method for eluting DNA from Agarose or Acrylamide gel slices without toxic or chaotropic materials." Biotechniques. 13: 205-206 (1992).
GenBank accession No. AB014440, version AB014440.1, Jul. 6, 1999, Ito et al.
GenBank accession No. AB063172, version AB063172.2, Jun. 12, 2001, Ito et al.
GenBank accession No. AB121219, version AB121219.1, Sep. 26, 2003, Ito et al.
GenBank accession No. AF270046, version AF270046.1, May 22, 2000, Taylor et al.
GenBank accession No. BK001539, version BK001539.1, Aug. 15, 2003, Mongkolrattanothai et al.
GenBank accession No. BX571856, version BX57156.1, Jun. 23, 2004, Holden et al.
GenBank accession No. U10927, version U10927.2, Nov. 1, 2001, Lin et al.
GenBank accession No. AF422691, version AR422691.1, Apr. 29, 2002, Oliveira et al.
GenBank accession No. AF411934, version AF411934.1, Mar. 5, 2002, Oliveira et al.
Gerberding, et al. Comparison of conventional susceptibility Tests with Direct Detection of Penicillin-Binding Protein 2a in borderline Oxacillin-Resistant Strains of *Staphylococcus aureus*. Antimicrobial Agents and Chemotherapy. 35(12):2574-79 (1991).
Guatelli, et al. "Isotherma, in vitro amplification of nucleic acids by a multenzyme reaction modeled after retroviral replication." *Proc. Natl. Acad. Sci. USA*, 87:1874-1878 (1990).
Hiramatsu et al. "Analysis of Borderline-Resistant Strains of Methicillin-Resistant *Staphylococcus aureus* Using Polymerase Chain Reaction." *Microbiol. Immunol.* 36: 445-453 (1992).
Hiramatsu et al., "Genetic Basis for Molecular Epidemiology of MRSA" J. Infect. Chemother. 1996, 2:117-129. XP001122060.
Hiramatsu, et al. "The emergence and evolution of methicillin-resistant *Staphylococcus aureus.*" *Trends in Microbiology*. 9(10): 486-493 (2001).
Hiramatsu, et al. "Molecular Cloning and Nucleotide Sequence Determination of the Regulator Region of mecA gene in methicillin-resistant *Staphylococcus aureus*." FEBS. 298(2.3):133-36 (1992).
Huletsky, et al. "New Real-Time PCR Asay for Rapid Detection of Methicillin-Resistant *Staphylococcus aureus* Directly from Specimens Containing a Mixture of Staphylococci." Journal of Clinical Microbiology. 42(5): 1875-84 (2004).
Inglis, et al. "Induced deletions within a cluster of resistance genes in the mec region of the chromosome of *Staphylococcus aureus.*" *Gen. Microbiol.* 136:2231-2239 (1990).
Inglis, et al. "Methicillin-Sensitive and Resistant Homologues of *Staphylococcus aureus* Occur together among Clinical Isolates." J. *Infect. Dis.* N167:323-328 (1993).
Ito et al. "Acquisition of Methicillin Resistance and Progression of Multiantibiotic Resistance in Methicillin- Resistant *Staphylococcus aureus*." Yonsei Medical Journal. 39(6):526-33 (1998).
Ito et al. Novel Type V Staphylococcal Cassette Chromosome mec Driven by a Novel Cassette Chromosome Recombinase, ccrC. Antimicrob. Agents Chemother. 48:2637-2651 (2004).
Ito et al., "Cloning and Nucleotide Sequence Determination of the entire mvc DNA of pre-methicillin--resistant *Staphylococcus aureus* N315," Antimicrob. Agents Chemother. US, Jun. 1999; vol. 43, No. 6, pp. 1449-1468. XP002238386;ISSN: 0066-4804.
Ito et al., "Structural Comparison of Three Types of Staphylococcal Cassette Chromosome Med Integrated in the Chromosome in Methicillini-resistant *Staphylococcus aureaus*." Antimicrob. Agents Chemother. U.S. May 2001, 45:1323-1336.
Katayama, et al. "A New Class of Genetic Element, *Staphylococcus* Cassette Chromosome mec, Encodes Methicillin resistance in *Staphylococcus aureus.*" *Antimicrob. Agents Chemother.* 44(6):1549-1555 (2000).
Kellogg, et al. "TaqStart Antibody™: "Hot Start" PCR facilitated by a neutralizing monoclonal antibody directed against Taq DNA Polymerase." *Biotechniques.* 16:1134-1137 (1994).
Kimmel, et al. "Preparations of cDNA and the Generation of cDNA Libraries: Overview." Methods in Enzymology. 152:307-316 (1987).
Kitagawa, et al. "Rapid Diagnosis of Methicillin-Resistant *Staphylococcus aureus* Bacteremia by Nested Polymerase Chain Reaction." Annals of Surgery. 224(5):665-71 (1996).
Kluytmans. Food-Initiated Outbreak of Methicillin-Resistant *Staphylococcus aureus* Analyzed by Pheno and Genotyping. Journal of clinical Microbiology. 33(5):1121-28 (1995).
Koshkin, et al. "LNA (locked nucleic acids): Synthesis of the Adenine, Cytosine, Guanine, 5-Methylcytosine, Thymine and Uracil Bicyclonucleoside Monomers, Oligomerisation, and unprecedented nucleic acid recognition." Tetrahedron. 54:3607-3630 (1998).
Kuroda, et al. "Whole genome sequencing of methicillin-resistant *Staphylococcus aureus.*" *The Lancet*. 357: 9264; pp. 1225-1240, (2001).
Kwoh, et al. "Transcription-based amplification system and detection of amplified human immunodeficiency virus type 1 with a bead-based sandwich hybridization format." Proc. Natl. Acad. Sci. USA 86:1173-1177 (1989).
Landegren, et al. "A Ligase-Mediated Gene Detection Technique." (1988) Science 241:1077-1080.
Lawrence et al. "Consecutive isolation of homologous strains of methicillin-resistant and methicillin-susceptible *Staphylococcus aureus* from a hospitalized child." *J. Hosp. Infect.* 33:49-53 (1996).

(56) References Cited

OTHER PUBLICATIONS

Lawrence et al. "Use of the Coagulase Gene Typing Method for Detection of Carriers of Methicillin- Resistant *Staphylococcus aureus.*" *Journal of Antimicrobial Chemotherapy*. 37:687-696 (1996).
Leach et al. "Theoretical Investigations of Novel Nucleic Acid Bases." (1992) J. Am. Chem. Soc. 114:3675-3683.
Lin et al. "Sequence Analysis and Molecular Characterization of Genes Required for the Biosynthesis of Type 1 Capsular Polysaccharide in *Staphylococcus aureus*." Journal of Bacteriology. 176(22):7005-16 (1994).
Lomell, et al. "Quantitative Assays Based on the Use of Replicatable Hybridization Probes." Clinical Chemistry. 35(9):1826-1831 (1989).
Luchansky and Pattee, "Isolation of Transposon Tn551 Insertions Near Chromosomal Markers of Interest in *Staphylococcus aureus*." Journal of Bacteriology. 159(3):894-99 (1984).
Luijendijk, et al. "Comparison of Five Tests for Identification of *Staphylococcus aureus* Clinical Samples." Journal of Clinical Microbiology. 34(9):2267-69 (1996).
Luong, et al. "Type I Capsule Genes of *Staphylococcus aureus* Are Carried in a Staphyloccal Cassette Chromosome genetic Element." Antimicrobial Agents and Chemotherapy. 46(4):1147-52 (2002).
Ma et al., "Novel Type of Staphylococcal Cassette Chromosome Mec Identified in Community-acquired Methicillin-resistant *Staphylococcus aureus* Strains." Antimicrob. Agents Chemother. vol. 46, No. 4, Apr. 2002, pp. 1147-1152.
Mantsch et al. "Structural and Enzymatic Properties of Adenine 1-Oxide Nucleotides." (1975) Biochem. 14(26):5593-5601.
Martineau, et. al. "Correlation between the Resistance Genotype Determined by Multiplex PCR Assays and the Antibiotic Susceptibility Patterns of *Staphylococcus aureaus* and *Staphylococcus epidermis.*" *Antimicrob. Chemotherapy.* 44(2): 231-238 (2000).
Mulligan, et al. "Methicillin-Resistant *Staphylococcus aureus*: a Consensus Review of the Microbiology, Pathogenesis, and Epidemiology with Implications for Prevention and Management." Am J Med. 94(3):313-28 (1993).
Murakami, et al. "Identification of Methicillin-Resistant Strains of Staphylococci by Polymerase Chain Reaction." *J. Clin Microbiol.* 29(10):2240-2244 (1991).
Muraki. Detection of Methicillin-Resistant *Staphylococcus aureus* using PCR and non-radioactive DNA probes (II). Rinsho Byori. 41(10): 1159-66 (1993).
Newton et al. "Instrumentation, Reagents and Consumables." PCR, 2nd Ed., Springer-Verlag (New York: 1997), Chapter 2, p. 8-28.
Nichols, et al. "A universal nucleoside for use at ambiguous sites in DNA primers." *Nature*. 369:492-493 (1994).
Oliveira et al., "Genetic Organization of the Downstream Region of the mecA Element in Methicillin- resistant *Staphylococcus aureus* Isolates Carrying Different Polymorphisms of this Region," Antimicrobial Agents and Chemotherapy. US, Jul. 2000, vol. 44, No. 7, pp. 1906-1910; XP002238385; ISSN:0066-4804.
Oliveira, et al. "Multiplex PCR Strategy for Rapid Identification of Structural Types and Variants of the mec Element in Methicillin-Resistant *Staphylococcus aureus*." Antimicrob. Agents Chemother. 46:2155-2161 (2002).
Oliveira et al., "The Evolution of Pandemic Clones of Methicillin-resistant *Staphylococcus aureus*: Identification of Two Ancestral Genetic Backgrounds and the Associated mec Elements." Microb. Drug Resist. vol. 7, No. 4, Jan. 2001, pp. 349-361.
Oliveira et al. "Secrets of success of a human pathogen: molecular evolution of pandemic clones of meticillin-resistant *Staphylococcus aureus*." Lancet Infect Dis. 2:180-9 (2002).
Partial International Search Report for International Application No. PCT/CA 02/00824 dated May 12, 2003.
Pattee, et al. "Genetic and Physical Mapping of the Chromosome of *Staphylococcus aureus*." Molecular Biology of the Staphylococci. VCH Publishers. 41-58 (1990).
Piccirilli et al. "Enzymatic incorporation of a new base pair into DNA and RNA extends the genetic alphabet." (1990) Nature. 343:33-37.

Saito, et al. "Immunological Detection of Penicillin-Binding Protein 2' of Methicillin-Resistant Staphylococci by Using Monoclonal Antibodies Prepared from Synthetic Peptides." *J. Clin. Microbiol.* 33(9): 2498-2500 (1995).
Simor, et al. "Characterization and Proposed Nomenclature of Epidemic Strains of Methicillin-Resistant *Staphylococcus aureus* in Canada." CCDR 25-12: 105-112 (Jun. 15, 1999).
Sooknanan, R. NASBA. A detection and amplification system uniquely suited for RNA. (1995) Biotechnology 13:563-564.
Stewart, et al. "IS257 and Small Plasmid Insertions in the mec Region of the Chromosome of *Staphylococcus aureus*." Plasmid. 31:12-20 (1994).
Suzuki, et al., "Distribution of mec Regulator Genes in Methicillin-Resistant *Staphylococcus* Clinical Strains." Antimicrobial Agents and Chemotherapy. 37(6):1219-26 (1993).
Suzuki, et al. "Survey of Methicillin-Resistant Clinical Strains of Coagulase-Negative Staphylococci for mecA Gene Distribution." *Antimicrob. Agents Chemother.* 36(2): 429-434 (1992).
Switzer et al. "Enzymatic Recognition of the Base Pair between Isocytidine and Isoguanosine." (1993) Biochemistry 32:10489-10496.
Thewell, et al. "Mode of action and application of Scorpion primers to mutation detection." (2000), Nucl. Acids Res. 28(19):3752-3761.
Tokue, et al. "Comparison of a Polymerase Chain Reaction Assay and a Convetional Microbiologic Method for Detection of Methicillin-Resistant *Staphylococcus aureus*." Antimicrobial Agents and Chemotherapy. 36(1):6-9 (1992).
Tor et al. "Site-Specific Enzymatic Incorporation of an Unnatural Base, $N^6$-(6-Aminohexyl)isoguanosine, into RNA." (1993) J. Am. Chem. Soc. 115:4461-4467.
Tyagi et al. "Molecular Beacons: Probes that Fluoresce upon Hybridization." (1996) Nat. Biotech. 14:303-308.
Ubukata, et al. "Homology of mecA Gene in Methicillin-Resistant *Staphylococcus aureus* to that of *Staphylococcus aureus.*" *Antimicrob, Agents Chemother.* 34(1):170-172 (1990).
Ubukata, et al. "Rapid Detection of the mecA Gene in Methicillin-Resistant Staphylococci by Enzymatic Detection of Polymerase Chain Reaction Products." *J. Clin. Microbiol.* 30(7):1728-1733 (1992).
Ubukata, et al. "Restriction Maps of the Regions Coding for Methicillin and Tobramycin Resistances on Chromosomal DNA in Methicillin-Resistant Staphylococci." Antimicrobial Agents and Chemotherapy. 33(9):1624-26 (1989).
Unal, et al. "Detection of Methicillin-Resistant Staphylococci by Using the Polymerase Chain Reaction." Journal of Clinical Microbiology. 30(7):1685-91 (1992).
Unal, et al. "Comparison of Tests for Detection of Methicillin-Resistant Staphylococci aureus in a Clinical Microbiology Laboratory." Antimicrobial Agents and Chemotherapy. 38(2):345-47 (1994).
Van Belkum, et al. "Comparison of Phage Typing and DNA Fingerprinting by Polymerase Chain Reaction of Discrimination of Methicillin-Resistant *Staphylococcus aureus* Strains." Journal of Clinical Microbiology. 31(4):798-803 (1993).
Van Brunt, J. "Amplifying Genes: PCR and its Alternatives." Biotechnology, 8:291-294 (1990).
Vannuffel, et al. "Specific Detection of Methicillin-Resistant *Staphylococcus* Species by Multiplex PCR." Journal of Clinical Microbiology. 33(11):2864-67 (1995).
Wada, et al. "Southern Hybridization Analysis of the mecA Deletion from Methicillin-Resistant *Staphylococcus aureus*." Biochem. *Biophys. Res. Comm.*, 176: 1319-1326 (1991).
Wallet, et al. "Choice of a Routine Method for Detecting Methicillin-Resistance in Staphylococci." Journal of Antimicrobial Chemotherapy. 37:901-909 (1996).
Westin, et al. "Anchored multiplex amplification on a microelectronic chip array." *Nat. Biotechnol.* 18:199-204 (2000).
Wilson, Ian. "Inhibition and Facilitation of Nucleic Acid Amplification." *Appl. Environ. Microbiol.* 63: 3741-3751 (1997).
Wu, et al. "Genetic Organization of the mecA Region in Methicillin-Susceptible and Methicillin-Resistant Strains of *Staphylococcus sciuri*." Journal of Bacteriology. 180(2):236-42 (1998).

(56) References Cited

OTHER PUBLICATIONS

Wu, et a. "The Ligation Amplification Reaction (LAR)-Amplification of Specific DNA Sequences Using Sequential Rounds of Template-Dependent Ligation." (1989) Genomics 4:560-569.
Holden, et al. "Complete genomes of two clinical *Staphylococcus aureus* strains: Evidence for the rapid evolution of virulence and drug resistance." PNAS. 101(26):9786-9791 (2004).
Zhang, et al. "Genome-based analysis of virulence genes in a non-biofilm-forming *Staphylococcus epidermidis* strain (ATCC 12228)." Molecular Microbiology. 49(6): 1577-1593 (2003).
Database EMBL [Online]. "*Staphylococcus aureus* DNA, type-IV.1 (Iva) staphylococcal cassette chromosome mec: strain CA05 (JCSC1968)", retrieved from EBI accession No. AB063172 (Nov. 21, 2001).
Ausubel et al., Current Protocols in Molecular Biology, 3rd Ed. Wiley Interscience Publishers (1995) [Table of Contents Only].
Bartels et al., "An unexpected location of the Arginine Catabolic Mobile Element (ACME) in a USA300-related MRSA." PLoS ONE 6(1): e16193 (Jan. 2011).
Bastos et al., "Molecular characterization and transfer among *Staphylococcus* strains of a plasmid conferring high-level resistance to mupirocin", Eur. J. Clin. Microbiol. Infect. Dis. (1999) 18(6):393-8.
Becker et al., "Thermonuclease gene as a target for specific identification of *Staphylococcus intermedius* isolates: use of a PCR-DNA enzyme immunoassay", Diagn. Microbiol. Infect. Dis. (Apr. 2005) 51(4):237-44.
BLAST Sequence-Alignment 1 between AB037671 (strain 85/2082) and SEQ ID No. 42, printed on Apr. 1, 2011, pp. 2.
Brakstad et al., "Detection of *Staphylococcus aureus* by polymerase chain reaction amplification of the nuc gene", *J. Clin. Microbiol.* (1992) 30(7):1654-60.
Brakstad et al., "Comparison of tests designed to identify *Staphylococcus aureus* thermostable nuclease", *APMIS* (1995) 103(3):219-24.
Chesneau et al., "Thermonuclease gene as a target nucleotide sequence for specific recognition of *Staphylococcus aureus*", Mol. Cell. Probes. (1993) 7(4):301-10.
Chongtrakool et al., "Staphylococcal cassette chromosome mec (SCCmec) typing of methicillin-resistant *Staphylococcus aureus* strains isolated in 11 Asian countries: a proposal for a new nomenclature for SCCmec elements", Antimicrob. Agents Chemother. (2006) 50(3):1001-12.
Costa et al., "Rapid detection of mecA and nuc genes in staphylococci by real-time multiplex polymerase chain reaction", Diagn. Microbiol. Infect. Dis. (Jan. 2005) 51(1):13-17.
Cuny et al., "PCR for the identification of methicillin-resistant *Staphylococcus aureus* (MRSA) strainsusing a single primer pair specific for SCCmec elements and the neighbouring chromosome-borne orfX."—Research Note, Clin Microbio Infect., 11(10): 834-837 (Oct. 2005).
Database Geneseq [Online]. "Polymorphic right extremity junction (MREJ) DNA #1." EBI accession No. GSN:ACD02065; Database accession No. ACD02065 (2003).
Domann et al. "Schneller und zuverlaessiger Nachweis multiresistenter multiplex-PCR." Deutsche Medizinische Wochenschrift. 125(20): 613-618 (2000). w/EN Abstract.
Fang et al. "Rapid Screening and Identification of Methicillin-Resistant *Staphylococcus aureus* from Clinical Samples by Selective-Broth and Real-Time PCR Assay." (Jul. 2003) 41(7): 2894-2899 and 1 page Erratum.
GenBank accession No. AB037671, "*Staphylococcus aureus* DNA, type-III staphylococcal cassette chromosome mec and SCCmercury: strain 85/2082", May 12, 2000, pp. 30.
Grisold et al., "Use of hybridization probes in a real-time PCR assay on the LightCycler® for the detection of methicillin-resistant *Staphylococcus aureus*", Methods Mol. Biol. (2006) 345:79-89.
Hanssen et al., "Local Variants of Staphylococcal Cassette Chromosome mec in Sporadic Methicillin-Resistant *Staphylococcus aureus* and Methicillin-Resistant Coagulase-Negative Staphylococci: Evidence of Horizontal Gene Transfer?" Antimicrob Agents Chemothera., 48(1): 285-296 (Jan. 2004).
Hanssen et al., Mini Review "SCCmecin staphylococci: genes on the move." FEMS Immunol Med Microbiol., 46: 8-20 (Sep. 2005).
Innis et al. Eds. PCR Protocols, a Guide to Methods and Applications, Academic Press (1990) Table of Contents.
Kang et al., "The enhancement of PCR amplification of a random sequence DNA library by DMSO and betaine: application to in vitro combinatorial selection of aptamers", J Biochem Biophys Methods. (Aug. 2005) 64(2):147-51.
Kearns et al., "Rapid detection of methicillin-resistant staphylococci by multiplex PCR." Journal of Hospital Infection. 43(1):33-37 (1999).
Kloos et al., "Updated on clinical significance of coagulase-negative staphylococci", Clin. Microbiol. Rev. (1994) 7(1):117-40.
Kovacevic et al., "Secretion of staphylococcal nuclease by Bacillus subtilis", J. Bacteriol. (1985), 162(2):521-8.
Levi et al., "Detection of methicillin-resistant *Staphylococcus aureus* (MRSA) in blood with the EVIGENE MRSA detection kit", J. Clin. Microbiol. (2003) 41(8):3890-2.
Maes et al., "Evaluation of a triplex PCR assay to discriminate *Staphylococcus aureus* from coagulase-negative Staphylococci and determine methicillin resistance from blood cultures", J. Clin. Microbiol. (2002) 40(4):1514-7.
McDonald et al., "Development of a triplex real-time PCR assay for detection of Panton-Valentine leukocidin toxin genes in clinical isolates of methicillin-resistant *Staphylococcus aureus*", J. Clin. Microbiol. (Dec. 2005) 43(12):6147-9.
Murray et al., Manual of Clinical Microbiology, 8th Ed., ASM Press (2003) [Content pages only].
NCBI BLAST Sequence Alignment 1 between AB037671 (strain 85/2082) and SEQ ID No. 42, printed on Apr. 1, 2011.
Okuma et al., "Dissemination of new methicillin-resistant *Staphylococcus aureus* clones in the community." J Clin Microbio., 40(11): 4289-4294 (Nov. 2002).
Oliveira et al., "Redefining a structural variant of staphylococcal cassette chromosome mec, SCCmec type VI", Antimicrob. Agents Chemother. (Oct. 2006) 50(10):3457-9.
PCR Methods and Applications, Cold Spring Harbor Laboratory Press (from 1991 to 1995), Contents pages only.
PCR Strategies, Academic Press, Inc. (1995), Contents pages only.
Poulsen et al., "Detection of methicillin resistance in coagulase-negative staphylococci and in staphylococci directly from simulated blood cultures using the EVIGENE MRSA Detection Kit", J. Antimicrob. Chemother. (2003) 51(2):419-21.
Ralser et al., "An efficient and economic enhancer mix for PCR", Biochem. Biophys. Res. Communi. (Sep. 2006) 347(3):747-51.
Schuenck et al., "Improved and rapid detection of methicillin-resistant *Staphylococcus aureus* nasal carriage using selective broth and multiplex PCR", Res. Microbiol. (Sep. 2006) 157(10):971-5.
Shittu et al., "Molecular identification and characterization of mannitol-negative methicillin-resistant *Staphylococcus aureus*", Diagn. Microbiol. Infect Dis. (2007) 57(1):93-5.
Sequence Alignment 3 printed on Mar. 31, 2011 aligning the Nucleotide Sequence of Staphylococcal aureas strains 85/2082, HDG2, and N315(d86934) downs stream of mecA, pp. 10.
Spiess et al. "Trehalose Is a Potent PCR Enhancer: Lowering of DNA Melting Temperature and Thermal Stabilization of Taq Polymerase by the Disaccharide Trehalose," Clin Chem., Jul. 2004, 50(7):1256-1259.
White, "Molecular Cloning to Genetic Engineering", in Methods in Molecular Biology Humana Press (1997) vol. 67, Contents pages only.
Wilson et al., "Detection of enterotoxigenic *Staphylococcus aureus* in dried skimmed milk: use of the polymerase chain reaction for amplification and detection of staphylococcal enterotoxin genes entB and entC1 and the thermonuclease gene nuc", Appl. Environ. Microbiol. (1991) 57:1793-8.
Wisplinghoff et al., "Related clonges containing SCCmec type IV predominate among clinically significant *Staphylococcus epidermidis* Isolates." Antimicrob Agents Chemothera. 47(11): 3574-3579 (2003).
Zhang et al., "New quadriplex PCR assay for detection of methicillin and mupirocin resistance and simultaneous discrimination of

(56) References Cited

OTHER PUBLICATIONS

*Staphylococcus aureus* from coagulase-negative staphylococci", J. Clin. Microbiol. (2004) 42(11):4947-55.
Zhang et al., "Novel multiplex PCR assay for characterization and concomitant subtyping of staphylococcal cassette chromosome mec types I to V in methicillin-resistant *Staphylococcus aureus*.", J. Clin. Microbiol. (Oct. 2005) 43(10): 5026-33.
Electronic File History of Inter Partes Reexamination Control No. 95/001,599, filed Apr. 8, 2011 containing Office Actions dated Apr. 19, 2011, Jun. 1, 2011 and Dec. 29, 2011, Requestor submissions Apr. 8, 2011, and Aug. 31, 2011 and Applicant Response filed Aug. 5, 2011.
Partial International Search Report dated May 12, 2003 for International Application No. PCT/CA02/00824, filed Jun. 4, 2002.
International Search Report dated Sep. 24, 2003 for International Patent Application No. PCT/CA02/000824, filed Jun. 4, 2002.
International Preliminary Report on Patentability (Rule 44bis) dated Apr. 16, 2008 for International Patent Application No. PCT/US06/39996, filed Oct. 10, 2006.
Extended European Search Report dated Aug. 10, 2011 for European Patent Application No. 10016072.0, filed Oct. 10, 2006.
Extended European Search Report dated Aug. 10, 2011 for European Patent Application No. 10016073.8, filed Oct. 10, 2006.
Extended European Search Report dated Jul. 20, 2011 for European Patent Application No. 10016074.6, filed Oct. 10, 2006.
Extended European Search Report dated Aug. 10, 2011 for European Patent Application No. 10016031.6, filed Oct. 10, 2006.
Extended European Search Report dated Aug. 10, 2011 for European Patent Application No. 10016019.1, filed Oct. 10, 2006.
Extended European Search Report dated Aug. 10, 2011 for European Patent Application No. 10016020.9, filed Oct. 10, 2006.
Partial International Search Report dated Dec. 19, 2008 for International Application No. PCT/US072/088004, filed Dec. 18, 2007.
International Preliminary Report on Patentability and Written Opinion dated Jul. 2, 2009 for International Application No. PCT/US072/088004, filed Dec. 18, 2007.
European Search Report dated Dec. 3, 2009 for European Application No. 07874372.1, filed Dec. 18, 2007.
European Office Action dated Sep. 28, 2011 for European Application No. 07874372.1, filed Dec. 18, 2007.
European Extended Search Report dated Apr. 18, 2011 in European Patent Application No. 10181533.0, filed Jun. 4, 2002.
European Extended Search Report dated Apr. 18, 2011 in European Patent Application No. 10181534.8, filed Jun. 4, 2002.
European Extended Search Report dated Apr. 18, 2011 in European Patent Application No. 10181535.8, filed Jun. 4, 2002.
European Extended Search Report dated Apr. 15, 2011 in European Patent Application No. 10181536.3, filed Jun. 4, 2002.
European Office Action dated Apr. 26, 2011 in European Patent Application No. 09174581.0, filed Jun. 4, 2002.
Third Party Observations dated Jan. 17, 2008 in European Patent Application No. 02740158.7, filed Jun. 4, 2002.
Notice of Opposition dated Aug. 4, 2010 in European Patent Application No. 02740158.7, filed Jun. 4, 2002.
Notice of Opposition dated Aug. 3, 2010 in European Patent Application No. 02740158.7, filed Jun. 4, 2002.
EPO Communication dated Sep. 10, 2010 in European Patent Application No. 02740158.7, filed Jun. 4, 2002.
Patentee Response to Opposition dated Mar. 17, 2011 European Patent Application No. 02740158.7, filed Jun. 4, 2002.
Notice of Opposition & Discussion filed Oct. 19, 2011against European Patent No. 1934613, issued Jan. 19, 2011 (Koenig et al.).
Notice of Opposition and Statement filed Oct. 18, 2011 against European Patent No. 1934613, issued Jan. 19, 2011 (BC).
EPO Communication dated Nov. 25, 2011 in European Patent No. 1934613, dated Jan. 19, 2011.
Australian Office Action dated Jun. 6, 2011 for Australian Application No. 2006302044, filed Oct. 10, 2006.
Office Action dated Sep. 11, 2012 for European Patent Application No. 10016072.0, filed Oct. 10, 2006.
Office Action dated Sep. 11, 2012 for European Patent Application No. 10016073.8, filed Oct. 10, 2006.
Office Action dated Sep. 11, 2012 for European Patent Application No. 10016074.6, filed Oct. 10, 2006.
Office Action dated Sep. 11, 2012 for European Patent Application No. 10016031.6, filed Oct. 10, 2006.
Office Action dated Sep. 11, 2012 for European Patent Application No. 10016019.1, filed Oct. 10, 2006.
Office Action dated Sep. 12, 2012 for European Patent Application No. 10016020.9, filed Oct. 10, 2006.
European Office Action dated Apr. 16, 2012 for European Application No. 07874372.1, filed Dec. 18, 2007.
Japanese Office Action dated Mar. 13, 2012 for JP Patent Application No. 2008-535692, filed Oct. 10, 2006.
Japanese Office Action dated Aug. 8, 2012 for JP Patent Application No. 2008-535692, filed Oct. 10, 2006.
Australian Office Action dated Sep. 5, 2012 for Australian Application No. 2007353522, filed Dec. 19, 2006.
EPO Communication dated May 10, 2012 re Oral Proceeding Schedule in European Opposition No. 02740158.7, filed Jun. 4, 2002.
Patentee Reply in European Opposition Proceedings filed May 30, 2012 in European Patent No. 1934613, issued Jan. 19, 2011.
Electronic File History of Reexamination Control No. 11/248,438, filed Oct. 11, 2005 for U.S. Appl. No. 11/248,438, filed Oct. 11, 2005 (U.S. Pat. No. 7,838,221) as of Oct. 3, 2012.
Dieffenbach et al. "General Concepts for PCR Primer Design." Genome Res. 3: S30-S37 (1993).
GenBank accession No. X53818.1, "*Staphylococcus aureus* IS431mec gene associated with methicillin resistance", Oct. 23, 2008.
Huletsky, A.—Declaration in Reexamination of U.S. Pat. No. 7,449,289 dated Jul. 30, 2011; pp. 3.
NCBI BLAST 2 Sequence—AF411934.1—*Staphylococcus aureus* strain HDG2 genomic sequence downstream of mecA, printed on Mar. 16, 2012, pp. 2.
Oliveira, D.—Email re Sequence Question with Hema Pande, Beckman Coulter, Inc. (Jul. 2010).
Oliveira, D—Declaration in Opposition to EP Patent 1397510 dated Nov. 29, 2012; pp. 2.
Random House Unabridged Dictionary, (1993) Definition of "extremity", p. 686.
Sanches et al., "Tracing the Origin of an Outbreak of Methicillin-Resistant *Staphylococcus aureus* Infections in a Portuguese Hospital by Molecular Fingerprinting Methods." Microbial Drug Resist. 2(3): 319-329 (1996).
Singh et al. "PCR Primer Design." Mol Biol Today 2(2): 27-32 (2001).
D3—Exhibit in European Opposition Proceeding: Applicant Response dated Dec. 2, 2009 in EP Application No. 06825875.5, filed Oct. 10, 2006; 5 pages.
D6—Exhibit in European Opposition Proceeding:: BLAST alignment of SEQ ID 46 from EP 1 397 510 and SEQ ID 19 from EP 1 934 613; 1 page.
D7—Exhibit in European Opposition Proceeding:: EP 1 93 4613 Claimed sequences with EP 1 397 510 primer binding sites shown; 3 pages.
D13—Exhibit in European Opposition Proceeding: CLUSTALW2 Multiple sequence alignment of rjmec primer from Cuny et al. and various MREJ type sequences; 1 page.
D14—Exhibit in European Opposition Proceeding: Primer binding sites of Cuny et al. in EP 1 934 613; 2 pages.
D17—Exhibit in European Opposition Proceeding: Primer binding site for SEQ ID No. 35 in SEQ ID No. 20 of EP 1 934 613; 1 page.
D18—Exhibit in European Opposition Proceeding: Overlap between ORFX2r primer binding sites of Cuny et al. and primer binding site of SEQ ID No. 45 from EP 1 934 613 in type xi MREJ sequences claimed in the EP patent; 6 pages.
D19—Exhibit in European Opposition Proceeding: Primer binding sites for primers of Cuny et al. in MREJ Types I-XX (sequences taken from EP 1934 613 and EP 1 397 510; 10 pages.
D32—Exhibit in European Opposition Proceeding: Lawrence et al. "Poisonous EPC Divisionals—Implications for Risk Management

(56) References Cited

OTHER PUBLICATIONS and Opportunistic Advantage." epi Information Feb. 2011; 54-61 (D32—Exhibit in European Opposition Proceeding).
D36—Exhibit in European Opposition Proceeding: Alignment of SEQ ID No. 18 from U.S. Appl. No. 11/248,438 and WO 2007/044873 with orfX sequence from Ito et al., AB014440; 3 pages.
D37—Exhibit in European Opposition Proceeding: Alignment of SEQ ID No. 19 from U.S. Appl. No. 11/248,438 and WO 2007/044873 with orfX sequence from Ito et al., AB014440; 1 page.
D38—Exhibit in European Opposition Proceeding: Alignment of MREJ type xi (SEQ ID No. 17) and mrej type iii (SEQ ID No. 184 from WO 2002/099034 showing asserted binding sites of primers pair (SEQ ID Nos. 64/98) from WO 2002/099034; 3 pages.
D39—Exhibit in European Opposition Proceeding: Alignment of MREJ type xi (SEQ ID No. 17) and MREJ type iii (SEQ ID No. 184 from WO 2002/099034 showing asserted binding sites of primers (SEQ ID Nos. 1-5) from EP 1 529 847; 1 page.
Patentee Response dated Nov. 19, 2012 to EP Summons to Oral Proceeding in European Opposition to Patent No. 1397510.
Opposer Hain Lifescience GmbH Response dated Nov. 26, 2012 to EP Summons to Oral Proceeding in European Opposition to Patent No. 1397510. (English Translation Only).
Opposer Beckman Coulter, Inc. further Response dated Nov. 30, 2012 to EP Summons to Oral Proceeding in European Opposition to Patent No. 1397510.
Patentee Reply filed May 30, 2012 in European Opposition to Patent No. 1934613.
EPO Summons to Oral Proceedings dated Nov. 23, 2012 in European Opposition to Patent No. 1934613.
Japanese Office Action dated Nov. 27, 2012 in Japanese Patent Application No. 2009-543155, filed Dec. 18, 2007.
Arakere, et al. "A novel type-Ill Staphylococcal cassette chromosome mec (SCCmec) variant among Indian isolates of methicillin-resistant *Staphylococcus aureus*." FEMS Microbiol. Lett. 292(1): 141-148 (Mar. 2009).
Barany et al., "Genetic disease detection and DNA amplification using cloned thermostable ligase," Proc Natl Acad Sci. USA (Jan. 1991) 88: 189-193.
Barski et al., "Rapid assay for detection of methicillin-resistant *Staphylococcus aureus* using multiplex PCR," Mol Cell Probes (1996) 10(6):471-475.
Beaucage et al. "Deoxynucleoside Phosphoramidites—a New Class of Key Intermediates for Deoxypolynucleotide Syntesis," Tetra Lttrs. (1981) 22(20): 1859-1862.
Becker et al., "Does Nasal Cocolonization by Methicillin-Resistant Coagulase-Negative Staphylococci and Methicillin-Susceptible *Staphylococcus aureus* Strains Occur Frequently Enough to Represent a Risk of False Positive Methicillin-Resistant *S. aureus* Determinations by Molecular Methods?", J Clin Microbiol. (Jan. 2006) 44(1): 229-231.
Benson et al., "Direct detection of mecA and nuc genes for rapid species and resistance determination of staphylococci from blood cultures," Abstracts of the Interscience Conference on Antimicrobial Agents and Chemotherapy, (1999) vol. 39, Abstract #877; pp. 208. cd-rom; 39th Interscience Conference on Antimicrobial Agents and Chemotherapy. San Francisco, California, USA. Sep. 26-29, 1999. American Society for Microbiology.
Bishop et al., "Concurrent Analysis of Nose and Groin Swab Specimens by the IDI-MRSA PCR Assay is Comparable to Analysis by Individual-Specimen PCR and Routine Culture Assays for Detection of Colonization by Methicillin-Resistant *Staphylococcus aureus*", J Clin Microbiol. (Aug. 2006) 44(8): 2904-2908.
Boye et al., "A new multiplex PCR for easy screening of methicillin-resistant *Staphylococcus aureus* SCCmec types I-V.", Clin Microbiol Infect. (Jul. 2007) 13(7): 725-727.
Brakstad et al., "Multiplex polymerase chain reaction for detection of genes for *Staphylococcus aureus* thermonuclease and methicillin resistance and correlation with oxacillin resistance," APMIS (1993) 101(:681-688.

Brakstad et al., "Simultaneous detection of the staphylococcal MecA and Nuc genes by a multiplex PCR," Zentralblatt für Bakteriologie (Inter'l J Med Microbiol.), (1994) Supplement 26, 246-248.
Brown et al., "Chemical Synthesis and Cloning of a Tyrosine tRNA Gene," Meth Enzymol. (1979) 68: 109-151.
Brown et al., "Real-time PCR detection of *S-aureus* and MRSA from wound, fluid and respiratory samples," Abstracts of the General Meeting of the American Society for Microbiology, (2006) vol. 106, Abs. C-074, pp. 110-111; 106th General Meeting of the American Society for Microbiology. Orlando, FL, USA. May 21-25, 2006.
Carroll, K.C. "Rapid diagnostics for methicillin-resistant *Staphylococcus aureus*", Mol Diagn Therapy, (Jan. 2008) 12(1): 15-24.
Cho et al., "Detection of methicillin resistance in *Staphylococcus aureus* isolates using two-step triplex PCR and conventional methods", J Microbiol Biotechnol. (Apr. 2007) 17(4): 673-676.
Denis et al., "Rapid screening of methicillin resistant *Staphylococcus aureus* carriers by direct PCR on enrichment broth culture of superficial swab samples," Abstracts of the Interscience Conference on Antimicrobial Agents and Chemotherapy, (2002) vol. 42, Abs. K-101, pp. 304; 42nd Interscience Conference on Antimicrobial Agents and Chemotherapy. San Diego, CA, USA. Sep. 27-30, 2002. American Society for Microbiology.
De San et al., Controlled Evaluation of the IDI-MRSA Assay for Detection of Colonization by Methicillin-Resistant *Staphylococcus aureus* in Diverse Mucocutaneous Specimens, J Clin Microbiol. (2007) 45(4): 1098-1101.
Desbouchages et al., "Direct screening of MRSA from swab specimens using duplex real-time PCR assay: implication for antibiotic prophylaxis," International Journal of Antimicrobial Agents, (2004) vol. 24 (212/47O, pp. S104-S105; 6th European Congress of Chemotherapy and Infection/24th Interdisciplinary Meeting on Anti-Infectious Chemotherapy. Paris, France. Dec. 1-3, 2004.
Desjardins et al., "Evaluation of the IDI-MRSA Assay for Detection of Methicillin-Resistant *Staphylococcus aureus* from Nasal and Rectal Specimens Pooled in a Selective Broth", J Clin Microbiol. (Apr. 2006) 44(4): 1219-1223.
Donnio et al., "Partial Excision of the Chromosomal Cassette Containing the Methicillin ResistanceDeterminant Results in Methicillin-Susceptible *Staphylococcus aureus*", J Clin Microbiol. (Aug. 2005) 43(8): 4191-4193.
Elsayed et al., "Development and Validation of a Molecular Beacon Probe-Based Real-Time Polymerase Chain Reaction Assay for Rapid Detection of Methicillin Resistance in *Staphylococcus aureus*", Arch Pathol Lab Med. (Jul. 2003) 127(7): 845-849.
Fan et al., "Rapid detection of methicillin-resistant Staphylococci by DNA probe," Linchuang Jianyan Zazhi 24(5) 351-352 (2006).
Francois et al., "Evaluation of Three Molecular Assays for Rapid Identification of Methicillin-Resistant *Staphylococcus aureus*", J Clin Microbiol. (2007) 45(6): 2011-2013.
García-Álvarez et al. "Meticillin-resistant *Staphylococcus aureus* with a novel mecA homologue in human and bovine populations in the UK and Denmark: a descriptive study," Lancet Infect Dis. (Aug. 2011) 11(8): 595-603.
Goldmeyer et al., "Identification of *Staphylococcus aureus* and Determination of Methicillin Resistance Directly from Positive Blood Cultures by Isothermal Amplification and a Disposable Detection Device," J. Clin. Microbiol. (2008) vol. 46 No. 4, 1534-1536.
Grisold et al., "Detection of Methicillin-Resistant *Staphylococcus aureus* and Simultaneous Confirmation by Automated Nucleic Acid Extraction and Real-Time PCR," J Clin. Microbiol. (2002) 40(7):2392-2397.
Gröbner et al., "Development of a real-time *Staphylococcus aureus* and MRSA (SAM-) PCR for routine blood culture," European Journal of Clinical Microbiology & Infectious Diseases (2007) (26)10:751-754.
Guintu et al., "Detection of MRSA Directly from Positive Blood Culture Bottles using MRSA Evigene (Advandx)," Abstracts of the Interscience Conference on Antimicrobial Agents and Chemotherapy, 45th Interscience Conference on Antimicrobial Agents and Chemotherapy. Washington, DC, US.; Abs. D-1716; (2005) vol. 45, pp. 151.

(56) References Cited

OTHER PUBLICATIONS

Hanaki et al., Loop-mediated isothermal amplification assays for identification of antiseptic- and methicillin-resistant *Staphylococcus aureus*, J Microbiol Meth. (2011) 84(2): 251-254; Epub Dec. 16, 2010.

He et al., "Identification of *Staphylococcus aureus* and detection of its multiple-resistant genes by multiplex PCR," Linchuang Jianyan Zazhi (2004) 22(4): 249-251.

Hiramatsu et al. "Analysis of borderline-resistant strains of methicillin-resistant *Staphylococcus aureus* using polymerase chain reaction," Microbiol Immunol. (1992) 36(5): 445-453.

Hope et al., "A PCR method for the identification of methicillin-resistant *Staphylococcus aureus* (MRSA) from screening swabs," Pathology (2004) 36(3):265-268.

Hougardy et al., "Direct and fast detection of methicillin resistant *Staphylococcus aureus* carriage by automated nucleic acid extraction and real time PCR" [English Abstract Only], Pathologie-Biologie, (Oct.-Nov. 2006) vol. 54, No. 8-9, pp. 477-481. Electronic Publication Date: Oct. 5, 2006.

Jayaratne et al., "DNA-based detection of methicillin-resistant *Staphylococcus aureus* (MRSA) from nosocomial screening: Comparison with culture and cost-benefit analysis," Abstracts of the Interscience Conference on Antimicrobial Agents and Chemotherapy, 38th Interscience Conference on Antimicrobial Agents and Chemotherapy. San Diego, California, USA. Sep. 24-27, 1998. American Society for Microbiology (1998) vol. 38, Abs. D-56; pp. 144-145.

Jiang et al., "Review on Progress of *Staphylococcus aureus* by PCR", Shipin Kexue (Beijing, China) (2006), 27(5): 265-269. [English Abstract].

Jonas et al., "Evaluation of the mecA femB duplex polymerase chain reaction for detection of methicillin-resistant *Staphylococcus aureus*," Eur J Clin Microbiol Infect Dis. (1999) 18(9):643-647.

Jonas et al., "Rapid PCR-based identification of methicillin-resistant *Staphylococcus aureus* from screening swabs," J Clin. Microbiol. (2002) 40(5):1821-1823.

Jovanic et al., "Rapid detection of methicillin-resistant *Staphylococcus aureus* by real-time PCR from clinical specimens", International Journal of Antimicrobial Agents, Abs P907; (Mar. 2007) 29(Suppl. 2): S235-S236.

Klotz et al., "Detection of *Staphylococcus aureus* Enterotoxins A to D by Real-Time Fluorescence PCR Assay," J Clin Microbiol. (2003) 41(10): 4683-4687.

Kobayashi et al., "Detection of mecA, femA, and femB genes in clinical strains of staphylococci using polymerase chain reaction," Epidemiol Infect. (1994) 113(2):259-266.

Kowalski et al., "Evaluation of the SmartCycler II System for Real-Time Detection of Viruses and *Chlamydia* from Ocular Specimens", Arch Ophthalmol. (Aug. 2006) 124: 1135-1139.

Lee et al., "Detection of MecA gene in clinical isolates of *Staphylococcus aureus* by multiplex-PCR, and antimicrobial susceptibility of MRSA," Journal of Microbiology and Biotechnology 13(3) 354-359 (2003).

Lem et al., "Direct detection of mecA, nuc and 16S rRNA genes in BacT/Alert blood culture bottles," Diagn Microbiol Infect Dis. 41(3):165-168 (2001).

Levenson, Deborah, "The Path to Better MRSA Control", Clin Lab News. (Aug. 2007) 33(8): 6 pages.

Levi et al., "Evaluation of an Isothermal Signal Amplification Method for Rapid Detection of Methicillin-Resistant *Staphylococcus aureus* from Patient-Screening Swabs", J Clin Microbiol. (Jul. 2003) 41(7): 3187-3191.

Ll et al., "Typing SCCmec Gene of Methicillin-Resistant *Staphylococcus aureus* by Novel Multiplex PCR Method," Journal of Modern Laboratory Medicine (2008) 23(1): 32-35. [English Abstract].

Liao et al., "Blinded comparison of repetitive-sequence PCR and multilocus sequence typing for genotyping methicillin-resistant *Staphylococcus aureus* isolates from a children's hospital in St. Louis, Missouri", J Clin Microbiol. (Jun. 2006) 44(6): 2254-2257.

Lizardi et al., "Exponential Amplification of Recombinant-RNA Hybridization Probes," BioTech. (Oct. 1988) 6: 1197-1202.

Louahabi et al., "Screening of methicillin-resistant *Staphylococcus aureus* directly from clinical specimens by real-time PCR," International Journal of Antimicrobial Agents, (Dec. 2004) vol. 24S, Abstract 365/79P, pp. S130. Meeting Info.: 6th European Congress of Chemotherapy and Infection/24th Interdisciplinary Meeting on Anti-Infectious Chemotherapy. Paris, France. Dec. 1-3, 2004.

Louie et al., "Rapid Detection of Methicillin-Resistant Staphylococci from Blood Culture Bottles by Using a Multiplex PCR Assay," J Clin Microbiol. 40(8):2786-2790 (2002).

Lu et al., "One tube multiplex PCR for simple screening of SCCmec I-V types of methicillin-resistant *Staphylococcus aureus*", J Chemother. (Dec. 2008) 20(6): 690-696.

Marin et al., "Molecular Diagnosis of Infective Endocarditis by Real-Time Broad-Range Polymerase Chain Reaction (PCR) and Sequencing Directly From Heart Valve Tissue," Medicine (2007) 86(4) 195-202.

Martineau et al., "Species-Specific and Ubiquitous-DNA-Based Assays for Rapid Identification of *Staphylococcus aureus*," J Clin Microb. (Mar. 1998) 36(3): 618-623.

Mason et al., "Multiplex PCR Protocol for the Daignosis of Staphylococcal Infection," J Clin Microbiol. 39(9): 3332-3338 (2001).

McBride et al., "Quantitative PCR Technology" in *Gene Quantification*, The Immune Response Corporation, Francois Ferre (Ed.), Birkhaeuser Boston (1998) pp. 97-110.

Menon et al., "Comparison of rapid method of DNA extraction using microwave irradiation with conventional phenol chloroform technique for use in multiplex PCR for mec A and fem B genes to identify genotypes of MRSA from cultures," Medical Journal Armed Forces India, (2001) 57(3): 194-196.

Merlino et al., "Detection and expression of methicillin/oxacillin resistance in multidrug-resistant and non-multidrug-resistant *Staphylococcus aureus* in Central Sydney, Australia," J Antimicrob Chemother. (2002) 49: 793-801.

Mongkolrattanothai et al. "Novel Non-mecA-Containing Staphylococcal Chromosomal Cassette Composite Island Containing pbp4 and tagF Genes in a Commensal Staphylococcal Species: a Possible Reservoir for Antibiotic Resistance Islands in *Staphylococcus aureus*." Antimicrob. Agents Chemother. (May 2004) 48(5): 1823-1836.

Narang et al. "Improved Phosphotriester Method for the Synthesis of Gene Fragments," Meth Enzymol. (1979) 68: 90-98.

Niemeyer et al., "Rapid DNA extraction for direct PCR identification of methicillin resistant staphylococci in clinical samples," Abstracts of the General Meeting of the American Society for Microbiology, (1998) vol. 98, Abs. C-419, pp. 201; 98th General Meeting of the American Society for Microbiology. Atlanta, Georgia, USA. May 17-21, 1998. American Society for Microbiology. Ohno, Akira, Japan Medical Journal (2001) 4051: 19-24.

Perez-Roth et al., "Multiplex PCR for Simultaneous Identification of *Staphylococcus aureus* and Detection of Methicillin and Mupirocin Resistance," J Clin Microbiol. 39(11):4037-4041 (2001).

Podzorski et al., Evaluation of the MVPlex Assay for Direct and Rapid Detection of Methicillin-Resistant *Staphylcoccus aureus* from Nares and Other Swab Speciments, (Abstract C-237), American Society for Microbiology 107th Meeting, Toronto, Canada May 21-25, 2007, p. 186.

Podzorski et al., MVPlex Assay for Direct Detection of Methicillin-Resistant *Staphylococcus aureus* in Naris and Other Swab Specimens, J Clin Microbiol. (Sep. 2008) 46(9): 3107-3109.

Ramos-Trujillo et al., Multiplex PCR for simultaneous detection of enterococcal genes vanA and vanB and staphylococcal genes mecA, ileS-2 and femB, Int Microbiol. (2003) 6(2):113-115.

Reischl et al., "Rapid identification of methicillin-resistant *Staphylococcus aureus* and simultaneous species confirmation using real-time fluorescence PCR," J Clin. Microbiol. (2000) 38:2429-2433.

RUIZ-Pérez de Pipaón et al., "Detection of methicillin resistance and identification of *Staphylococcus* spp. from positive blood culture bottles using the mecA and nucA genes with the LightCycler System", [English Abstract Only] Enfermedades infecciosas y microbiologia clinica (2005) vol. 23, No. 4, pp. 208-212.

(56) References Cited

OTHER PUBLICATIONS

Rupp et al., "Be Aware of the Possibility of False-Positive Results in Single-Locus PCR Assays for Methicillin-Resistant *Staphylococcus aureus*", (Jun. 2006) 44(6): 2317-8.
Rushdy et al., "Detection of methicillin/oxacillin resistant *Staphylococcus aureus* isolated from some clinical hospitals in Cairo using Meca/Nuc genes and antibiotic susceptibility profile," Internaitonal Journal of Agriculture and Biology (2007) 9(6):800-806.
Sabat et al., "Comparison of PCR-based methods for typing *Stapholococcus aureus* isolates," J Clin Micrbiol. 44(10) 3804-3807 (2006).
Sabet et al., "Simultaneous species identification and detection of methicillin resistance in staphylococci using triplex real-time PCR assay", Diagn Microbiol Infect Dis. Sep. 2006;56(1):13-8. Epub May 2, 2006.
Saiful et al., "Detection of methicillin-resistant *Staphylococcus aureus* using mecA/nuc genes and antibiotic susceptibility profile of Malaysian clnical isolates," World J Microbiol Biotechnol. (2006) 22: 1289-1294 [online: Apr. 20, 2006].
Saiki et al., "Enzymatic amplification of beta-globin genomic sequences and restriction site analysis for diagnosis of sickle cell anemia," Science (Dec. 1985) 230(4732): 1350-1354.
Sekiguchi et al., "Rapid and simple method for detecting qacA, mecA and femB in antiseptics—and methicillin-resistant *Staphylococcus aureus* by loop-mediated isothermal amplification," Abstracts of the General Meeting of the American Society for Microbiology, (2006) vol. 106, pp. 108; 106th General Meeting of the American Society for Microbiology. Orlando, FL, USA. May 21-25, 2006. Amer Soc Microbiol.
Shore et al. "Characterization of a Novel Arginine Catabolic Mobile Element (ACME) and Staphylococcal Chromosomal Cassette mec Composite Island with Significant Homology to *Staphylococcus epidermidis* ACME Type II in Methicillin-Resistant *Staphylococcus aureus* Genotype ST22-MRSA-IV." Antimicrob Agents Chemother. (May 2011) 55(5): 1896-1905.
Simor, et al. "Characterization and proposed nomenclature of epidemic strains of methicillin-resistant *Staphylococcus aureus* in Canada." Can J Infect Dis. Sep.-Oct. 1999; 10(5): 333-336.
Singleton P., DNA Methods in Clinical Microbiology, (2000) Dordrecht, Boston: Kluwer Academic. TOC only.
Sinsimer et al., "Use of a Multiplex Molecular Beacon Platform for Rapid Detection of Methicillin and Vancomycin Resistance in *Staphylococcus aureus*", J Clin Microbiol. (2005) 45(9): 4585-4591.
Stratidis et al., Use of real-time polymerase chain reaction for identification of methicillin-resistant *Staphylococcus aureus* directly from positive blood culture bottles, Diagn Microbiol Infect Dis. (2007) 58(2): 199-202.
Tan et al., "Rapid identification of methicillin-resistant *Staphylococcus aureus* from positive blood cultures by real-time fluorescence PCR," Journal of Clinical Microbiology (2001) 39(12):4529-4531.
Tang et al., StaphPlex System for Rapid and Simultaneous Identification of Antibiotic Resistance Determinants and Panton-Valentine Leukocidin Detection of Staphylococci from Positive Blood Cultures, J Clin Microbiol. (Jun. 2007) 45(6): 1867-1873.
Thomas et al., "Development of a real-time *Staphylococcus aureus* and MRSA (SAM-) PCR for routine blood culture," J Microbiol Methods (2007) 38(2):296-302 [Online: Oct. 12, 2006].
Tijssen, Laboratory Techniques in Biochemistry and Molecular Biology—Hybridization with Nucleic Acid Probes, (1993) Part I, Chapter 2, pp. 19-78 (Elsevier, New York).
Towner et al., "Development and evaluation of a PCR-based immunoassay for the rapid detection of methicillin-resistant *Staphylococcus aureus*," J Med Microbiol (1998) 47(7):607-613.
Van Hal et al., "Methicillin-Resistant *Staphylococcus aureus* (MRSA) Detection: Comparison of Two Molecular Methods (IDI-MRSA PCR Assay and GenoType MRSA Direct PCR Assay) with Three Selective MRSA Agars (MRSA ID, MRSASelect, and CHROMagar MRSA) for Use with Infection-Control Swabs", J Clin Microbiol. (Aug. 2007) 45(8): 2486-2490.
Vanguilder et al., "Twenty-five years of quantitative PCR for gene expression analysis", Biotechniques 25th Anniversary (2008) 44(5): 619-626.
Walker et al., "Strand displacement amplification—an isothermal, in vitro DNA amplification technique," Nucl Acids Res. (1992) 20(7): 1691-1696.
Wang at al., "Rapid detection of methicillin-resistant *Staphylococcus aureus* with duplex real-time PCR assay," Zhongguo Kangshengsu Zazhi (2007) 32(4) 225-228 [w/English Abstract].
Warren et al., "Detection of Methicillin-Resistant *Staphylococcus aureus* Directly from Nasal Swab Specimens by a Real-Time PCR Assay", J Clin Microbiol. (Dec. 2004) 42(12): 5578-5581.
Wei et al., "Detection of *Staphylococcus* isolates and their multidrug resistance genes by multiple PCR," Zhongguo Renshou Gonghuanbing Zazhi (Sep. 2004) 20(9), 814.
Wichelhaus et al., "Rapid molecular typing of methicillin-resistant *Staphylococcus aureus* by PCR-RFLP", Infect Cont Hosp Epidem. (May 2001) 22(5): 294-298.
Wittwer et al., "Fluorescence Monitoring of Rapid Cycle PCR for Quantification" in *Gene Quantification*, The Immune Response Corporation, Francois Ferre (Ed.), Birkhaeuser Boston (1998) pp. 97-110.
Woron et al., "Multiplex rt-PCR detection of MRSA from bacterial isolates," Abstracts of the General Meeting of the American Society for Microbiology, (2004) vol. 104, Abs C-116, pp. 143; 104th General Meeting of the American Society for Microbiology. New Orleans, LA, USA.
Wren et al., "Rapid molecular detection of methillin-resistant *Staphylococcus aureus*," Journal of Clinical Microbiology (2006) 44(4):1604-1605.
Wu et al., "Rapid detection of *Staphylococcus aureus* and methicillin resistance from blood cultures using a real-time PCR SmartCycler assay," Abstracts of the General Meeting of the American Society for Microbiology, 105th General Meeting of the American-Society-for-Microbiology. Atlanta, GA, USA; Abs. C-085; (2005) vol. 105, pp. 119.
Zhang et al., "Novel multiplex PCR assay for simultaneous identification of community-associated methicillin-resistant *Staphylococcus aureus* strains USA300 and USA400 and detection of mecA and Panton-Valentine leukocidin genes, with discrimination of *Staphylococcus aureus* from coagulase-negative staphylococci", J Clin Microbiol. (Mar. 2008) 46(3): 1118-1122; Epub Dec. 26, 2007.
Japanese Office Action dated Dec. 24, 2013 in Japanese Patent Application No. 2009-543155, filed Dec. 18, 2007.
European Extended Search Report dated Aug. 10, 2010 in European Patent Application No. 09174581.0, filed Jun. 4, 2002. [D33].
Response to Extended Search Report filed Mar. 3, 2011 in European Patent Application No. 09174581.0, filed Jun. 4, 2002. [D34].
Supplementary Response to Extended Search Report filed Nov. 16, 2011 in European Patent Application No. 09174581.0, filed Jun. 4, 2002. [D35].
Electronic File History [Part 2] Inter Partes Reexam Control No. 95/001,599, filed Apr. 8, 2011 including Examiner's Answer Aug. 2, 2013, Rebuttal Brief of Sep. 3, 2013, and Third Party Request for Oral Hearing Oct. 1, 2013.
PTO Action closing prosecution dated Sep. 20, 2013 of Inter Partes Reexamination Control No. 95/002,216, filed Sep. 13, 2012 for U.S. Appl. No. 11/248,438, filed Oct. 11, 2005 (U.S. Pat. No. 7,838,221) Part 2.
Comparison of the nucleotide sequence of MRSA strains V14 (deposited under Accession No. AB425427) with the nucleotide sequence of SEQ ID No. 165 from the Patent. Primer binding sites for some of the primers claimed in claim 4 of the EP2236621 [D12] cited on May 8, 2013; pp. 1-7.
Nucleotide Sequence of MRSA strain M08/1026 ACME/SCCmecCI of ST22-MRSA-Ivh deposited in Genbank Accession No. FR753166 with orfX and SCCmec portions of Seq ID No. 165 highlighted thereon. Also shown are primers binding sites for the primers of SEQ Id Nos. 64 and 112 from claim 5 of the EP2236621 [D14] cited on May 8, 2013; pp. 1-16.

(56) References Cited

OTHER PUBLICATIONS

Alignment of SEQ ID Nos. 42-46 and 51 with HDG2 sequence; GenBank Accession Version No. AF411934; Exhibit D9a in European Opposition of Patent No. 1397510, issued Mar. 17, 2004; pp. 10.
ClustalW2 Multiple nucleotide sequence alignment (generated using ClustalW2). The sequence of each of MREJ types I to xx (excluding type x) is aligned around the integration site. The sequence of the rjmec primer from D7 is also included; [D9] cited on May 8, 2013; p. 1.
Nucleotide Sequence alignment of SEQ ID No. 165 of EP2236621 [D17] with *Staphylococcus epidermidis* strain ATCC 12228 (Accession No. AE015929.1) cited on May 8, 2013; p. 1.
BLAST Sequence-Alignment between the orfX sequence from *Staphylococus aureus* and the equivalent *Staphylococcus epidermidis* sequence taken from a number of strains; [D19] cited on May 8, 2013; pp. 1-6.
SEQ ID No. 6—Figure 19 of D1 and D2. Primer biding sites for SEQ ID Nos. 64 and 98 from EP2236621 as underlined; [D22] cited on May 8, 2013; p. 1.
European Decision T 1496/11 of the Technical Boards of Appeal in re EP Patent No. 930979 [D28] of Sep. 12, 2012; pp. 1-28.
Annotated version of figure 4A of EP 2236621 cited on May 8, 2013; p. 1.
Sequence Alignment of SEQ ID No. 64 and SEQ ID No. 98 on SEQ ID No. 165 and SEQ ID No. 166 of EP2236621 [D31] cited on May 8, 2013; pp. 1-3.
Minutes of the Oral Proceedings on Jan. 30, 2013 in European Opposition to Patent No. No. 1397510 [D37] mailed Apr. 5, 2013.
EPO Decision of the Opposition Division of Apr. 5, 2013 in European Opposition to Patent No. No. 1397510 [D36].
Notice of Opposition filed May 8, 2013 against European Patent No. 2236621, granted Aug. 8, 2012.
EPO Board Decision and Minutes of Oral Proceedings dated Aug. 2, 2013 in European Opposition to Patent No. 1934613.
PTO 2nd Action closing prosecution dated Feb. 18, 2014, Patentee Response and 3rd PartyComments in Inter Partes Reexamination Control No. 95/002,216, filed Sep. 13, 2012 for U.S. Appl. No. 11/248,438, filed Oct. 11, 2005 (U.S. Pat. No. 7,838,221) Part 3.
International Search Report and Written Opinion dated Aug. 13, 2013 for International Patent Application No. PCT/IB2013/000900, filed Mar. 14, 2013.
Patentee Appeal dated Jun. 3, 2013 and Grounds for Appeal dated Aug. 12, 2013 against EPO Decision of Apr. 5, 2013 to Revoke Patent No. 1397510 [T 1294/13-3.3.08].
Opponent Beckman Coulter's Response dated Dec. 16, 2013 to Patentee's EPO Appeal and Grounds for Appeal in T 1294/13-3.3.08 against EPO Decision in Re EP Patent No. 1397510.
Patentee Reply filed Dec. 23, 2013 in EP Opposition proceedings against Patent No. 2236621.
Patentee Appeal dated Sep. 12, 2013 and Grounds for Appeal dated Dec. 11, 2013 against EPO Decision of Aug. 2, 2013 to Revoke Patent No. 1934613 [T 2002/13-3.3.08].
Opponent Koenig et al. Response dated Apr. 30, 2014 to Patentee's EPO Appeal and Grounds for Appeal in T 2002/13-3.3.08 against EPO Decision in Re EP Patent No. 1934613.
U.S. PTAB Record of Oral Hearing dated Jul. 16, 2014 in Inter Partes Reexam Control No. 95/001,599 [Appeal No. 2014-002900]; 66 pages.
U.S. PTAB Decision on Appeal dated Aug. 28, 2014 in Inter Partes Reexam Control No. 95/001,599 [Appeal No. 2014-002900]; 43 pages.
Requests for Rehearing and PTAB Decision for Requests dated Sep. 26, Sep. 29, 2014 and May 26, 2015 in Inter Partes Reexam Control No. 95/001,599 [Appeal No. 2014-002900]; 45 pages.
PTO 3rd Action closing prosecution dated Sep. 3, 2014, Patentee Responses and 3rd Party Comments in Inter Partes Reexamination Control No. 95/002,216, filed Sep. 13, 2012 for U.S. Appl. No. 11/248,438, filed Oct. 11, 2005 (U.S. Pat. No. 7,838,221); 74 pages.

Third Party [Applicant Requestor] Appeal Brief dated Nov. 26, 2014 in Inter Partes Reexamination Control No. 95/002,216, filed Sep. 13, 2012 for U.S. Appl. No. 11/248,438, filed Oct. 11, 2005 (U.S. Pat. No. 7,838,221).
Respondent's Brief on Appeal dated Dec. 29, 2014 in Inter Partes Reexamination Control No. 95/002,216, filed Sep. 13, 2012 for U.S. Appl. No. 11/248,438, filed Oct. 11, 2005 (U.S. Pat. No. 7,838,221); 409 pages.
Australian Office Action dated May 1, 2015 for Australian Application No. 2013200217, filed Jan. 16, 2013.
Australian Office Action dated May 1, 2015 for Australian Application No. 2013200218, filed Jan. 16, 2013.
Australian Office Action dated May 1, 2015 for Australian Application No. 2013200220, filed Jan. 16, 2013.
Canadian Office Action dated Feb. 13, 2014 for Canadian Application No. 2,673,357, filed Dec. 18, 2007.
Canadian Office Action dated Jul. 23, 2014 for Canadian Application No. 2,625,072, filed Oct. 10, 2006.
European Extended Search Report dated Aug. 25, 2014 in European Patent Application No. 14168417.5, filed May 15, 2014.
European Office Action dated Dec. 9, 2014 in European Patent Application No. 14168417.5, filed May 15, 2014.
European Extended Search Report dated Aug. 25, 2014 in European Patent Application No. 14168420.9, filed May 15, 2014.
European Office Action dated Dec. 17, 2014 in European Patent Application No. 14168420.9, filed May 15, 2014.
EPO Interlocutory Decision of Apr. 10, 2015 in EP Opposition proceedings against Patent No. EP 2236621.
Bustin S.A., "Absolute quantification of mRNA using real-time reverse transcription polymerase chain reaction assays", J Mol Endocrinol. (2000) 25: 169-193.
Lowe et al., "A Computer Program for Selection of Oligonucleotide Primers for Polymerase Chain Reactions", Nucl Acids Res. (1990) 18(7): 1757-1761.
NCBI BLAST AX720590: Sequence 167 from Patent WO02099034; [D16—Exhibit in European Opposition Proceeding: EP 2 322 655] downloaded on Aug. 21, 2015; 57 pages.
Shore et al. "Detection of Staphylococcal Cassette Chromosome mec Type XI Carrying Highly Divergent mecA, mecl, mecR1, blZ, and ccr Genes in Human Clinical Isolates of Clonal Complex 130 Methicillin-Resistant *Staphylococcus aureus*", Antimicrob Agents Chemother. (Aug. 2011) 55(8): 3765-3773.
Tyagi et al., "Molecular Beacons: Hybridization Probes for Detection of Nucleic Acids in Homogeneous Solutions," in *Nonradioactive Analysis of Biomolecules* (Part D); Springer Lab Manuals pp. 606-616; [Exh. D29]; 2000; 8 pages.
D7—Exhibit in European Opposition Proceeding: EP 2 322 661, EP 2 322 664 and EP 2 322 655; MREJ type viii sequence (SEQ ID No. 167) with orfX and SCCmec portions highlighted—WO2002099034 Sequence 1; 1 page.
D8—Exhibit in European Opposition Proceeding: EP 2 322 661, EP 2 322 664 and EP 2 322 655; MREJ type i, ii and iii sequences with orfX and SCCmec portions highlighted —WO2002099034 Sequence 1; 14 pages.
D9—Exhibit in European Opposition Proceeding: EP 2 322 661, EP 2 322 664 and EP 2 322 655; Alignmeht of type ii (SEQ ID No. 2) and type viii (SEQ ID No. 167) MREJ sequences confirming lack of MREJ specificity of primers in patent; 2 pages.
D10—Exhibit in European Opposition Proceeding: EP 2 322 661, EP 2 322 664 and EP 2 322 655; Alignment of type ii (SEQ ID No. 2) and type ix (SEQ ID No. 168) MREJ sequences confirming lack of MREJ specificity of primers in the Patent; AX720425; 2 pages.
D11—Exhibit in European Opposition Proceeding: EP 2 322 661, EP 2 322 664 & 2 322 655 Alignment of type iii (SEQ ID No. 104) and type vii (SEQ ID No. 165) MREJ sequences confirming lack of MREJ specificity of primers in the patent; 1 page.
D12—Exhibit in European Opposition Proceeding: EP 2 322 664 and EP 2 322 655; Alignment of type vi (SEQ ID No. 171) and *S. haemolyticus* MREJ sequences confirming lack of MRSA specificity of primers in the patent; 2 pages.
D12a—Exhibit in European Opposition Proceeding: EP 2 322 661; Example of overlap between type ix (SEQ ID No. 168) and other

(56) References Cited

OTHER PUBLICATIONS category of MRSA sequences confirming lack of MREJ specificity of primers claimed in the Patent; AB774374; 3 pages.
D12b—Exhibit in European Opposition Proceeding: EP 2 322 661; Example of overlap between type ix (SEQ ID No. 168) and other category of MRSA sequences confirming lack of MREJ specificity of primers claimed in the Patent; HF569115; 2 pages.
Cuny et al., "Rare Occurrence of Methicillin-Resistant *Staphylococcus aureus* CC130 with a Novel mecA Homologue in Humans in Germany", Plos One (2011) 6(9):e24360; 5 pages.
Turlej et al., "Staphylococcal Cassette Chromosome mec (SCCmec) Classification and Typing Methods: an Overview", Polish J Microbiol. (2011) 60(2):95-103.
International Working Group on the Classification of SCC Elements [IWG-SCC]. "Classification of staphylococcal cassette chromosome mec (SCCmec): guidelines for reporting novel SCCmec elements", Antimicrob Agents Chemother. (2009) 53(12):4961-4967.
Stegger et al. "Rapid detection, differentiation and typing of methicillin-resistant *Staphylococcus aureus* harbouring either mecA or the new mecA homologue mecALGA251", Clin Microbiol Infect (Online: Nov. 7, 2011); (2012) 18:395-400.
Supplementary European Search Report dated Apr. 7, 2009 for European Application No. 06825875.5, filed Oct. 10, 2006.
D57—Exhibit in Appeal Procedure—2nd Declaration by Prof. Mark C. Enright on Jan. 19, 2018 re 1st declaration of Sep. 29, 2017 in 2 pages.
D75—Exhibit in European Opposition Proceeding/Appeal: EP 2 322 661; Maloy S.R., (1990) *Experimental Techniques in bacterial genetics*. Jones & Bartlett Learning; Genetic Nomenclature—2 page excerpt.
D78—Exhibit in European Opposition Proceeding/Appeal: EP 2 322 661; Third Declaration of Prof Mark C. Enright dated Mar. 9, 2018 in 5 pages.
D79—Exhibit in European Opposition Proceeding/Appeal: EP 2 322 661; Declaration of Dr Duarte C. Oliveira dated Mar. 13, 2018 including Appendices in 16 pages.
EPO Interlocutory Decision in Opposition Proceedings and supporting documents dated Apr. 19, 2018 against EP 2322664; (263 pages).
Patentee/Appellant Submission re Appeal dated Aug. 18, 2018 and Grounds for Appeal dated Aug. 16, 2018 against EPO Decision of Apr. 19, 2018 to Revoke Patent No. 2322664 [T 1582/18-3.3.08]; 236 pages.
EPO Notice re Beckman Coulter Response to Summons to Oral Proceedings dated Dec. 6, 2017 against European Patent No. 2322655, granted Nov. 26, 2014 (154 pages).
Patent Proprietor's Reply to both Oppositions and supporting documents filed Apr. 11, 2016 in EP 2322661 granted Nov. 26, 2014 (446 pages).
EPO Notice re Beckman Coulter Response to Summons to Oral Proceedings dated Dec. 6, 2017 against European Patent No. 2322661, granted Nov. 26, 2014 (153 pages).
EPO Interlocutory Decision of Apr. 19, 2018 in EP Opposition proceedings against Patent No. 2322661, granted Nov. 26, 2014 (38 pages).
EPO Notice re Appeal (No. T1521/18-3.3.08) filed Aug. 29, 2018 by Beckman Coulter in EP Opposition proceedings against Patent No. 2322661, granted Nov. 26, 2014 (70 pages).
Patentee's/Appellant's Statement re Grounds of Appeal ((No. T1521/18-3.3.08) filed Aug. 28, 2018 EP Opposition proceedings against Patent No. 2322661, granted Nov. 26, 2014 (19 pages).
Opponent Beckman Coulter's Submission in Opposition Appeal No. T1146/15-3.3.08 (EP 2236621) dated Nov. 30, 2017 in 221 pages.
Patentee's/Appellant's Written Submission on Grounds of Appeal filed Sep. 26, 2018 and additional Appendices/Exhibits in Opposition Appeal No. T1146/15-3.3.08 (EP 2236621); in 227 pages.
EPO Interlocutory Decision of Jul. 5, 2018 and Minutes of Oral Proceeding in EP Opposition against Patent No. 2781604; 40 pages.
Patentee's/Appellant's Written Submission on Grounds of Appeal filed Nov. 15, 2018 and additional Appendices/Exhibits in Opposition Appeal No. T2255/18-3.3.08 (EP 2781604); in 188 pages.
Diekema et al., "Survey of infections due to *Staphylococcus* species: frequency of occurrence and antimicrobial susceptibility of isolates collected in the United States, Canada, Latin America, Europe, and the Western Pacific region for the SENTRY Antimicrobial Surveillance Program, 1997-1999", Clin Infect Dis. (2001) 32(Suppl. 2):S114-132.
Jones, R.N., "Use of Surveillance Programs as a Platform for Testing New Antimicrobials Against Multidrug Resistant Bacteria, Recent Experiences", Tufts University School of Medicine, Presentation of JMI Laboratories (61 pages).
D49—Exhibit in European Opposition Proceeding: FDA Approval of K033415 (IDI-MRSA Assay) to market; Letter, Mar. 18, 2004 with Summary & Indications for Use; 7 pages.
D51—Exhibit in European Opposition Proceeding: Gentechnische Methoden: Eine Sammlung von Arbeitsanleitungen fur das Molekularbiologische Labor. Publ. Gangolf Schrimpf (2002) Spektrum Akademischer Verlag GmbH; 3rd Edition; pp. 147-168.
D63—Exhibit in European Opposition Proceeding: NCBI—Nucleotide H569115-569102/4. *Staphylococcus aureus* subsp. *aureus* SCCmec . . . ; (Dec. 2012); 3 pages.
D55b—Exhibit in European Opposition Proceeding: NCBI—Nucleotide AY267380.1; AY267381.1; AY267376.1; AY267377.1. *Staphylococcus aureus* strain CCRI-1311 SCCmec . . . ; (2004); 6 pages.
European Office Action dated Aug. 2, 2018 in EP Application No. 15195621.6, filed Nov. 20, 2015.
EPO Notice re Beckman Coulter's Response to Summons to Oral Proceedings dated Nov. 30, 2017 in Opposition of European Patent No. 2322663, granted Nov. 26, 2014 (306 pages).
EPO Interlocutory Decision in Opposition Proceedings and supporting documents dated Apr. 11, 2018 against EP 2322663; (52 pages).
Patentee/Appellant Submission re Appeal filed Jun. 18, 2018 and Grounds for Appeal dated Aug. 21, 2018 against EPO Decision in European Patent No. 2322663 [T 1522/18-3.3.08]; (111 Pages).
Reply by Beckman Coulter to Opposition Appeal on Jan. 7, 2019 in EP 2322663, granted Mar. 18, 2015 (157 pages).
Reply by Opposer Beckman Coulter to Opposition Appeal on Jan. 10, 2019 in EP 2322664 [T 1582/18-3.3.08];(158 pages).
Further Reply by Opposer Beckman Coulter to Opposition Appeal re Reinstatement on Mar. 1, 2019 in EP 2322664, [T 1582/18-3.3.08]; (14 pages).
EPO Interlocutory Decision in Opposition Proceedings dated Mar. 27, 2018 against EP 2322655; (29 pages).
Patentee/Appellee's Submission re Appeal dated Aug. 6, 2018 and Grounds for Appeal against EPO Decision of Mar. 27, 2018 in re Patent No. 2322655 [T1421/18-3.3.08] (82 pages).
Opponent/Respondent Beckman Coulter Reply to Opposition Appeal on Dec. 19, 2018 in EP 2322655; [T1421/18-3.3.08] (258 pages).
Patentee/Appellee's Submission re Opposition Appeal dated Jan. 14, 2019 in re Patent No. 2322661 [T1521/18-3.3.08] (118 pages).
EPO Opposition Notice dated Dec. 2, 2016 with supporting documentation by Beckman Coulter Inc. against European Patent No. 2781603, granted Mar. 2, 2016; 234 pages.
Reply of the Patent Proprietor to Notice of Opposition dated May 19, 2017 in European Patent No. EP 2781603; 49 pages.
EPO Decision to Revoke EP 2781603 & Minutes of Oral Proceedings in Opposition Proceedings dated Jun. 25, 2018 ; 37 pages.
Patentee/Appellee's Submission re Appeal dated Sep. 5, 2018 against EPO Interlocutory Decision including Grounds for Appeal filed Nov. 5, 2018 in EP Opposition proceedings against Revocation of Patent No. 2781603; [T2261/18-3.3.08]; (27 pages).
Opponent/Respondent Beckman Coulter's Reply dated Mar. 18, 2019 to Patentee's Grounds for Appeal filed Nov. 5, 2018 in EP Opposition proceedings against Revocation of Patent No. 2781603; [T2261/18-3.3.08]; (102 pages).
EPO Opposition Notice dated Dec. 2, 2016 with supporting documentation by Beckman Coulter Inc. against European Patent No. 2781604, granted Mar. 2, 2016; 186 pages.

(56) References Cited

OTHER PUBLICATIONS

Reply of the Patent Proprietor to Notice of Opposition dated May 19, 2017 in European Patent No. EP 2781604; 35 pages.
Patentee's/Appellee's Reply to Appeal dated Apr. 9, 2019 to Opponent/Respondent Beckman Coulter's Grounds of Appeal filed Apr. 1, 2010 in EP Opposition proceedings against Revocation of Patent No. 2781604; [T2255/18-3.3.08]; (66 pages).
EPO Minutes of Oral Proceedings dated May 24, 2017 in Appeal No. T2002/13-3.3.08 against revocation of EP Patent No. 1934613; 6 pages.
EPO Board Decision dated Nov. 9, 2017 in Appeal No. T2002/13-3.3.08 against revocation of EP Patent No. 1934613; 32 pages.
Chaudhary et al., "Analyzing Immunoglobulin Repertoires", Front Immunol. (Mar. 2018) 9: 462 in 18 pages.
GenBank accession No. FR823292, "*Staphylococcus aureus* Staphylococcal Cassette Chromosome mec element XI (SCCmec XI), strain M10/0061", Aug. 2, 2011 in 15 pages.
GenBank accession No. FR821779, "*Staphylococcus aureus* subsp. *aureus* LGA 251 complete genome sequence", Aug. 23, 2011 in 1 page.
Hiramatsu et al., "Molecular genetics of methicillin-resistant *Staphylococcus aureus*," Int J Med Microbiol. 292: 67-74 (2002).
Ito et al., "Insights on antibiotic resistance of *Staphylococcus aureus* from its whole genome: genomic iland SCC." Drug Resistance Updates 6(1): 41-52 (2003).
Shulzhenko et al., Specificity of alternative splice form detection using RT-PCR with a primer spanning the exon junction. Biotechniques (2003) 34(6):1244-1249.
Simor et al., "Laboratory Characterization of Methicillin-Resistant *Staphylococcus aureus* in Canadian Hospitals: Results of 5 Years of National Surveillance, 1995-1999", J Infect Diseases (Aug. 2002) 186: 652-660.
Tarantul, V.Z., Explanatory dictionary of biotechnology. Russian-English, M. Yaziki slavyanskih kultur, 2009, p. 553.
Tickler et al., "Mobile genetic elements responsible for discordant *Staphylococcus aureus* phenotypes and genotypes in the same blood culture bottle," Diag Microbio Infect Disease (2020) 98: 115175 (6 pages).
Yadav S. et.al., Detection of methicillin-resistant *Staphylococcus aureus* (MRSA) from nasal samples by multiplex real-time PCR based on dual priming AT-rich primers. Folia microbiologica (Jan. 2012) 57(1):37-45.
Zhang et al., "Comparison of Two Versions of the IDI-MRSA Assay Using Charcoal Swabs for Prospective Nasal and Nonnasal Surveillance Samples", J Clin Microbio. 45(7): 2278-2280 (2007).
Baba et al. "*Staphylococcus aureus* subsp. *aureus* MW2 Dna, complete genome", retrieved from EBI Database accession No. AP004822 (May 27, 2002), replaced by Accession No. BA000033.
Cheng et al., "Effective amplification of long targets from cloned inserts and human genomic DNA," Proc Natl Acad Sci. USA, (Jun. 1994) 91: 5695-5699.
Crisóstomo et al., "The evolution of methicillin resistance in *Staphylococcus aureus*: Similarity of genetic backgrounds in historically early methicillin-susceptible and -resistant isolates and contemporary epidemic clones", Proc Natl Acad Sci USA, (Aug. 2001) 98(17): 9865-9870.
Database Geneseq [Online]. Sequence provided in Fig. 4 of JP11056371. Retrieved from EBI accession No. GSN:AAX32450 (Jun. 22, 1999).
Database Geneseq [Online]. "Identification method" JP1999056371, Retrieved from EBI accession No. EM-PRO:E60314 (Feb. 22, 2001).
Database Geneseq [Online]. "Sequence of Primer KC1". Retrieved from EBI accession No. GSN:AAX32446 (Jun. 22, 1999).
Diefenbach, Dveksler. "PCR Primer: a Laboratory Manual", 1995, Cold Spring Harbor Laboratory Press (Cover & Contents pages only).
Edwards et al., "Multiplex PCR: advantages, development, and applications", Genome Res. (1994) 3: S65-75.

Hagen, et al. "Development of a real-time PCR assay for rapid identification of methicillin-resistant *Staphylococcus aureus* from clinical samples." International Journal of Medical Microbiology, Urban and Fischer, DE. 295(2):77-86 (2005).
Ito et al. "*Staphylococcus aureus* DNA, 3' flanking region of mecDNA, strain 64/4176." GenBank accession No. AB014434, Jan. 7, 2000—Abstract only.
Kobayashi et al., "Genomic diversity of mec regulator genes in methicillin-resistant *Staphylococcus aureus* and *Staphylococcus epidermidis*", Epidemiol Infect. (1996) 117(2): 289-295.
Lee et al., "Nucleic Acid Amplification Technologies: Application to Disease Diagnosis", 1997, Eaton Publishing (Cover pages Only).
Lewin, "Genes IV", 1990, John Wiley & Sons, Chapter 3, Genes are Mutable Units, pp. 41-56.
Ma et al. "*Staphylococcus aureus* DNA, type-IV.2 (Ivb) staphylococcal cassette chromosome mec: strain JCSC1978 (8/6-3P)", EBI GenBank accession No. AB063173, Nov. 21, 2001.
Oliveira et al. "*Staphylococcus aureus* strain HDE288 type-VI SCCmec element, complete sequence" GenBank Accession Version No. AF411935, Mar. 5, 2002, pp. 8.
Oliveira et al. "*Staphylococcus aureus* strain PL72 genomic sequence upstream of mecA" GenBank Accession Version No. AF411936, Mar. 5, 2002, pp. 3.
Sambrook et al., "Molecular Cloning: a Laboratory Manual", 1989 Cold Spring Harbor Laboratory Press (Cover & Contents pages only).
Seki et al., Amplification of long targets of approximately 50 kb from cloned cosmid inserts of *Arabidopsis thaliana*, DNA Research (Jul. 1996) 3: 107-108.
Turbeville et al., "Amplification of the complete mitochondrial genome of two protostome worms: a useful technique for comparative studies of metazoan mitochondrial DNA", Mol Marine Bio Biotech., 6(2): 141-143 (1997).
Van Leeuwen et al., "Genetic diversification of methicillin-resistant *Staphylococcus aureus* as a function of prolonged geographic dissemination and as measured by binary typing and other genotyping methods," Res Microbiol, 149: 497-507 (1998).
Walker, et al., "Isothermal in vitro Amplification of DNA by a Restriction Enzyme/DNA Polymerase System," Proc Natl Acad Sci. USA, 89: 392-396 (Jan. 1992).
Watson et al., "Molecular Biology of the Gene", 1987, The Benjamin/Cummings Publishing Company (Cover pages only).
Ciardo et al., "GeneXpert Captures Unstable Methicillin-*Resistant Staphylococcus* aureus Prone to Rapidly Losing the *mecA*Gene," J. Clin. Microbio. (Aug. 2010) 48(8):3030-3031.
Database EMBL [Online]. "Staphylococcus aureus DNA, 3' flanking region of MecDNA, strain 64/4176", Retrieved from EBI accession No. AB014434 (Jan. 7, 2000).
Database EMBL [Online]. "Staphylococcus aureus M type 1 capsular polysaccharide biosynthesis gene cluster, complete sequence and unknown genes", Retrieved from EBI accession No. SA10927 (Nov. 8, 1994).
Database EMBL [Online]. "Staphylococcus aureus DNA, type-IV.1 (Iva) staphylococcal cassette chromosome mec: strain CA05 (JCSC1968)", retrieved from EBI accession No. AB063172 (Nov. 21, 2001).
Database Geneseq [Online]. "Staphylococcus aureus downstream junction sequence Psj10-3J3rc.", Retrieved from EBI accession No. GSN:AAT84818 (Mar. 23, 1998).
GenBank accession No. D86934.1, "Staphylococcus aureus genes, mec region, partial and complete cds.", Jul. 3, 1999.
Huletsky, et al. "Identification of Methicillin-Resistant *Staphylococcus aureus*Carriage in Less than 1 Hour during a Hospital Surveillance Program." Clin. Infect. Dis. (Apr. 2005) 40: 976-981.
Kobayashi et al., "Analysis on distribution of insertion sequence IS431 in *clinical isolates of staphylococci*", Diag. Micro. Infect. Dis. (2001) 39: 61-64.
Partial European Search Report dated Mar. 31, 2011 for European Patent Application No. 10016072.0, filed Oct. 10, 2006.
Partial European Search Report dated Mar. 31, 2011 for European Patent Application No. 10016073.8, filed Oct. 10, 2006.
Partial European Search Report dated Mar. 31, 2011 for European Patent Application No. 10016074.6, filed Oct. 10, 2006.

(56) References Cited

OTHER PUBLICATIONS

Partial European Search Report dated Mar. 31, 2011 for European Patent Application No. 10016031.6, filed Oct. 10, 2006.
Partial European Search Report dated Mar. 30, 2011 for European Patent Application No. 10016019.1, filed Oct. 10, 2006.
Partial European Search Report dated Mar. 30, 2011 for European Patent Application No. 10016020.9, filed Oct. 10, 2006.

\* cited by examiner

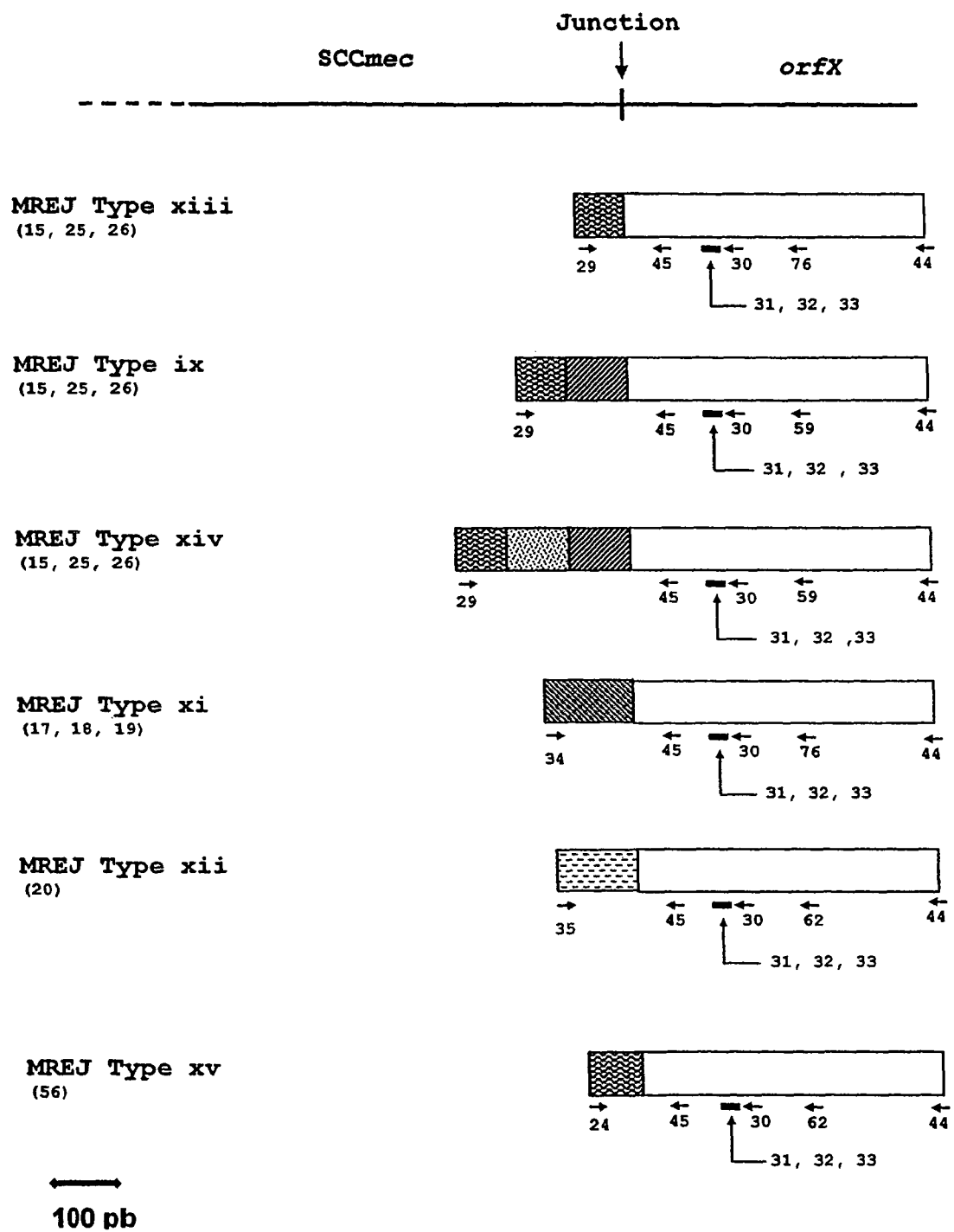

| | |
|---|---|
| FIG. 3A | FIG. 3B |
| FIG. 3C | FIG. 3D |
| FIG. 3E | FIG. 3F |
| FIG. 3G | FIG. 3H |
| FIG. 3I | FIG. 3J |
| FIG. 3K | FIG. 3L |
| FIG. 3M | FIG. 3N |
| FIG. 3O | FIG. 3P |
| FIG. 3Q | |

| | 260 | | | 280 | | 300 |
|---|---|---|---|---|---|---|
| | * | | * | | * | |
| mrej_i | AAGATGCTAT | CTTCCGAAGG | ATTGGCCCAA | GAATTGAACC | AACGCATGAC | CCAAGGGCAA |
| mrej_ii | AAGATGCTAT | CTTCCGAAGG | ATTGGCCCAA | GAATTGAACC | AACGCATGAC | CCAAGGGCAA |
| mrej_xvi | ---------- | ---------- | ---------- | ---------- | ---------- | ---------- |
| mrej_ix | AAGATGCTAT | CTTCCGAAGG | ATTGGCCCAA | GAATTGAACC | AACGCATGAC | CCAAGGGCAA |
| mrej_xiv | AAGATGCTAT | CTTCCGAAGG | ATTGGCCCAA | GAATTGAACC | AACGCATGAC | CCAAGGGCAA |
| mrej_xiii | AAGATGCTAT | CTTCCGAAGG | ATTGGCCCAA | GAATTGAACC | AACGCATGAC | CCAAGGGCAA |
| mrej_viii | AAGATGCTAT | CTTCCGAAGG | ATTGGCCCAA | GAATTGAACC | AACGCATGAC | CCAAGGGCAA |
| mrej_iii | AAGATGCTAT | CTTCCGAAGG | ATTGGCCCAA | GAATTGAACC | AACGCATGAC | CCAAGGGCAA |
| mrej_iv | AAGATGCTAT | CTTCCGAAGG | ATTGGCCCAA | GAATTGAACC | AACGCATGAC | CCAAGGGCAA |
| mrej_v | AAGATGCTAT | CTTCCGAAGG | ATTGGCCCAA | GAATTGAACC | AACGCATGAC | CCAAGGGCAA |
| mrej_vi | AAGATGCTAT | CTTCCGAAGG | ATTGGCCCAA | GAATTGAACC | AACGCATGAC | CCAAGGGCAA |
| mrej_vii | AAGATGCTAT | CTTCCGAAGG | ATTGGCCCAA | GAATTGAACC | AACGCATGAC | CCAAGGGCAA |
| mrej_xi | AAGATGCTAT | CTTCCGAAGG | ATTGGCCCAA | GAATTGAACC | AACGCATGAC | CCAAGGGCAA |
| mrej_xii | AAGATGCTAT | CTTCCGAAGG | ATTGGCCCAA | GAATTGAACC | AACGCATGAC | CCAAGGGCAA |
| mrej_xv | AAGATGCTAT | CTTCCGAAGG | ATTGGCCCAA | GAATTGAACC | AACGCATGAC | CCAAGGGCAA |
| mrej_xvii | AAGATGCTAT | CTTCCGAAGG | ATTGGCCCAA | GAATTGAACC | AACGCATGAC | CCAAGGGCAA |
| mrej_xviii | ---------- | ---------- | ---------- | ---------- | ---------- | ---------- |
| mrej_xix | ---------- | ---------- | ---------- | ---------- | ---------- | ---------- |
| mrej_xx | ---------- | ---------- | ---------- | ---------- | ---------- | ---------- |
| Consensus | AAGATGCTAT | CTTCCGAAGG | ATTGGCCCAA | GAATTGAACC | AACGCATGAC | CCAAGGGCAA |

```
          *         560          *          580         *         600
    TGTGAATTGC TGTTATGTTT TTAAGAAGCT |  |  |  |  |  |  |  |  |
    TGTGAATTGC TGTTATGTTT TTAAGAAGCT |  |  |  |  |  |  |  |  |
    TGTGAATTGC TGTTATGTTT TTAAGAAGCA |  |  |  |  |  |  |  |  |
    TGTGAATTGC TGTTATGTTT TTAAGAAGCA TATCATAAAT |  |  |  |  |
    TGAGAATATT TGCTATGTTT TTATGAAGCG ATACGATGTT TATAGAGTGT TTAATAAACC
    ATGAAAATATT GGATTATACC TTGCAATATC TATCCTCTTT AGTAGCGGTT TTTATCTGTA
    AGAAAACAAT AAAGTAGAGA TGGATTTCCA ATATTATAAT GTGAAACACA AAATAATAAT
    ACTTTTATT AAGAATAAT TCTAGTTGAT GAATTTAAGA GGTCATGAAA ATAGACTTAA
    TCAAATTTAA ATAAAGGGGT TTTTAAGTAT AGATTAAGAA TTTCCATTAT TTAATACATG
    TATTAAGTTT GATAATTTAG GTACAAGTAA AACTATAGCT TTGTAAACTA AAATGTAAAT
    GTTAACTTAC GATAATGCTT TTCGATAATC ACACTAGTGA AGATGATTTG
    AAATAAATAG AAAATGTTAG TTATAAAATCA TTCGATAATT TATGCAACT AATACATTGA
    CAAAAATTAT TGAAAGGGAA CTGTACCTTAG AAATTGAATC CACCAGGCTG TCTGGTAAAT
    ATCTAAGTAC TTATTTAATA ATTGATTGAA CTGTGATTGG GTGTAAAGAA ATCACAAATC
    CTTCACAGAA TAGCGAAGGA CTCCCATTAA ATATATTATG TAAAATGCAC TTAGCGACAT
    ATTATTTAAG CAGGTTTTTC AAATTAAATA ATAACAAGAA GCGCATATAA CTTAAGTAGT
    ATCCACGTTC ATTCAATATA TAAGATATAT CACGATAATT
    AKTAAATTAC TGTTATGTTT TTAAAAAGMA AWATATAATT KATCAAGTAA WTAAAATAAT
```

| | | | 980 | | * | | | 1000 |
|---|---|---|---|---|---|---|---|---|
| mrej_i | GTAGTTAAAA | AATCTGATTG | GGATAAAGGT | GATCTATATA |
| mrej_ii | GTAGTTAAAA | AATCTGATTG | GGATAAAGGT | GATCTATATA |
| mrej_xvi | GTAGTTAAAA | AATCTGATTG | GGATAAAGGT | GATCTATATA |
| mrej_ix | AGTTTGATGA | GGAATGGAAAT | AAAAGGAAAT | TAGGTGAAGT |
| mrej_xiv | AGTTTGATGA | GGAATGGAAAT | AAAAGGAAAT | TAGGTGAAGT |
| mrej_xiii | AGTTTGATGA | GGAATGGAAAT | AAAAGGAAAT | TAGGTGAAGT |
| mrej_viii | CGCCTGTATG | AACAATTTTA | TTTCTCATAC | CATAGTAATC |
| mrej_iii | TTTGAGAAAA | TTTTATGGGG | CATAGGGAAA | GTTTTATTGA |
| mrej_iv | GAATAGGATT | ATCATCAATA | TAAAGTGAAC | TACAGTCTGT |
| mrej_v | GTTTGAGTTC | CGTTTTGCTA | TTCCATAATT | CCAAACCATT |
| mrej_vi | TGAGGATAAT | ATTAAAGAAC | CACTTTCAAC | GATAAATAC |
| mrej_vii | AGCATCTACA | ATTACATTAA | TAAATATATA | AATGATGATT |
| mrej_xi | AAAATGGTGG | GTAATTATTA | TTATAGTAAT | CATAATTTGT |
| mrej_xii | GCTGACAAAG | ATCCAGTTAA | TGCTTTTTAT | AGTTGGAAGA |
| mrej_xv | ATGAAAAAAT | TTTATATAAT | AATTGCGTAA | AATATAAAA |
| mrej_xvii | AAGAAAGAAT | CGCAGGGATG | GTATTGAACA | ATTAAAAACA |
| mrej_xviii | ATGAAAACAA | TTTCAAGAAT | ACATTATAAA | CATAAAGTAT |
| mrej_xix | TTAACAGAAT | TAGCTTCGGA | ATTGAATATT | AAGTCCAAAA |
| mrej_xx | TTGCGAGACT | CATAAAATGT | AATAATGGAA | ATAGATGTAA |
| Consensus | ATARTRAAAA | ATTATGGWWA | AAATARAAAT | AATATAAAGA |

SEQUENCE LISTING

<160> NUMBER OF SEQ ID NOS: 97

<210> SEQ ID NO 1
<211> LENGTH: 21
<212> TYPE: DNA
<213> ORGANISM: Artificial Sequence
<220> FEATURE:
<223> OTHER INFORMATION: Synthetically prepared nucleic acid sequence

<400> SEQUENCE: 1
gcaggaacaa acagatgaag a                                              21

<210> SEQ ID NO 2
<211> LENGTH: 19
<212> TYPE: DNA
<213> ORGANISM: Artificial Sequence
<220> FEATURE:
<223> OTHER INFORMATION: Synthetically prepared nucleic acid sequence

<400> SEQUENCE: 2
tcggctctac cctcaacaa                                                 19

<210> SEQ ID NO 3
<211> LENGTH: 19
<212> TYPE: DNA
<213> ORGANISM: Artificial Sequence
<220> FEATURE:
<223> OTHER INFORMATION: Synthetically prepared nucleic acid sequence

<400> SEQUENCE: 3
tcgcagggat ggtattgaa                                                 19

<210> SEQ ID NO 4
<211> LENGTH: 19
<212> TYPE: DNA
<213> ORGANISM: Artificial Sequence
<220> FEATURE:
<223> OTHER INFORMATION: Synthetically prepared nucleic acid sequence

<400> SEQUENCE: 4
caccctgcaa gatatgttt                                                 19

<210> SEQ ID NO 5
<211> LENGTH: 25
<212> TYPE: DNA
<213> ORGANISM: Artificial Sequence
<220> FEATURE:
<223> OTHER INFORMATION: Synthetically prepared nucleic acid sequence

<400> SEQUENCE: 5
ttcgttgaaa gaagagaaaa ttaaa                                    25

<210> SEQ ID NO 6
<211> LENGTH: 27
<212> TYPE: DNA
<213> ORGANISM: Artificial Sequence
<220> FEATURE:
<223> OTHER INFORMATION: Synthetically prepared nucleic acid sequence

<400> SEQUENCE: 6 gcttttttttt ctttattatc aagtatc                                 27

<210> SEQ ID NO 7
<211> LENGTH: 25
<212> TYPE: DNA
<213> ORGANISM: Artificial Sequence
<220> FEATURE:
<223> OTHER INFORMATION: Synthetically prepared nucleic acid sequence

<400> SEQUENCE: 7
aatggaattt gttaatttca taaat                                    25

<210> SEQ ID NO 8
<211> LENGTH: 25
<212> TYPE: DNA
<213> ORGANISM: Artificial Sequence
<220> FEATURE:
<223> OTHER INFORMATION: Synthetically prepared nucleic acid sequence

<400> SEQUENCE: 8
ttccgaagtc ataatcaatc aaatt                                    25

<210> SEQ ID NO 9
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 9
ttccgaagct aattctgtta ata                                      23

<210> SEQ ID NO 10
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 10
aggcgttaaa aatcctgata ctg                                      23

<210> SEQ ID NO 11
<211> LENGTH: 22
<212> TYPE: DNA
<213> ORGANISM: Artificial Sequence
<220> FEATURE:
<223> OTHER INFORMATION: Synthetically prepared nucleic acid sequence -continued

```
<400> SEQUENCE: 11
aagccaattc aatttgtaat gc                                               22

<210> SEQ ID NO 12
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 12
aacccctcct ctgtaattag tg                                               22

<210> SEQ ID NO 13
<211> LENGTH: 21
<212> TYPE: DNA
<213> ORGANISM: Artificial Sequence
<220> FEATURE:
<223> OTHER INFORMATION: Synthetically prepared nucleic acid sequence

<400> SEQUENCE: 13
agcggtggag tgcaaataga t                                                21

<210> SEQ ID NO 14
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 14
ttgctggaca tcaacagtat cat                                              23

<210> SEQ ID NO 15
<211> LENGTH: 4149
<212> TYPE: DNA
<213> ORGANISM: Staphylococcus aureus

<400> SEQUENCE: 15
accattttag ctgtagggaa actaaaagag aaatattgga agcaagccat agcagaatat      60
gaaaaacgtt taggcccata caccaagata gacatcatag aagttccaga cgaaaaagca     120
ccagaaaata tgagcgacaa agaaattgag caagtaaaag aaaagaagg ccaacgaata      180 ctagccaaaa ttaaaccaca atccacagtc attacattag aaatacaagg aaagatgcta     240
tcttccgaag gattggccca agaattgaac caacgcatga cccaagggca aagcgacttt     300
gtattcgtca ttggcggatc aaacggcctg cacaaggacg tcttacaacg cagtaactac     360
gcactatcat tcagcaaaat gacattccca catcaaatga tgcgggttgt gttaattgag     420
caagtgtata gagcatttaa gattatgcgt ggagaagcat atcataagtg atgcggtttt     480
tattaattag ttgctaaaaa atgaagtatg caatattaat tattattaaa ttttgatata     540 tttaagaaa gattaagttt agggtgaatg aatggcttat caaagtgaat atgcattaga     600
aaatgaagta cttcaacaac ttgaggaatt gaactatgaa agagtaaata tacataatat     660
taaattagaa attaatgaat atctcaaaga actaggagtg ttgaaaaatg aataagcaga     720
caaatactcc agaactaaga tttccagagt ttgatgagga atggaaaaaa aggaaattag     780
gtgaagtagt aaattataaa aatggtggtt catttgaaag tttagtgaaa accatggtg      840 tatataaact cataactctt aaatctgtta atacagaagg aaagttgtgt aattctggaa     900
aatatatcga tgataaatgt gttgaaacat tgtgtaatga tactttagta atgatactga     960
```

```
gcgagcaagc accaggacta gttggaatga ctgcaattat acctaataat aatgagtatg    1020
tactaaatca acgagtagca gcactagtgc ctaaacaatt tatagatagt caatttctat    1080
ctaagttaat taatagaaac cagaaatatt tcagtgtgag atctgctgga acaaaagtga    1140
aaaatatttc taaaggacat gtagaaaact ttaattttt atctcctaat tacactgaac    1200
aacaaaaaat aggtaatttc ttcagcaaac tcgaccgcca gattgagtta aagaagaga    1260 aacttgaact cttagagcaa caaaagcgtg gatatattca gaagattttt tctcaagatt    1320
taagatttaa agatgaaaat ggaaacagtt atcctgattg gtctattaaa aagattgaag    1380
atatttctaa agttaataaa gggtttactc caaatacaaa aatgataaa tactgggatg    1440 aattaaatga aaattggtta tctatagcag gtatgacaca gaaatatttg tataaggaa    1500 ataaaggaat tactgaaaaa ggtgcatcaa agcatgtaaa agtagataaa gatactctaa    1560
taatgagttt taaattgact ttaggtaagt tagctatagt aaaagagcct atctatacaa    1620
atgaagctat atgccatttc gtatggaaag aaagtaatgt taatactgag tatatgtact    1680
actatttaaa ttctataaat ataagtactt ttggtgcaca ggcagttaaa ggagtaacat    1740
taaataacga tgcaattaat agtattatag taaagttacc agtgatacaa gaacaaaata    1800
aaatagcata cttttcaat aaattagata aattaattga aaaacaatct tctaaagtag    1860
aattattaaa acaacgcaaa caaggatttt tacagaaaat gtttgtttaa ttcttataaa    1920
gttctattat gtaaaatatt aaatagagat aacattatga aagcgagccc aagacataaa    1980 gttttttgaat aaataaaaaa gataatttct atcaaattaa tatagaaatt gtcttttta    2040 taaatttttt gattattttt agctgattga gctgttactt ttcttataat aagtgctatt    2100
agcacaaatc ctagttctct tttggctttg tttattcctc ttacggacat tcgagtgaaa    2160
cccattttaa ttttattaga agtaatttag gtttgaaccc acctaaataa atatatgagt    2220
tattttttta tgctacaaaa tatattcaga tttcaataat gacataaaat aggcatcttt    2280
atatttacct ttagtgtaga attgctcttt gagtaatcct tctgttttaa atccttgtga    2340
ctcgtatata tgcacagctt ttttgttatc tgtatcaaca tatagataaa ttttgtgcat    2400
gtttaatata tcgaatgcat aatttatcgc ttttcgaat gcgaattttg cataaccttt    2460
accactgaac tcaggtttaa taattatttg tatttcacaa ttacgatgga tgtaattaat    2520
ttctactaat tcaacaatac ctacgacttg attttcatct tcaacaataa aacgtctctc    2580
tgattcatct aataaatgct tatcaaataa atattgaagt tccgttaagg attcatatgg    2640
ttcttcaaac caataagaca taatagaata ttcattattt aattcatgaa caaaaagtaa    2700
atcactatac tctaatgctc ttagtttcat aattccactc ccaaaatttt ctcatatatt    2760
tgcattataa atataaataa cgaataagtc atcattcact gtgaatactc tattttaaca    2820
attcaccaca tactaattct catttcttg ttattctcga tttattactc ttactatgaa    2880
acctataaaa ttctcacatt tgtttgtatt aagaataaat acgtcgatag taacaataaa    2940
aaaataaata ataaagcatc cctcaccgta aaagtgaagg atgctctagt tttattgaaa    3000
tatacatttc attttgttaa ataattatta ataatatttt gaaaatcatt attacgtgaa    3060
atcttcatag atttttatcaa gtatttcttt gccttcaatt gctgtgaagt gatgtaccaa    3120 tctatttta caatcatatg taattttgtg acgctaggta attagtaatt gttcgtcagt    3180
ctgattgtat agtatcaagt ttcatagata atactctttg attttaatgt ccactttgac    3240
gtgctttaag attgagtata tacataatgt cattgtggaa tgttaaaaat cctacaaatg    3300
```

```
tttattcatc tgcaggattt ttaaatctcc aagaataaaa atcatcatag gacaactgga    3360
ttattgtttg gataaataac gtaaacaata attaggtact attatttatt tttgtttatt    3420 cttttccta acaaaataaa gaaagaata aacgcaattg ttaaaaatat gtgtcctaaa      3480
ccagcaatac cagcaatagc aggacttaca cttagatctt taatggtaga aataccgttc   3540
acgaattgca ttgccacagt aacaagcaca cctaaatggt atatataaaa gaaactgtta   3600
aacagctttg tatgagttgt taatttgaat tggccctcga taatcatgaa aattaagaac   3660
ataattgtac ctagtactaa taaatgtgta tgtgtaacat ttaattgaga aaaccgcta    3720 aaatcttccg cttttgtcat ttctctataa aatagaccac ttaataaccc taatagtgta   3780
tagagcgctg aactatacat taatcttttc atttttaattc cccctatttt taattacgag  3840
ataagtatag cggtagttta tgaactgagt atgaacttac aacaaaaaaa ttaatgaagt   3900
actttacaat aaaactcaatt tattagatgg tggagggacg aaaaaggatt ttagaaaaat  3960
aaattaatat attttatttt tgataagtaa taattaataa tatcttggaa atcattgtta   4020
agtattgttg taatacaatc gtcattcata aaatcttcat agttttatc aagaatttct   4080 tcatcttcga tagatgtgaa atgattagct aaccctttta taatttaagt gtaatttgtg  4140
aatctaaac                                                          4149

<210> SEQ ID NO 16
<211> LENGTH: 4353
<212> TYPE: DNA
<213> ORGANISM: Staphylococcus aureus

<400> SEQUENCE: 16
accattttag ctgtagggaa actaaaagag aaatattgga agcaagccat agcagaatat     60
gaaaaacgtt taggcccata caccaagata gacatcatag aagttccaga cgaaaaagca   120
ccagaaaata tgagcgacaa agaaattgag caagtaaaag aaaagaagg ccaacgaata    180 ctagccaaaa ttaaaccaca atccacagtc attacattag aaatacaagg aaagatgcta   240
tcttccgaag gattggccca agaattgaac caacgcatga cccaagggca aagcgacttt   300
gtattcgtca ttggcggatc aaacggcctg cacaaggacg tcttacaacg cagtaactac   360
gcactatcat tcagcaaaat gacattccca catcaaatga tgcgggttgt gttaattgag  420
caagtgtata gagcatttaa gattatgcgt ggagaagcat atcataaatg atgcggtttt   480
ttcagccgct tcataaaggg attttgaatg tatcagaaca tatgaggttt atgtgaattg   540
ctgttatgtt tttaagaagc atatcataaa tgatgcggtt ttttcagccg cttcataaag   600
ggattttgaa tgtatcagaa catatgaggt ttatgtgaat tgctgttatg tttttaagaa   660
gcatatcata agtgatgcgg ttttttattaa ttagttgcta aaaatgaag tatgcaatat    720 taattattat taaattttga tatatttaaa gaaagattaa gtttagggtg aatgaatggc    780
ttatcaaagt gaatatgcat tagaaaatga agtacttcaa caacttgagg aattgaacta    840
tgaaagagta aatatacata atattaaatt agaaattaat gaatatctca aagaactagg    900
agtgttgaaa aatgaataag cagacaaata ctccagaact aagatttcca gagtttgatg   960
aggaatggaa aaaaggaaa ttaggtgaag tagtaaatta taaaaatggt ggttcatttg   1020
aaagtttagt gaaaaaccat ggtgtatata aactcataac tcttaaatct gttaatacag   1080
aaggaaagtt gtgtaattct ggaaaatata tcgatgataa atgtgttgaa acattgtgta  1140
atgatacttt agtaatgata ctgagcgagc aagcaccagg actagttgga atgactgcaa  1200 ttataccta ataatgag tatgtactaa atcaacgagt agcagcacta gtgcctaaac    1260
```

```
aatttataga tagtcaattt ctatctaagt taattaatag aaaccagaaa tatttcagtg    1320
tgagatctgc tggaacaaaa gtgaaaaata tttctaaagg acatgtagaa aactttaatt    1380
ttttatctcc taattacact gaacaacaaa aaataggtaa tttcttcagc aaactcgacc    1440
gccagattga gttagaagaa gagaaacttg aactcttaga gcaacaaaag cgtggatata    1500
ttcagaagat ttttctcaa gatttaagat ttaagatga aatggaaac agttatcctg       1560 attggtctat taaaaagatt gaagatattt ctaaagttaa taaagggttt actccaaata    1620
caaaaaatga taaatactgg gatgaattaa atgaaaattg gttatctata gcaggtatga    1680
cacagaaata tttgtataaa ggaaataaag gaattactga aaaaggtgca tcaaagcatg    1740
taaaagtaga taaagatact ctaataatga gttttaaatt gactttaggt aagttagcta    1800
tagtaaaaga gcctatctat acaaatgaag ctatatgcca tttcgtatgg aaagaaagta    1860
atgttaatac tgagtatatg tactactatt taaattctat aaatataagt acttttggtg    1920
cacaggcagt taaaggagta acattaaata acgatgcaat taatagtatt atagtaaagt    1980
taccagtgat acaagaacaa aataaaatag catactttt caataaatta gataaattaa     2040
ttgaaaaaca atcttctaaa gtagaattat taaaacaacg caaacaagga ttttacaga    2100 aaatgtttgt ttaattctta taaagttcta ttatgtaaaa tattaaatag agataacatt    2160
atgaaagcga gcccaagaca taaagttttt gaataaataa aaaagataat ttctatcaaa    2220
ttaatataga aattgtctt tttataaatt ttttgattat ttttagctga ttgagctgtt     2280
acttttctta taataagtgc tattagcaca aatcctagtt ctcttttggc tttgtttatt    2340
cctcttacgg acattcgagt gaaacccatt ttaattttat tagaagtaat ttaggtttga    2400
acccacctaa ataaatatat gagttattt tttatgctac aaaatatatt cagatttcaa     2460
taatgacata aaataggcat ctttatattt accttagtg tagaattgct ctttgagtaa     2520
tccttctgtt ttaaatcctt gtgactcgta tatatgcaca gctttttgt tatctgtatc     2580 aacatataga taaattttgt gcatgtttaa tatatcgaat gcataattta tcgcttttc    2640 gaatgcgaat tttgcataac ctttaccact gaactcaggt ttaataatta tttgtatttc    2700
acaattacga tggatgtaat taatttctac taattcaaca atacctacga cttgattttc    2760
atcttcaaca ataaaacgtc tctctgattc atctaataaa tgcttatcaa ataaatattg    2820
aagttccgtt aaggattcat atggttcttc aaaccaataa gacataatag aatattcatt    2880
atttaattca tgaacaaaaa gtaaatcact atactctaat gctcttagtt tcataattcc    2940
actcccaaaa ttttctcata tatttgcatt ataaatataa ataacgaata agtcatcatt    3000
cactgtgaat actctatttt aacaattcac cacatactaa ttctcatttt cttgttattc    3060
tcgatttatt actcttacta tgaaacctat aaaattctca catttgtttg tattaagaat    3120
aaatacgtcg atagtaacaa taaaaaaata aataataaag catccctcac cgtaaaagtg    3180
aaggatgctc tagttttatt gaaatataca tttcattttg ttaaataatt attaataata    3240
ttttgaaaat cattattacg tgaaatcttc atagatttta tcaagtatt ctttgccttc     3300 aattgctgtg aagtgatgta ccaatctatt tttacaatca tatgtaattt tgtgacgcta    3360
ggtaattagt aattgttcgt cagtctgatt gtatagtatc aagtttcata gataaactc     3420 tttgattta atgtccactt tgacgtgctt taagattgag tatatacata atgtcattgt     3480
ggaatgttaa aaatcctaca aatgtttatt catctgcagg attttaaat ctccaagaat     3540 aaaaatcatc ataggacaac tggattattg tttggataaa taacgtaaac aataattagg    3600
```

```
tactattatt tattttttgtt tattcttttt cctaacaaaa taaagaaaag aataaacgca    3660
attgttaaaa atatgtgtcc taaaccagca ataccagcaa tagcaggact tacacttaga    3720
tctttaatgg tagaaatacc gttcacgaat tgcattgcca cagtaacaag cacacctaaa    3780
tggtatatat aaaagaaact gttaaacagc tttgtatgag ttgttaattt gaattggccc    3840
tcgataatca tgaaaattaa gaacataatt gtacctagta ctaataaatg tgtatgtgta    3900
acatttaatt gagaaaaacc gctaaaatct tccgcttttg tcatttctct ataaaataga    3960
ccacttaata accctaatag tgtatagagc gctgaactat acattaatct tttcatttta    4020
attcccccta tttttaatta cgagataagt atagcggtag tttatgaact gagtatgaac    4080
ttacaacaaa aaaattaatg aagtacttta caataaactc aatttattag atggtggagg    4140
gacgaaaaag gattttagaa aaataaatta atatatttt attttgataa gtaataatta     4200
ataatatctt ggaaatcatt gttaagtatt gttgtaatac aatcgtcatt cataaaatct    4260
tcatagattt tatcaagaat ttcttcatct tcgatagatg tgaaatgatt agctaacccct   4320 tttataattt aagtgtaatt tgtgaatcta aac                                 4353
```

<210> SEQ ID NO 17
<211> LENGTH: 1100
<212> TYPE: DNA
<213> ORGANISM: Staphylococcus aureus

<400> SEQUENCE: 17

```
accattttag ctgtagggaa actaaaagag aaatattgga agcaagccat agcagaatat     60
gaaaaacgtt taggcccata caccaagata gacatcatag aagttccaga cgaaaaagca    120
ccagaaaata tgagcgacaa agaaattgag caagtaaaag aaaagaagg ccaacgaata     180 ctagccaaaa ttaaaccaca atccacagtc attacattag aaatcaagg aaagatgcta    240 tcttccgaag gattggccca agaattgaac caacgcatga cccaagggca aagcgacttt    300
gtattcgtca ttggcggatc aaacggcctg cacaaggacg tcttacaacg cagtaactac    360
gcactatcat tcagcaaaat gacattccca catcaaatga tgcgggttgt gttaattgag    420
caagtgtata gagcatttaa gattatgcgt ggagaagcgt atcacaaata aaactaaaaa    480
ataagttgta tataacttat tttgaaattg gttaagtata taatatctcc aataaaatgt    540
agttaactta cgataatgct gaactatagc tttgtaaact aaaatgtaaa taattacaat    600
caaattgcaa caatatagtt caagaatgct acaatttgag gacagattga tagcattaat    660
ccctttaaaa tgaagctagg agataactta cattatgatt agtaaacaaa taaggatttt   720
acgaaagcaa cataattata ctcaagaaga gctagctgaa aaattaaata cttcaagaca    780
aacaatttct aaatgggaac aaggtatttc agaaccagac ttaattatgc ttatgcaatt    840
gtcacaatta ttttctgtta gtacagacta tctcattaca ggaagtgaca atattattaa    900
aaaagataat aaaagctatt atgaaatgaa ttttttgggca tttatgtctg aaaaatggtg    960
ggtaattatt attatagtaa tcataatttg tggaacaata ggacaaattt tttcaaacta   1020
atgtaagtat ctctcaaata ttttgggagg ttttattatg aaaatcaaaa aattattaaa   1080
gacattatta attattttat                                                1100
```

<210> SEQ ID NO 18
<211> LENGTH: 1109
<212> TYPE: DNA
<213> ORGANISM: Staphylococcus aureus

<400> SEQUENCE: 18

-continued

| | |
|---|---|
| accattttag ctgtagggaa actaaaagag aaatattgga agcaagccat agcagaatat | 60 |
| gaaaaacgtt taggcccata caccaagata gacatcatag aagttccaga cgaaaaagca | 120 |
| ccagaaaata tgagcgacaa agaaattgag caagtaaaag aaaagaaagg ccaacgaata | 180 |
| ctagccaaaa tcaaaccaca atcaacagtc attacattag aaatacaagg aaagatgcta | 240 |
| tcttccgaag gattggccca agaattgaac caacgcatga cccaagggca aagcgacttt | 300 |
| gtattcgtca ttggcggatc aaacggcctg cacaaggacg tcttacaacg cagtaactac | 360 |
| gcactatcat tcagcaaaat gacattccca catcaaatga tgcgggttgt gttaattgaa | 420 |
| caagtgtaca gagcatttaa gattatgcgt ggagaagcgt atcacaaata aaactaaaaa | 480 |
| ataagttgta tataacttat tttgaaattg gttaagtata tagtatctcc aataaaatgt | 540 |
| agttaactta cgataatgct gaactatagc tttgtaaact aaaatgtaaa taattacaat | 600 |
| caaattgcaa caatatagtt caagaatgct acaatttgag gacagattga tagcattaat | 660 |
| cccttttaaaa tgaagctagg agataactta cattatgatt agtaaacaaa taaaggattt | 720 |
| acgaaagcaa cataattata ctcaagaaga gctagctgaa aaattaaata cttcaagaca | 780 |
| aacaatttct aaatgggaac aaggtatttc agaaccagac ttaattatgc ttatgcaatt | 840 |
| gtcacaatta ttttctgtta gtacagacta tctcattaca ggaagtgaca atattattaa | 900 |
| aaaagataat aaaagctatt atgaaatgaa ttttgggca tttatgtctg aaaatggtg | 960 |
| ggtaattatt attatagtaa tcataatttg tggaacaata ggacaaattt tttcaaacta | 1020 |
| atgtaagtat ctctcaaata ttttgggagg ttttattatg aaaatcaaaa aattattaaa | 1080 |
| gacattatta attattttat tatgttttg | 1109 |

<210> SEQ ID NO 19
<211> LENGTH: 1159
<212> TYPE: DNA
<213> ORGANISM: Staphylococcus aureus

<400> SEQUENCE: 19

| | |
|---|---|
| accattttag ctgtagggaa actaaaagag aaatattgga agcaagccat agcagaatat | 60 |
| gaaaaacgtt taggcccata caccaagata gacatcatag aagttccaga cgaaaaagca | 120 |
| ccagaaaata tgagcgacaa agaaattgag caagtaaaag aaaagaaagg ccaacgaata | 180 |
| ctagccaaaa tcaaaccaca atcaacagtc attacattag aaatacaagg aaagatgcta | 240 |
| tcttccgaag gattggccca agaattgaac caacgcatga cccaagggca aagcgacttt | 300 |
| gtattcgtca ttggcggatc aaacggcctg cacaaggacg tcttacaacg cagtaactac | 360 |
| gcactatcat tcagcaaaat gacattccca catcaaatga tgcgggttgt gttaattgaa | 420 |
| caagtgtaca gagcatttaa gattatgcgt ggagaagcgt atcacaaata aaactaaaaa | 480 |
| ataagttgta tataacttat tttgaaattg gttaagtata tagtatctcc aataaaatgt | 540 |
| agttaactta cgataatgct gaactatagc tttgtaaact aaaatgtaaa taattacaat | 600 |
| caaattgcaa caatatagtt caagaatgct acaatttgag gacagattga tagcattaat | 660 |
| cccttttaaaa tgaagctagg agataactta cattatgatt agtaaacaaa taaaggattt | 720 |
| acgaaagcaa cataattata ctcaagaaga gctagctgaa aaattaaata cttcaagaca | 780 |
| aacaatttct aaatgggaac aaggtatttc agaaccagac ttaattatgc ttatgcaatt | 840 |
| gtcacaatta ttttctgtta gtacagacta tctcattaca ggaagtgaca atattattaa | 900 |
| aaaagataat aaaagctatt atgaaatgaa ttttgggca tttatgtctg aaaatggtg | 960 |

```
ggtaattatt attatagtaa tcataatttg tggaacaata ggacaaattt tttcaaacta   1020
atgtaagtat ctctcaaata ttttgggagg ttttattatg aaaatcaaaa aattattaaa   1080
gacattatta attattttat tatgttttgt attgtctgtt attgtgcaaa atatttcaat   1140
gctatggcat attgtgagc                                                1159
```

```
<210> SEQ ID NO 20
<211> LENGTH: 1125
<212> TYPE: DNA
<213> ORGANISM: Staphylococcus aureus

<400> SEQUENCE: 20
accattttag ctgtagggaa actaaaagag aaatattgga agcaagccat agcagaatat     60
gaaaaacgtt taggcccata caccaagata gacatcatag aagttccaga cgaaaaagca    120
ccagaaaata tgagcgacaa agaaattgag caagtaaaag aaaaagaagg ccaacgaata    180
ctagccaaaa tcaaaccaca atccacagtc attacattag aaatacaagg aaagatgcta    240
tcttccgaag gattggccca agaattgaac caacgcatga cccaagggca aagcgacttt    300
gtattcgtca ttggcggatc aaacggcctg cacaaggacg tcttacaacg cagtaactat    360
gcactatcat ttagcaaaat gacattccca catcaaatga tgcgggttgt gttaattgaa    420
caagtgtata gagcatttaa gattatgcgt ggagaggcgt atcataaata aaactaaaaa    480
acggattgtg tataatatat tttaaatata aaaaggatta ttttatgtt aaataaatta    540 gaaaatgtta gttataaatc attcgataat tacactagtg aagatgattt gactaaagta    600
aatatatttt ttggaagaaa tgggagtgga aaaagctcat taagtgaatg gttaagaaga    660
ctagataatg aaaaaagtgt tatctttaat actggttact aaaaaataa tattgaagaa    720 gttgaagaaa tagatggtgt gaatttggtt attggagaag aatctataaa tcatagtgac    780
caaattaagc atttaaatag cgctataaat agtttagaaa attttattac tcggaaaaat    840
agtgaactta agcattcaaa agaaagaatt tacaataaaa tgaatatcag actaaatgaa    900
gctagagaaa gatttgaaat aggtagtaat gtggttaagc agaagaggaa tgctgacaaa    960
gatccagtta atgctttta tagttggaag aaaaatgcta acgatataat tcaagagatg   1020
actattgaat ctttagatga attagaagaa agaataacaa gaaaagaagt cttattaaat   1080
aatataaaaa caccaatttt agcttttgat tataatgatt ttagt                   1125
```

```
<210> SEQ ID NO 21
<211> LENGTH: 818
<212> TYPE: DNA
<213> ORGANISM: Staphylococcus aureus

<400> SEQUENCE: 21
aatattggaa gcaagccata gcagaatatg aaaaacgttt aggcccatac accaagatag     60
acatcataga agttccagac gaaaaagcac cagaaaatat gagcgacaaa gaaattgagc    120
aagtgtatag agcatttaag attatgcgtg gagaagcata tcataaatga tgcggttttt    180
tcagccgctt cataaaggga ttttgaatgt atcagaacat atgaggttta tgtgaattgc    240
tgttatgttt ttaagaagct tatcataagt aatgaggttc atgattttg acatagttag    300 cctccgcagt ctttcatttc aagtaaataa tagcgaaata ttctttatac tgaatactta    360
tagtgaagca agttctagc tttgagaaaa ttctttctgc aactaaatat agtaaattac    420
ggtaaaatat aaataagtac atattgaaga aaatgagaca taatatattt tataatagga    480
gggaatttca aatgatagac aactttatgc aggtccttaa attaattaaa gagaaacgta    540
```

```
ccaataatgt agttaaaaaa tctgattggg ataaaggtga tctatataaa actttagtcc    600
atgataagtt acccaagcag ttaaaagtgc atataaaaga agataaatat tcagttgtag    660
ggaaggttgc tactgggaac tatagtaaag ttccttggat ttcaatatat gatgagaata    720
taacaaaaga aacaaggat ggatattatt tggtatatct ttttcatccg gaaggagaag    780
gcatatactt atcttgaatc aaggatggtc aaagataa                            818
```

```
<210> SEQ ID NO 22
<211> LENGTH: 27
<212> TYPE: DNA
<213> ORGANISM: Artificial Sequence
<220> FEATURE:
<223> OTHER INFORMATION: Synthetically prepared nucleic acid sequence

<400> SEQUENCE: 22
aacaggtgaa ttattagcac ttgtaag                                         27
```

```
<210> SEQ ID NO 23
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 23
gagcggattt atattaaaac tttg                                            24
```

```
<210> SEQ ID NO 24
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 24
gttgccatag attcaatttc taag                                            24
```

```
<210> SEQ ID NO 25
<211> LENGTH: 1081
<212> TYPE: DNA
<213> ORGANISM: Staphylococcus aureus

<400> SEQUENCE: 25
accattttag ctgtagggaa actaaaagag aaatattgga agcaagccat agcagaatat    60
gaaaaacgtt taggcccata caccaagata gacatcatag aagttccaga cgaaaaagca   120
ccagaaaata tgagcgacaa agaaattgag caagtaaaag aaaaagaagg ccaacgaata   180
ctagccaaaa tcaaaccaca atcaacagtc attacattag aaatacaagg aaagatgcta   240
tcttccgaag gattggccca agaattgaac caacgcatga cccaagggca aagcgacttt   300
gtattcgtca ttggcggatc aaacggcctg cacaaggacg tcttacaacg cagtaactac   360
gcactatcat tcagcaaaat gacattccca catcaaatga tgcgggttgt gttaattgaa   420
caagtgtaca gagcatttaa gattatgcgt ggagaagcat atcataagtg atgcggtttt   480
tattaattag ttgctaaaaa atgaagtatg caatattaat tattattaaa ttttgatata   540
tttaaagaaa gattaagttt agggtgaatg aatggcttat caagtgaat atgcattaga   600 aaatgaagta cttcaacaac ttgaggaatt gaactatgaa agagtaaaata tacataaatat   660 taaattagaa attaatgaat atctcaaaga actaggagtg ttgaaaaatg aataagcaga   720
```

```
caaatactcc agaactaaga tttccagagt ttgatgagga atggaaaaaa aggaaattag    780
gtgaagtagt aaattataaa aatggtggtt catttgaaag tttagtgaaa aaccatggtg    840
tatataaact cataactctt aaatctgtta atacagaagg aaagttgtgt aattctggaa    900
aatatatcga tgataaatgt gttgaaacat tgtgtaatga tactttagta atgatactga    960
gcgagcaagc accaggacta gttggaatga ctgcaattat acctaataat aatgagtatg   1020
tactaaatca acgagtagca gcactagtgc taaacaatt tatagatagt caatttctat    1080
c                                                                   1081

<210> SEQ ID NO 26
<211> LENGTH: 1054
<212> TYPE: DNA
<213> ORGANISM: Staphylococcus aureus

<400> SEQUENCE: 26
accattttag ctgtagggaa actaaaagag aaatattgga agcaagccat agcagaatat     60
gaaaaacgtt taggcccata caccaagata gacatcatag aagttccaga cgaaaaagca    120
ccagaaaata tgagcgacaa agaaattgag caagtaaaag aaaaagaagg ccaacgaata    180
ctagccaaaa tcaaaccaca atcaacagtc attacattag aaatacaagg aaagatgcta    240
tcttccgaag gattggccca agaattgaac caacgcatga cccaagggca aagcgacttt    300
gtattcgtca ttggcggatc aaacggcctg cacaaggacg tcttacaacg cagtaactac    360
gcactatcat tcagcaaaat gacattccca catcaaatga tgcgggttgt gttaattgaa    420
caagtgtaca gagcatttaa gattatgcgt ggagaagcat atcataagtg atgcggtttt    480
tattaattag ttgctaaaaa atgaagtatg caatattaat tattattaaa ttttgatata    540
tttaaagaaa gattaagttt agggtgaatg aatggcttat caaagtgaat atgcattaga    600
aaatgaagta cttcaacaac ttgaggaatt gaactatgaa agagtaaata tacataatat    660
taaattagaa attaatgaat atctcaaaga actaggagtg ttgaaaaatg aataagcaga    720
caaatactcc agaactaaga tttccagagt ttgatgagga atggaaaaaa aggaaattag    780
gtgaagtagt aaattataaa aatggtggtt catttgaaag tttagtgaaa aaccatggtg    840
tatataaact cataactctt aaatctgtta atacagaagg aaagttgtgt aattctggaa    900
aatatatcga tgataaatgt gttgaaacat tgtgtaatga tactttagta atgatactga    960
gcgagcaagc accaggacta gttggaatga ctgcaattat acctaataat aatgagtatg   1020
tactaaatca acgagtagca gcactagtgc taa                                1054

<210> SEQ ID NO 27
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 27
ttcttaagta cacgctgaat cg                                              22

<210> SEQ ID NO 28
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 28
```
taatttcctt tttttccatt cctc                                          24

<210> SEQ ID NO 29
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 29
tgataagcca ttcattcacc ctaa                                          24

<210> SEQ ID NO 30
<211> LENGTH: 19
<212> TYPE: DNA
<213> ORGANISM: Artificial Sequence
<220> FEATURE:
<223> OTHER INFORMATION: Synthetically prepared nucleic acid sequence

<400> SEQUENCE: 30
ggatcaaacg gcctgcaca                                                19

<210> SEQ ID NO 31
<211> LENGTH: 37
<212> TYPE: DNA
<213> ORGANISM: Artificial Sequence
<220> FEATURE:
<223> OTHER INFORMATION: Synthetically prepared nucleic acid sequence

<400> SEQUENCE: 31
cccgcgcgta gttactgcgt tgtaagacgt ccgcggg                            37

<210> SEQ ID NO 32
<211> LENGTH: 37
<212> TYPE: DNA
<213> ORGANISM: Artificial Sequence
<220> FEATURE:
<223> OTHER INFORMATION: Synthetically prepared nucleic acid sequence

<400> SEQUENCE: 32
cccgcgcata gttactgcgt tgtaagacgt ccgcggg                            37

<210> SEQ ID NO 33
<211> LENGTH: 37
<212> TYPE: DNA
<213> ORGANISM: Artificial Sequence
<220> FEATURE:
<223> OTHER INFORMATION: Synthetically prepared nucleic acid sequence

<400> SEQUENCE: 33
cccgcgcgta gttactacgt tgtaagacgt ccgcggg                            37

<210> SEQ ID NO 34
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 34
caaattgtag cattcttgaa ctat                                          24

<210> SEQ ID NO 35
<211> LENGTH: 24
<212> TYPE: DNA

<213> ORGANISM: Artificial Sequence
<220> FEATURE:
<223> OTHER INFORMATION: Synthetically prepared nucleic acid sequence

<400> SEQUENCE: 35
ctcccatttc ttccaaaaaa tata                                           24

<210> SEQ ID NO 36
<211> LENGTH: 29
<212> TYPE: DNA
<213> ORGANISM: Artificial Sequence
<220> FEATURE:
<223> OTHER INFORMATION: Synthetically prepared nucleic acid sequence

<400> SEQUENCE: 36
gtcaaaaatc atgaacctca ttacttatg                                      29

<210> SEQ ID NO 37
<211> LENGTH: 1256
<212> TYPE: DNA
<213> ORGANISM: Staphylococcus aureus

<400> SEQUENCE: 37
gctgtaggga aactaaaaga gaaatattgg aagcaagcca tagcagaata tgaaaaacgt    60
ttaggcccat acaccaagat agacatcata gaagttccag acgaaaaagc accagaaaat   120
atgagcgaca agaaattga gcaagtaaaa gaaaagaag ccaacgaat actagccaaa     180 attaaaccac aatccacagt cattacatta gaaatacaag gaaagatgct atcttccgaa   240
ggattggccc aagaattgaa ccaacgcatg acccaagggc aaagcgactt tgtattcgtc   300
attggcggat caaacggcct gcacaaggac gtcttacaac gcagtaacta cgcactatca   360
ttcagcaaaa tgcattccc acatcaaatg atgcgggttg tgttaattga gcaagtgtat   420
agagcattta agattatgcg tggagaagca tatcataaat gatgcggttt tttcagccgc   480
ttcataaagg gatttgaat gtatcagaac atatgaggtt tatgtgaatt gctgttatgt   540
ttttaagaag catatcataa gtgatgcggt ttttattaat tagttgctaa aaaatgaagt   600
atgcaatatt aattattatt aaattttgat atatttaaag aaagattaag tttagggtga   660
atgaatggct tatcaaagtg aatatgcatt agaaaatgaa gtacttcaac aacttgagga   720
attgaactat gaaagagtaa atatacataa tattaaatta gaaattaatg aatatctcaa   780
agaactagga gtgttgaaaa atgaataagc agacaaatac tccagaacta agatttccag   840
agtttgatga ggaatggaaa aaaggaaat taggtgaagt agtaaattat aaaaatggtg   900
gttcatttga aagtttagtg aaaaaccatg gtgtatataa actcataact cttaaatctg   960
ttaatacaga aggaaagttg tgtaattctg gaaatatat cgatgataaa tgtgttgaaa  1020
cattgtgtaa tgatacttta gtaatgatac tgagcgagca agcaccagga ctagttggaa  1080
tgactgcaat tatacctaat aataatgagt atgtactaaa tcaacgagta gcagcactag  1140
tgcctaaaca atttatagat agtcaatttc tatctaagtt aattaataga aaccagaaat  1200
atttcagtgt gagatctgct ggaacaaaag tgaaaaatat ttctaaagga catgta      1256

<210> SEQ ID NO 38
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 38

```
gaggaccaaa cgacatgaaa atc                                             23
```

<210> SEQ ID NO 39
<211> LENGTH: 756
<212> TYPE: DNA
<213> ORGANISM: Staphylococcus aureus

<400> SEQUENCE: 39

```
tgacattccc acatcaaatg atgcgggttg tgttaattga gcaagtgtat agagcattta    60
agattatgcg tggagaagcg tatcacaaat aaaactaaaa aataggttgc gcataatata   120
attagaaagg aattagacat aaattaggag tccttcacag aatagcgaag gactcccatt   180
aaatatatta tggtgtaaag aaatcacaaa tcaatatata tacttaatac catatattaa   240
cttgtactat tataaagtac gacatcagta ttaggtatca ctttgaacac atgaatttca   300
ttatcacttt tattattcac aaaaaatttt ccaattctca attactgaat tatgtgtata   360
catgttgtta aaaattaata aaggatattt atgtttgttt aaagcatatc acaagtgatg   420
cggtttttta taaagattta cttgttagtg attttgataa aaatgcttaa tactatttca   480
ataatatgta tttaaaaatt agattaatag tatttaactt caaatggcct cgtataaact   540
catagcaaat taacgtaaat caatgaaata aaatgaaaac aatttcaaga atacattata   600
aacataaagt atacaaaaaa taatgagcg tatttgttta aacgtataca ctcattttta   660
ttaaattaat ttattatatt ttacgattgt tatttatgaa attaacaaat tccatttttg   720
atagtgaaat taaaagcttt atcacttatt attgat                             756
```

<210> SEQ ID NO 40
<211> LENGTH: 771
<212> TYPE: DNA
<213> ORGANISM: Staphylococcus aureus

<400> SEQUENCE: 40

```
tgacattccc acatcaaatg atgcgggttg tgttaattga gcaagtgtat agagcattta    60
agattatgcg tggagaagcg tatcacaaat aaaactaaaa aataggttgc gcataatata   120
attagaaagg aattagacat aaattaggag tccttcacag aatagcgaag gactcccatt   180
aaatatatta tggtgtaaag aaatcacaaa tcaatatata tacttaatac catatattaa   240
cttgtactat tataaagtac gacatcagta ttaggtatca ctttgaacac atgaatttca   300
ttatcacttt tattattcac aaaaaatttt ccaattctca attactgaat tatgtgtata   360
catgttgtta aaaattaata aaggatattt atgtttgttt aaagcatatc acaagtgatg   420
cggtttttta taaagattta cttgttagtg attttgataa aaatgcttaa tactatttca   480
ataatatgta tttaaaaatt agattaatag tatttaactt caaatggcct cgtataaact   540
catagcaaat taacgtaaat caatgaaata aaatgaaaac aatttcaaga atacattata   600
aacataaagt atacaaaaaa taatgagcg tatttgttta aacgtataca ctcattttta   660
ttaaattaat ttattatatt ttacgattgt tatttatgaa attaacaaat tccatttttg   720
atagtgaaat taaaagcttt atcacttatt attgataatt ttgactgcat c            771
```

<210> SEQ ID NO 41
<211> LENGTH: 680
<212> TYPE: DNA
<213> ORGANISM: Staphylococcus aureus

<400> SEQUENCE: 41

```
ttcagcaaaa tgacattccc acatcaaatg atgcgggttg tgttaattga acaagtgtac      60
agagcattta agattatgcg tggagaagcg tatcataagt agcggaggag ttttttacct    120
tgtgacttat cataaagtac gatgtttatg taagtgatta tcattattta agcaggtttt    180
tcaaattaaa taataacaag aataaaatgc acttagcgac attgaaattt attaatctag    240
taaactaata gatttataga aaatttatt tgcaagggga taattttgaa aagtagtatt     300
ttctatcttt ccataataca ttgtaattac aacggagggg atattgtgat gaagtgtata    360
gataaaacgt gggttagcta ttataaagaa ttagctgata agttaacaga ttatcaaaat    420
aaacgttatg aattaattga aatagtgaag gaagtatata aaaaaacggg aataaaattc    480
cctactttag caagtgataa tgtattgatg gacatagatc cttttacaat atttgcatta    540
tttaataaaa attccatgag agaaactaat aaggtaaaaa tattaacaga attagcttcg    600
gaattgaata ttaagtccaa aattccgtca gtttttgaca gtattccaac agtcaataat    660
ctgaatgcta catattataa                                                680

<210> SEQ ID NO 42
<211> LENGTH: 1119
<212> TYPE: DNA
<213> ORGANISM: Staphylococcus aureus

<400> SEQUENCE: 42
gacattccca catcaaatga tgcgggttgt gttaattgag caagtgtata gagcatttaa     60
gattatgcgt ggagaggcgt atcataagta aaactaaaaa attctgtatg aggagataat    120
aatttggagg gtgttaaatg gtggacatta aatccacgtt cattcaatat ataagatata    180
tcacgataat tgcgcatata acttaagtag tagctaacag ttgaaattag gccctatcaa    240
attggtttat atctaaaatg attaatatag aatgcttctt tttgtcctta ttaaattata    300
aaagtaactt tgcaatagaa acagttattt cataatcaac agtcattgac gtagctaagt    360
aatgataaat aatcataaat aaaattacag atattgacaa aaaatagtaa atataccaat    420
gaagtttcaa agaacaattt ccaagaaatt gagaatgtaa ataataaggt caaagaattt    480
tattaagatt tgaaagagta tcaatcaaga aagatgtagt ttttttaataa actatttgga    540 aaataattat cataatttaa aaactgacaa tttgcgagac tcataaaatg taataatgga    600
aatagatgta aaatataatt aaggggtgta atatgaagat taatatttat aaatctatt     660 ataatttttca ggaaacaaat acaaattttt tagagaatct agaatcttta aatgatgaca    720
attatgaact gcttaatgat aaagaacttg ttagtgattc aaatgaatta aaattaatta    780
gtaaagttta tacgtaaaa aaagacaaaa aactattaga ttggcaatta ttaataaaga    840
atgtatacct agatactgaa gaagatgaca atttatttc agaatccggt catcattttg     900
atgcaatatt atttctcaaa gaagatacta cattacaaaa taatgtatat attataccttt   960 ttggacaagc atatcatgat ataaataatt tgattgatta tgacttcgga attgattttg   1020
cagaaagagc aatcaaaaat gaagacatag ttaataaaaa tgttaatttt tttcaacaaa   1080
acaggcttaa agagattgtt aattatagaa ggaatagtg                          1119

<210> SEQ ID NO 43
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 43
```

-continued cattttgctg aatgatagtg cgta                                    24

<210> SEQ ID NO 44
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 44
gaggaccaaa cgacatgaaa atc                                     23

<210> SEQ ID NO 45
<211> LENGTH: 21
<212> TYPE: DNA
<213> ORGANISM: Artificial Sequence
<220> FEATURE:
<223> OTHER INFORMATION: Synthetically prepared nucleic acid sequence

<400> SEQUENCE: 45
atcaaatgat gcgggttgtg t                                       21

<210> SEQ ID NO 46
<211> LENGTH: 26
<212> TYPE: DNA
<213> ORGANISM: Artificial Sequence
<220> FEATURE:
<223> OTHER INFORMATION: Synthetically prepared nucleic acid sequence

<400> SEQUENCE: 46
aaacgaaaat actggtgaag atatta                                  26

<210> SEQ ID NO 47
<211> LENGTH: 25
<212> TYPE: DNA
<213> ORGANISM: Artificial Sequence
<220> FEATURE:
<223> OTHER INFORMATION: Synthetically prepared nucleic acid sequence

<400> SEQUENCE: 47
ttgcctttct caagtcttta caact                                   25

<210> SEQ ID NO 48
<211> LENGTH: 20
<212> TYPE: DNA
<213> ORGANISM: Artificial Sequence
<220> FEATURE:
<223> OTHER INFORMATION: Synthetically prepared nucleic acid sequence

<400> SEQUENCE: 48
cgaggagaag cgtatcacaa                                         20

<210> SEQ ID NO 49
<211> LENGTH: 27
<212> TYPE: DNA
<213> ORGANISM: Artificial Sequence
<220> FEATURE:
<223> OTHER INFORMATION: Synthetically prepared nucleic acid sequence

<400> SEQUENCE: 49
agttgccata gattcaattt ctaaggt                                 27

<210> SEQ ID NO 50
<211> LENGTH: 27
<212> TYPE: DNA

```
<213> ORGANISM: Artificial Sequence
<220> FEATURE:
<223> OTHER INFORMATION: Synthetically prepared nucleic acid sequence

<400> SEQUENCE: 50
aacaggtgaa ttattagcac ttgtaag                                         27

<210> SEQ ID NO 51
<211> LENGTH: 26
<212> TYPE: DNA
<213> ORGANISM: Artificial Sequence
<220> FEATURE:
<223> OTHER INFORMATION: Synthetically prepared nucleic acid sequence

<400> SEQUENCE: 51
ctattgttcc acaaattatg attact                                          26

<210> SEQ ID NO 52
<211> LENGTH: 26
<212> TYPE: DNA
<213> ORGANISM: Artificial Sequence
<220> FEATURE:
<223> OTHER INFORMATION: Synthetically prepared nucleic acid sequence

<400> SEQUENCE: 52
cttcttttct tgttattctt tcttct                                          26

<210> SEQ ID NO 53
<211> LENGTH: 20
<212> TYPE: DNA
<213> ORGANISM: Artificial Sequence
<220> FEATURE:
<223> OTHER INFORMATION: Synthetically prepared nucleic acid sequence

<400> SEQUENCE: 53
ctaaatcata gccatgaccg                                                 20

<210> SEQ ID NO 54
<211> LENGTH: 20
<212> TYPE: DNA
<213> ORGANISM: Artificial Sequence
<220> FEATURE:
<223> OTHER INFORMATION: Synthetically prepared nucleic acid sequence

<400> SEQUENCE: 54
atgctctttg ttttgcagca                                                 20

<210> SEQ ID NO 55
<211> LENGTH: 1073
<212> TYPE: DNA
<213> ORGANISM: Staphylococcus aureus

<400> SEQUENCE: 55
tattggaagc aagccatagc agaatatgaa aaacgtttag gcccatacac caagatagac     60
atcatagaag ttccagacga aaaagcacca gaaaatatga gcgacaaaga aattgagcaa    120
gtaaaagaaa aagaaggcca acgaatacta gccaaaatca accacaatc cacagtcatt    180 acattagaaa tacaaggaaa gatgctatct tccgaaggat tggcccaaga attgaaccaa    240
cgcatgaccc aagggcaaag cgactttgta ttcgtcattg gcggatcaaa cggcctgcac    300
aaggacgtct acaacgcag  taactatgca ctatcattta gcaaaatgac attcccacat    360
caaatgatgc gggttgtgtt aattgaacaa gtgtatagag catttaagat tatgcgtgga    420
gaggcgtatc ataagtgatg cttgttagaa tgatttttaa caatatgaaa tagctgtgga    480
```

```
agcttaaaca atttgtttat ctaagtactt atttaataat tgattgaact gtgattggca      540
ccaggctgtc tggtaaattg agaagttggg ttttggagcg tataaatgat agaattaata      600
taaaattcaa tttgaggagt aggagattat gtcgaatata aaacaacac tagagacgtc       660 cgtaggacta gaaaaagaca acgataagct atttgattat ataactgaat tagagattca     720
aaacacgcct gaaaccggg aagcaaaagt tgttattgaa gaaaggttac ataaagaata      780
taaatatgaa ttagatcaaa tgacaccaga gtatggaata caaaaaggca gtgttagaat     840
aggtcatgca gatgttgtaa tatttcatga ttctaaagat aaatctcaag agaatattaa    900
aataatagta gagtgtaaaa gaaagaatcg cagggatggt attgaacaat taaaaacata   960
tcttgcaggg tgtgagtctg cagaatacgg cgtttggttt aatggagaag atatagtata  1020
tataaaacga ttgaaaaaag caccacattg gaaaacagta tttaatatac cga          1073
```

<210> SEQ ID NO 56
<211> LENGTH: 2031
<212> TYPE: DNA
<213> ORGANISM: Staphylococcus aureus

<400> SEQUENCE: 56

```
accattttag ctgtagggaa actaaaagag aaatattgga agcaagccat agcagaatat      60
gaaaaacgtt taggcccata caccaagata gacatcatag aagttccaga cgaaaaagca     120
ccagaaaata tgagtgacaa agaaattgag caagtaaaag aaaagaagg ccaacgaata     180 ctagccaaaa tcaaaccaca atccacagtc attacattag aaatacaagg aaagatgcta    240
tcttccgaag gattggccca agaattgaac caacgcatga cccaagggca aagcgacttt    300
gttttcgtca ttggcggatc aaacggcctg cacaaggacg tcttacaacg cagtaactac    360
gcactatcat tcagcaaaat gacattccca catcaaatga tgcgggttgt gttaattgaa   420
caagtgtaca gagcatttaa gattatgcga ggagaagcgt atcacaaata aaactaaaaa   480
atagattgtg tataatataa aaggagcgga tttatattaa aactttgaat tcaaaaatta   540
ttgaaaggga agctacctta gaaattgaat ctatggcaac taatacattg aaaataaacc  600
cggatattaa ttcaaacgat acaaaaatgt ctttcgatgg agaattggaa gtgtatgatt  660
ctgaaaattt gagtaaaaaa aatttcgttg gaaaaataca agttcaagtt aaaggaaagg  720
aagtagctaa aagaggaggt aaggttattc atcgaagtaa tgtcaaaatg aatgatttaa  780
aggcatacca acgagaaggt ggtgtgtatt actttgtcgt gtatttaatc gttgagaata  840
aaaaagttgt tgagaagcag gtttatggta acaattaca tcaattagat ttacaatttt  900
tactgcaaaa aaagcagaaa agcgtcacta taaaaatgta tgaaattgaa atgaaaaaa  960 ttttatataa taattgcgta aaatatataa atgaaaagag attacaaaat caagtaggtc  1020
aagttaaagt aaagaacata gaaaaagctt tatcatatat agctacacct gaaaatattg  1080
tgatggatca tagaggttta ccattaaatg attttttatgg ctatataaaa attaattcat   1140
ctgaattaga tgtaactata ccagatggag tattaagtat ggaaaaagta aaaagagtga    1200
acaaaaagca gataataaaa gaaggcaagt tattatttga aggtatggta ggtattgaaa    1260
cttcaaagga gtccatctct ataactatag atgatatttt caaaattcaa acatttgaaa    1320
gtgataacaa aagtatatat acaatgttac catttaaaaa attaaatata gccgaacaat   1380
cttttaatgt tataaacgaa ttgtcgaaag gcggcgaatt ctttttggat caaatccaat   1440
tagtaatcca acctttttgaa attaatatta ttgaaataaa agaaacaata aataagttga   1500
```

```
atattaaatt atcagagtat agtaacttgc tttcgtttga tgtgagtcta aaatctacag    1560
aatttgataa gcagatgaat gagataaaag gtttattaga attattggaa tataaaaatt    1620
ttaaagattt taaaatgcat aataatggat actataaaat gaagttttgt ggaaaattta    1680
tattattatt taaagacaat acatcattgt ataatgtcta ctctaatgac tttgtagata    1740
gatttgaggc tgttacaaaa gaaagagttg tacagatgcc aattgtttac acattaacaa    1800
gagatatgat tgtagatgta ctgaattttg atataaatgt tattaaagaa tgtattgaat    1860
cagataaaat tgctattcaa tctgacatta aatgggagaa attaaataac tttgcattag    1920
aattaatcgc agcctatgat gaaactcaaa gaaccgattt attagaatta gctgaatatg    1980
tattaaataa tttgctgaat tttgataatg ataaaatatt tatgaactta a             2031
```

<210> SEQ ID NO 57
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 57
cgtggagagg cgtatcataa gt                                              22

<210> SEQ ID NO 58
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 58
gctccaaaac ccaacttctc aa                                              22

<210> SEQ ID NO 59
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 59
gccaaaatta aaccacaatc cac                                             23

<210> SEQ ID NO 60
<211> LENGTH: 30
<212> TYPE: DNA
<213> ORGANISM: Artificial Sequence
<220> FEATURE:
<223> OTHER INFORMATION: Synthetically prepared nucleic acid sequence

<400> SEQUENCE: 60
aatctttgtc ggtacacgat attcttcacg                                      30

<210> SEQ ID NO 61
<211> LENGTH: 30
<212> TYPE: DNA
<213> ORGANISM: Artificial Sequence
<220> FEATURE:
<223> OTHER INFORMATION: Synthetically prepared nucleic acid sequence

<400> SEQUENCE: 61
cgtaatgaga tttcagtaga taatacaaca                                      30

```
<210> SEQ ID NO 62
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 62
gccaaaatca aaccacaatc cac                                              23

<210> SEQ ID NO 63
<211> LENGTH: 27
<212> TYPE: DNA
<213> ORGANISM: Artificial Sequence
<220> FEATURE:
<223> OTHER INFORMATION: Synthetically prepared nucleic acid sequence

<400> SEQUENCE: 63
attgctgtta atatttttg agttgaa                                           27

<210> SEQ ID NO 64
<211> LENGTH: 21
<212> TYPE: DNA
<213> ORGANISM: Artificial Sequence
<220> FEATURE:
<223> OTHER INFORMATION: Synthetically prepared nucleic acid sequence

<400> SEQUENCE: 64
tattgcaggt ttcgatgttg a                                                21

<210> SEQ ID NO 65
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 65
tcaccgtctt tcttttgacc tt                                               22

<210> SEQ ID NO 66
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 66
cagcaattcw cataaacctc ata                                              23

<210> SEQ ID NO 67
<211> LENGTH: 26
<212> TYPE: DNA
<213> ORGANISM: Artificial Sequence
<220> FEATURE:
<223> OTHER INFORMATION: Synthetically prepared nucleic acid sequence

<400> SEQUENCE: 67
caggcatagc tatatatgat aaagca                                           26

<210> SEQ ID NO 68
<211> LENGTH: 26
<212> TYPE: DNA
<213> ORGANISM: Artificial Sequence
<220> FEATURE:
<223> OTHER INFORMATION: Synthetically prepared nucleic acid sequence
```

```
<400> SEQUENCE: 68
atgcctttaa atcattcaca ttgaca                                          26

<210> SEQ ID NO 69
<211> LENGTH: 4340
<212> TYPE: DNA
<213> ORGANISM: Staphylococcus aureus

<400> SEQUENCE: 69
cttcatatga cgtctatcca tttatgtatg gcatgagtaa cgaagaatat aataaattaa      60
ccgaagataa aaagaacct ctgctcaaca agttccagat acaacttca ccaggttcaa       120 ctcaaaaaat attaacagca atgattgggt taaataacaa aacattagac gataaaacaa     180
gttataaaat cgatggtaaa ggttggcaaa aagataaatc ttggggtggt tacaacgtta     240
caagatatga agtggtaaat ggtaatatcg acttaaaaca agcaatagaa tcatcagata     300
acattttctt tgctagagta gcactcgaat taggcagtaa gaaatttgaa aaaggcatga     360
aaaaactagg tgttggtgaa gatataccaa gtgattatcc attttataat gctcaaattt     420
caaacaaaaa tttagataat gaaatattat tagctgattc aggttacgga caaggtgaaa     480
tactgattaa cccagtacag atcctttcaa tctatagcgc attagaaaat aatggcaata     540
ttaacgcacc tcacttatta aaagacacga aaaacaaagt ttggaagaaa atatattttt    600
ccaaagaaaa tatcaatcta ttaactgatg gtatgcaaca agtcgtaaat aaaacacata     660
aagaagatat ttatagatct tatgcaaact taattggcaa atccggtact gcagaactca     720
aaatgaaaca aggagaaact ggcagacaaa ttgggtggtt tatatcatat gataaagata     780
atccaaacat gatgatggct attaatgtta aagatgtaca agataaagga atggctagct     840
acaatgccaa aatctcaggt aaagtgtatg atgagctata tgagaacggt aataaaaaat     900
acgatataga tgaataacaa aacagtgaag caatccgtaa cgatggttgc ttcactgttt     960
tattatgaat tattaataag tgctgttact tctcccttaa atacaatttc ttcatttca    1020 ttgtatgttg aaagtgacac tgtaacgagt ccattttctt tttttatgga tttcttattt    1080
gtaatttcag cgataacgta caatgtatta cctgggtata caggtttaat aaatttaacg    1140
ttattcattt gtgttcctgc tacaacttct tctccgtatt taccttcttc tacccataat    1200
ttaaatgata ttgaaagtgt atgcatgcca gatgcaatga tacctttaaa tctactttgt    1260
tctgcttttt ctttatctat atgcatatat tgaggatcaa aagttgttgc aaattggata    1320
atttcttctt ctgtaatatg aaggcttttt gttttgaatg tttctcctac tataaaatca    1380
tcgtatttca tatatgtctc tctttcttat tcaaattaat ttttttagtat gtaacatgtt    1440 aaaggtaagt ctaccgtcac tgaaacgtaa gactcacctc taactttcta ttgagacaaa    1500
tgcaccattt tatctgcatt gtctgtaaag ataccatcaa ctccccaatt agcaagttgg    1560
tttgcacgtg ctggttttgtt tacagtccat acgttcaatt cataacccgc ttcttttacc    1620
atttttactt ttgctttagt aagtttggca tcttcagtgt ttactatttt agcattacag    1680
taatctaaaa gtgttctcca gtcttcacga aacgaagttg tatggaatat aactgctctg    1740
ttatattgtg gcatgatttc ttctgcaagt ttaacaagca caacattaaa gcttgaaatg    1800
agcacttctt gattctgatt taagtttgtt aattgttctt ccacttgctt aaccatactt    1860
ttagaaagtg ctagtccatt cggtccagta ataccttta attctacatt taaattcata    1920
ttatattcat ttgctatttt tactacatca tcgaagttg gcaaatgttc atctttgaat    1980
ttttcaccaa accaagatcc tgcagaagca tctttaattt catcataatt caattcagtt    2040
```

| | |
|---|---|
| atttccccgg acatatttgt agtccgttct aaataatcat catgaatgat aatcagttgt | 2100 |
| tcatcttttg taattgcaac atctaactcc aaccagttta taccttctac ttctgaagca | 2160 |
| gctttaaatg atgcaattgt attttccgga gctttactag gtaatcctct atgtccatat | 2220 |
| acagttagca tattacctct ccttgcattt ttattttttt aattaacgta actgtattat | 2280 |
| cacattaatc gcactttat ttccattaaa aagagatgaa tatcataaat aaagaagtcg | 2340 |
| atagattcgt attgattatg gagttaatct acgtctcatc tcattttaa aaaatcattt | 2400 |
| atgtcccaag ctccattttg taatcaagtc tagtttttcg gttctgttgc aaagttgaat | 2460 |
| ttatagtata attttaacaa aaaggagtct tctgtatgaa ctatttcaga tataaacaat | 2520 |
| ttaacaagga tgttatcact gtagccgttg gctactatct aagatataca ttgagttatc | 2580 |
| gtgatatatc tgaaatatta agggaacgtg gtgtaaacgt tcatcattca acggtctacc | 2640 |
| gttgggttca agaatatgcc ccaattttgt atcaaatttg gaagaaaaag cataaaaaag | 2700 |
| cttattacaa atggcgtatt gatgagacgt acatcaaaat aaaaggaaaa tggagctatt | 2760 |
| tatatcgtgc cattgatgca gagggacata cattagatat ttggttgcgt aagcaacgag | 2820 |
| ataatcattc agcatatgcg tttatcaaac gtctcattaa acaatttggt aaacctcaaa | 2880 |
| aggtaattac agatcaggca ccttcaacga aggtagcaat ggctaaagta attaaagctt | 2940 |
| ttaaacttaa acctgactgt cattgtacat cgaaatatct gaataacctc attgagcaag | 3000 |
| atcaccgtca tattaaagta agaaagacaa ggtatcaaag tatcaataca gcaaagaata | 3060 |
| ctttaaaagg tattgaatgt atttacgctc tatataaaaa gaaccgcagg tctcttcaga | 3120 |
| tctacggatt ttcgccatgc cacgaaatta gcatcatgct agcaagttaa gcgaacactg | 3180 |
| acatgataaa ttagtggtta gctatatttt tttactttgc aacagaacca tattttatgt | 3240 |
| gttgttgttt gtggtgcatt agcagcaaac attcgtggtg aaagtgatgc tgttttagca | 3300 |
| tttgataatt tgaatgttgc tgattgagtt ggttttgtg ttgaggcttg ttgtgcatct | 3360 |
| acgtcgcgcg tttcgtttac tgttgttgaa actgctgtag atggtttgtt agatggtgcg | 3420 |
| ttggatgtta cttttgttgtt tgtatcatca gctgttccct gtactgatgc tgatacgttg | 3480 |
| gttgccgctt cttcaccaga ttgatgagcc gcttcctttg ttggcgttac ttgttgctta | 3540 |
| tctgttgttg ctgcttgtgc tttcattggt gtatgctgct cagccgcgtt cgagacatgc | 3600 |
| cataatccca tcacactaaa aagcaaaacg agccatacac ttgttttaag taataaagct | 3660 |
| ttcatttcgt tccctccatt aactgtcata caccaatata ttatcataat ccttatatta | 3720 |
| aaatgtttga tttatgtaa attatttata aattacattt aatatcgaat tattttacac | 3780 |
| atttcaatca atccgattca actcaacaac agccatttcc caccaacaac ataaaaaagc | 3840 |
| acccgataaa gtcgtttcac agcagtgcgg aactttatcg gatgactctc atttatattg | 3900 |
| tatatattgg tgttggaata gctttatccg tatcacatag caatacttct ttttccgtat | 3960 |
| caatatcgtt tcgttcaat acttggccaa cactcatacg cgccaaatct ttcatattat | 4020 |
| tatcttgtga taaatgcgat aagtaaatac gtttcgtgtt acctgtaatc acgtctgtca | 4080 |
| tcgcatgacc cgcatcctca ttagatacat gacccatatc gcctaaaatg cgttgtttcg | 4140 |
| tcttccatgg ataacgacac attctcaaca tatcgacgtc atgattactc tcaaaaataa | 4200 |
| atgcatcgct gccacgtatc ataccttca tacgatcaga cacgtaaccc gtatctgtta | 4260 |
| aaatcgtaaa cttcttatag ttattatgga aaatataaaa ttgcggatct atcgcatcat | 4320 |
| gtgacacgtt aaacgattca | 4340 |

```
<210> SEQ ID NO 70
<211> LENGTH: 29
<212> TYPE: DNA
<213> ORGANISM: Artificial Sequence
<220> FEATURE:
<223> OTHER INFORMATION: Synthetically prepared nucleic acid sequence

<400> SEQUENCE: 70
atttcatata tgtaattcct ccacatctc                                    29

<210> SEQ ID NO 71
<211> LENGTH: 29
<212> TYPE: DNA
<213> ORGANISM: Artificial Sequence
<220> FEATURE:
<223> OTHER INFORMATION: Synthetically prepared nucleic acid sequence

<400> SEQUENCE: 71
caaatattat ctcgtaattt accttgttc                                    29

<210> SEQ ID NO 72
<211> LENGTH: 29
<212> TYPE: DNA
<213> ORGANISM: Artificial Sequence
<220> FEATURE:
<223> OTHER INFORMATION: Synthetically prepared nucleic acid sequence

<400> SEQUENCE: 72
ctctgcttta tattataaaa ttacggctg                                    29

<210> SEQ ID NO 73
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 73
caagctccat tttgtaatca ag                                           22

<210> SEQ ID NO 74
<211> LENGTH: 27
<212> TYPE: DNA
<213> ORGANISM: Artificial Sequence
<220> FEATURE:
<223> OTHER INFORMATION: Synthetically prepared nucleic acid sequence

<400> SEQUENCE: 74
cactttttat tcttcaaaga tttgagc                                      27

<210> SEQ ID NO 75
<211> LENGTH: 27
<212> TYPE: DNA
<213> ORGANISM: Artificial Sequence
<220> FEATURE:
<223> OTHER INFORMATION: Synthetically prepared nucleic acid sequence

<400> SEQUENCE: 75
acaaactttg agggattttt tagtaaa                                      27

<210> SEQ ID NO 76
<211> LENGTH: 23
<212> TYPE: DNA
<213> ORGANISM: Artificial Sequence
<220> FEATURE:
<223> OTHER INFORMATION: Synthetically prepared nucleic acid sequence
```

-continued

```
<400> SEQUENCE: 76
gccaaaatca aaccacaatc aac                                             23

<210> SEQ ID NO 77
<211> LENGTH: 23
<212> TYPE: DNA
<213> ORGANISM: Artificial Sequence
<220> FEATURE:
<223> OTHER INFORMATION: Synthetically prepared nucleic acid sequence

<400> SEQUENCE: 77
accacgaatg tttgctgcta atg                                             23

<210> SEQ ID NO 78
<211> LENGTH: 25
<212> TYPE: DNA
<213> ORGANISM: Artificial Sequence
<220> FEATURE:
<223> OTHER INFORMATION: Synthetically prepared nucleic acid sequence

<400> SEQUENCE: 78
acgcaattgt taaaaatatg tgtcc                                           25

<210> SEQ ID NO 79
<211> LENGTH: 20
<212> TYPE: DNA
<213> ORGANISM: Artificial Sequence
<220> FEATURE:
<223> OTHER INFORMATION: Synthetically prepared nucleic acid sequence

<400> SEQUENCE: 79
tggcaatgca attcgtgaac                                                 20

<210> SEQ ID NO 80
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 80
ttccactccc aaaattttct ca                                              22

<210> SEQ ID NO 81
<211> LENGTH: 25
<212> TYPE: DNA
<213> ORGANISM: Artificial Sequence
<220> FEATURE:
<223> OTHER INFORMATION: Synthetically prepared nucleic acid sequence

<400> SEQUENCE: 81
aatcgagaat aacaagaaaa tgaga                                           25

<210> SEQ ID NO 82
<211> LENGTH: 20
<212> TYPE: DNA
<213> ORGANISM: Artificial Sequence
<220> FEATURE:
<223> OTHER INFORMATION: Synthetically prepared nucleic acid sequence

<400> SEQUENCE: 82
ttggcgaaca gttgctagtt                                                 20

<210> SEQ ID NO 83
```

<211> LENGTH: 26
<212> TYPE: DNA
<213> ORGANISM: Artificial Sequence
<220> FEATURE:
<223> OTHER INFORMATION: Synthetically prepared nucleic acid sequence

<400> SEQUENCE: 83
tctctttata atttgagctt ggttga                                          26

<210> SEQ ID NO 84
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 84
tggaaaaagt aaaagagtg aaca                                             24

<210> SEQ ID NO 85
<211> LENGTH: 24
<212> TYPE: DNA
<213> ORGANISM: Artificial Sequence
<220> FEATURE:
<223> OTHER INFORMATION: Synthetically prepared nucleic acid sequence

<400> SEQUENCE: 85
tggttataga aatggactcc tttg                                            24

<210> SEQ ID NO 86
<211> LENGTH: 22
<212> TYPE: DNA
<213> ORGANISM: Artificial Sequence
<220> FEATURE:
<223> OTHER INFORMATION: Synthetically prepared nucleic acid sequence

<400> SEQUENCE: 86
acccggacat taattcaaac ga                                              22

<210> SEQ ID NO 87
<211> LENGTH: 46392
<212> TYPE: DNA
<213> ORGANISM: Staphylococcus aureus

<400> SEQUENCE: 87
aaaatatcaa aaactgcaaa aaatattggt ataataagag ggaacagtgt gaacaagtta      60
ataacttgtg gataactgga aagttgataa caatttggag gaccaaacga catgaaaatc     120
accattttag ctgtagggaa actaaaagag aaatattgga agcaagccat agcagaatat     180
gaaaaacgtt taggcccata caccaagata gacagcatag aagttccaga cgaaaaagca     240
ccagaaaata tgagcgacaa agaaattgag caagtaaaag aaaagaagg ccaacgaata      300 ctagccaaaa tcaaaccaca atcaacagtc attacattag aaatacaagg aaagatgcca     360
tcttccgaag gattggccca agagttgaac caacgcatga cccagggca aagcgacttt      420 gtattcgtca ttggcggatc aaacggcctg cacaaggacg tcttacaacg cagtaactac     480
gcactatcat tcagcaaaat gacatttcca caccaaatga tgagggttgt gttaattgag     540
caagtgtaca gagcgtttaa gattatgcgt ggagaagcgt atcataaata aaactaaaaa     600
ataggttgtg tataatataa aaggagcgga tttatattaa aactttgaat tcaaaaatta     660
ttgaaaggga agctaccta gaattgaat ctatggctac aaatacattg aaaataaacc       720
cggacattaa ttcaaacgat acaaaaatgt cttttgatgg agaattggaa gtgtataatt     780

```
ctgaaaattt gagtaaaaaa atttcgttgg aaaaatacaa gttcaagtta aaggaaaaga    840
agtacctaaa agaggaggta aggttattca tcgaagtaat gtcaatgtga atgatttaaa    900
ggcataccaa cgagaaggtg gtgtgtatta ctttgtcgtg tatttaattg ttgagaacca    960
agtttatggt aaacaattac atcaattaga tctacaactt ttactgcaaa aaaaatagaa   1020
aactgtcact ataaaaatgt gtgaaattta aaatgaaaaa aattatataa taactgttta   1080
aaatatataa atgaaaagcg attacaaaac caagtagatc aagttaaagt aaagaaaaaa   1140
gaaaatgctt tatcatatat agctatgcct gaaaatattg tgatggatca cagaggttta   1200
ccattaaatg attttatgg ctatataaaa attgattcat ctgaattaga tgtaactata    1260
ccaaacgaag tattaagtat ggaaaagta aaagagtga acaaaaagca gataacaaaa    1320
gaaggtaaat tattatttga agtatggta ggtattgaaa cttcaaagga gtccatttct    1380
ataaccatag atgatatttt caaaattcaa acatttgaaa gtgataataa agtacatat    1440 acaatgttac catttaataa attaaatata gccgaacaat cttttaatgt tataaacgga   1500
ttgtcgaaag ttggctaatt ctttttttgat gaaattcaat tagtaataga acttttgaaa  1560
ttaatattaa tgaaataaaa gaaacaataa ataaattaaa aattaagtta tcagagtata   1620
gtaacttgct ttcgtttaat gtgagcctaa aacctacaga atttgataag caaatgaatg   1680
aaataaaagg tttattagaa ttattggaat ataaaaaatt taaagataat acatcattat   1740
ataatgtata ttctaatgaa tttatggata gatttgaagc tattacaaaa gaagaatctg   1800
tacaaatgcc aattgtgtac acattaacaa gagatatgat tgtaaatgta ctaaatttttg  1860 atataaatgt tattaaagaa tgtgttgaat cagataaaat cgctattcaa tctggcatta   1920
aatgggagaa actaaataat tttgcattag aattaatcgc agcctatgat gaaactcaaa   1980
gaatcgattt attagaatta gctgaatata tattaaataa tttgctgaat tatgataatg   2040
ataaaatgtt tatgaacttg atcaaccaag ctcaaattat aaagagaaga aaaagtatgg   2100
tagattaaaa attgttaagc gacttatttg aattgaaaga taaattagtt gatatttata   2160
aggttgatat gaagaaattt caaaaaaatt ctggggaaag tgaaagggca gcttatagtt   2220
tcaatggtat tgcttttgat atattatgtg tcttattaaa taatatgaca gatgataata   2280
taccaaaagc aattacggat gaagatgtaa ggctgagaaa agatgcgata aaaaatattg   2340
atattaccca atatgcgaat tttattaaaa atgttaagaa tgatatagat aaaattgaat   2400
ttaaaccatt aaagttacat atacatgcac aaaaagcata ccaagatgta aaaggtgtt    2460 tgattcaggc agtaaaataa acgataagtt acaattagct tctgaagtaa tgagtcaatt   2520
acctatagat aaacaagtgg aattaagtga caaaattgca cttgctataa atgaagttgt   2580
ttactcaaca ttttcagaaa gtaaatataa tgaacgaatt gatgaacaca atcaaacgag   2640
tgaaaagtca agtcaatatg atttttcgata taattatttt gtaaatcaat taatagataa   2700
tgtaataaca gaagatatag atgaagagaa agcatttata tatgatagaa atgaacaatt   2760
agattggtta ttagttaaga tactaaataa agttcaaaga gctgcggatg gatggggaat   2820
gagaaatgct aaacttcatc acagaacaca aacatttaga gatatggaac attatttcct   2880
cagagatata tcgaaaatga tagataaaga gcttaacaaa aaggaaaact taaataagca   2940
atctaaaaaa tatgacttcg ataataagat aaaggtcata aatgacaata ttgagttttt   3000
taatgaagat gaacaaatta gaaaacattt actagagtta cgcaagcgat tagactttca   3060
ttctgcagca gtattagata agaaaaatca ttcacacata gggaatgaaa tgttccaata   3120
```

```
ttttatggat gatatgcagc aagttgtaac attgatagac cgatacatta ataagactga    3180
acattataat gatatgaaaa atggctatat taatgaatat aaatcatttt ataatgctta    3240
taataatgaa attgaagtga ctaagacgca cgaaaataac atcccaatgg caatgttaat    3300
gaagcaattt aagaatcaac tgttaaaaag aaggaataac cgaaaaagct ctaattgaag    3360
ttaagtagaa atttaataaa taattggtaa gctcaatccc tcatataaag ggattgagct    3420
tatttgcttg gtgggaattt ttttgaattt ttttgccact tcatcaacga cctctattta    3480
gtattaagat tgtcttgtca aaacgttttg aacaaatttt aagttgaaag tgagcgcgcc    3540
actttcaacc ataaaggaga agatttacat ggagacaaga gacaaactga tgtcgttgac    3600
tcagagtaac aaaatacagc aatggttaat ggacaaatca tctaaccaag atgaggttca    3660
acaattgcag caaccaattc agtcagccag ctagatcaac aatataatgc acttttagct    3720
gatgaaaaag ctaagttaga ccaatacgtg gaagtacatc aaggattgga atcattaaag    3780
gaagagattg aatcagaacc tattacgatt aatatcgata aattacccga tatcaaagca    3840
acaatgcttg aaagagccaa gaatgatgaa cattctgata agatcgaaaa gctatttgaa    3900
aggttagaac aggcattaag tggtacgaat cgattatata cgcaattatc gttgattggt    3960
acacgaacac atagaattac aactaaaaat tttaatcttc aaggcttacc taaagcagtt    4020
caacatacga ttttaccttc aaaatttaag aaggtgtata caatcgattt caactcattt    4080
gaaccttcgg ttgttgcgta catgactcaa gattcaaaac tgattgactt tttaaatcag    4140
aaagacggac tgtatgacgc attgctaagt gaattaggct tatcagatga gctacgagta    4200
tttgttaaac gtgcatttat tggttcgttt ctatttggcg gcaacttcca tagccctaaa    4260
ttcaagttga acattatgt aagtgaagtg caatggttgg atgcggtcag ccaatttaca    4320
aaagtcattg aacttaagaa acaaatcgaa gagcataaaa ccatgcctat gccttacggc    4380
attgaacatg atatgagcgc atttttaagt agcagtatta tggcatttta tgtacaaact    4440
gtagcgagtt atattttcaa acacattcta ttggaagttt ataaagcgca gtgtacacaa    4500
aagagctttc aaatcatttt gccaattcat gatgccatta tgattgagtg cgacgatgaa    4560
gaaacagccc aaagtgtagc ccaactaatg aaaagtaaag ctaataaatt gtttaatggt    4620
gagtttgcgc acgtgacagt ggaagcatta ggaggtgtaa gcaatgaata atgatagagg    4680
tcaaagttta caaattccaa aatgcacctc actaacagaa ggctatatat acgttgcttc    4740
attatattct gtaatccaaa cagatttcaa tggtgatgtt aaacaccagt ttacgtatga    4800
aataaagata gatcagaaag ttattttatgt gaatcgtagt atttcaaaag atgctaccga    4860
taagcagtta tcaattactg attggcttaa acgtcatagt aattatagtt ccactcatga    4920
gaattataac ccttacattg atagaaagca tttaatctat gtgggtgtca atataacgga    4980
aactattatg ttcaagatgt agcaccatta gatggatttg gaggggtatt gtaatgaatc    5040
atattttaga aatgttaata aaattattaa aagtgggtat ggaggcaatc gaccgtaaag    5100
gtctgattgc catcctaaca agtagtattg gaaatgatga aatggatgat tctgaacaag    5160
ctgtaatggt gtataacgag cttatcgata aactacagct taacattcct aaagatgtcg    5220
actatagacc taacatatac agttattttg gtattcaaaa aaagccaaat gacacaatat    5280
tagtggaaat gatgataagt atttttaata tcaagcgttt tgattcagag ttgtttgttt    5340
tcaaagataa aggttggcaa aaggtaaatg aagatgaatt gcaaggactg atatctaaaa    5400
tgatacaagt gttgctagtt gattataagc cctcgttaag tattctaaag aatgtagtgg    5460
ttggcttaca aaattcaata gatgtagaag aactagttga gaataaacag tccattgcat    5520
```

| | |
|---|---|
| gcggtcataa catgtttaat ctagacgcat ttgaagtggt tgaaaattct ataaagattt | 5580 |
| tctccgcaac acggttgaat ttagagttgg ttaaaagtga tgtcataact gaaaaaacac | 5640 |
| ctccacattt taatcgatac atgttagagt ttgctaattt tgattctgat ttacagtact | 5700 |
| ttcttttca acatatagcg gtgcttctta cagctaacac aaagtatcgc agagccttac | 5760 |
| tattatatgg tggatctaag aatgggaaat ccgtagttat taatttagtt aggtcatttt | 5820 |
| tctacagcga agacattgtg tctaaagcac ttaacgagct ttaaggccgt tttgacaaag | 5880 |
| agagcttggt gggtaaaaaa cttatggcaa gtgacgaaat tggggaatca aggattcaag | 5940 |
| aaaagattgt aaatgactta aaaaagttag tatctgttga accagtacac gttgatcgta | 6000 |
| aaggtaaaac acaagttgaa actactttgg atttaaaact tgcttttggt acaaatgcaa | 6060 |
| gacttaattt tccatctgct catgcgaagg cactagagcg tcgaattgct gttattccat | 6120 |
| gtgaatatta tgttgaaaaa gctgaccctg acttaattga aaagttacag gatgaaaaga | 6180 |
| aagaaatctt tctttacttg atgtatgtgt ataagcaaat tgtaaaaaat gatatcgagt | 6240 |
| acctccaaaa tgatcgtgtt actgaaattt ctcatgattg gttaaatttt ggatatgaat | 6300 |
| ttgtttctag taaatcagca agtattgaaa atcagaaagc gtgtattaat ttactcagaa | 6360 |
| aacttataaa aatcaaacca ggatcacgaa tcaaagtatc cgagttaaat acaagttatt | 6420 |
| aatgaagaaa taaggtgag ttctcaggtt attaaacagt taattcaagc aaactttgat | 6480 |
| actcaaacca aactatacaa tggctacgat tattggattg atttaggttg gaaagaagcc | 6540 |
| gataaaaaag agattcatga tatttcggaa aaagataata ttatttcatt agataaaaat | 6600 |
| gaaaatataa cagacgatga ggcattagat gaagagaatt tagactttga ttgggaggac | 6660 |
| tttgacgatg aataatgaac aaattgaagc atttgtagaa gtgtttgtgc ctatcataga | 6720 |
| agaacgtatc aataaaggta agtactcata tgattaagtg gtaaaagtga taaaaagaaa | 6780 |
| tgaaattata aatatatatt atccatatga tgttacaaga ccgatggtct gtagcaataa | 6840 |
| tctaataaaa ggagcggtac attatgagta agaaaattgc actgtactca cgtgtaagta | 6900 |
| catctgagca atctgaacgt ggttattcaa tccatgaaca agagcaagtg ctcatcaaag | 6960 |
| aagttgtgaa aaatttcccg ggttatgact atgagacata tactgactca ggcatttcag | 7020 |
| gtaaaaatat tgaaggtcgt ccggcaatga acgtctatt acaagatgtt aaggataata | 7080 |
| aaattgaaat ggtattaagt tggaaattga atcgtatttc tcgctcaatg agagacgtgt | 7140 |
| ttaatattat tcatgaattc aaagagcttg acgtaagtta tcaatcgatt tctgagaata | 7200 |
| ttgatacatc caatgcttct ggagaagtac tcgttacaat gtttggttg ataggatcaa | 7260 |
| tagaacgttc aacactgatc agtaatgtca aaatgtcgat gaatgctaaa gcacgtagtg | 7320 |
| gagaggctat tacagataga gtgctcggtt acaagttgaa actcaatcca cttacacaga | 7380 |
| aaaatgattt ggttatcgat gaaaatgaag ctaatatcgt acgtgaaatt ttcgatttat | 7440 |
| acttggatca taataaagga ctcaaagcca ttacatcagt actgaatcaa aaggggtatc | 7500 |
| gtactattaa ttaaaagcca ttttcagttt atggtgttaa atatatttg aataatccag | 7560 |
| tctataaagg ttatgtcaga ttcaataacc atcaaaattg ggctgtacag cgaagaagtg | 7620 |
| gcaaagtga taaaaatgat gtgatattgg tcaaggtaa acatgaagcc attataagtg | 7680 |
| aagaggtatt tgaccaagtt catgaaaaat tagcttctaa aagttttaaa ccgggcagac | 7740 |
| ctattggtgg agatttctac cttcgtgggc tcaataaatg tccagagtgt ggcaataata | 7800 |
| tggtatgtcg tcggacttat tataaaacga aaaagtcgaa agaacggaca atcaaacgct | 7860 |

-continued

```
attacatttg ttctttattc aatcgttcag ggagttctgc ctgtcatagt aatacgatca    7920
atgctgaagt cgtcgaacgt gtaatcaatg ttcatctaaa tcgtattttg tctcaaccgg    7980
atgtgattaa aaagattgcg tcaaatgtga tagaaaaact gaaacaaaag catagtaaac    8040
aaacagaaat aaaatatgat attgatagtc tagaaaaaca aaaagcaaaa gttaaaacac    8100
aacaagaacg attattggaa ttgttcttag atgatgaaat ggacagtgaa attttaaaag    8160
ctaaacaaag tcaaatgaat caacagttag aagtattaga ccagcaaatt aaagaagcaa    8220
aacaagcata tcaatcacaa gctgaaatac ccaattttga taagttaaaa ggacgactca    8280
ttttaatgat aacacgattc agtgtgtatt ttagaaaagc cacacccgaa gctaaaaatc    8340
aacttatgaa aatgttaatt gattcgattg aaattacgac agataaacag gtgaaactag    8400
tacgatataa aattgatgaa agtcttatcc ctcaatcttt gaaaaaagat tgggggtctt    8460
ttttatgccc aaattccaat tcgaaatata tggtcaaaat gattatttca tcaaccaaat    8520
taccactttt accacttagt tattagtgaa aaaagtgaga gaaatgaaat aaaaatcaaa    8580
tatatatcat ctaaatgata tatcacatgt atacatcaac caaatacatt aggaggttat    8640
aacaatgaca ttagaactac aactcaaaca ctatataacc aatttattca acctaccaaa    8700
ggatgaaaag tgggaatgtg aatctatcga ggaaatcgct gatgatatcc tacctgacca    8760
atatgtaagg cttggggcac tcagtaataa aatacttcaa acctataccl actactctga    8820 tacacttcac gaaagtaata tctaccctlt cattctctac tatcagaaac agctcatagc    8880
catcggctat atcgatgaaa atcacgatat ggatttctta tacctacaca acaccatcat    8940
gccacttttg gatcaacgat acttactaac aggaggacaa taatatgcat aaatatatca    9000
aaattacaca attagtaatc acaatactaa gtgaaatcat catttggatg aaagagtcag    9060
aacgaaagga agtctcttat gaatagatat atcaccegtg gtatcgccaa caacttacct    9120
actgcattac aacatcaatt atggcaattt gtagcacaac gtgaaaacga acagtccaag    9180
gaactagaag caatagatta ttttcatgta ttccagttca acatgcacaa taatcaatta    9240
tatgtaaaac acaaacaaga acgtcctgag tatgtcaaaa ttcataaagc gaattattcg    9300
aaagatctca atattaataa ggtctacatt atccgagaat atgatgtaga cttttcttla    9360 ctatgtcatg ttactacccg aagaatatta ataggaggca tcaatcatgc agaatataca    9420
atgtacatta gaaactgaag caatatttag tgacgataat caacatcgtt acttactcaa    9480
aaaacatggg acaatgataa aaagataatt tcagttataa cttgttatcc aaattttgaa    9540
ggaacgaaaa aattagattt aacgactcaa ctaattatga acaaagttgt agaaatggat    9600
gaatttggtt ccatcaattt tgtgaatcta tactctaata ttacaacacc gattaatttc    9660
aaacatttag aaaccctcta tgatgcctat gataagcata cagatattca aattatgaag    9720
gcagccaagg agtcagatga agtaatagaa atgttgaaac cacataagaa gaaagtgaaa    9780
caactcatta accccgaaag ctcgtcgcaa gtggatatat aaacaaaaca ctatttaaaa    9840
taattataca aaagcgaagg tatttaatgt attttaataa gaaaaagcaa gaaaaaattg    9900
actaatataa aaattacatt cgagaaatta tattaaacgg aaaacaagtg atttgttgca    9960
taaatttata aagtagtgaa aattatgaga acgtatagct gtattgattg ctacatttat   10020
tttgatgaca atattataga tatcgttgtt gtatggagct atggcgataa gtatatttgg   10080
tggaaatgat gaaatgttaa ataaagaact taattcactg caagaagcga tatgaaagta   10140
tgttaaggga gtaaaatatg acattaccaa atttattaaa ttattattaa tgcaattttt   10200
atgtgtattt cttgtagtac aagtaggact tgtatctgga ggtagtgttc tacttgcagt   10260
```

```
agtatatctt gaaattttag ggtcttattt taaaaggatt tttacaatta aatggccact   10320
cggtaaagat gtagcaaaaa ttatagaaaa ttactttggt gaacctgtat aaatcagaga   10380
ataattatta aaaatagaac atttcctacc tttcatagta ggaaatgttc tatttaattt   10440
atattttttc taacgaaact agaatacacc tactttgata acttaattaa cataagtaga   10500
ggtatagtcg tattttgtca ctttccaata tttacaaact atcttcaaag tcaatgcttt   10560
atctgaaaaa aattttcaaa gattttctta aaatttacga aggaatgact tattgtgaaa   10620
aacttgtttt ttaacatata acttaaagga gataatatat tggattgtgt ataccgattg   10680
tacgaaagca gatcatggat aagtacaccc aaagtaatta agtatgatta taaatcgaaa   10740
gttataatat tgaacaagat aaaagttaaa atatgtattt tatgtatgat attttggctg   10800
atatttatta tattgctcca aaattaaacc gttacttttta gcaatatctt aaattttaat   10860
cataaaacat catgcaaata aacgaagtaa gttgttaatg aattttgatc gctttgaaat   10920
taatgaaaat cgatcaacaa taacaatcgt atcaatcgtc acacgagcat aaatgaaaa   10980 atctaaatac aatcaaaaac ttttaaatct atattgattt aatttcaatg tttgattttc   11040
aattaattta acaattaatt tgggagatct atatcaaaga cattaataaa atgaaattaa   11100
agatacccaa taaatagaac cacagtataa attatatcag tatgcttata taattttttga   11160 aatctttaaa caaatgaagt aataattgag aaaagtgtag ttaaattatt tttcttgaaa   11220
ttatttgtta catagcattt cgatgtaaaa ttcactttt ataagtaaat ttaaaagag   11280 tttgcaaaat atacagggga ttatatataa tggaaaacaa gaaaggaaaa taggaggttt   11340
atatggaaag tacaattgat ttatctgaat tattaggaag agtaagaaaa aatatgaaat   11400
tattaataat attaccactt ttaggtctgc taattagtgc aataatttct tttttctttt   11460
tagatgtaaa gtaccaagct tctactcaaa tattagtgaa tcaaaaagga aatgactcac   11520
aaattatggc acaagaagtt caaagtaata ttcaactagt aaacacatat tcagagatag   11580
ttaaaagccc acgtattcta gataaggttt ctaaagaatt agatgataaa tattcacgta   11640
gtgagatatc aagtatgtta accgttacca accaagcaga gtctcaagta ttaaatattg   11700
atgttgaaag taaagtggt agtaattcag aaaaaattgc taataaaata gcagaagtat   11760
ttagtgatga agtgcctgat attatgaatg ttgataatgt ttctgtttta tctacagcgg   11820
ataatacagg aaaacaagtt gcaccaaaac ctatggttaa tttagttgtt ggtttagtaa   11880
taggattggt tatcgcatta ttaataattt ttataaaaga agtgtttgat aaacgtatta   11940
aaacagaaga agaagttgaa aatgaattgg tgatacctgt actgggttca atccaaaaat   12000
ttgattaagg agggttttat ctatggcaaa aaagaaaagc actatatcac cactatatgt   12060
tcatgataaa cctaaatcga cgataagtga aaaatttaga ggtattcgat caaatatcat   12120
gttttctaat gctgaaaatg aaataaaaag cttgttgata acttctgaaa aatccgcatc   12180
tggtaagagc atactttcgg caaacattgc agtaacatat gcacaggcag gttacaaaac   12240
attaattata gatggagata tgagaaagcc tacacaacat tatatctttg atttgcctaa   12300
taatagtggg ctatctaatt taattattaa taaaactaca tatagcgatt caattaaaga   12360
aactagagta gagaatttaa acgttttaac agcaggacca acaccgccta atccttcaga   12420
attaattgct tctagcaaat ttgcaactat atttaatgaa cttttgaatc attatgactt   12480
cattgtgata gacacacctc cgattaatac agtaacggat gctcaagtat atgcgcgaat   12540
agtaaaaaat tgtgtgcttg tcatagatgc tgaaaaaaat aatgagagtg aagttaagaa   12600
```

```
agcgaaaggt ttacttacta aagccggtgg gaaagtatta ggcgcagttt taaataaaat   12660
gccaattgat aaaaattcta gctactatta ctactatgga gaagattaag aatggttgat   12720
atacataatc atattttggt tgatgtagat gatggaccaa aaagcattaa tgaagcaatt   12780
gagttgctta aacaagccca aagtgaaaat gtaacagata tagttgcaac acctcaccat   12840
cttcataaga gatatagtaa tgatattgaa aaagtgaaaa taaaattaaa tgaattaaaa   12900
aataactcag aaataaaaaa attaggactt aatttatatg ttggacaaga gattcgtata   12960
acggatcaaa ttatagaagg tataaaaaat aaagagattg aaggaattaa tgaatctagg   13020
tatttgttaa tagaatttcc tagcaatgag attccttatt atacgaatca attattctat   13080
gagttacaaa caatgggata tattccaatc attgcgcatc cagaacggaa taaagcgata   13140
gttcaaaatt tagatttact atttgaatta ataaatggtg gtgcattaag tcagattaca   13200
gcttcttcat tattgggaga ttttgggaat aacataagaa aattatcatt aaaaatgata   13260
gatagtaatt tagcacattt tattgcatca gatgcacata gtataacaaa tcgaccttt    13320 atgctaaaac agttgtttaa tgatagaaag ttaaaagctt attatgagga attagaaagt   13380
tatttaaaaa acgggaagtt agttttaaca aatgaaagaa tttccaaaca gataccaact   13440
caagattata agcagaaaaa atggtttggt ctttttataga aaaagtgagt gaggggatta   13500
aaagtgacaa gtatttctgc gaaattgcga ttttaatat taattattat agattcgttt   13560
attgttacat tttcagtatt tttaggatat gcaatattag aaccgtattt taaggatat   13620 tcaatagatt tattagtatt atcatctgtt atattgttgg tatcacatca tatattcgca   13680
tatgtattta atttatatca tcgagcgtgg gagtatgcga gtgtaagtga attgatgtca   13740
gttttaaaag cggttacaag ttcaatagtg gtaacacttt tattagtttc attacttata   13800
agtgaaagtc catttctaag gttatatttt ataacgtgga tgatgcattt gctattgatt   13860
ggtggctcta gattgttttg gcgggtttat agaaggtatt ttattgataa cgctgtcgaa   13920
aaaaaagcca cattagtagt aggggctgga caaggcggat ctgttttaat tcgtgaaatg   13980
ttaagaagcc aagatatgcg tatgcaacca gttttagctg ttgatgacga taaaaacaaa   14040
caaaaaatga ctattactga acgtgttaaa gttcaaggtt atgttgaaga tataccggaa   14100
ctagtaaaaa aatttagaat aaaaaagatt attattgcta taccgacatt aagccaaaaa   14160
aggttaaatg aaattaataa aatatgtaat attgagggcg ttgaattatt taaaatgcct   14220
aatatagaag atgtgttatc tggagaatta gaagtcaata atttgaaaaa agtagaagta   14280
gaagatttac ttggaagaga tccagttgaa ctagacatgg cattaattcc aagagaatta   14340
acgaataaaa caatattggt aactggagct ggaggatcaa taggttcaga aatttgcaga   14400
caagtaagta aatttgatcc tcaaaaaatt attttgttag acatggaga gaacagtatt   14460 tattcaattc atcaagaatt aagtaaaact tatggaaata gaattgaatt tgttcctgtt   14520
atagctgatg tacaaaataa aacacgtatt ttagaagtca tgaatgaatt taagccatat   14580
gctgtttatc atgctgcagc acataagcat gtaccattaa tggaatacaa ccctcatgaa   14640
gctattagaa ataatatttt aggtactaaa aatgtagctg agtctgcaaa agaaggagaa   14700
gtaagtaaat ttgtaatgat ttcaacagat aaagctgtaa atccatctaa tgtaatggga   14760
gcaacaaaac gcattgctga aatggtaata caaagtttaa atgaagataa ttctaagaca   14820
agttttgtag cagtaagatt tggaaatgtg cttggatcaa gaggatcggt catacctcta   14880
tttaaaaatc aaattgaatc aggtggtccg gttacagtaa ctcaccctga aatgacacga   14940
tatttcatga ctataccaga agcatcaaga cttgtattac aggccggggc attggcacaa   15000
```

```
ggtggcgaag tatttgtgct agacatgggt aaaccagtta aaatagttga tttagctaag   15060
aatttaatac ggttgagcgg taaaaaagaa gaagatattg gtattgaatt ttcagggatt   15120
agaccaggag aaaaattata tgaagaatta ttaaataaaa atgaaattca tccgcagcag   15180
gtatatgaaa aaatttatag aggcaaagtt gaccactata ttaaaacgga agttgatttg   15240
attgtggaag atttaataaa taatttctca aaagagaagc tcttaaagat agcaaataga   15300
taaatataaa atgtatattg gagttttaaa atgaaactaa agtacaaagt aattttaatt   15360
ataaattttg ttacagtatt atttagtata tttacattca tcggttattt aaataacttg   15420
ataggtttta gagttgttac aatatcatta tgtataacta tagctatgac cgtgtactta   15480
ctttacaaaa aaagaaaagg ttttttatta gtttatttaa tatatttatt tttaactaat   15540
tttggtgtat ttgtaacaaa tatattttta gccaatcctt tagtggagta tcacggtgat   15600
ttatcttggt attatataaa tacatctaat ttgtttagca ttgctacttt tgcgatatta   15660
acttttacaa ttttaagtaa ttttattagt gtgtttagca aaataaatcc aagtagaaag   15720
tttgatatta aaagtaaagg aaataattta ttctactaca caggaatatt atttatcatt   15780
ggatttacta tacaatttct ttttatatt ataactggtc gattagcaat taatacttat   15840
ggagattatg taagtagcat acaagaatta ccaatgtata cgtacggtat attctttttt   15900
tcaattggga ttgcatttgc attttctaat gtaaaaaaaa cacatattaa atatctagta   15960
attatattaa ctccccaagt gttattttt ttaataaccg gaaatagggg agaagtattt   16020
tatccaattc tatctgcact tggagtgtta atagtaagga attataaaat taaatggtgg   16080
atgataatta caattgtttt tacattattt tttgtaatac catttattaa agtctttaga   16140
aatatggata gtagctcaat tgaaaaggtt gatataaatt ggttttcttc acttgttgaa   16200
ataggctaca cactgcgccc tttaggttat gtaactaggt ggattgacgg tggggaaagc   16260
atagtttatg gcaaaagtta cttagcacct attcaaaata tattttcata tattatacca   16320
gggttacaac ctgtaaacta tgaaatggtt ggttacggtt ttaggtatag actacctggt   16380 atgggttttta atgtaatagc agaagcgtat tacaatggtg caattgttgg agtattgatt   16440
gtaatggtgt tattagtgct tttactttgg aaatttacaa attttaaatc ttttgaaatg   16500
ctgtcaatgg gtactgcaat tgtaagtgta ttaatcaata atataagaaa cgcatttca   16560 ttcgtacctg catacatatt aattatcatt gtaatagtga ttatattgct gtttatagat   16620
agttatttaa aaaagaaac gaaggccgat taaagtggtt aaaaatttta attatatgtt   16680
tgttgctaat atactgtctg cattgtgcaa attttaatt ttactagtaa tagttagatt   16740
aggaacacct gaggatgtag gacgttataa ttatgcttta gttataactg ctccaatttt   16800
tttatttata tccctgaaaa taaggtctgt aattgtcacg aatgataaat atagtccaaa   16860
tgaatatata tcagcaattt tatcattaaa tattattact ttaatatttg ttgcaatttt   16920
tgtttatgta ttaggaaatg gtgatttaac tactatatta atagtatcgt taataaatt   16980 atttgaaaat ataaagaag taccttatgg aatatatcaa aaaaatgaga gtctcaaatt   17040
actcggaatc tcaatgggta tttataatat actaagttta attttgttt atattatata   17100 ttcttttca cacaacttga atatggcact tttattttta gtaatatcct gtatattctc   17160
atttgctatt atcgatagat ggtatctaag taagtattat aatataaaac tacactataa   17220
taacaacatt gcaaagttta aggagatttt tattcttaca atacctcttg cttttttcaag   17280 tgcgttagga tcattaaata caggaattcc tagaatagta ttagaaaatc tatttggaaa   17340
```

```
atatacatta ggtatatttt ctacaattgc gtatgtactg gtaatcggtg ggttattcgc    17400
aaattcaatc agtcaagttt ttttacccaa attaagaaaa ttatataaag atgaaaaaaa    17460
aattgaattt gaaaagttaa ctagaaaaat ggtgtttatt ggaatttta ttggtatgtg     17520 ctcggtaata ttgagtttgt ttttaggtga ggccttgtta tcattgttat ttggtaaaga    17580
atatggtgaa aataatataa tattaatcat tctttctttt ggtttgcttt ttatactcag    17640
tggtattttt ttggggacaa ctataatagc cactggaaag tataatgtga attacaaaat    17700
ttctctaata ctattgtttt gtattttgat atttagtttc ttattaatac caaaatattc    17760
tttattaggt gctgctttaa ctattactat ttcacaattc gttgctttaa taagctatta    17820 ctattttac aaaaggatat tttgaggtgg aaaatatgaa aaaattattt ttaaagttaa      17880
tgaaaaggaa tctatctgaa gataagataa ggaaattggg tgtacaagtt ggaaatgatt    17940
gtaggttttt aagtgttgat agatcaacat ttggatctga gccttacctg attcaaatag    18000
gaaatcatgt aacaataact agtggtgtaa aatttgctac ccatgatggt ggggtatgga    18060
tttttagaaa aaaatatcct gagatagata atttttcatag aatatttatc ggtaataatg    18120
ttttcatagg gattaattca ataattttgc caggagtaac aataggaaat aatgttgtag    18180
taggtgctgg gagtgtggta acgaaagatg tacctgataa tgtaattatt ggtggtaatc    18240
ctgccaaaaa aattaaaagt atagaggcct atgaaactaa atatattagaa aatgcggatt    18300 acacaaaaaa acttaattat aatgaaaaga agatatattt attaaataaa ttcaaagaga    18360
ataggtataa ttaatgatta aagttatgca tatatttagc agaatgaatc gtggcggtgc    18420
agaattaaga actatggata caatgaaact attaaatagg gagtttgagt ttcatgtatg    18480
tgctacatca ggaaaaaggg gcgaattaga tgatgaatta gaatctatgg gtattacgat    18540
acattattta gatattaaaa aatttagttt tcctttcaag ttcataaagt tattgaaaaa    18600
gaaaaatata gatgttgtac atagtcacat acttttatg agtggattga ttcaattact     18660 ttcttttca gcaaatgtaa gaaatagaat aacacacttt agaacttcca aagatagtaa     18720
agaacaatat aataaaataa gaaaagctag aaataaagta ctgaaagcca ttatagaaat    18780
ctttagtacg aaaatcttat atgtaagtaa tatagcaaat aggaatttaa tctcaatgaa    18840 acttttccg aaaaaacata aaactattta caatggattt gaaataagta atataaacaa     18900 aaatttaaa aagaggaaa atagtttat ttatgtcggt aggttcattc atactaagaa        18960
ccaattattt ttgttagatg taatagaaat tttaaaaaaa gaatttaata ctaacattga    19020
aattactttt gttggcaata ttcaaactga ttatggaaaa aaattcttga gtatagcaaa    19080
tgaaagaggt ttaaataaaa atattaaggt tattggagaa gtgaataacc cattagatta    19140
tttaaaaacg agtgaatatt ttttgtttcc tagtgaatta gagggattac cgggagcatt    19200
gatagaagcg catcatcaca attgtattgt tatatcttcg aatataaaag aaaattctga    19260
agtaaatcaa tattttaaag actcttcatt tgaattagaa ttaattccaa aaacttgggc    19320
ctcaactatc aaaaagctaa tttcaaggaa aaagcatata agtttttaatg attctaatgt    19380 ttttgatatc aatatgacta cacaagaatt aaaagaaatt tatatgagta aaactttata    19440
gatgaaggga ttgattttca tgaaaatatt aatcacaggt acagcaggtt ttattgggtc    19500
acatcttgcg aaaaaactaa ttaaacaagg tcattacgtt ataggtgtag atagcataaa    19560
tgattattat tcagtttctt tgaaagagga tagattaaaa tcaataggga aagagaattt    19620
cacttttaat aaagtgaaat tagaaaatta tgacgattta tctaaagtat ttgtagatga    19680
acaaccagaa gtagtagtta atttagctgc tcaagcaggt gttagataca gtattgagaa    19740
```

```
tccaaggacg tatattgatt ctaatattgt cggttttatg aacattttag aatgcagtag   19800
gcattttaat attcaaaatt taatttatgc ttcatctagt tctgtttatg gtgcaaatac   19860
ttctaaacca tttagcactt cggataatat tgatcatccg ttaagtttat atgcagcaac   19920
taaaaaatca aatgagctaa tggcacatac gtatagtcat ttatacaatt tacctacaac   19980
aggattgaga tttttcacag tatatggtcc atggggagga ccagatatgg cgctatttaa   20040
atttacaaaa gcaatcgtaa atgatcaagc tatagacgtc tataatcacg gaaatatgat   20100
gagagacttt acttacgtgg atgatattgt tgaagcaatt agtaggcttg ttaagaaacc   20160
agcgtcccct aataaagaat ggtcaggggc cgaccctgac cctggttcct catatgcacc   20220
atataaagtc tacaatattg ggaacaacag tccagttaga ttgatggaat tgtagaggc    20280 tatagagaat aaattaggca agaagctag gaaaaactac atggatttac aaccaggaga    20340
tgtacctgaa acttatgcaa atgtagatga cttgtttaga gatattgatt tcaaaccaga   20400
aactacaatt caagatggtg taaataaatt tgttgattgg tacttagaat attataaaaa   20460
atgaagaaaa agggtgtttt aatatgcaat tactctttgt acatgatttc ccagttgaaa   20520
aatataaaga taattattac tcaataggct tctctcacaa aatttggaat cgatatttaa   20580
ccatttttga taaaatgctc ataaattcaa gagtgaaaaa tgtagataat ggggaaatta   20640
ttaataaatc gaatggagaa aaagtgaatt tcaaaacaat agatagctat aaatcaccta   20700
aatctctaat tttaaacat aaaaaaatat ttgaagccct tacaatttct atcaagaaaa    20760
gtgatggtgt tttaattagg gtaccaagtg ttttaggatt tattgcagct ctaatatgta   20820
aaaaaatcaa taaaccttat atggtggaag tagttggtgc agcatttgac gcatattggt   20880
ttcatggatc aatatttgga aaaatttat cgttacctat ggaatattta caaaaaaatg    20940
cagtgaaaaa tgctagcata gcgatttatg taactaagaa atatttgagt aacaaatatc   21000
cttgtaacgg gaaagagttt aaaggcattt caaacgtaca atctgtagaa aaatttaata   21060
agaatttaga tattgggaat aaaattaaaa ttggacttat tggatctacg tttgttgatt   21120
ataaaggaca taacgtagct ataaaatcaa taagtaattt ggtgaatgaa ggttataaca   21180
ttgaattaga atttgtgggt gatgggccca gtaagaaatt tatggaaatg gctaaaaaat   21240
acaatgttga aaataatgtt atatttaaag gtaaaattta tgacaagaca gcgttaaata   21300
attggtttag aaatttagat ttgtatattc aaccaagttt aacagaggga cattgtcgag   21360
caattgtgga agcaatagga aatggagtgc ctacattagc gtctaatgct ggtggtaatt   21420
cggatagtgt taacaaagaa tatttgttta aaccaaaaga tgtagttaaa ttaacaaaac   21480
taattaatag atctattttg tctaagcaat atcgagaaga aaatgtttta gaaacaaaa    21540 aaaatatttc aggttacaac ctggaaaata ttcaaataga aagagaaaaa gcactactta   21600
attataaaaa aataataaat gatttttatt tagcgaaagg aataaataaa aatgcttaat   21660
tatatatata atcattcacc aataattttc caaaatttaa tggtttcaat aaagggtaaa   21720
atattcatga aacaaagata tactaaacat tattatgaag aaataaagag acttagagag   21780
tgtaatgatt tatttgaact tcaaaatcaa agatttgaag aattttataa ttatatcaaa   21840
aaaaatagtg aattttattc tgaaataatt aaaaaaaata atctaagcgg taaaaaaatc   21900
actgttgcaa atataaacca attgcctgaa attacgaaag atgatattag aaaaaatgtt   21960
gataaaatta ttactaaaaa gaaaatataa cttataaaaa tgggcactgg cggttcgact   22020
ggtaaaagta tggttttta tactaatgca tatgatatgt ctagaaaaat agcttaccct   22080
```

```
gattattta  aagaacaaca  tgggtatat   aaaggtatga  aaagagttag  tgtaggtggt   22140
agaaaaattg  taccaattaa  acaaaaaaag  aaagtatttt  ggcgatataa  taaaccacta   22200
aatcaattaa  tgatatctgc  ttatcatgct  gatggtgaaa  atcttaaata  ctacattaaa   22260
aaattaaata  aatttcagcc  tgaaactttg  gatggctata  ctacagttat  tcataggatt   22320
gcgagatata  ttttagataa  caatatagaa  ttaagtttta  caccaattgc  tatttttcct   22380
aatgcagaaa  ctttaactga  tttaatgagg  gatgatattg  aaaaagcttt  taattgtcca   22440
gtgcgtaatc  aatatgcttc  ttctgaagga  gcaccttta   ttacagaaaa  caaagaaggc   22500
gaactagaaa  ttaatgtagc  tactggagtg  tttgagtgta  aacaaattca  tggtaatatc   22560
tatgaattaa  tagtgacagg  ttttatact   actactacac  cattattgag  gtataaaatc   22620
ggagattcag  tagaattaga  aaatgagctt  cccgtaaatt  atcaacaaaa  agatataaaa   22680
attaaaagaa  ttatcggtcg  taacaatgat  tttttacagt  ctagagaaaa  aggaattgta   22740
actaatgtga  atttgtcaac  agcaataaga  tttgttgaga  atgatgttat  tgaatcgcaa   22800
tttgtacaga  atgatattga  taacattatt  gtgtatttag  taattagtaa  tgatgcggat   22860
aaaaataata  ttataaagaa  attaaaatat  gagttgaaat  tcaggtttgg  tacaaatact   22920
aatttccatt  ttgaatttgt  taataagata  ccatcaacac  ctggtggaaa  aaaagatttt   22980
gcaattaata  acattaaata  aggggataag  aaaatgaata  gaaatattgc  agtagtaggt   23040
ttaggttatg  taggtttacc  agtagctgta  acttttggga  ataaacataa  agtaatcgga   23100
tttgatatta  tgaatcaag   aattaaagaa  ttaaaaaata  attatgatag  aacaaatgaa   23160
gtaacagaaa  ataaattaaa  aaacacgaat  atagaatata  cttcaaatgc  agaagatttg   23220
aaaaaggctg  attttattat  tatagctgtg  ccaacaccaa  tcgataagca  taataaacct   23280
gatttattac  cattattaaa  agccagtgaa  actgttggga  aggtaattac  tccagacaca   23340
atcgttgtat  atgaatctac  agtttatcct  ggcgcaacag  aagaagaatg  tgtacctgta   23400
ttggaaaaat  attctggact  cgtttgtggt  aaagattttt  ttgttggtta  ctcacctgaa   23460
agaattaatc  ctggggataa  ggtacatact  tttgaaacca  ttactaaggt  tgtatctggc   23520
caaacgcttg  aagtattaga  aatagttgca  gacgtatata  gttcagtagt  cacagcagga   23580
gttcataaag  catcttctat  taaagtagca  gaagcagcaa  aagtcattga  aaacacacaa   23640
cgtgatgtaa  atattgccct  aatgaatgaa  ttggcaatta  ttttttgataa  attagatata   23700 gatactaacg  aggtattaaa  agcttcagga  acaaaatgga  acttcttgaa  ttttaaacca   23760
ggattagtag  ggggacattg  cattggtgtg  gacccatatt  attaacaca   taaagctcag   23820 gaagttgggc  accatcctga  agtgatttta  gcaggtagaa  gaataaatga  taatatggct   23880
aaatatattg  cttctaacgt  tattaaagag  ttattgaagc  aaggattaga  agtcaaagga   23940
gcaacagtta  atgtgctagg  tcttacattt  aaagagaatt  gtccggattt  aagaaataca   24000
aaggttattc  atattattga  agaactgaaa  gagtatggat  taaacgtaac  agtgaatgat   24060
gttgaagcgg  ataaaaatga  agctaaaaag  ttctttggtt  tagatttgat  agatacaaaa   24120
gaattaaaaa  tggtggatgt  agtgttattt  gcagtgccac  ataaagacta  tatggaaaat   24180
aaaaaggatt  atatcaattt  agttaaagat  tgtggcatag  tgtttgacat  taaaggcata   24240
atcaatagtg  atgaacttaa  tgtaagtcaa  cgattatgga  gattataagt  gtaaaattac   24300
attgtgaggt  tttgtatgaa  aaatcaaaaa  atatttcatt  tagttactgt  ttctaagagt   24360
attccactta  tgagaggaca  aatagaattt  ttaagaaaaa  aaaatatgga  tgttcacatt   24420
gtttcgagtg  atggtaagga  attaaagcag  tatgataatg  aaatagctca  tgttataccct  24480
```

```
atgaaaagag atatagcatt attcagtgat ttaaagtcat tattaaaaat gatattacta    24540
tttcacaaag aaaaaccatt tattgttaat tctggtactc caaaagcagg attaatagga    24600
acaatagctg cgtttattac ccaaagacct attagaatat atactgtgag aggtttaagg    24660
cttgaaacag ttaaaggatt caaatatttt gtattgtatt tgatggaaaa gatagcaatg    24720
ttttgtgcaa ctgatataat agcaatttct gaaagtttaa agcataaaat tattacatct    24780
aatttggcta aggaaaataa aattactgtt tgggatttg gtagttctaa tggtatacaa     24840
tttgaaaaat tccaattaga taacaataaa ttagaagaaa ataccataa attattaaat     24900 gataattttg ttattggcta tgtaggaaga attgtaaaag ataaaggtat acatgaatta    24960
attcagtcat ttaaaattat tgtaagtaaa ggatataatg tcaaattgct tgttattggt    25020
agtttagaga cagaaaattc tattgatgaa tctgactatt tatttttaac tcaaaatcct    25080
aatgtagtac taatcaagca tgtttcagat ccaatttcat tttataataa tatgaatgta    25140
tttgtttttc caactcatag agaagggttt ggaaatgtta gtatagaggc tcaagcactt    25200
gaagtgccag taattactac taatgttaca ggcgctattg atactgtagt aaatggagaa    25260
actggattta ttgttgaaaa aggtgactt aaagcaatcg ctgaaaaaat tgaaaaatta     25320
attaatgacg agagtttaag agaaactatt ggtcataatg aagaaagag agtggaaaat     25380 aaattttcaa gccaaattat atgggaagaa ttggaaagta tgtacaatac ttttctaaaa    25440
gaaagtgagg gaaagtaatg aaaagaatat ttgatatatt tagttcatta tatgcaatta    25500
ttatattttt gccgctgctc tttctagtgt ctattgcaat taaaatagag tctaaaggtc    25560
cgattgtatt taaacaggac cgaccaggcg taaagaacaa attatttaaa atttataaat    25620
ttagatctat gagacaagat accccaaatg tagcaactga taggttagac cctgcagatt    25680
atattacaaa aactgggaag ttcattagaa aaacatcatt agatgaatta ccacagttat    25740
ttaatatttt aaaaggtgat atggcagtag ttgggcctag acctgcttta tataatcagt    25800
atgaacttat tgaaaaaaga actaatgtaa atgttcattt ggttaagcca ggattaactg    25860
gcttagcaca agttatgggc agagataaca atacggacga ccaaaaagtt caatatgata    25920
agttttatgt tgaaaaccaa tctttcaaat tagatatgta tattatttat aaaaccataa    25980
aaaacactat atcttctgaa gggttagtc actaatgaaa aatatattaa tcacagggaa     26040
aaatggattt gtaggtaatc aatttcaatt attattaaat aatgataatt ataaagtcga    26100
tagagtcagt ttgaaaaata atgattggaa gttttgttca tttgaaaatt atgacgtaat    26160
cattcattta gcagcattgg ttcataataa tcaacccaat gctaaaataa ttgattatat    26220
gaatacgaat taccatttaa ctagagaact agctaaaaaa gctaaagatg acggtgtaag    26280
tcaatttata ttttttagta ctatgggtat ttttggcatg aatggtttaa ttaataaaaa    26340
atgtgaaatc actcaattaa ctccatataa acctaaaagt gcatacgact attctaaatt    26400
gttagcagaa agagatattc aaaaattaat tgatgacaaa tttgtggtaa atatcgttag    26460
accgccaatg atatatggta aaaagggacc gggtaatttc gctaaactta taaaagttgc    26520
aaatttatca agaatatttc ccaaatatca taatgaaaga agtgttatac atatagataa    26580
cttatataaa catatttta acttattgaa gaatgaaaaa tctgatatca cacatccaca    26640
gaatatggaa tatatgaaca ctaatactgc tttatcattg attagaaatc atttaggaaa    26700
atcgagtgaa cttatagaaa ttccagtgcc aaatttcatt aataaaatta ttgaaaaatc    26760
aaatattgcg aacaaaatat atggaaattt aacatactca aaaaatatag acgatagaga    26820
```

-continued

| | | | | | |
|---|---|---|---|---|---|
| aataaataat | atgcattttg | acaattttaa | tcaaactatt | agtaaaactt | taaaataaaa | 26880 |
| aattatatga | taaagatttt | gttatgataa | ataaatcgtt | aacgaaaaaa | taggcttaac | 26940 |
| tgttataatt | ataccaatat | tattattatt | tatagtaggt | tttgttttta | taaattaata | 27000 |
| gttttaaata | gcttaattaa | tgatctacta | gaaaaggcag | gttcccattt | ctattgacta | 27060 |
| ttttcgatta | atgtgaaagg | tcaaaaaata | gatgtgatca | gtgctttacc | tgagtacaca | 27120 |
| cactaaaatt | gtcggtagag | gtacataaga | aaagattaat | catgtgtatg | tgtgttgtga | 27180 |
| atcgtacatg | gcagtaaaat | ctattgaaaa | attaattaat | gtgccaattg | gcattcatta | 27240 |
| tgcaacgatt | aatttagatg | gtgatgaaca | ttactttatg | gagtgaatgg | tgtcgatgtt | 27300 |
| gtgagtaaca | gtgatttta | tccccaatta | tcccttctct | aaaggtcaaa | aaataccaca | 27360 |
| tggatggtaa | agaatcttca | gcgtttatac | gtaatagaaa | agaagcgggt | gctggtagtg | 27420 |
| gaggaaatag | acaagcgaga | caacagcacg | ttattgaagc | agttactaaa | aaactatgaa | 27480 |
| tccaacctct | atcatgagaa | ccaattcaat | taataaaggg | gcaaaacacg | ttaggtgttg | 27540 |
| gtcgacttca | ttacttctat | cctggtgata | atgaagatat | tattcaagca | tatcgagaca | 27600 |
| atttgaattt | aaataaaatt | ttagtaaaca | tcaattgctc | atttagcggt | tggtgttttt | 27660 |
| tatagattaa | aatatatgga | aacacagatg | taaataacct | ttttattaaa | gttatactta | 27720 |
| cagcatttga | gttttggagg | agttggtatt | aaatgaaact | acaggcagtt | ttgatttatg | 27780 |
| atatctaatt | gaattggcac | atataattta | ttattataat | tcgagtataa | aagttaggaa | 27840 |
| tgaagaaaag | ctattttagc | catttataca | tagctatgtt | gtaaatattt | agcaaaataa | 27900 |
| ctaatatggg | gaggcgtatc | ataagtaggg | gggatgttga | taagcttccc | cttgttagtt | 27960 |
| atttggctaa | aaaagactag | ctgttcatta | tatttacatg | gtatgtcaac | attttttaga | 28020 |
| cagttttcat | gtgtgtattt | ttaaatgcca | ctgacgtcaa | atactttaat | gaagaatgtg | 28080 |
| gtctagaatt | gttgtaccaa | tttacataat | caaataattc | tgtttctaac | tgttctaagt | 28140 |
| tttcaaattg | catttgtttt | acaaattctg | ttttcattgc | tttcatcgtt | gcttccgcaa | 28200 |
| ctgcgttatc | ataaggacaa | tctttggtac | ttcatgaacg | tttcatttta | aatgtttcta | 28260 |
| gaacttcatc | tatcaaatga | ttattaaatt | ctttgcctct | atcggtgtga | aatagtttga | 28320 |
| tttattctgc | tgattgcttt | tgatactata | tttgcgtcct | tatttttaac | tgcactgtaa | 28380 |
| ccaacaattt | ttctattaaa | tagatctata | aataaacata | tgtagtgcca | tgttcctgcg | 28440 |
| acttttacgt | atgttaaatc | acttactaat | gcttccattg | gttgctctct | attaaaagct | 28500 |
| tcattcaaat | gatttttaat | ttgtcttgta | ccaagacctt | tctattagaa | ttaaaaatat | 28560 |
| ttatgattgc | acgttctacg | tttgaatcat | ctttagtgat | tttattatct | tttcttttta | 28620 |
| tagaatcata | ataggtactt | cttggtattt | ttaggacttt | acatattgct | ggtactgaat | 28680 |
| attgatgtgc | attcttttga | atgacttcta | ttttcgtctc | ataatcagct | ctgcttgctt | 28740 |
| taaaatatcg | ttctccattt | ttatatgttt | aacttctttg | cgtaatttaa | tcagctcttt | 28800 |
| ttcttcatct | gataaattat | cttgatgatt | gaacaaacct | gtgtattgat | gttgctttat | 28860 |
| ccatttcct | aacacctagg | aatgaaacct | aaccatttgt | aacttaaact | ctgaactaaa | 28920 |
| cgatttctt | tctcttgtca | taataaaatc | acctactttc | ttaaattaac | aatatctact | 28980 |
| ctcatagaat | ttgtccaatt | aagtgtagac | gattcaaaat | atcaaattta | tatgtatagc | 29040 |
| acttcttgct | ttttatgatt | aacttagcaa | aaaatacaaa | tcaacaataa | ataaaattta | 29100 |
| attacttaat | atatatttat | taccattaga | gtctgtttac | agcatccttt | ttgatttgtt | 29160 |
| catcagattt | ttcttttccat | gcatgaggtg | aaaagttaaa | tgtaatacta | tggtcatcaa | 29220 |

```
aaaactcata aagggcaggt cttaaccttt ttgcttttc atttcttctt tctgatcttt    29280
ttcgaccctc tgataaacgt gtaacacctg tacaataaat tttatccatt tctttgatat    29340
catctttata tagttccttt gataaagaaa tattttttct ttacttgaat taacatttac    29400
ttcgttagga attgcttcat taagactctc ataaaaagga aatagcccctt taccaaaact    29460 agatgattcg atgccaaaaa aattatatag catactgtaa tcatctacta ttaatccatt    29520
attatttgct tcaactacca aggaattttt catagttgac tctttataaa atgttaattg    29580
aactttcgcg aatttattta ttcttttaat aaattttcct ttaaatctgc ggataaagac    29640
taaataattt tcattttat atttaaattt aaatgaatca ataatataat ccttatcacg     29700
catatcgtca aatattaatt gaattttaga caagtgtaaa ttgttcatag ttatctactc    29760
cctatatata agtggatttc tacataatta ttctcctagg aaccctaaaa tcggcattat    29820
atctttcaaa aatgtacctc ataaaaagaa taggttgata tcgactttaa tttactctct    29880
ttctttatta ctaaatacac tttaacacat ttgtaaaatc ataatcattc actctaacat    29940
agtaaaattc ataatttttt cttaagtata ttaattgtat attttcatat taaagtccaa    30000
tgaatatact ttattcattt attagtcgaa ttttcatat ttcattaacc aactacctac     30060
ttaaattatt taatcttatt cttactcatc atttcaaagt gttggatatg tctaagtttt    30120
tcaaagacta acttaaagac tcttttataa tttctcatac ttgctccatc aaaggtaata    30180
acaaaatcat cacttataaa atgtgatccg tcatttattc ctgaaataag tgatttacat    30240
aatattttgt ctataccgtc aaatttatta atacatcttt cataatccat gcccctataa    30300
tattaaaata atattatagt attctacgca ttgtattaaa tgatgttatt ggtgacattt    30360
cttcagaatt aagttctttc cacattaatt gatatgaaga ttttatagca ttattctcat    30420
aagtattaaa ataacttata ttatccttt ttctaataat tccatacatt acttcattaa     30480
gcgaaaacct ttctctactt cctaaaaaag tgatttcttt atgaaagtaa atattgtgag    30540
taagattgaa tacttgttgt attctattct tattatttct acagtcattt atcaaattt     30600 taactaaagt actaacaata aataatacat tactatctaa actagaaatt ggatcatcta    30660
taatagcgat tttatttgaa gttacacttg tactctcatg actaccataa ataaaattta    30720
tttttttagg ttttatttct acataatttc ataggtcgc aatgttttga agcgaaattt     30780
ttttaatcat tcataatacc ccaatcccctt atttttaatta gtaaagacac tatatttatc   30840
aactgctaac tgtgggcttt agatttattt ctgataatca aaattatgtc tgagatgtta    30900
ctaatgtatt taatattatt tttagtattt aatctccccc atacttatga tacgcctctg    30960
cttatcagtt aataatggct ctatgtcaaa ttggactgat aagttcaata ttggaagtta    31020
ggcaactaaa cattgcttaa cttccttttt actttttgga gcgtaaagtt ttgaacataa    31080
taatattcga ttgcgtaaat gattgtaact tccataacca aaagatatac gtttaattaa    31140
ttttattttg ttatttatac cttctaaagg accatttgat aaatttgtaat aatcaaatgt   31200 attttttata aagtatgcat gtttgtttag tgtcttaatt gctcgttgga caaatgaatg    31260
cgcttgagat aatggcatat gttttaattc gtgaataaag ccttcataat cattatgttt    31320
aagtttgaat cgtaattgat tgatatattg gtaggcgtca ttcagtgagt catcttgatc    31380
taatatatac ttgacgatac cttttgtgt cttccattcc ttaaataaag cgactttacg     31440
atattcaaat gcctctaaat cttcttcagg ttttaataat aatttcgcat atctttttaaa   31500 cttattatat aaaggttgat tcgtcgttct taattcattc ataacagcga tgtcaatagc    31560
```

```
ggtttaaaat actgttttat ggcggtttga aaatatcgtt ttttagcggg ttaagaatat   31620
cgtgctttta atgcgctttt acttttattt attctcatgt ttacgttctt catagcaatt   31680
tttagtttag ataaatctga aagagtagca gcttcaaaat ttgcatttat atctaaaaat   31740
aattttaaaa tagacatgtt taaacaatca aaagtgtgca ttgctaaatc atcattttca   31800
aaagtttatg gatagaacaa ttatatgtaa acatatttat ttaagtttta aaaaagtagg   31860
acttaattat cgcaatattt ggtctatata aatgaaatat gatttaagtg aagaaataat   31920
actttgatat ctacagaatt aataggagtg atcagtcgta taacagtaat tgcaatttgt   31980
gaaagttaat tttgtaattg tatcaacaat ttttaaataa gattattagg taagtcataa   32040
atagccctgt taagggataa atgatataat agtgctatat aggaggcgat atcgtgatta   32100
ctattgactc aaagattaac aaacaaatcg ctaaaacctt tcacttgaag gtatgtatgt   32160
tacaaaagaa caacaaatac aaattcttca tgcaattaat aataagaaat tacaaatgag   32220
cttattcgta aaatcgcttt taaataatga aatatgatgg aatacagcaa gacgaatatt   32280
tattaaattc taatatgctt ggtgtcaaaa cttctgatga attaaagcga cttggaaaag   32340 ttgcttttttt aattgctgaa gcttccgttg aagaggaagg atataaattc tatttcccctt   32400 atcgtttaaa gtgaatttca agataattat caaaaaagca tatatactat attaaaagtg   32460
gacgtaggga cagtcattaa aatataaaag gattattaaa gtgcaatttg ttgtaatata   32520
ataattaaat tttaaaaatt atagttacat taagtgaata tatgttataa aataacaacg   32580
gttgataagg gtcaactaaa ttaattatat attcaagagg agtaatatga gaaaagtatt   32640
tatactaatc actttgttat ttggttatag tagctattct ttgttggaag ctaaagcaga   32700
gacacaaaat gatccaaata taagtgaatt aaacaaatct agtcaatata cgggttcgtg   32760
gcataatata tggtatttat ataatagtga tccagttaat gctaaaaaaa taagctaag   32820 tgacaaattt ttgagtcatg aattcattgt tccaataaat aaccctagtc attacgacta   32880
tgttaaaact gagttaaaag acagtacaat ggctagttca tttgatggga aagaagtcga   32940
tatttttggc gtcaattatt ttgatcaatg ctatttttta aatgaaaata tacagtgtga   33000
tagtaatcaa ggagctggaa gcaaaaaaac ttgtatgtat ggtggtataa cattaaatga   33060
gaacaatacc aataatagaa ttcagcctat tgttgtaaaa gtttacgaga atgacagtgt   33120 tactcttttct tttgatatca atattgataa agagactgta actattcaag agttagatta   33180
taaagtgaga aataaattaa tttctaaaat caatttatac catttaggtg gcacttcata   33240
tgaaacggga tacattaaat ttatagaaaa tggtaatcga tattattggt atgatatgat   33300
gccagaccct ggctttactc agtctaaata tttgatgata tatcggggta atgaaacagt   33360
tgaatcagcc aaaacggaaa tagaagtgca cttaactaaa aagtagacat agagcaactt   33420
atcaataata atttatggct agattaaagt aaataaaaat attttgatga attaaagcga   33480
cttggaaaag ttgcttttttt taattacttc tttaaaaagt aggtgcatta gtctttaata   33540
caaacaaaaa aggaggaaca ttacattcct cctcaacctt tattactcat actataattc   33600
aattttaacg tcttcgtcca tttgggcttc aaattcatct agaagtgctc ttgcttctgc   33660
aattgattgt gtgttcatca attgatggcg aagttcgcta gcacctctta tgccacgcac   33720
atagatttta aagaatctac gcaaactctt gaattgtcgt atttcatctt tttcatattt   33780
gttaaacaat gataatgcaa tctcaacaga tctaatagtt ccttgcttgt gtgttcacgt   33840 ggttctttttt caaaagcgaa tggattgtgg aaaatgcctc taccaatcat gacgccatca   33900
atgccatatt tttctgcaag ttcaagtcct gttttttctat cgggaatatc accgttaatt   33960
```

```
gttaacaatg tatttggtgc aatttcgtca cgtaaatttt taatagcttc gattaattcc   34020
caatgtgcat ctactttact catttcttta cgtgtacgaa gatgaataga taaatttgca   34080
atgtcttgtt caaagacatg ctttaaccaa tctttccatt catcgatttc atagtagccg   34140
aggcgtgttt taacacttac cggaagccca cctgctttag ttgcttgaat aattttggca   34200
gcgacatcag gtcttaagat taagccggaa cccttaccct ttttagcaac atttgctaca   34260
ggacatccca tatttaagtc aataccttta aagcccattt tagctaattg aatactcgtt   34320
tcacggaact gttctggctt atctccccat atgtgagcga ccatcggctg ttcatcttca   34380
ctaaaagtta agcgtccgcg cacactatgt atgccttcag ggtggcaaca gctttcagta   34440
tttgtaaatt cagtgaaaaa cacatccggt ctagctgctt cacttacaac gtgtcgaaag   34500
acgatatctg taacgtcttc cattggcgcc aaaataaaaa atggacgtgg taattcactc   34560
caaaaatttt ccttcataat atatttatac cctctttata attagtatct cgattttta   34620 tgcatgatga tattaccaca aaagacgaac ttatacaaaa ggaattttag ctgatacaac   34680
catttgaaag ggaagtctac gagtagtcta aaatgaatat tgtggttagt tgatcagtat   34740
acaaatcaag gattatcgta ttagattgtt cattattaat gatacactac ttattaatat   34800
gattcagaat tttctttagc tacatataca ataccgtgat ttttacgtta tcttataaca   34860
aagacaaatt tataaggtg atattatgga agatttaaaa cactctttaa aaggtttagg   34920
ttggtatgac ttattttta cagtacctat gtttctacta ttcgtgtatc tgccgaatta   34980
taatttcata actatattta ttaacattgt tattattatt ttcttttcca taggtttgat   35040
tttaactact catataatta taggtaacat taagaacaac tctaaatgat ttattaatac   35100
aaatatggtt aaacataaaa ctgaaggagc gattacaatg gcgactgaga agatgtaaa   35160 tgatttattt ttaaatcatg tgaattcaaa tgccgttaaa actagaaaga tgatgggaga   35220
atatattatt tattatgatg gtgtggttat aggtggtttg tatgataata gattattggt   35280
caaggcgact aaaagtgcac gtcatcaatt tcaagataat acattagtat cgacgtatcc   35340
tggtgccaag gaaatggttt taattccaca ctttgtcaaa gtaacaactc taaatgattt   35400
atttgagctc ataaaaaatg atttgcaaaa gtgaagtgcg aatagagaga gaaataaaag   35460
cggataatat gtccgtcttc gccaccctta aaatatatta ttgtaccttt tatgaggtaa   35520
gtagctaaag gttgttcgaa ctaagcacta gtacttcatt ttctatttca attctttctt   35580
aatttgatta ggagatttcc tctcctttaa aggtcgttgc ttttagtaaa tttctttttg   35640
ctttgtatgt tcgaggtata tcattattaa aaaatgccta caattaatga ggactatagc   35700
aaatgtagta ccgataatga ttagaatgtt ttttgatat gatatcaact ccgatattgg   35760
taaggacata ggagcaatta caatttccaa acaaggtaca cgagtgccat tgaatatttt   35820
attcagatca aaagtacacg cactaaaata agcatttatt tctatgtaac ttacatcttt   35880
gatactacag aagttcatgc atatgttcaa tcgtctcata atttttaaat acccctgatt   35940
cccatagtta aatacattat tcaaatcgta attaaaacat agaagtattt gaatcaccat   36000
attcaacttt taagtttgta ctactatgaa gtaatctaac taccacttta gtcaatacaa   36060
atataacgga aagataatca agtgagtgct cattcagggg tgctctttt tcatgtattt   36120 attgaacaaa aataaagatg cttaaggccc atttaaaaag ctacggaagt catttgagaa   36180
ataatatagt tacagtaaaa agttatacat aaatatcttca tcagtgaaag cccttttaaaa   36240 tatagaactt tgatttaagt aagaaaaatt taattcatgt gatatttatg aatgtttaga   36300
```

```
ttaaagatga tatatactat taataacagt attacttgaa aattaactac cttgtatatt    36360
tgaatataat aatatgatgt gactgttttt atacaatcta atttaaaact aaactgccaa    36420
tattgaatat tatggggtat agacaagtta tatgtagcca cttttttgaga gtactttatt   36480 ataatagtct tgtagtcaat ttgcagtgac aagagctaaa aaagaatttt atgtaattgg    36540
ggacatgcaa agaatacaga caaaaccatt ttatgaaacc attttttgaag aaagaaatgt   36600 agaataacat acaaaaaaag tatatagagg gagttattt catgcaaaat agaaatgatt     36660
ttatagaaaa actattagac agagctcaaa ttgaagaagg tatgcgtgta ctggatatag    36720
gttgtgcgac tggtgaggtc actcaattaa ttgcaaaacg tgtgggggcg aatggtgaag    36780
tcgtcggtgt tgatgtgaat gaatcattac ttaaaattgc aaatgaaaac aatcaatata    36840
acaatgtatc atatcaatat tctgatatat atcacttgcc agacactatg gggcattttg    36900
atgcgattgt tggtagaaga gtattgatgt acttaccaga tgctgaaaag tgtttacaaa    36960
ttttgaatca atttttaaaat ctgagggtat attatgtttt caagaaagtg atgctattaa   37020
tacaggcgtt ggtgcagatg cactacccttt acatcaatcg gcaattcaat ggatttggga   37080
aacagtgaag caagaaggtg gcaatattca tattggtcaa aatttatata atttgtttaa    37140
taataatgga atgtatgttg tagattactt tgcagaggca gtgattcaaa cgtcaatgga    37200
taatgattta gcatggcttg tagatgtaat gctaccaaga atgaaagcgc atggtgtcat    37260
taatgatgat ttttcactag atgagtttaa atcaaacctt gaacatgaag caataaacaa    37320
tcaatgtgca tttatacgtg aaatggcgtt tggtattatc ggaaaagcgt agtttaaaaa    37380
acgctgaaag tagcatatta ttatcaacaa tgttttaatt tgtgaagtta ttaatggaat    37440
ttgaaatgac agcatttcta taggctaatc aagtgatact taattaccga gcaatttata   37500
cattttaaaa ggagtaaaat tgaataatga agaaatttaa caactggata ttaaatgcaa    37560
taagtggatc tcaaacagac aagaatggaa caactgaaga attaaaaggg gcaaaattta   37620
tcattttata tgcatattca atgctcgttt tgcttgcgtt agtaatttct aacatattca    37680
ttcacatttt ggagcctaaa ttatcaatca ccactcaaat catcatcgtt ttgatttaa    37740 ttgaatcact aattggacta cgtttcttgc aaagggtacg atgttaggcg tggcaaagat    37800
aaagaaaata agaaaaatag taaggatttc gttaaactaa aatcaatttt agtagcaatt    37860
ttatttacat cattggtgct gacagcaggc actgtagctg atatatacgg tttcactgac    37920
ttaggaaata ctagaagtga ttaatcgttt ggagcatagg tggtattata tttggcctcg    37980
taagttacac aatggaagat aaaaaataac gataaggagt tggcgattat aaagctagct    38040 cctttttaa cttatttatg taaagaacta tcccgcgggt gtttaatcat atgtcaataa     38100
ttcctataat acattgttaa aacatcaatt aaataagttt taaaattta cccatatttt     38160 tatttgaaaa agatgtataa ttaatgtatt gaatatagaa agaatttgat attatgaaaa    38220
agtgtattaa gactttgttt ttaagtatca ttttagtagt gatgagtggt ttatatcatt    38280
cagcacatgc gtcagattcg ttgagtaaaa gtccggaaaa ttggatgagt aaacttgatg    38340
aaagcaaaca tttaactgag attaatatgc caggctcaca tgatagtggc tcattcactt    38400
taaaggatcc agtaaaatcg gtttgggcaa agactcaaga taaagattac cttacgcaaa    38460
tgaagtcagg agtcaggttt tttgatatta gaggtagagc aagtgctgat aatataattt    38520
cggttcatca cggcatggtt tatttgcatc atgaattagg aaaatttctc gatgatgcta    38580
aatattattt gagtgcctat ccaaatgaaa caattgtgat gtctatgaaa aaggactatg    38640
atagtgaccc taaagttatg aagacatttg aagaggtttt tagagaatat tattataata    38700
```

```
acccgcaata tcagaatctt ttttacacag gaagtaatgc gaaccctact ttaaaagaga    38760
cgaaaggtaa aattgttcta ttcaatagaa tgggggggcac atacataaag agtggttatg    38820
gtgctgacac gtcaggtatt caatgggcag acaatgcgac atttgaaacg aaaattaata    38880
atggtaactt acatttacag gtacaagatg agtataaaga ttattacgat aagaaagtag    38940
aagctgttaa aaatttattg gctaaagcaa aaacggatag taacaaagac aatgtatatg    39000
tgaatttctt gagtgtggcg tctggaggca gcgcatttaa tagtacttat aactatgcat    39060
cacatataaa tcctgaaatt gcaaaaacga ttaaagcaaa tgggaaagct agaacgggtt    39120
ggctgattgt tgactatgca ggatatccgt ggcctggata tgatggtatc gtaagcaaaa    39180
ttatagatag taataaataa ggattaaata atgacattaa gacgagtatg aaaatagtta    39240
gattctaatt attttcacta ctcgttttta ttttgaaaat aagtaataat tcaacaatat    39300
tataaattga acagattttt tgtgaaattt ttgataatat taaagtgaaa aagtgttata    39360
aattgataaa tatatgtaat tcgaaaaagt gaatcatttt aaaaagaaga gagtgatgaa    39420
atgataaaac gtgtaaataa attagtgctt ggtattagtc ttctgttttt agtcattagt    39480
atcactgctg gttgtgatat gggtaaagaa gaggaaataa agaaaagttt tgaaaaaaca    39540
ttaagtatgt atccgattaa aaacctagag gatttataag ataagaagg ttatcgtgat    39600 gatcaatttg ataaaaatga taaaggtaca tggattattg gttctgaaat ggcaactcaa    39660
aataagggtg aagctctgaa agttaaaggt atggtcttat atatgaatag aaatacaaga    39720
agtgcaaaag gattttacta tgttaatgca gtaaagaaag atgaagatgg tagacctcag    39780
gataataaaa tagaatatcc ggttaaaatg gtcgataata aaatcatccc tactaaagat    39840
attaaagatg gaaacataaa aaaagaaatc gaaaacttta agttcttcgc gcaatatggt    39900
acctttaaag atttgtcgaa gtacaaagat ggagatattt catataatcc agaggtaccg    39960
agttattcag ctaaatatca attaactaat gatgattata atgtaaaaca attacgaaaa    40020
agatatgata taccaacaaa taaagcgcca aagctgttgt tgaaaggttc gggagactta    40080
aaaggttcat cagttggata taaagacatt gaatttactt ttgtggagaa aaaaggggaa    40140 aatactttt ttactgatag tctacatctt gaaccaagtg aggataaata atcatgacca    40200
ataaagagta tgaaatcgat cccggaaaaa gagagtgatg aaatgataaa acgtgtaaat    40260
aaattagtgc ttggtattag tcttctgttt ttagtcatca gtatcgctgc tggttgtggc    40320
attggtaaag aagcggaaat taagaaaagt tttgagaaga cattgagtat gtatccgatt    40380
aaaaatctag aagatttata cgataaagaa ggttatcgtg atgacgaatt tgataaaaat    40440
gataaaggaa cgtggactat tagttctgaa atggcaattc agaaaaaggg agaagcatta    40500
aatataaaag gtatggtttt gaagttaaat agaaatacaa ggagtgcaaa aggatttat    40560 tatgttaatg cgataaagaa ggatgaagat ggaagacctc aggataatca aatagaatat    40620
cctgttaaaa tggtcgataa taaaatcatt ccaacaaaag aaattaaaga tgacaacata    40680 aaaaagaaa tcgaaaactt taagtttta gttcaatacg gtaactttaa agatttgtcg    40740
aagtacaaag atggcgatat atcatacaat ccagaggtgc cgagttattc agctaaatat    40800
caattaacca atgatgatta aatgtgaaa caattacgaa aagatataa tataccaacg    40860 aataaagcac caaagttatt gttgaaaggt acaggtaatt taaaaggctc atcagttgga    40920
tataaagata ttgaatttac tttcgtggag aaaaaaggtg aaaatatata ctttagtgat    40980
agtttacatc ttaaaccgag tgaggataaa taacctcatt gtctcccaca cgattcaaca    41040
```

```
cgaatttcaa atatgttgct gtaaaataat gtaaaataaa cgtattcata ttactgaatt   41100
gagggatagt atgcaacgtg attatttaat tcgagtagaa actgagagta tgtcagattt   41160
caaaaggctc aatggtttaa tgattggttt tgttattaaa ggtgaggcac atatttatga   41220
tgaaaataat atgacgcaat gcaacagtgg cgacattttc atcattaacc accgcgactt   41280
gtatcgattt caacttcaac aagatggcat catatgttat atccaattcc aaatgaaata   41340
tttagcagac aagtttgatg atgcgcattg tctatatttt cacttaacag atgcgaccac   41400
aacaaagaat aaacatcaac tgagaaatat aatggcaaga ctggtttcaa cacatatccg   41460
acataatgag ttgtctaaat tgactgagca acaacttgtg attcagttgc ttatgcatat   41520
gattcattat gtcccgcgta catatcattc gaaccaaagt atcttaaatg atgataaagt   41580
gaatcaagta tgcgactata ttgagttaca ttttcatgaa gatttaagcc tttcggaatt   41640
aagcgaatat gttgggtggt cagagagcca tctgtctaaa aagtttgcag aatcactagg   41700
tgtaggattc cagcatttct taaatacgac gcgaattgag catgcgaaac tcgatttgac   41760
atatacagat gaaatgatta ctgatattgc attgcaaaat ggcttttcaa gtgcagcgag   41820
ctttgcgaga acatttaaac acattacgca tcaaacacct aaacagtatc gaggtgatcg   41880
tccagcagtc actgaaaacc agcaatcggc acaacatgat tatcacgacc gtgaattgat   41940 attacttta aatgactaca ttgaagaaat gaatcatttc attgaagata ttgaaatgat   42000
gaactataaa gagattacct ttcaaccaac caatcaacaa ctaaatcaat ttaatcatat   42060
cattcaagtg ggctatttga ggaatttgct caatacacag tatcaatcac agttgcttac   42120
atgtcatcat gattttcaag tcaatgaagt attagcatat gatgtgatgc catatatcat   42180
gaaaaagctc aatgcgccat tcacgtatga tgcagaaatt tcgaatatat tttatgatat   42240
tgatttgtgt ttagactttt tattagatca taattttagt ctgaccatgc atttggatta   42300
gtatgactca cgagattata tcgatgcatt caaagtattt atccatcacg ttgccctgca   42360
tgtcagtcat agaaaagatt tgaagttcaa cttgtatgtg acgacattgc acacgtcttt   42420
gattgaaatg attgattatt ttaaagcatt attccctaat ggtggcttgt acattcactt   42480
agatcaagct acggaaaggc agctaccatt gttgaaacga cttgagccac acatcgacca   42540
ttttgtattt gatgccaatt caaataatgc tgttgatttt aataaaatga atgatgatga   42600
atttaaaact gcaagtcaaa tgattattaa taaaacgaat taccttatcg atttaatgca   42660
tcgtcatcat ctaaagcgtc cactcatttt actcaattgg aatacattga cgggtgatac   42720
atttattaca aacggcgaat gttttagagg tggtatcatc attgagcaat tattaaaatt   42780
aagttctaaa gtagagggta tcgggtattg gttgaattat gacttgcacg tcagtcattg   42840
tagaaatgaa cgggattata tgaattctat tgaactgttt catcaatata tggaaaacg   42900 tccggtctat ttcacggcat tgctatttaa taaattaaca agcaatattt tatattctga   42960
tgatacatgt attgtcacgg gaactgattc aaattttcaa atattgttat atgatgcaaa   43020
gcattttaat ccgtacttag cgttggacaa tcaaatgaat atgcgtgcaa cggaaatgat   43080
ccatttgaac attaatgccc tggaagaagg tatgtataag attaaacatt ttaccttaga   43140
taaagaaaat ggtgcattat ttaatctttg gcgcaaacat catacgatac atggtatgga   43200
caaggactct atagattacg ttaatcgaat gagttttcca aaattagaag tgtacgatat   43260
agatatgacg gatacgctgg cattaaatat taaaatgatt acaaatggaa ttcacttaat   43320
tgaagtaaaa cgttacccaa gttcataaaa tgatcacaaa tcacaaattt tgatatacag   43380
aatttgtgat ttttatatt caaagttaaa attgcaaaaa attaatggtt aacatctctg   43440
```

```
ttgttggcaa tataaataat gattaatcat ttatgatgta actaaggaga tgaatgatat    43500
gaatcaacaa ttaattgaag ctttaaaatc aaaagaagac aaaatgattg agatcagacg    43560
ttatttacat cagcatccag aattatcttt tcatgaaggt gaaacggcga aatacatcgt    43620
tgaattttac aaagataaag atgtagaagt agaaacgaat gccggaccac gtggaattaa    43680
agtaacgatt gattcaggga gacctggtaa acattagca atccgtgcag actttgatgc    43740
attacccatt actgaagata caggattgtc ttttgcatca caaataaag gtgttatgca     43800 cgcatgtggt cacgatgcac atacagcata tatgcttgta ttagcagaga cgcttgctga    43860
aatgaaagat agttttacag aaaggtcgt tgtgatacat caaccagctg aagaagtacc     43920
accaggtggt gctaaagcaa tgattgaaaa tggtgtatta gacggtgttg atcatgtatt    43980
aggcgtacac gtcatgagca caatgaaaac aggtaatgtg tattacagac ctggttatgt    44040
tcaaacagga cgcgcattct tcaaattgaa agttcaaggt aaaggtggtc atggttcatc    44100
accacatatg gccaatgatg ccattgttgc aggtagctac ttcgtcacag cgttacaaac    44160
agttgtatct agacgactaa gtccatttga aaccggcgtt gtcacaatcg gttcatttga    44220
cggtaaaggt caattcaatg tcattaaaga tgttgttgaa attgaaggtg atgtacgtgg    44280
attaacagat gctacaaaag caacaattga aaagaaatt aaacgtttat caaaaggatt     44340
agaagcattg tatggtgtaa cttgcacatt agaatataac gatgattatc ctgcattata    44400
taatgatcca gagtttactg agtacgtggc taagacgcta aaagaagcag acctggaatt    44460
tggtgtcgaa atatgtgaac cacaaccacc ttcagaagac tttgcatatt atgctaagga    44520
acaaccaagt gcctttattt atacaggtgc agctgtggaa gatggtgaaa tttacccaca    44580
tcatcatcct aaatttacca tttcagaaaa atcattactt atttcggaag aagctgtagg    44640
gacagttgtt ttagattacc ttaaaggaga taactaacat gaatgaaacg tatcgcgggg    44700
gcaacaagtt aatcttaggt attgtattag gtgttattac attttggttg tttgcacaat    44760
cacttgtaaa tgttgtacca aatttacaac gaagttttgg tgcagatatt ggaacaatta    44820
gtattgcggt aagtctaacc gcactatttt caggcatgtt tgttgttgga acaggcggcc    44880
tagcagataa aattggacgc gtgaaaatga cgaatatcgg cttattatta agtattattg    44940
gttcagcatt aattattatt acaaatttac cagcattgct aatttaggt cgtattatac      45000 aaggcgtatc agcagcgtgt attatgcctt ccacattggc cattatgaaa acttattatg    45060
agggtgctga acgtcagcgt gccttaagct actggtctat cgtttcttgg ggtggaagtg    45120
gtatctgttc actcttcggt ggggcagttg cgacaactat gggttggaga tggattttca    45180
tcttctcaat tatcgttgcc gtactttcaa tgttactcat caaagggacg cctgaaacga    45240
aatcagaagt taccaataca cataaatttg acgttgcagg tctaattgtt ctagtagtta    45300
tgttgctaag tttaaacgtt gtcattacta aaggtgcagc acttggttat acatcattat    45360
ggttctttgg tttgattgca atcgtaattg tagcattctt tattttctta aatgttgaga    45420
aaaaataggt acatcatcgt taagaccaac aagtgcttca gaaacatttc gtgaatgata    45480
accgatacgt tcaagaacac caatcatatc gatatatagt aatccgcctt ttgttgtaca    45540
ttcaccacga ttaaggcgtt taatatgacc tttgcgtagt ttatgttcaa tattaaatga    45600
ttctctacta cgctctacaa tttcatcttt tttcgttttg tcataaacat ctaacatgtc    45660
gatggcttta tcaaatgact cagcaacatg gttgaataat ttatccatac cgcgttgtgc    45720
atcttctgta atgcgaatat cttcatcatg ttggcgtttt aattgagcga catactcttc    45780
```

```
tgttagctct gctactttta aaatagagcg attgacatca aacataactg ctaaacgctc    45840
aacgtctgcc ttcgtaatgg cttttgtaga aattctaact aaataatttc gaatactatc    45900
attgattgtt tcaacagctt ggtgcttttg ttcaagcttt ttgatcaatt ttttatcgtc    45960
ttttgtaatt tcgcgaatgt cttcaaacat tgataagaca atctgaccca cattttgtaa    46020 ttcttttga gtttcttgta atgcaacacc aggtgcgtga taaacaagat ctttgtttaa    46080
gtgctgaggt ttatagtcat cagcaatatc tttacctggg acaagctttg taactatcca    46140
tgctaaacct gctacaaatg gtaattgaat caaagtattt gttatgttga agataccatg    46200
tgatactgca atcgtcatcg ctggttttaa gtgccataca tcttgtaaca aactaatcaa    46260
atgaatcaca actggcaaga aaattgtgaa gataattacc ccgattaagt taaagatgac    46320
gtgtacaagc gccgcacgtt ttgcagcgat tgagccggct aaactagcta agatagctgt    46380
aatcgtggta cc                                                        46392

<210> SEQ ID NO 88
<211> LENGTH: 57474
<212> TYPE: DNA
<213> ORGANISM: Staphylococcus epidermidis

<400> SEQUENCE: 88
cgaagcatat cataaatgat gcggtttttt tagccgcttc atgaagaaaa ttagagttag      60
cacaatactt ttgttaaaat ataaagacaa atatttggaa atataaaaat aattaataat     120
taataaattc tcttattttt ccatttgaat ctctatataa attttttttgc aaaaggacat    180 cttcttcaga ttcaatatct acactatcta ccaattttttt atttctaaca tcagtaagtc    240
gtgtataaaa aaatatata aaaggaatta ataaaaagaa tcttaatttt ttcatagaaa      300
ttaccttcct tattcaatag ctataaactt aaaataacat ttatttttaat attagtaaat    360 atatttttga atattaaata acaatcgtta agaatgtata acacttataa atatattatt    420
aaaagtagat gtatataatg aaaaattatc aaaaagtagt aaaattaaaa tttacctttc    480
acagcacatt tgttaaaatt attcatgata tgtaaatttg atgtaaagat taaattataa    540
tatatgcata tgagaaaact atgctcttta gtattaggtg aacattttag ggaggaaaat    600
agtttgcgat attcaatagt tatgccttat aaagaaacag atacaaagat gtttaatgat    660 tgttagata gtcttaataa tcaaactttt aaagattttg aggtattatt tatacatgat    720
ggagattcaa atttgcatga cgaaataaaa aatattaatt ttaatcataa agttttagaa    780
tctaatgttt catcaaatcc tcaatattat agaaatatag gtattaagga agctacgggt    840
gaatatatct tgtttatgga tagtgatgat tacttacacc ctaattcgtt aatttatgcc    900
aatgaaatca taaatgaaga acacgatttt gtggttaagc taggagtaaa aaaaactcac    960
tataccaaaa gtttaacttt caaggaaaac actcgaagtt tttataaacc tgaaatttcc   1020
gaaaaaataa gaaagctact taccgatata aataagaaaa atgtatctaa tccgagtttt   1080
attaataaac tatatgagct tgaattagta aagcatagtt ataataatat taaacaaaat   1140
aaatttttag acaatattaa ttatcgttta aaatctaatg ggttaataat taatagacaa   1200
ttcataatag atcatgaact aggatttgat acaactaaca gttatatgg agatattccg   1260 tttgttatca aattatataa tttagtagat agaataaaac agacaagagt aaaattatat   1320
tttaaattaa tacataacga tagtattagt tatccgtcac atacacaaaa attaaagaa    1380 actaaaagct attataaatt attagcgtat gataaagcat tgaattattg tcctaattta   1440
aacttagcga gaaaattaaa aggttttgct acaagagaat atttatatta tgtatgtaaa   1500
```

```
ggtgaagatt tcgaaactc atttaacaat gtaaaaccaa tatattcaat tttacgagat    1560
ttactaaata aaccttcaaa aagactcaaa atcaatttgc gtcataaatt ggaaattaat    1620
cctattaaga acggggaata cagaaaagcc tataataggt caagaagaag agttaagttg    1680
tataatgctt atgaattttt gaaacctaaa atgaaagat atagaaaaaa agttatacaa     1740
aaaaattttt ttgcaaaatt gccaatacgt aaagatttga tcgtttatga aagttttta    1800 gggaaaaatt actctgatag ccctaaatca attttgaat atcttaaatc atctgagagc     1860
gataaattta aacatgtttg gattttgaat aataaagata ttttagaaga ttatccaata    1920
ttaaatgata aaaatgtgaa aattatcgat agatttagct gggaatattt ttattatgta    1980
actgtcgcaa agtattttat actaaatatg agacagccca aatggttagt taaaaagaaa    2040 gatcaaaacta ttttatctac atggcatggc actcctttaa agagattagt atttgatatg   2100
gataatgtaa cttcagcaag taaaagttat aaacaagatt tttatcagca atcaagaaat    2160
tgggattacc taattgctgc taataaatat agtgagcaaa ttttcgagag agcattcaaa    2220
tatcctactt caaatattt aacttatggt tatcctcgaa atgatatctt aagtaattat     2280
aatcaagaat ataaaattaa ggttaaacaa aaattaaata tacctacaga taaaaaagtc    2340
gttctttatg ctcctacttg gagagatgat gaatatcatg gagtaggtca atacaaattt    2400
tcattaaatt tagacttaga acaaatgaga caagaattgg gggaagaata tatcgtacta    2460
cttagaatgc attactttat atcagataga ttagatattt cagaatatga aggatttgcg    2520
tttgattttt ctaaatataa tgatgtaaat gacctttata ttgtaagcga catattgatc   2580
acagattatt cttcagtttt ctttgattat gctaatctga agagacctat tttattctat    2640
acttatgact tagataaata taagatgaa ctgcgtggtt tctatataga tatggaaaaa     2700
gatttaccag gaccgctttt atttgattca tcggaagtta ttaataatat aaaaaatatt    2760
gaggttataa ataataatta taagagaga tacgaattat tttataataa attctgttta    2820
ttagatgatg gaaaagcaac aaaaagagtc gttgaaaagg ttattaacta atatttttaa    2880
atgaaaaaat aaattaatag agcatcccctt accgcaaagt gaaggatgct ctattttgt    2940 tgaaattaat ataagcttca ttctgataga tagtcattaa taattgtttg caaatcgtta    3000
ttaagtaccg ttgttacagc gtcatcatcc ataaaatcct cgtagatttt atcaagaatt    3060
tattcctctt acagacattc gcgagaagtc cgttttaatt ttattagaag taattcaggt    3120
ttgaacctac ctaaatgaat atatgagtta tcttttatac tacaaaatat attcagattt    3180
caataatgac ataaaatagg catcttata tttacccttta gtgtagaatt gctctttgag     3240
taatccttct gttttaaatc cttgtgactc gtatatatga atagcttttt tgttatctgc    3300
atcaacatat agatagatct tgtgcatatt taaaatattg aatgcataaa ttatcgcttt    3360
ttcgaatgcg aattttgcat aaccttacc actgaactca ggtttaataa ttatttgtat     3420
ttcacaatta cgatggatgt aattaatttc tactaattca acaataccta cgacttgatt    3480
ttcatcttca acaataaaac gtctttccga ttcatctaat aaatgcttat caaataaatg    3540
ttgaagttcc gttaaggatt cataaggctc ttcaaaccaa taagacataa tagaatattc    3600
attatttaat tcatgaacaa aaagtaaatc actatattct aatgctctta gtttcataat    3660
tccactccca aaatcttcat atatatttgc attataaata taaataacga ataagtcatc    3720
atcactgtga acactttttt taacaattca tcacatatta attctcattt tcttattatt   3780
ctcgatttat tactcttact atgaaatcta taaaattctc atatttgttt atattaagaa    3840
```

```
taaatacgtc aatagtaaca ataaaaaata aataatagag catccctcac cgctaagtga    3900
aggatgctct agttttattg aaatatacat ttcattttgt taaataatta ttaataatat    3960
tttgaaaatc attattacgt gaaatcttca tagattttat caagtatttc tttgtcttca    4020
attgctgtga agtgatgtac caatccttt ttacaatcat atgtaattt gtgacgctag      4080 gtaattagta attgttcgtc agtctgattg tatagtatca agtttcatag ataatactct    4140
ttgattttaa tgtccacttt gacgtgcttt aagattgagt atatacataa tgtcattgtt    4200
gaatgttaaa aatcctataa atgtttattc atctgcagga ttttttaatc tccaagaata    4260
aaaatcatca taggacaact ggattattgt tggataaaat aacgtaaaca ataattaggt    4320
actattattt attttttgttt attcttttc ctaacaaaat aaagaaaaga ataaacgcaa    4380
ttgttaaaaa tatgtgtcct aaaccagcaa taccagcaat agcaggactt acacttagat    4440
ctttaatggt agaaataccg ttcacgaatt gcattgccac agtaacaagc acacctacat    4500
ggtatatata aagaaactg ttaaacagct ttgtatgagt tgttaatttg aattggccct     4560
cgataatcat gaaaattaag aacataattg tacctagtac taataaatgt gtatgtgtaa   4620
catttaattg agaaaaaccg ctaaaatctt ccgcttttgt catttctcta taaaatagac    4680
cacttaataa ccctaatagt gtatagagcg ctgaactata cattaatctt ttcattttaa   4740 ttcccctat ttttaattac gagataagta tagcggtagt ttatgaactg agtatgaact     4800
tacaacaaaa aaattaatga agtactttac aataaactca atttattaga tggtggaggg    4860 acgaaaagg attttagaaa aataaattaa tatattttta ttttgataaa taataattaa    4920
taatatcttg gaaatcattg ttaagtattg ttgtaataca atcgtcattc ataaaatctt    4980
catagatttt atcaagtatt tcttcatttt caatcgctgc gaaatgatgt actaatcctt   5040
ttacaattga tacataactt tgcgatgcta acaactagc aactgtatgc caatctgatt     5100
gtttagtttc atggttcata gataatcatc ctttatttca atgtccattt ttgacgtgct    5160
ttaggattaa gcggatgcat aatatcattt gttgctggat ttatcaactt tttcaccttc   5220 ttttatgag gttttaacat ttccattacc tgtgatacac gttcaacgac agttggccgc    5280
ttcgcataag ctccataggc tagaatcact gtgtcacttt cacttatcgc tttcatcaag   5340
tgaatatcag tgtgctcatc atatggattt ttgatgtgtt tgagattttc tggactttta   5400
atattagaga atagatttac aagatataca gcgccatatt gttcagaatt agctaattgg    5460
ttgaggataa gaacagttgt gagatcgagt gataatacac cgtctaaatg aggatacatc    5520
gttatcactg tgcatgcagc tttcttttca tcccatgttt tcttgagtaa atagcggtgc    5580
tgttcatcat cgctaaatat ggcttctgtg tgtatcgtac ttttgattgt attcatcatc    5640
gtcacttcct ttagtattct tctggtaaaa gcatcacata ataaaaagcg tccacgtcat    5700
cttcacgaat gacgtagact ttcttaggta atgcattttg atttttttca tagtttgtat    5760
agtgatattc caatttgtat gtgggttgtt cttgttcatg cgtaactgac aacatattat   5820
catcttcttg tagtttgaaa atgtgtaggt aatcggtatg agagtggtta tctctttctt    5880
ttaccatatt ccaaagtatg atttgaaggt ctagagatag ttgttcacta atgcctcttg    5940
tgatgtatcg attgattttc atactatttg cctccatttt gcttttcttt catgatgtca    6000
atcacttcgt taatgactgt aacagatatt tgtgccactt tgatccaatt attcatggtc    6060
ctgacctcct tgttttagta aatgacgttc atcaataatg atattttgag tatctgtaag    6120
gtacagaaag tccatatcaa aatgatccag ataaccaata ctgatgagtt ggttattggc    6180
atacattaga aatggataga tacttagctc atgtagctca tcattatagt aggtataagt    6240
```

```
ctcgagtgtg agttgtacca gtggagaatc attaataaaa cgttccggta gaatattttc   6300
tgctgcttcc tccagcgctt cacattccca agcttcgtta ttagatagtt ggaataagtg   6360
ggtcatatat tgtttgagtt cttgagtgat ggttttcata ttattgcctc ctagatagtg   6420
taatagtgat gtagttcata tacatcattg agataatata tatttgattt gtcatttatt   6480
acgaatcccg gtgggaataa gagaaaattc catatgaaaa accgcttcaa accttggtat   6540
gacaaggaaa tcccgaaatt ccgcctgttt tgacgaacaa tcaactcatt atttataagt   6600
attgatgata gtggcgggtc tttacttcct tatatatatt atttatttat aaagaataac   6660
gggattttgg gattgtgctt gcacaatcct tctgcttctt cgaatctgca aatcccattc   6720
ctttcccgat aaaaaatcat cgtgggatgt tctttagcaa tttcaatata agcttcgtgt   6780
agtagtagat agatactgtc aattcgctct ctcattagat aagtgttatt gaattgata    6840 aagagaattc tcaaaaattt ttagaaaaag aaagaggaag tatgtagata taaaatagat   6900
ttattaaata gtaagatata atgtttgcgg taaaaataaa gacgaagtgc tggaatacac   6960
ttcgtcgata ataaggtaat tgaagtctcg attattttaa attgatcatt ttaagcctac   7020
aaattcctct aatgtttcac cagatttgta cacttttgtc gccttctttt ttcctaaata   7080
acgtaaatgc caaggttcat attgatatcc tgtgatgctt tctttgtttt taggatatct   7140
tataataaat ccataattat gggcattctt agctatccag cgtccttcct cagttttacc   7200
aaaactagca tatagatttt tatctgaatc gacgccacca acatcaaatg taagacctgt   7260
ttgatgttca gaatagcctg gacgcgcact atatttatct gctgcttttt taccatcacg   7320
cttcacataa ttattatata gcttaacttg tgtaggatag cttctatatc cacttatttt   7380
atataagtga atatcatctt tttgtgcacc atcaaataat tgttttaagg cttttttgtgc  7440 ttttggattt tcacccggat tataagagga gggtaaatca atattttgt ttacaattaa    7500 aattccatct gcatacgtcc gaccattctt aacaactttt tgatgcttct tttggttgtt   7560
atcgttattt tgggcttgat ttgtatgtgc agttttactt tcattttgt cattgtggct    7620 ttcagattga tgtgaacaag ctgaaagtaa taaagcgcta gtcatcaata ttacagataa   7680 tttttttcata ttaatactcc ttttgctaat acaaaaatat taaatgctaa atataacata  7740
acatatactt tgagctctat atataatatt taatattta taatgattca attaatgcgt    7800 atataaattta tattatgtta ccattaaata tacatgatac gagttgattt aaagtaagtc  7860
gttcattttt aatatcaaag tcacaaatat aaaatagaaa ttgaggaata tgaattgaaa   7920
aaaatatttt tgattatgtt gatatcttta ttttgttgta gttttttcac aaatactaca   7980
tatgctttga ctcctgttga aatcactaat aattcaaaag cacaacttga tgaaggattg   8040
aaccctagag gagcagtcgt gacaacaacg aatggacaaa tattatataa gtatcataag   8100
gataagaaag ttgatcctgc atcaacaaca aagttgatga caatgctagt tatatatgac   8160
gacattaatc atagtaaagt gagcttaaaa gacaaggtta aaatatctga gagatatcaa   8220
aaaatgtcac aattacctaa tttaactacc tttccattaa aaaagggca aacatatacg    8280 attgaacagt tactaaaaca agctgcctta aattctagta atgcagcaac gctagtatta   8340
gcagaacata tagatggaga tatttcaaaa ttcactgata gaatgaaccg tgaagcgcaa   8400
ttattaggta tgaatcaaac gcacttact aatcccagtg gtgccaacaa taaaattata    8460
aaaccctatg aacccaaaaa atataaggat gaaactagct catatacgac agcaaatgat   8520
atggctattt taacaaatca cttattacgc aagtatccta atatttttaaa aatgactcaa   8580
```

```
ttggaaacag atactcaata caatcaacaa ttacataaca cgaatttatc actgcctcat    8640
caatcactcg gcatgaaaaa tgtggatgga ttgaaaacgg ggacaagcaa agaaggatat    8700
aatttagcat taaccgctaa aaaagatcaa ttaagagtga atacaaattt atttaatatc    8760
cagccatatc ctagtgaaaa agctaaattt gcacgccaca aggttgctaa cgcactcacc    8820
caaaacgcat ttaaaaatta tacgtatcgc aaagtgatat cgaaaggtgc acatcaaatt    8880
gatggtaaaa cttacaacgt gaaagaagac ttatatgatg tagtacctaa ggataacagt    8940
aaatatgaat taaaaatatc ggaaaaaaac caactatcag ttaaatacaa tcgacaattt    9000
actaaagggg agcatattcc tagcgttaaa gtagaaccaa agtttaactt cttgtctgta    9060
ttatttcaaa tcacttttagc aattgtcggt ataatattgg tttctgtcat tgttattata    9120
gcgatcaaag tgtacataaa aaaatatagt aaaaattaaa ttaatttctt tttaagaaat    9180
agaacatgtg taacaaatgt ataaattaaa gtagatgcaa cttttttgtgt taatattctc    9240
tattttata taatttatat atttaaaata attatattat tcatatagta ctaaagatta    9300
aagtattata ttttgaataa aggcgaagtg ctacaaagca cttcgccata atatccagca    9360
tttttattaa ttaatacttg tgtatcaatg tagatgtgcg ctagtttctt caacttctcc    9420
tctagctgtt ttttcgtaca tttctagttg cttctcataa tatgatttat atcatattaa    9480
ggtgtgagac ctcagccagt ctgtgacatg acatttttt catattgggc ttcttttga    9540
ggggagtcaa attttccaac gtaatcgatt tcgtttttgg ttttgtgtat aacttctcca    9600
ctttcattcg ttcttatgtc atttattatt acgttattat ttgcattagg ttgagcaatt    9660
gtattatttt ttgaatttag attatcaccg ctgtcatttc attcaacagg ctcttctttt    9720
ttatctttat cattttgctt gttctttatt tttggtagtt ttatgagctt gagagtcttg    9780
tttttttatt gttcatatct ataacagtct tgtaactaaa tactaacgat acaataatta    9840
cacttattaa agcgactgta gataatatag gggaaaaata tttcttataa acctctctca    9900
atataaattta atcctatatt gcattaattt aaaaaaacata ccactgaaat tatattgtta    9960
aataaaaagg ttggggtaaa aataaagacg aagtgctaag gagcacttcg tcgagaggaa   10020
tatcattgaa aacctgttta attacttcat tatcaagttt gagtgttaca taaaactgtt   10080
ttttgtgatt gctgtctttt ctaatatcta tgcgatcaat cactgctaag tacagtgctt   10140
taagttgaga ttttttcatt ttctcaatat tatgaaagac gtatcgcaat attttaccaa   10200
ttttttttggc attatatgag ggtttatctt cattttgttg ttttttgagt tgattgattt   10260
gactcataat gtcattaagt tgcttatcat attttttgaat cgacggcctg attactgatg   10320
ttaagtccgg attatcctcg atggttttaa tcaagttatt tagtttgatt cttacttcat   10380
catattgttg ttgcttataa gcgatatcgt gatgaagtga cgcacaatca acttgatttt   10440
cttgattaac acgtgctaca acgcgttgaa tgactttatc acttttgact atttcgagta   10500
tttgcttcat cacataatct tcaatcacat cagctcttac actgtttgcc gaacatactt   10560
tggacccctt gttgcgaaaa ttactacatg aatagtaacg tatacgtttc ttggttccat   10620
ctttaagtgt attcgttgta ttgcttgctg ccataggtgc gccacattgg ggacagtgaa   10680
taatgcctgt aagcagattt gttcctttgc catggacttg gggtttttga ctgacttgtt   10740
ttttacgtat ttgtacttta ttccataaat cttgattaat aatgggggaa tgcttccctt   10800
cagctatcac tggtttatca ttaagcccctt tacgacgttt ttcactccaa tctttgtatt   10860
tcgcaaattg aattttgccg atatagaatg ggttagctaa tatatatgtg atagaactaa   10920
tactaaaagg tttacccttt ttagtgacat agcctttgtg attcaatgca ttggctattt   10980
```

```
tacgatagcc atgtcctttg gcataggact cgaatatata ttttacaata ttagcttcat   11040
gttggttaat cattagctcg tgtttactat ctggtatttt gtcataacct agtggtaaat   11100
tgccttgata atagccttct tgggcacgtc tcgtttgccc cataaataca ttctcgacaa   11160
tgttattacg ttcgaattct gagaaactcg caagtatttg taacatgagt ttaccagaag   11220
aagtattgac ttccatacgc tctgataaac tgaaaaattc gacattttgt ttatgcaaat   11280
cttcgacgat tttcagaaga tccgatgtat tacgagctaa tcggtttgtt ttgtagatca   11340
taacacaatc tatattgcct tcttttgcat ctttcaacat acgttggagc tcaggtctgt   11400
tcataaattt acctgaaata ccacgatcag cgtatatatc tttgacctca aaatgatgga   11460
agtcacagta ttctttgatt tgattgattt gtccatcgat actataacct tctgtgcttt   11520
gcatttctgt tgaaacacgt acatagatac cgacacgttt tgttttaagt tgttgcatta   11580
tgttacatcc tttcttcatt tatgcaatcg atgattgcat ggcttgattg acgatattga   11640
gtggttcatt tttgaaatag attcctataa gattttttatc tttcgtaatg tgaatggttt   11700
caatataggg gtacaatatg tttaacgtga aacgttttg aataatattt tgaatggtgt   11760
gttgtatttg atgcccatt atagatgtag tgcgttgcgg ttgttgacgt aatgattgcg   11820
tttgttctct gaacgtttct gcatcaatga tgccttgtgc caacttttct atcagttgtt   11880
cttgagtcaa tatgtgatgt ttttctatgt ttctttgtct tttgatgcgt ttgtcaatcg   11940 caccttaat ttttgtgtag atgcgttgat tttgataaaa gtctcggcac acttctaata   12000
ctttatcttc aagtgtttgt gcattgatgc ctttaaaatc acagacaaag cgtgaagcat   12060
tcatgttttt aggacagacg tagtaacgta atgtatgatt ctttttctcta atggtcatat   12120 ttgtaagtgt tgcattacaa catgggcatt tgattttttg tttgagttga ttatccgaag   12180
atgtctgttt ggtttgtttt tgcgatcgaa gtctctgcgc ttgctcatat atacttgtgg   12240
aaacaataga aggaaacata ttgtcgaatt gaccatattg attgttgaca cgaccacaat   12300
aattaggatt gatgataatg ttacgaactt gataggttg tcgattgata tacgtgttat   12360
cttcttctaa taactgtgca attttcttat aaccatgacc tttaatgtaa taattgaata   12420
cagcctttac cgttggtgac tcattttgat tgatgatgaa tgttccgttg tgataatcgt   12480
aaccaaaagg tgcatgtgtt gtaatcaatc gaccttgctt tgcttttct tgaagcccat   12540 ttctgacttg ttctccaatg ttatccgatt caagttcggc taaactgatg aagatattaa   12600
gcttgagtcg gtcgaaagct tgatccatat caaagtaacc atcatgtacg cttaagatat   12660
gaacatggta cgtttgacat aatttgatga gttttaatgc attttttcaga ttacgatgca   12720 acctattaag acgataacag cataatatgt cacattgtcc ttgttgaatt aattgtgtta   12780
cttgtcgata cccactacga ttatctttgc gtcctgattg tttgtcgcta taaaagttga   12840
tatgttgaat atgatgtttt tcggctattg cttcgatagc ttgtttctgt gctgcaagag   12900
attgttgttt catcgtactt tgacgtaaat agcctataac ttgttcata tcggctcctc   12960 ctttcacagt gataatatat atttatagat gaattgatat ataagcccaa catcaatgag   13020
atgttgggcg tccatattag tcattcgttt gattgatttc ttcaattacc aaatcggcta   13080
atatctcgat aagttcatcc atgtttttca ctccgttatt tgttctatct tcaatacgtc   13140
gattattcag tttgatgctt cacggttgta tgataaagac aatcagaaat cttcgtgaac   13200
tcctgaaggg cctatcccct cattagcgga tttaaaaagt tctttcgcag ctttgttatc   13260
atttgccggt gtccaatttt gaattaacga cttatcttta gttaatccca ggatagatgc   13320
```

```
aaactctaca tctaatttta gatggtaaaa tacaagtgat tgttttttac cgctattatc    13380
tttgacactt cttttagttg tttggcgtcc acggtcagct aatatgaaac ctttatctct    13440
taaggcgttg acaacattat taacatcttg aaattgatga ttgtttagca tctgtttaaa    13500
aacgtttgca atcatttta cttcgatatg gtcatctttt aatgagatta atccatagtt    13560
ctcaaacata ttttcaaag caccttcatc tgaaaactta cctctgtttt gtgctacaaa    13620
ttgaatgatg acatcgatag ctttatcagc taatgagcgt tcagagattg tatgaccatg    13680
ataatcaata aagtagtctc ttattttagc gatatcaata tctgtagcta aaacacgacc    13740 taatatttt gcagatgttg taatgactgc ataacgctta acatacgat tgcctgtgtt      13800 gcttttatca tctttcaatt tagcttcaaa ccaatctact tccttgtaaa accattgaat    13860
aacttcatct tcacgattta taagatattt agctactaac ggtaaaacat gaccatagtt    13920
tagtgctaca gcttttttaa tattgtcagc attggtcgca tttgtagtga attgttcatt    13980
aatctcgatg gttcttacac gtaatccatc gttttgagct gaatcattaa aaatactgtg    14040
ttctgacgtt gaaatgacag aagtaccccca attcttaggc gttttaactt ctccatgaac    14100
gtttgaacgt tgacgacctt gaccttcagt gatggagtac aataaccccg ttgtatctct    14160
aaaagttgct gatgagagtt catcaaatac aataggtata ccaaaattgt tactcaagta    14220
accttcaagt gcattacgtg tggcattcca atttctaaag agagtttcat tacctttggt    14280
agggttacca gcgactgata cagctaaaga agctgcagtt gacttaccgg ttgaggattg    14340
acctgtaaaa ctaaaaatga ttccggcaaa ttcggtttca tgtttgtgct tcaggaaact    14400
cgtcactaag gcagaaatac caaatacgac tgctaattct aaaagaagag aacctttaac    14460
ctcttttaga tacatgttaa accaattatc aaatgtacct ttaggagtta agtcataagc    14520
attatcacaa atggcgtcag atggagattt attatcaaat tctttagtag tatagatttc    14580
acttaacgat acaataggac caaacggtgt tccagtata cctaccccctt catataagta    14640 ggaaatgggt aattgattgc gcatttgttg caacgcataa cctaaatctt ttgtatattt    14700
ttcattaata ctaaatccat acttcattaa agatggcagt ttttgtgtcg ttaaaatatc    14760
actagattca acaatttctt tttgatcttc gtctgtgata attagttttt cagtattagt    14820
tttagggtca ataaacttat tttcgataac gataggacct gcgatttcaa cttcagtagg    14880
cattcctcct ttttcttttg ggggcgtgtc tttataccaa cctttttttg atttgtatcg    14940
tggtgaagga ttaaatgaaa ggttagtttg agccattagc aatcacctcc tttcgaaggg    15000
ttgctgttat ggtgtggatt aggacctgtt ttaagataaa ctaagtgacc gtgagtatcc    15060
ttaccgataa taataaatgg aacacgtggc gcatgtttta caaaatatgc gaaccaacgt    15120
ccaacatttt gttgtacagc ttttgaacat tgtacatttg cacgactgtt caagtcatga    15180
aatgtaaatt cttctccttc aggtaaattg aatgaaatac ctaatatttt cttttttaac    15240
tgctcgaatt tatctgattg attgaaatac atttaacttc ctcctactaa tgaactaaga    15300
taggaaaatt aaatatgcgc acaattaact ttcttaagtt catttagcc aagaagttat     15360 catttgaaag cttgtaaaaa tatgttagaa attccgtact aaattaagat ggattttgt      15420 tgacaaaata aaaacgctg atttaacagc gctttaaata aaaattaatc tgaagttata     15480
taaaagtagt cagaaggagt ggtgttatta tcattataat aatctagtgc tttattgatt    15540
tcttttatta atttatcatg atgttctttt gttattttct ttggatattt gagttctttt    15600
tcttctaagt cttttggaga cactaggtca ctatttaaaa ttaatgataa cagcatattt    15660
ttaggtgccg aagctctggt gtctcgatga gtaatatatt ttgctaaatt actgttttata   15720
```

```
cttactttt   cattttctaa   aaagtttgta   ctattttca    catgagcatc   agcaattttg   15780
gtacttattt  cagtgtttaa   atcgtctatt   tcatctaaat   aatattcaag   aatctgaagt   15840
ttatctttag  aagtgatacc   tttttcagtg   aaaatcttaa   taatgataga   tttgattcca   15900
atttctatat  tactgtctac   tagaaaatag   agataataat   tagtcagagc   atgttcataa   15960
tctctttgat  cagtaatttc   atgattgatg   aaataatata   agttctcttt   gatacgatta   16020
gaagaatcta  tatctttgtc   attgataccg   tttttaaaaa   agtgtagata   aactgagttg   16080
tttgagagta  tatcatataa   tacaaataaa   cttttggtt    taaatacata   tgatttcct    16140
gatttaaagt  ttgctatgtt   tattcctaga   gcgttgcaga   atttattaaa   attagttgta   16200
aaattatttt  tttcttgaat   aaacatgtcg   ttgtcattta   attctgaact   atgatttta    16260
atcatattga  tattttcttc   aatcttgtca   ctatttaaat   tttccatgca   aagtatacta   16320
tatcttacta  tatcacttat   atttatggaa   aaatctttag   gagaacgatt   taaagtatcc   16380
tttttattat  cttgatctac   agccctacat   gaatcatcaa   aaacttcttt   gacatttatt   16440
ttatcaatgt  tcaaaattat   gtctactaat   gcattttgaa   attttcatt    atatatgtct   16500
ctcttattca  taatatcact   accttatca    attataataa   tatattatat   cttaatattt   16560
gtagaagtac  ttgatgagag   gttagataaa   acaccacatt   tctctggtta   gtaaaaacat   16620
aacttctaag  acttttttc    atatactaat   aaattatatt   ataaatattt   ttgaaaataa   16680
aagtagtgta  taaaaatgta   tgcaaagaag   gtgttttagt   atagattta    aggcattcat   16740
ttttaatata  aaatatttat   aatattttat   attaaaaatg   attatccttt   caaaattttt   16800
gcaacgagta  attttacttt   agttatatta   taaagtagaa   ttaatagtaa   ttaaaggaac   16860
gtttgttcct  gttttatat    gtaaatacga   gaacgattga   atagataaag   aaggataaaa   16920
ttgacttcga  aatagaatat   ttaatttcaa   gaaggagagt   attggatgtt   aaagcataaa   16980
ataataaatt  taatacaaga   aaagagagaa   gggagttact   gggattttaa   agcagaatat   17040
cataaagata  aagcagaatt   attacatgat   ataatttgtt   tatcaaataa   cttgttgaat   17100
caagaagctt  atttaattt    aggagtcgca   gataacggtc   atattctggg   ggttgcaggt   17160
gattcaaatc  gaaaaaacca   agaagaatta   atatcattta   ttactggaaa   aaaatttgct   17220
gcgggtaggc  accccaagat   ttcattaatg   acatttgaat   atgaagaaaa   ggaaatcgat   17280
gtcattataa  taaatcctaa   aggatatgta   ccatactatc   tggagagagc   agaaaccgat   17340
caaaaaagta  aaaaaaacaa   aacagtcaat   gcaggtagca   tttatacaag   agttgaagat   17400
aaaaatacc   caatagattc   tactgcaagt   ccattagata   cagaaatatt   atggaaaatg   17460
cattttggtt  tatatcctac   tcctataaag   aggttacaga   attatttact   aactcctgag   17520
aaatggatgc  agaactcaac   aggttattt    catagtgaat   cgccagagta   tatagtatac   17580
aaaatgagg   acattgaaga   aaaagaaaat   tatttttaatt  tagtaagtcc   attttatgcg   17640
tataatcaaa  tcaatagtaa   cactttatac   tcatattacg   aatttaaata   tcatagtaca   17700
gttttatatg  gttgccggtg   tatctcttta   gattcaggta   tctacacaac   accagtacct   17760
gaactaggtg  agataaattt   taatatgcat   agagatgata   ctatttatta   tcgttatttc   17820
attgaagaga  cgatgcttta   taatattcat   cttttatgt    ataagggtga   ttcgatggaa   17880
gagaaatttg  caatggataa   attttagaa   tgtgttttgg   tttataaaag   tgatgtagaa   17940
aaggaacttt  ttgaaaatta   tatattagat   aattgggata   aagttaatca   gtcaattaat   18000
gaaaataata  aacgtgtatt   tggaactgaa   catttgtcac   aacttgaaaa   agaagatatc   18060
```

```
actaaaaaag taaaaacagt taaagttttta aaagatgaac ttgagaactt tagaacttga    18120
gaaaaattat tggttaatag gagaaaatca tgaaaaaatc aacactcatt gataaatttt    18180
tagacttact ttcttcaaga agctcactca gagaaattca gaataatttt attgatgcaa    18240
acattatgag agatagttct ataaatcaaa aatataacgg acaacgtaaa tcgttagcgt    18300
gggaatatat tagtacttta aatttagaag atgaagctga attttctaaa ttacttaatg    18360
ttatagaaac gtatttgttt caatggaatc tgtatatcca tgaagttgat gaagacgaag    18420
aaattaatag attaataaaa ataattaatg tattaggtta tgaatataat aaagatacag    18480
gaaaaataac taaaaatgaa agagaagtta atttaagtac tattaaatct ttggcaataa    18540
aatttgatat tgaatatgta ttaaaagaat gtaatagaat tgaaaaagag gcactaacgg    18600
atccagagga cgcaattaca tctgcaaaat cgatggttga gagtactttg aagcatattt    18660
tagattctga aggagaaaaa tttaataata atgaaaccctt gagaggttta tataaaaaag    18720
taagtaatat tatgaatctt tctcctggtg gacataatga aaatactttt aaaacaattt    18780
tgagtggaat gataaatgta attaacggtc tggacgaagt aaggaatgaa tatggtgacg    18840
cacatggtaa atcaaagaaa aattataggc ctgaaactag acatgctttt ctagcaatca    18900
acgcagcacg tacgataact gaatttcttt tagcttcata taaaaagtaa aagctatttg    18960
atgaatagca atcaaatata ttggttataa aaaccgcat catcaactga taagcagaag    19020
catatcataa gtgatgcggt ttttattaat tagttgctaa aaaatgaagt atgcaatatt    19080
aattattatt aaattttgat atatttaaag aaagattaag tttagggtga atgaatggct    19140
tatcaaagtg aatatgcatt agaaaatgaa gtacttcaac aacttgagga attgaactat    19200
gaaagagtaa atatacataa tattaaatta gaaattaatg aatatctcaa agaactagga    19260
gtgttgaaaa atgaataagc agacaaatac tccagaacta agatttccag agtttgatga    19320
ggaatggaaa aaaaggaaat taggtgaagt agtaaattat aaaaatggtg gttcatttga    19380
aagtttagtg aaaaaccatg gtgtatataa actcataact cttaaatctg ttaatacaga    19440
aggaaagttg tgtaattctg gaaaatatat cgatgataaa tgtgttgaaa cattgtgtaa    19500
tgatacttta gtaatgatac tgagcgagca agcaccagga ctagttggaa tgactgcaat    19560
tatacctaat aataatgagt atgtactaaa tcaacgagta gcagcactag tgcctaaaca    19620
atttatagat agtcaatttc tatctaagtt aattaataga aaccagaaat atttcagtgt    19680
gagatctgct ggaacaaaag tgaaaaatat ttctaaagga catgtagaaa actttaatttt    19740
tttatctcct aattacactg aacaacaaaa aataggtaat ttcttcagca aactcgaccg    19800
ccagattgag ttagaagaag agaaacttga actcttagag caacaaaagc gtggatatat    19860
tcagaagatt ttttctcaag atttaagatt taaagatgaa aatggaaaca gttatcctga    19920
ttggtctatt aaaaagattg aagatatttc taaagttaat aaagggttta ctccaaatac    19980
aaaaaatgat aaatactggg atgaattaaa tgaaaattgg ttatctatag caggtatgac    20040
acagaaatat ttgtataaag gaaataaagg aattactgaa aaaggtgcat caaagcatgt    20100
aaaagtagat aaagatactc taataatgag ttttaaattg actttaggta agttagctat    20160
agtaaaagag cctatctata caaatgaagc tatatgccat ttcgtatgga agaaagtaa     20220
tgttaatact gagtatatgt actactattt aaattctata aatataagta cttttggtgc    20280
acaggcagtt aaaggagtaa cattaaataa cgatgcaatt aatagtatta tagtaaagtt    20340
accagtgata caagaacaaa ataaaatagc atactttttc aataaattag ataaattaat    20400
tgaaaaacaa tcttctaaag tagaattatt aaaacaacgc aaacaaggat ttttacagaa    20460
```

```
aatgtttgtt taattcttat aaagttctat tatgtaaaat attaaataga gataacatta    20520
tgaaagcgag cccaagacat aaagtttttg aataaataaa aagataatt  tctatcaaat    20580
taatatagaa attgtctttt ttataaattt tttgattatt tttagctgat tgagctgtta    20640
cttttcttat aataagtgct attagcacaa atcctagttc tcttttggct ttgtttattc    20700
ctcttacgga cattcgagtg aaacccattt taattttatt agaagtaatt taggtttgaa    20760
cccacctaaa taaatatatg agttatttt  ttatgctaca aaatatattc agatttcaat    20820
aatgacataa aataggcatc tttatattta cctttagtgt agaattgctc tttgagtaat    20880
ccttctgttt taaatccttg tgactcgtat atatgcacag cttttttgtt atctgtatca    20940
acatatagat aaattttgtg catgtttaat atatcgaatg cataatttat cgcttttcg     21000
aatgcgaatt ttgcataacc tttaccactg aactcaggtt taataattat ttgtatttca    21060
caattacgat ggatgtaatt aatttctact aattcaacaa tacctacgac ttgattttca    21120
tcttcaacaa taaaacgtct ctctgattca tctaataaat gcttatcaaa taaatattga    21180
agttccgtta aggattcata tggttcttca aaccaataag acataataga atattcatta    21240
tttaattcat gaacaaaaag taatcacta  tactctaatg ctcttagttt cataattcca    21300
ctcccaaaat tttctcatat atttgcatta taaatataaa taacgaataa gtcatcattc    21360
actgtgaata ctctatttta acaattcacc acatactaat tctcattttc ttgttattct    21420
cgatttatta ctcttactat gaaacctata aaattctcac atttgtttgt attaagaata    21480
aatacgtcga tagtaacaat aaaaaaataa ataataaagc atccctcacc gtaaaagtga    21540
aggatgctct agttttattg aaatatacat ttcatttgt  taaataatta ttaataatat    21600
tttgaaaatc attattacgt gaaatcttca tagatttat  caagtatttc tttgccttca    21660
attgctgtga agtgatgtac caatctattt ttacaatcat atgtaatttt gtgacgctag    21720
gtaattagta attgttcgtc agtctgattg tatagtatca agtttcatag ataatactct    21780
ttgattttaa tgtccacttt gacgtgcttt aagattgagt atatacataa tgtcattgtg    21840
gaatgttaaa aatcctacaa atgtttattc atctgcagga tttttaaatc tccaagaata    21900
aaaatcatca taggacaact ggattattgt ttggataaat aacgtaaaca ataattaggt    21960
actattattt attttgttt  attctttttc ctaacaaaat aaagaaaaga ataaacgcaa    22020
ttgttaaaaa tatgtgtcct aaaccagcaa taccagcaat agcaggactt acacttagat    22080
ctttaatggt agaaatac cg ttcacgaatt gcattgccac agtaacaagc acacctaaat    22140
ggtatatata aagaaactg  ttaaacagct ttgtatgagt tgttaatttg aattggccct    22200
cgataatcat gaaaattaag aacataattg tacctagtac taataaatgt gtatgtgtaa    22260
catttaattg agaaaaaccg ctaaaatctt ccgcttttgt catttctcta taaaatagac    22320
cacttaataa ccctaatagt gtatagagcg ctgaactata cattaatctt ttcattttaa    22380
ttccccctat ttttaattac gagataagta tagcggtagt ttatgaactg agtatgaact    22440
tacaacaaaa aaattaatga agtactttac aataaactca atttattaga tggtggaggg    22500
acgaaaaagg atttagaaa  aataaattaa tatattttta ttttgataag taataattaa    22560
taatatcttg gaaatcattg ttaagtattg ttgtaataca atcgtcattc ataaaatctt    22620
catagatttt atcaagaatt tcttcatctt cgatagatgt gaaatgatta gctaacccct    22680
ttataattta agtgtaattt gtgaatctaa acaactagca actgttcgcc aatctgattg    22740
tgtagtgtca tggttcatag ataatcctcc ctttattta  atgtccattt ttgacgtgct    22800
```

```
ttagggttaa gtggatgcat aacttcgttc gttactggat taatgagttt tttgactttc    22860
tttttatgag gttttaacat ttccatcact tgctcaacac gttcgacgac aacaggccgc    22920
ttcgcataag ctccataggc tagaatcact gtgtcacttt cactaatcgc tttcattaag    22980
tgaatgtctg tgtgtttgtc ataaggctct ttcctacgat tagtcaagta cttataatta    23040
aaataagcat tacttaacta aaccgttcat tttaattttt ttgaataagg tgttaaacta    23100
tatttaattg tacgtttggc taatgtggtg acatttgata atcgtacaat ttatgattca    23160
ttacaagata atgaattgtt tttaataatc gatttataca agcaatgatg gcagtcttat    23220
gaggtttctc attaggctgc tttcttagtt tgtagtaata atcgacgaca tgattgtcat    23280
aatgatgctg ccctcttatt atattcataa tcacccaaaa taaaagtttt ctcgcttttt    23340
tattaccacg cttgttgatg gtatctctac agtgtgtatg acctgattga tatcgtttga    23400
tatcaatgcc aacaaaagca ttgagttgtt tatttgattt aaatcgctta atatcaccaa    23460
tctccccaat aatcatagct gtgcttagct taccaatacc aggtatcgaa tgaatatttt    23520
caaaataatc gagttgttgt gctaattgaa tcatggcatc atctaattgt ttgagatgat    23580
gaatagattg ttttaattgt tgaataagta agcgtaattt ttcgactaga aaggaatgtc    23640
tatcgacatt aggatagctt tcttgagcaa tcactcttaa ttgaagtgca tattttgtag    23700
ctttatccat tgacattccc ttatctgtag aattgaatat atgtgtaatc agtacatcct    23760
tgtcgatatc aagaaccatg tctggatgag taaagatttc tgcgatgttg agtgcaatga    23820
ttgaatatcg actactaaat aatctttcta aaccagggaa tgtttgatgg agtaattcaa    23880
ggatctgaaa tttaagtcga ttttgttcat tctcgatttc tagatgaaaa cggacgcgtt    23940
ctcttaattc aaagaatatt aactcatgta taggtaagct gtctgtttgt ttaagcgtcg    24000
gtcctaaaca agcaagctta tgagcatctg cctgatcagt tttccatgat cttagagcgc    24060
tcgtttaaaa tttggcttct aacggattca tttgaatata gttaatttga tttacacaac    24120
aaaatcgttc catacctctt gaatagatac ctgtagattc aaaaatgagt tgtgggtggt    24180
ctaagtcatt caaatacttg agtaaataat tgtaaccatt tttattattc tggatgaaaa    24240 actcttttg gaattttcca ttttataat gtgcaactac actacttctt ttactaatat    24300
caacacctaa gtaatcgata aaaaaacctc ctttgaataa ttgagaagct aaaaacttta    24360
cttaaccttt ctcatttcat tttcctatac acggtttcaa gaacccaaca tactacaaac    24420
gaatttcaaa aggcgagagt aaagctgact tgttttttat acggatttaa aatccaagag    24480
tctggacagt ctacttctct ctataactat aaaaaatagc tatgaaaaaa tctatcgtca    24540
tagatttctt catagctaat cttagtatgt ttaatatgtt taaggttttc aggtgtttta    24600
atattagaga atagatttac tagatataca gcaccgtatt gttcagaatt agctaattgg    24660
ttgagaatga gaacagtggt aagatcgagt gataatacgc catctaaatg tggatacatc    24720
gttatcactg tacaagaggg tttctttca tcccatattt tcttgagtaa gtagcggtgt    24780
tgttcatcgt cgctaaatat agcttctgtg tgtatcgtac ttttgattgt attcatatat    24840
cgttacccct tttaatattc ttctggtaaa agcatcacat aataaaaagc gtctacgcca    24900
tcttcacgaa tgacgtagac tttccttaggt aatgcatttt gattttttac atagtttgta    24960
tagtgatatt ccaatttgta tgcaggttgt tcttgttcat gtgtgattga gagtatattc    25020
tcatcttctt gcagtttaaa aatgtgtagg taatctgtat gaggttgatt gtcccgttct    25080
tttaccatgt tccaaagtaa gatttgaagg tctagagata ggtgttcact aatgcctctt    25140
gtgatatatc gattgatgtt catactattt tcctccattt tgcttttctt tcataatgtc    25200
```

```
aatcacttcg ttaatgactg taacagatat ttgtgccact ttgatccaat tattcatggt    25260
gattccctcc ttgttttagt aaatgacgtt catcgataag cgtgttttta gtgtctgtga    25320
ggtagagaaa gtccatatca aaatgatcca ataaccaat gctgatgagt tggtcattgg     25380
cgtacataag aaatggatag atacttagct catgtagctc atcattgtag taggtataag    25440
tgttgagtgt gagatgcgca agtagagaat tattaataaa acgttccggt agaatatttt    25500
ctgctgcttc ctcaagtgct tcacattccc atgtttcgtt gttagatagt tggaagagac    25560
gagttatata ttgtttgagt tcttgagtgg ttgttttcat atcattgcct cctagatagt    25620
gtgatagtga tgtagttgat atacatcatt gggataatat atatttgatt tattatttat    25680
tacgaatccc ggtgggaata agagaaaatt ccatataaaa acccgtgata aatgttggtg    25740
taacaaggaa atcccggaat cccactcatt ttgacgaaca atcaactcat tatttataag    25800
tattgatgat agggttgtgt ctctgcttcc ttatatatat tatttattta taaaaaataa    25860
cgggattttg ggattgtgct tgcacaatcc ttctgcttct tcgaatctgc aaatcccatt    25920
cctttcccgg taaaaaatca ttgtgggatg ttctttagca atttcaatat aagcattgtg    25980
tagtcatgaa aaaatgacg gcaatgactg tttcattaga taagtgttat tgaaattgat     26040
aaagagaatt ctaaaaatgg ttagataaaa taagtgaaag aatagcagtg tagttattgt    26100
ttattcaata gttatatata aagtttgtgg caaaaataaa gacgaagtgc tagggagcac    26160 tcgtcgagt ggatggttat taaatagttg tttgattata tcattattta acttgagcgt     26220
aacataaaat tgcttcttat gatgctcatc ttttcttatg tcaatgcgat cgatgattgt    26280
tagatatagt gatttcaact gagatttctc taatttgtct atatctttga atattgcttg    26340
tagtacattc gcaatcatat cagcatcata atgtggagct tctgcttgtt tatcttgttc    26400
tagttgatag atttgattat ttatttgatt caattcatct tggtagctaa gtattgttgg    26460
ttttaatacg ctatctaagt caggtgagtc ttcaatagtt ttcgttaatg tatgcatttt    26520
tgcttttatt tcttcacatt gtgactgttt ataggcaata tcatggttca agaagagac    26580 gtctatttga cttttttcat ttaccttttc aaccaattgc ttcaatacct ttttgctttt    26640 gataaatttcc aatatctgat ccataacata tttttctagt acatctgctc taacgctatt    26700
ggcagaacaa acttttgaac ctttatttct aaaattgcta catgagtaat atctgattct    26760
tttcttagtg ccatctttta atgtattagt tgtattactt gcctccattg ctgcaccaca    26820
tttcggacat tttacaatcc cagtcagtag gtttgttcct ttgccgtgaa cttgtggttt    26880
cttgcgactc tcttgacgtt taaactgtac tttatcccat aggttctat caataatagg     26940 cgcatgttta ccatcagcga taatcggttc ctcattgagt cctttttcgtc ttttatcgct   27000 ccagtgtcta tacttcgcaa actgtatctt tccaatgtaa aaagggtttg agatgatgta    27060
ggtaatggac gaaatactaa aaggttccc tttcttagtc acataacctt tatgattcaa     27120
tgcgttcgca atcttacgat aaccatgacc tttagcgtat gaatcaaaaa tatatttaac    27180
aatattcgct tcatgttgat tgatcatgag ctctttttta ctgtcaggta ctttatcgta    27240
gcctagaggt aaattacctt gataataacc ttcaatagca cgttgtcttt ggccattgta    27300
gacattctct acaatcgtat tacgttcaaa ttctgcgaag ctggctaaaa tttggagcat    27360
caatttacct gttgaactgg caatttctat tttttcagtt agactaaaaa attcgacatt    27420
aatcttatac aattcctcga caatatttaa caaatctgag gtatttctag ctaaacgatt    27480
tgttttgtag accataatac aatctaattt accttcgttg gcatctttta acatacgttg    27540
```

```
taattctgga cgttgcattg ttttacctga tataccacga tcggtgtatt cattgacgac   27600
ttcatagcct tgaaattgac aatactctgt aagttgattc aattgacctt gaatactgta   27660
accatccgtt tgcatttcag tcgatacacg tgcatataat ccaatacgtt tctttttgag   27720
ttgtttcata ttacttcatt cctttcagga gttattaaat gtgattgttc aacgatattg   27780
agtggactgt ttttaaagta gattccttgt aattgtttag tttgagttat tttgatgcaa   27840
tcgataaaag gtgctatatc ctgtaaagtt attttatttt ttatgacata ttttaatttg   27900
tcatcgattt ggtaggttga ataagtagag taattctctt cacttttaca actagcagat   27960
aaacgtttga acgttttttac atcaatacga ttttgagcta gcttttcgat aagttgttct   28020
tgtgttagat gggtttcttt atgcttcatt tgttgctgtt ttaggacttt gagtattgtg   28080
ttattcaatc gttatgaaa cgattgttct tcaaaatact ttttacaagt gtcgagcact   28140
tcactttcaa gttctggtgc attgatactt ttaaatgggc atgtacgata agcgtcattc   28200
atatttttag gacaaacata gtaacgtaga gaatagttct cttttttttat cgttaagttt   28260 gttaatgttg attgacagta aggacatttg attcgtcgct ttagcttatt tctagaattg   28320
gatcgattga gttgtttatg aatacgacgc tcttgtgctt cttcaaatgt atcaatatca   28380
ataataggtg gaacgatatc attaaacgtg ccatatttat tgatgacacg accgcaatag   28440
ttagggttca agagaatatt tctaacttga tagggcttac gaggaataag gttaggatta   28500
ctatccaaat gttgggaaat ctttttgtag cctagacctt gtaagtacca gcgataaacc   28560
gatttaactg tatacgcttc ttcttcttgt acaacaaaac aaccttttct ataacgatag   28620
ccaaacggag catgagttgt gattagctta ccttgtttgg cttttctct aatcccattt    28680 tttgtttgtt cgctgatatt gtttgattcc atttccgcta gactcataag tatgttcaaa   28740
cgaaagcaat caaactcttt agacaaatca aaatatccat cgttaacact gatgattgtg   28800
atgtgatgct ttttacaaat ttcaaagaat tgtatggcat ttttcaaatt acgatgtagt   28860
cggttcaagc gatagcaaca caatacttta cattttccag acgtaattat ttctaccatt   28920
ttttgataac ctgaacgttt tgtatgtcga cctgttttct tatcatcata aaacgccaca   28980
ttagaccatc catattgctt agcggtatcc ataatgagcg attttttgagt agctaagctt   29040 tgttgtttga gtgtactttg acgtacataa gcaatcgctt cttccatgtt atacacctcc   29100
aaaaagataa tatatatttg tgagtaaatt agaatgaaag gtccaacgtg cttttaacac   29160
gttggaccgt cgtgattagt tatcgttctg tagctcttca acgactaaat cagctagtaa   29220
ttcaatcaat tcatccatttt tatctactcc tgtacgattt catctttaag ttattaaaaa   29280
tcaattaaat catcgttctg ttttttccat gattcaagta tcttttttgtt atccaagtta   29340 atttcagctt taataggttc agcatcttta gttagaccaa aaatagacgc atattttgaa   29400
tctagcttta aatggtaaaa gacaagtgac tgtttcttgc catagtcatc tttaactgct   29460
cttttcgtag ttattcgatc acggtcagat tcgataaatc ctttatccct tagtgcattc   29520
acaacattgt tgacatcttg gaaatgatgc tctatcaaca tattcttaaa tacagatgca   29580
atgattttaa cttcgatata atcatctttt aaggcaatta gtccatagtt ctcaatcata   29640
ttctttaatg ctgtatcatc agaaaactta ccacggtttt gtgctacaaa ttgcgtaatg   29700
acttcaatcg ctttatcagc cagtgatcgt tcagagactg tatgagcatg ataatcaata   29760
aagtagtctc ttattttagc gatatcaata tctgtagata aaacatgact aagaatcttg   29820
gccgaagtag tgatagccgc atagcgctta acatacgaa taccagtatt attgtttca    29880 tccttcaatt tatctttaaa ccaatgatgt aattcaaaaa cggatcaaaa aacaaaggc    29940
```

```
cctagaaact aggagcacac ttacacaaga acaattgata gataaattag ctaaaggagc    30000
catcgatgca gaaacgttca gaaaacaatc tcaatcgtta cttcaacaat caaaaccaac    30060
actatcaata aatgagcaac aaattcaaag gtcttttgaa aatgtaattc aacaacactt    30120
cacgttaagc atgttatacc gatatattga tgaaattcat atttctaaaa acaaaagcct    30180
tgtgggaatc tatttcaaaa atgaaccgct aaacattgta aaccaagcta cgcaatcatc    30240
gattgcttaa ttaatgaaag gatgaaaaat atgaaagaaa tgaaaagaaa atctgtagga    30300
tgttatgtta gagtttcaac aatttctcaa gacattgata aatttagtat taatggtcaa    30360
attacacaaa taaggaata ttgccaacag ggaaattatg aattgctata ctgataatta    30420
aaagtacccc cgatcgaacg aaaatatctt tttgatgact attagtgata attgtaattt    30480
tatccattaa tagatgaatg gattggaata atactaagcc tattgctatt ccaccgagta    30540
aaattaccca cccgcctaat tcaatacttt ccggaatcat ttcaaaaaat aataagccaa    30600
ttataaggcc tgcacataat gaataaataa agccatgacc actttgaaaa ccttccatta    30660
tccaagcgag tccaccgcca acaccaattc caagtgcgga agctaacgcc cgatcatcca    30720
tactgcactc atcccactat tcttaaaaag gctttgttta ttttactcta aaaaatcaaa    30780
acaaaatata tgaattcata ttaaatatta tttgactctt tattcagatg gttatatcat    30840
atatatgaac atatattaat atatgtagat aaatagtgat tattatatat aaggttttga    30900
attgaaacct aaagtgaggg aaggataatg gaagaaaaaa aggaattaga ggaagtaaat    30960
aataaggact tagatgatga acattatttt gtcgtatcgc aaacatttaa agcgttaggt    31020
gatcctacga gaatccggat tctccatttg ctcttttata aggagtattc ggtaaacggt    31080
attgctgaaa cgctacatct tagacaatca acagtttccc atcaattgcg gttcttgaaa    31140
aatttacggt tagtaaaatt ccgaagggaa ggcacaacat tgttttattc ccatgatgat    31200
gaacatacta tgaatatgct aaaacaggcg atcgatcacg cctgtcatca ctagtattcc    31260
gtaaaccagt aatgagtgtt aataataatt cacgtcatta atattgttat atgatcatat    31320
aaaaatatta taggcatatg aaaaggggt tttgcaatgg atatggaaaa caaaaaaaca    31380
gaatggaaag cgttgtatga tatctcgaag gaaagtgaga tgggtgtagc agagagggtt    31440
agtgaatacg gttgataaat tcataggatg tattattgga tacaaaaagt ttggatgtgg    31500
tcaattaacg tcctggttta gtaaagctta ctgcgaatat attggaaccc gatatatcat    31560
atttatttag aaaggtgata gaaatgaaaa atattcaaga gcaacaagca cacgaaagtc    31620
atagccacga tcatagtcat gatcatgatc acggaaaaat gccaattatt tcatatttta    31680
ttggcttagt gttggctata attgggcttt ttttaagtga tgcaaattta ttaatacaaa    31740
acatcttatt ttcaattgcc acaatcacag ccggctacca tgtaattatt ctcgaaggaa    31800
ttggagagac agttgaaaat actaaattaa agggaaaatt cactcctaat tctcatattc    31860
taatgggatt agctgcaatc ggggcttctc tgatagggag ttttttgggaa ggaaccettt    31920 tgatacttat ttttttccggc gctcattttc ttgaagatta cgctgaagga aaaagtaaaa    31980
gagaaattac taagctactc gaaatgaacc caacgacagc taaattaatc ttacctgatg    32040
gaaacacaaa aattgttgat gtcagtgaat taaaagttgg agatcaactc caagtgctga    32100
acggtgatca agttccaatt gatgggataa ttttatccgg tactacctca attgatgaat    32160
cttctattaa tggagaaagt ataccgaaag agaagtctaa gggtgacgaa gttttttgaa    32220
gtacgattaa tggaacaggt acttttacta tggaagtcac taaggaaaac aaggatactg    32280
```

```
tattctctaa aattttacaa ttagttagtc aaaaccaaga taatcaaaca aaagctgcca    32340
gtatcattca aaaattcgag cctaaatatg ttaatatagt tttaatcgca ataccattag    32400
taatgttact tgctccttttt ctatttgatt ggacatggtc gcaaagtgtt tacaggggat    32460
tagtgctttt agtcgcagct tcaccgtgtg ctttggcagc agctactgta tctgtaacat    32520
tgtctacaac atctaaccta gctaaaaaag gcgtgctttc aaaaggaagt acttacctat    32580
cacaattagc ggatatagat gcaattgcct tcgataaaac aggaacccct acgaacggag    32640
aacctaaagt aacaaattac tatttcactc attctgtgaa cgaagaaaat attattgata    32700
ttatagtcgc ccttgaaaag gaatccaatc acccactcgc taatgctatt ttagaaaaat    32760
ttgaagttaa aaataaaata gacatcgaag ttactaatca aattggaaaa ggtctgacag    32820
gagattataa tggaaaaaat tatcgtattg gtaagcctac ttcttttgaa agtgcttctg    32880
aagagtatac ccagttcaat catgattggg catcagaagg aaagacggtt gtatacgtag    32940
cagaaaatga agaagttatt gggattatag ctctaatgga tattccgaat gagcatgcta    33000
aagaaacaat taattacttt aagaaacttg gtatccacac gactttaatt actggtgatt    33060
cggaaatgac gggaaaagct gtaggcgaac aattgggaat agacgaagtt atcgctaatg    33120
taatgcctga agataaatcc agaattatag aagaacaaaa agaaaaattt ggagttactg    33180
ccatggttgg agatggtgtg aacgatgcac cggcccttgt taatgctgat gttggtatag    33240
ctatgggggg cggtactgat gtggcagtag aagtatctga tttggtttta atgcagaaca    33300
atttatctaa attagtacag tctcataaaa tttcctcaaa tatgggtcgt gttattaggc    33360
aaaatattat tttttcaatg gcagttgttg cctttttagt tgtcgttagt ttgttaggat    33420
taactgatat tacaatcagt gtaattgttc atgaaggaag tactttagtt gttatactaa    33480
atggacttcg attattaaga tctaaataat gaacgaatcg attgacatga atgaactttg    33540
aagtgtggat tctacaatgt tcccataaca ttggacacta aaaaacagag caatctaata    33600
aagatgttat gagtaaaaac aatgccttgc ataccgttt tatcatacgg gcggtcaaat    33660
aagcaattaa agagcatggg aagcataaaa tcataaacag tgacttaagg cagccagttt    33720
acattcaaaa gttaaattga ctgtattaaa agtttcgaaa cgattaatat ccgtatgggg    33780
gcaagcgtcg agccaaagat aatgccagga cagagcgtct ttttccgttc ttttaagtgg    33840
gaaaggtttt accttctcta tgccaagaca gtcccagagc taaagggcc agttgctctt    33900 tttgggcgtt tgtgaacggt aatcgcagga aggggatttt cccaaccgca cctggttttc    33960
catcacaata aagttggcgg catttgttct gatattcttg ggaatactta cactatgaat    34020
ggccgtatta agtgatacag gagctgctat tattgtaata ctgaatgctc tccgcctttt    34080
gagggtaaaa gaataaaagt aaggataact aggtaaagct gttcaatcaa aaattgaaca    34140 gcttatttt catcaaaatc aaaaacgttt attataatac ctacacttgt tctgttaaat    34200
gtaccgattt tttaacctta ttgtatcagt aatatcttga aacgaagtaa gcgactaaaa    34260
tttctctttt atcatacgtt tataaaaata cacttttaag aacggtttga aaattttga    34320 aatagatcaa aataatcttc tggttaaaaa acctgtagat atgatttctc tcttaaattt    34380
ttgtttgatt agattagacc ctaataagac gcattcaata tgtctacacg tgaatttagt    34440
ctttgaaaat gtaaggacca ttattattat aaaaaccccca gtataaaacg atacgctgaa    34500
gcgtaccaca aataaaacta aaaaaatgaa tattataatg atatattaac aattaaaagt    34560
ttgaactttt ttggcaatga tgttaaggca aaaatgtatt gaagaaagtt aagagtttgg    34620
gacataaagt tctaggataa gtgaaaaaag acaatttcta ttgaagtaat ataaaaattg    34680
```

-continued

```
tcttttttat aattttttg  attattttca  gatcgttgag  ctgttacatt  tcttatatta    34740
agtgccatca  gcacaaattc  tagttctctt  ttgtcttttt  tattcctcga  acggacattc    34800
gagtgaaatc  caaaatggcc  ttaataaatc  caaaaaacag  gctccacatc  aacttttttt    34860
gactgtagat  ggttttgtt  tttgatttga  agtttatact  ttatacattg  gtgtttcaga    34920
ggacattctg  aacaatcatc  acattcatat  aatttaaagt  ctcgtttaaa  aactatattt    34980
atcatgacta  taggcatatc  ttttaaatcc  tagtcttta   ttattcggac  aagtgaattc    35040
atcgttaatt  tcgtcataat  ccccattttg  agtattaaga  aatgtcactt  ttatatttt    35100 tagttttatc  ttttataaac  atttcataag  ttatgagtgg  cattcgatta  aaatgataga    35160
atgctttaga  gtctttattc  atccttgact  caggttttga  atactatttt  tccatacaaa    35220
tgtatatcga  ttggcatttg  cctcaacttt  cgtatcatca  ataaaaatgg  cttgatcatc    35280
tctaagattt  tacttcaaac  actgaatatg  aaattgaata  aataacgttt  ctaataaagc    35340
atcactttgg  gatttactct  aaatcgatta  atcgttttat  aagaatgctt  tagattttgt    35400
gacagccaca  ccattcggat  tctatcattg  agcaatttt   ctatcttacg  tcctgaaaac    35460
acagattgtg  tgtaggtata  tagaactact  tttaacatca  tttttggata  gtatgatgtt    35520
gcaccatgat  aatgtctgaa  ttcatcgaat  tcagtctcgg  gaattgtttc  tacaatatca    35580
tttggggtga  gtattatttg  atgaaagctg  aagataaaag  ttagaataaa  attactaaat    35640
atagatttga  catctttata  aattaagaat  ttgtcaaaat  aaagggaggc  attctataga    35700
taatggtgaa  tgatgatttt  acgaatgagt  tatatcaact  tatagttcct  atggatgata    35760
aaataaaaga  aaacattgat  gaagtattat  ctttctacaa  tattaatttc  aaaaaatatt    35820
tatttagtat  ctcttcgtta  gtaacctttg  aaaagtgtaa  taaattacga  ggaagaattg    35880
ctaaatatcc  tattttaca   attttatatg  aaaaagtaga  atatgatgaa  aaagggatta    35940
agattataat  taatagtaaa  attcttaatg  acatacaaac  gcatgtgagt  catattccta    36000
atactactga  aatttatttg  gttaactttta ataacctaaa  catttctgaa  aaaacaaaga    36060
aagaattggt  taaagaatta  aataaaatgt  ttaacgacca  gaaaaaaaga  aagttagccc    36120
atcaagttgt  aaatattata  gagataataa  aattggatag  tcatggtaag  tctctaattg    36180
atatcggcta  tttctatta   ggtgctaaaa  atagtgcttt  aaagtttcaa  aaaatacata    36240
ttcaagaaaa  aatggactat  cggggaaagt  aatttcaaat  cgatttgaat  tattaagaga    36300
tatctatgat  atagacatga  atcaatttca  accctatttt  gataagaaag  atagtaaaac    36360
aaaaagatca  aattatgaat  ttgatatgga  gcaattcgaa  tctataagta  cattagtaga    36420
tttgttagag  aattacccac  ttcctaaaag  tgaaaataat  attaaacatt  tagaaagtat    36480
taagaaaaat  atatttagtg  ataacgcaga  tgaatacgaa  aagtatttta  atgaaggtat    36540
agataaactt  aaagaaggtg  catttgaatt  acaaaagcaa  ttatataacc  agtatccatt    36600
tcaattactt  atgcgatttc  agtatgaatt  aactgaatta  attaagcata  ttagtatgta    36660
ttttaaacaa  gtaaatcagt  caaatatata  tgaagctacg  actttatacg  aaaaattaaa    36720 caatttatt   ttaagaagtc  tacttgagaa  taactcagaa  aaagttaatt  ttaaaaactt    36780
tttgaatgga  gtaaaatttg  aagaatcaac  aatcaatgca  gatgaggaaa  taattgttaa    36840
aaaatacaat  gattttgtag  ataatattga  gtttaataaa  gatgattttg  ataaactata    36900
tgatcaatat  gaggtgttta  atagtataac  taaattagtt  acattaaatg  aagatgaaat    36960
aaaatgggat  catatatttg  tatataaata  taaattaaaa  accccttca   ttgataaaat    37020
```

```
aatcattgat aacttgaaaa acattaaaag tcaatatatt gatagtaaaa ctatgttgga  37080
aagagaatac aataaaaatg gtaatttat ttttgatttt ttaaatttag caaaatgtaa    37140
agatgagaat gaattagatg aggaaataga tgagttactc ttcaatcttg ataatatagg   37200
taacagatta ctaaagaaag ttgtattagg tcactctaaa aatataaaat attcaaacgc   37260
actattaaaa gaaattcgga gaatgataaa ggttttaaat ttatattctt cacaaaaaaa   37320
tcaatccaac atggttgtca cttaccatca attgcaaaag agcgataatg aatttgataa   37380
tagaattaat ttacttacaa aggaattagt ttatctaaga gtaaagaaag aacttttaa    37440 taacagtaaa tatactcata atgatgatag atagacattt aatttgaata atgaataagt   37500
ttaagctaac tcaattgagt tagcttttt ggcttccccc tctttaatga attttgggga    37560
agctaacgat tagttctaaa aatgttgata aagtatatct tgtaacgtta ctaataaaga   37620
tttcccgggc aatcaaactt gggggtgagt ttaaaaatgg aaagcaaagt agttgtaaaa   37680
gtagaacatg ataacgataa attacgagtt gagctaaacg tttcgaaaag agatgacttt   37740
aactatcaaa tgcactttgc aataagtgaa cgtgcatatg cattactaac tgtaatgatt   37800
ggtagagcgt taatgttacc aagagggaca gtattctcat gctatgaaag gttctgttgc   37860
aaagttgaat ttatagtata atttaacaa aaaggagtct tctgtatgaa ctatttcaga    37920
tataaacaat ttaacaagga tgttatcact gtagccgttg gctactatct aagatatgca   37980
ttgagttatc atgatatatc tgaaatatta agggaacgtg gtgtaaacgt tcatcattca   38040
acggtctacc gttgggttca agaatatgcc ccaattttat atcgaatttg gaagaaaaag   38100
cataaaaaag cttattacaa atggcgtatt gatgagacgt acatcaaaat aaaaggaaaa   38160
tggagctatt tatatcgtgc cattgatgca gagggacata cattagatat ttggttgcgt   38220
aagcaacgag ataatcattc agcatatgcg tttatcaaac gtctcattaa acaatttggt   38280
aaacctcaaa aggtaattac agatcaggca ccttcaacga aggtagcaat ggctaaagta   38340
attaaagctt ttaaacttaa acctgactgt cattgtacat cgaaatatct gaataacctc   38400
attgagcaag atcaccgtca tattaaagta agaaagacaa ggtatcaaag tatcaataca   38460
gcaaagaata cttaaaaagg tattgaatgt atttacgctc tatataaaaa gaaccgcagg   38520
tctcttcaga tctacggatt ttcgccatgc cacgaaatta gcatcatgct agcaagttaa   38580
gcgaacactg acatgataaa ttagtggtta gctatatttt ttactttgca acagaacctc   38640
caatatcatt aaagcaacac cagaaactat gaaaacatca gcgagattaa agataggata   38700
atcaatgagc cgaaaatcaa ggctatctat tacttctcct ctaatcaagc ggtcaaaaaa   38760
gttccctaat gctccaccta gcaacagtga taaggcaaaa gagattcgtc ggttattcct   38820
tccttctgtt tgtaaataat aaatgatacc cagtacaaca attaacgtta caataataaa   38880
aaaccagcgt tgaccttgca aaattccaaa tgctgctcct ttatttcgaa gagaagtaat   38940
atggaatact ccttcccata aaggaatggt ttgacctatt tccattcatt tgacaatcgc   39000
agatttccat agttgatcaa tgattaaaac gatgactgca atgatatagt agatcctgat   39060
tctcctcctc caatattcat tatttttaaag tataccatga tataacgaaa aatgtatat   39120 tttattgttg caataaaacg ttatattatt tatactaata tatatacaaa taataatttg   39180
aatgttattt tatacactaa ttacagagga ggggttgttt tgagtattac ttccataaat   39240
aaaaaagaac atgatttaga tggtataaaa tcaaggggaa aagatgcttg tgagacattt   39300
atatttgacc cagaaaaggt tgagcgccgt cagcaggaag tcggtcaaac ggatggctta   39360
tcacaattgt ttaaagtttt tgcggatgat acacggttga aaattgttta tgcacttacg   39420
```

```
caagaagatg aaatgtgtgt ctgtgatgta gcaacgatta ttggttctac gaatgctact   39480
gcttcacacc acctacgtat gttacgtaat atggggtttg ccgagtacca taaaaaaggg   39540
aagatagttt tttataggct agtaagtaat catgtgcatc accttatgca agaagcacta   39600
cagttgaagg aaaagaagta aatgtgatga gtgttgggaa aaattagtta aaatgttaca   39660
aacaactcag tcctccgttt tacatgatgg aatgcagttg ctcaaaaata aaccataaaa   39720
attacctaag aaaagaccag tagataaaaa atcatctcag gagatttaag acctggtatc   39780
cactagggct taaatcttgt tttttctctg aattgtaccc tgatggtcca aattatttgt   39840
gaaatggaat gaattaaagt aaggagagtt tgtaatgttc tcatggactg tagtatctct   39900
tgtgttactc acaagtatag ctaatcttgt tggaggattt attgtcgtga gaaaagaatg   39960
gtcccccaaa gctcttacat atttaatggc ttttagtgca ggttttcttt tatccatagg   40020
tattcttgat ctaatgccag aaggattaga aaattcacct gaaaatggaa tctatatatt   40080
aataggattt ttagtattat tttcctttca aagaatcctc acaactcatt ttcatttcgg   40140
ctatgaaaca catgaggata aactcagtaa aaaaacgggc ggtttaggtg cctttatcgg   40200
aatgaccatt catagtttct ttgatggggt ctccattgtt gcgggattcg aagtaagcag   40260
tgaattaggt ttccttgtgt ttgttgctgt attacttcat aaaataccag atggcttaac   40320
catttcttcg attgttcttg tagtatttaa tgacaggaaa aaggcgttta ttgcctctgc   40380
agtactggct ttggctacta tatttggagg agctttagta tggctactca gtgacacaga   40440
atttgcagct gaagtacttg gcgattcttt tgcaagaatt gctttgtcct tttcagcagg   40500
tgtttttcta tatgttgcag caacggactt acttccagtt gttaatcaat ctgaaaatcg   40560
aaaaactggt ctttacgttt tgcttggtgt agccgttttc tatatagctt cttggatcat   40620
aggagttgtt gggttggaat gaaaatatta aaggaatagc cttgaataat cagttgagga   40680
aattaaacag aaaagttgag tttagtctta gcaaaaaaag aaataaaata caatcaaata   40740
atcatttgac tatctatatg tgtggatata taataacaac agaacataac gtaatattca   40800
aatgaatatc ataatgagag atggccaaga atataggaat tccacatgca ttgattgata   40860
aaagatacat tggttaatta agaaggaggt tattaaatat gagtgaagca acgaagccat   40920
tagaggagaa atatgtctat cgtgttgatg gattttcatg cgcaaactgt gcaggaaagt   40980
ttgaaagaaa tgttaaaaaa attccgggag tagaggatgc aaaagtaaat tttggagcat   41040
ccaaaatttc cgtttacgga gaagcaacgg ttgaagaatt agaaaaagca ggtgcctttg   41100
agaaccttaa agtggctcca gaaaaaccta ggcggcaggc tccgcaagag gttaaaaaag   41160
acaaaaatat atatcgtgtt gaagggtttt catgcgcaaa ctgtgcagga agtttgaaa   41220 gaaatgttaa aaaaattccg ggagtagagg atgcaaaagt aaattttgga gcatccaaaa   41280
tttccgttta cggagaagca acgattgaag aattagaaaa agcaggtgct tttgagaatc   41340
ttaaagtggc ctctgaaaaa cctgtacggc aagctacaca agagattaac caggaaaaag   41400
aggatgaaaa agaagaaaaa gtgccattct ataaaaagca cagtacttta ctctattcga   41460
ccttattgat tgttttcgga tatctttcag tctttgttaa tggggatgag aacattgtta   41520
ctacattatt atttgtagca tcgatgttaa taggaggatt atcgcttttt aaagttggtt   41580
tccaaaactt gttacgcttt gaatttgaca tgaaaacact tatgactgtt gcagttatag   41640
gtggtgcgat tataggagaa tgggcagaag tttctgttgt tgtcatactc tttgcaatta   41700
gtgaagctct agaacgattt tctatggata aagcgagaca atcaattcga tcattaatgg   41760
```

```
atattgcacc taaagaggca cttgttagac gaaaaggtca agaaatgatg gttcatgtag    41820
atgatattgc agttggagat attatgattg tcaaacctgg tcaaaagatt gccatggacg    41880
ggatggttgt aagtgggtac tctgctgtta atcaagctgc cattacaggt gagtcagtcc    41940
ctgttgaaaa agcggttgat gatgaagtat ttgcaggtac tctaaatgaa gaaggattac    42000
ttgaagtaga aataactaaa ttagtagaag atacaaccat ttcaaaaatt attcatcttg    42060
tagaggaagc acagggagaa cgagcaccat ctcaagcctt tgtagaaaaa tttgcgaaat    42120
attatactcc gatcatcatg atcatagctg cgttagttgc tgtagttcca ccattattct    42180
ttggggctag ttgggaaaca tgggtttatc aaggtttagc tgttttagtc gttggttgtc    42240
catgtgcgtt ggttatttcc accccgattt cgattgtttc agcaattgga aatgcagcga    42300
aaaagggtgt cctaataaaa ggtggcgttt atttagaaga aatgggtgcc ttaaaggcca    42360
ttgctttcga taaaacaggt actttgacaa aaggtgtccc tgttgtaact gacttcaatg    42420
tgttgaacaa acaggtagat gaaaatgaaa tgctatccat cattactgca ttagagtatc    42480
gttctcagca ccctcttgca tcagcaatca tgaaaagagc agaagaggcg aatatttctt    42540
attcagatgt tgtgatagat gacttctctt ccattacagg aaaaggaatt aagggtactg    42600
tagacggaac gacctattat attggaagtc caaaactatt taaggaactg tcaaactcta    42660
gttttgataa gaatttagag aaaaaagttg caactcttca aaatcaaggg aaaactgcta    42720
tggttgttgg aactgacaaa gaaatactag ctattattgc agtagcagat gaagtacgtg    42780
aatcaagtaa agaagtcatt caaaaactac atcaacttgg catcaaaaat acaattatgc    42840
ttaccggtga taataaaggt actgcgaatg ccattggaag tcatgtcgga gtaaaagaag    42900
ttcaggctga attaatgcct caggataaat tggattatat taaacaattg aaatcggaat    42960
acaacaacgt agctatgatt ggcgatggtg tcaatgatgc acctgcattg gcagcttcca    43020
ctgttggaat tgcaatgggt ggagctggta ctgatacagc attagaaacg gcggacgttg    43080
cactaatggg agatgattta agaaaaacttc cgtttacggt aaaactaagt cgaaaagcgc    43140
taaacataat aaaagctaac attacttttg caattgctat taaatttatt gccttattat    43200
tggttattcc aggttggtta acactctgga ttgcgattct ttcagatatg ggtgcaactc    43260
ttcttgtagc gttgaacagt ttacgactta tgcgagtgaa agattaagag taaaaagagt    43320
gtgggacata aagtcccagg ataagtaaaa aaagacaatt tctattgaaa taatatagaa    43380
attgtctttt ttattatttt tttgattatt ttcagctcgt tgagctgtta cttttcttat    43440
attaagtgcc attagcacaa atcctaattc tcttttggct ttatctatcc ctcgaacgga    43500
cattctagtg aaacccaaaa tagccttcat aaatccaaaa acaggctcca catcaatttt    43560
tctttgactg tagatggttt ttgttttttgg ttctgaaagc ttttttattaa tttgggcttt    43620 aaaatattcc caattataat ttttcattat tttttttattt gttttttgaat tgaagttcat    43680 acattgttgt ttcagagggc attctgaaca atcatcacat tcatataatt taaagtctcg    43740
tttaaaacca tatttatcat gacgataggc atatctttta aatcctagtc tttttattatt    43800 cggacaaatg aattcatcgt taatttcgtc ataatcccaa ttttgagtat taaagatgtc    43860
acttttatat tttttagttt tatcttttat aaacattcca taagttatga gtggcgttcg    43920
attaaaatta tctataattg ccatataatt ggcttcgcta ccataacctg cgtcagctac    43980
aatatattca ggtaaatgac cgtaggtctc ttgtattgta tttaaaaaag gtatcattgt    44040
tcttgtatca gtcggatttt gatacacatc ataaaataaa acaaattgag aatttgtcgc    44100
tatttgtaaa ttataccccg gtttaagttg tccatttttc atatgatctg ttttagaata    44160
```

```
actatttcta tcctttaaaa tagattttg gacttcgtat ttatgctttc gctgagagta   44220
atcattaatt tgcttttgt attttttaat tttagttctt ttgagccgta tttgttttct   44280
tattttagta cattttcat tatcgatatg ttggtttaaa tcttcgattt ctttatctaa   44340
atgactacca atcaaatcta tttcttcttt tgttaagtca ttatcatgat ctttttaat   44400 ctcaggtatg attttattta tcaccaattc atgatagagt gctttagagt tttcattcat   44460
tcttgactca tggttttgaa tactctttt ccatacaaat gtatatcgat tggcatttgc   44520
ctcaactttc gtaccatcaa taaaaatggc ctgatcatca ataagatttt gtttcaaaca   44580
ctgactatga aattgaataa ataatgattc taataaagca tctactttgg gatttactct   44640
aaatcgatta atcgttttat aagaaggctt ttgattttgt gatagccaca tcattcggat   44700
actatcattg agtaattttt ctatcttacg tcctgaaaac acagattggg tgtaggcata   44760
taaaactact tttaacatca ttttggatg gtatgatgtt gcacctcgat gatgtctgaa   44820
ttcatcgaat tcagtctcgg gaattgtttc tacaatatca tttacatgtc gtgaaatatc   44880
atttgtgggg ataagaactg aagtttccat tggtagagta agttgagtca tgttataatc   44940
tttatacata aggcacctcg ttaatttagt ttagtgatgt ttattaaatt atacgaaagg   45000
gccttatttt tttaaagtat tttaatgtaa aattacatat gaatacaaag tattttggcg   45060
agactcttga gggaacagga caagctgaag actacaggct gaagctgtcc cctaagaaag   45120
cgagccaaca atacgaagta ttgtaaataa agaagccagt aaatgaattt atgaaaactc   45180
atttactggc tattttgata ggaattatgt cccaggccct tttaatcaaa atgtagatta   45240 tttttataa attgtctaat aagagaagaa aaataggtga aaataagaaa aaggttagat   45300
acatattaca caactatatt cttgagtaca aatagtaatt atagttactt atcaaaggag   45360
gaatctagga tgactggaga agtgaaaaaa tatgtagacc ttttagtgat aggagcaggg   45420
tctggaggtt atgtggcggc aatacgtgct gcccagttag gaaaaaaggt ggtactggtt   45480
gataaggcgg agttaggagg agtttgcctt aatcgagggt gtatcccttc aaaagctctt   45540
attagtgcat ctgaacgagt caaacacatt aaacatgcca atacaatggg gcttaaggtt   45600
tcgggtgagg ttcaagttga tatgccagaa gtagtaaagt ggaaggacgg aatcgtgaac   45660
aagctaacag atgggattcg caccttgtta aaaggaaatg gtgtagaggt catcagtggg   45720
gaagcctatc tcactgaagc acatattgca aaaataaaaa tagaggacga ggaacagatt   45780
ttttcctaca aagatttaat tcttgcaata ggttctttgc cagtcgagtt aaaaagtatg   45840
ccatttgatc aaaaaagaat catttcttca acggaggcat tgcaactaca ggaagtaccc   45900
aatcatttag ttgtggtagg tggtggttat atcggtttag agttaggtac tgcttatgca   45960
aagtttgggg caaagtgac catccttgag ggatcggata caattttgtc cgggacagat   46020
cctatcctaa caaaaacagt aaaacgtcat ttaaaggaaa ttggaatcac tgttataacg   46080
gatgcccttg ttcaaggtgg agaaaataca ggcgatgaag ttaacgtcca tgttcaagtt   46140
gatggaaagg aagaaattat tcaatgtgat tattgcttag tttctattgg gagaaaacca   46200
aacacaggta aaattggtct ggaaaatatc ggagtagtat tagacgacca aggatttatt   46260
aagataaata acaaatgtca aacaaacatt gaacatgttt atgcaatagg ggattgtgct   46320
ggtggtgacc tccttgctca taaagctagt tatgaagcaa agatagcagc cgaagtgatc   46380
agtggtcaaa atagtgtgat tgattttcaa gcgatgcctt ttgttatctt cagcgatcct   46440
gaagtagcct atacaggttt aacagagaag gaagcaaagg aaaaaggata cgaaacagta   46500
```

```
tccagtcgtt ttccattcca agcaaatgct agggcgttat ctgtctcgga tgcagatggc   46560
tttgtacaag ttgtagccga aaagaatacg aaaagagtgt taggagtaca gatggttgga   46620
ccagaggtat cctctctgat tgcagaggct gttttttgcga ttgaggctgg ggcaaatgcg  46680
gaagatctta gccttacgat tcatgctcat cctaccttac cagagccact tatgaaagca   46740
gcagaaggtg tgatgggaca tgctacacat atgttgaata aaaagcaata atgtgaatgc   46800
aggccaacct gcacttttc ataagtgcag gttgaatttt tattaatgga tggagactca    46860
tgcacatttt gtattgatag atgtattact gtataaaatt cctgatggta tggattaatc   46920
actattcatg aatttctaat gaactgggtt aatacaaatt atgaaatata tcaaatcgtt   46980
tttctgactg tttatgaacg atgaaggagt tgatataaat gaatttaatt ttaactattc   47040
tctctgcttt aggttctttt atagtaacca atgtcgatga tattttttgtc ttgatgttac  47100 tgttctctca agcaaggtca caagctaaaa cgggtaacag tggaatagtt agcatggagt   47160
cgaaaggaaa ccgtatttat ccaagagata tagtcattgg ccaatatctt ggttttgcac   47220
ttttagtttt aatcagtctt ttagcaacat ttggagtaac actcattcct gatcagtggg   47280
taggtttgct aggattaata ccgatatatc taggagtaaa actctttata aagggtgaag   47340
atgaggatga aggtaacatt cttttccaact taaacaaatt taataagttc tatttaagtg   47400
tagcctttat cacattcgcc aatggcggag acaatattgg aatttatgtt ccattctttt   47460
ctaccttaaa taacaaccaa ctgataatta cagttgttac tttctttata atggttgctg   47520
tctggtgttt aattggctat cgtctagcaa ggttcagata tgtttctgaa cacttgaga    47580 aatacggccg ctggattatc ccaattgtgt ttataggatt aggaatatat attatggtgg   47640
agaacgaaac tttccgcgcc attttgagtt tagtgaatta aaaatttctc aaaagtacct   47700
ctgatttaca gtaggacttt gatatttaga gtaaatattt atcctctgac aaataattct   47760
atggatacgc tcatctatat tttgcttagc gtacaaaatt tccgaaatgt tggctgtacc   47820
ccaataagca attagaatat tatcaaaatt gttaattaag aatagccctc gaaaaaatcg   47880
ggggctttgc ttttggcata agacggccaa acaaagccg aaccaaaagg agtgaatgtg    47940
atgtgcataa cgcacacaca tcacattcac attaaaacta aattcaaaat ggagggaaag   48000
tgaagattca cttcccttt attttcattt ttagaattta ttttttttgtg ttgaaacgct    48060 cacacgtaca atcaaagatt gtacttttaa caagcctact caatcttaca aggggcaata   48120
aaacttttta ggttctgttg caaagtaaaa aatatagcta accactaatt tatcatgtca   48180
gtgttcgctt aacttgctag catgatgcta atttcgtggc atggcgaaaa tccgtagatc   48240
tgaagagacc tgcggttctt tttatataga gcgtaaatac attcaatacc ttttaaagta   48300 ttcttttgctg tattgatact ttgataccatt gtctttctta ctttaatatg acggtgatct   48360
tgctcaatga ggttattcag atatttcgat gtacaatgac agtcaggttt aagtttaaaa   48420
gctttaatta ctttagccat tgctaccttc gttgaaggcg cctgatctgt aattacccttt  48480 tgaggtttac caaattgttt aatgagacgt ttgataaacg catatgctga atgattatct   48540
cgttgcttac gcaaccaaat atctaatgta tgtccctctg catcaatggc acgatataaa   48600
tagctccatt ttcctttat tttgatgtac gtctcatcaa tacgccattt gtaataagct     48660
tttttatgct ttttcttcca aatttgatac aaaattgggg catattcttg aacccaacgg   48720
tagaccgttg aatgatgaac gtttacacca cgttcccttta atatttcaga tatatcatga   48780
taactcaatg catatcttag atagtagcca acggctacag tgataacatc cttgttaaat   48840
tgtttatatc tgaaatagtt catacagaag actccttttt gttaaaatta tactataaat   48900
```

```
tcaactttgc aacagaacca tttgcgatac aacgaggcga cattagccgt taatttgctt   48960
aactgtagaa gatttaaaag aaccccttgc catatattta acaatgttgt ccgggataac   49020
aacacagtga atccaccgtt tagttaagat gatggatttt ttcaaactgt ggatgaggta   49080
cagagtttca ttagataaaa acagggaaaa cttattaaag agtgatttct gtgaggagga   49140
taatgatgac aaagaaatac gatcttattg tgattggtac aggttctgcg gggtcaatca   49200
cagcagcaaa atgtaataaa gccggctgga atgtagctat ggtagatgac aggccgtttg   49260
gaggcacgtg tgcactacgt ggatgtgacc caaaaaaggt tctacatggt gctgccgagc   49320
ttattgattg aacaaacgg atggttaaga atggagtacc gtctgaagtc tccatcaact    49380
ggaaagatct tatgaatttt aaaagaacct ttacagatga tgtcccggaa aaaaagagg    49440 aagcattgaa taaacaggga atcgatacgt atcatggcaa tgcatctttc gtgagtgagg   49500
acaaacttga agtgaataaa gaagtgctcg aggggagtca tttcttgatc gctagtggtg   49560
cgaaacctac cccttaccc ataaaaggag aagaacatct tacttatagt gatgagtttt    49620
tggagttgga tgaattacca caaagaatcg tctttgttgg tggtgggtat atttcgtttg   49680
aatttgctca tatcgcggca cgtgctggat cagaagttca tattatccat cgaggtcaaa   49740
gacctttgga gaattttgat atagatcttg tagatatcct tttagaaaag tcgaaagaga   49800
ttggcataca ggtacatctt caacattccg ttgaatccat tgaaaaagaa caggaaagt    49860 ttcatgtgta cgctcgaaaa aaagaggata taacgcggtt tgaagcagac attgttattc   49920
atggtgctgg acgggtccct gccttagata tgaatcttga aaaagggaat atagaaagga   49980
aaaaacatgg tgtccatgtt aatgagtatt tgcaaagtgt aagtaacccg aatgtctatg   50040
cagctggaga tgctgcagca acggatggct tgcccctcac acctgtagcc agtgcagatt   50100
ctcatgtcgt agcatctaat ttattgaaag ggaacagcaa aaaaattgaa tatcccgtga   50160
ttccatctgc tgtatttacc gtacctaaaa tggcatcggt aggtatgagc gaggaggaag   50220
ccaaaaactc tggccggaat attaaagtaa agcagaaaaa catctccgac tggtttacgt   50280
ataaacggac aaatgaggac tttgctgcgt ttaaagtgct aattgacgag atagtgatc    50340 aagttgtcgg tgctcatttg attagtaatg aagccgatga actaattaac cactttgcaa   50400
cagccattcg ctttggaatt tcaaccaaag aattgaaaca aatgatatt gcctatccaa     50460 cggcagcttc ggacattgca cacatgttgt aagtttgcgt tttgtgagat gtttataaac   50520
cactttatcg tctaatcttg ttatatgatc ttagaatcaa aaagaaaata acttttttga   50580
cagccacatt tttcaacgga agaatgtggc ttcttggcgt gaagagcaga tatctttatt   50640
cttaaacttc taaaaaagct tatgtgaaca cttgataaat aaggttttt atctgaccta    50700 ttttataaga ttattctata aagaaaaaa taatgtatga cttgaccgtg tactatagta    50760
cagggtttat acttttttatt gaggtgacaa tatggagatg aaaatcagtg aattggctaa   50820
agcgtgtgat gtgaataaag aaaccgttcg gtattacgag cggaaggat tgatagccgg    50880 gcctcccaga aacgaatcag ggtatcgaat atattcagag gaaacagcag atcgggtacg   50940
gtttattaaa cgaatgaagg aattggattt ctcgctaaag gaaatccacc tgttgtttgg   51000
tgtggttgat caagatgggg agagatgtaa agatatgtac gcctttaccg ttcaaaaac    51060 caaagaaatc gagcggaaag tgcaggattt gttacgaatc caacggttat tagaggaatt   51120
aaaagaaaag tgtccagatg aaaaggcgat atatacctgt cctattattg aaacgttaat   51180
gggagggcct gataaataaa tgggggaaga tttgaatgaa aaaacgcatt tccttcaccg   51240
```

```
ctataatgac ggtgttgtta atcggtttaa cagcttgtgg agcagaatct gataccgcga   51300
atgaatcaaa ggttcaagac attcaaggaa atccagtcag cctacctaat gagaaaccca   51360
cactcattta ttttatggca acctggtgtc catcttgtat atacaatgag gaaatcttta   51420
aggaaattca tcaactaaac ccgaacgatg ttcaattgat cacagttagt ttagaccta    51480
acacagatac aaaagaaagc tttgcgaaat ttaaacagga ttatggcggg gattggcccc   51540
atgttttaaa gataggagtg gaattatgag ttttttcgttt ctcttcattc tgaccgctgg  51600
aatggttgcg gcctttaatc cttgtggtat cgccttgctt ccttcttata tctcctattt   51660
aattggaggc gaaacaaagg atcattcgtt ccgctatgca attttttaaag gattagggct  51720
tggtggagcg atgaccacgg ggttttttaac gattttttgta ttggctggtt tgttgatagg  51780
aggattggga agcgcactaa cagggatttt tccgattctt tcattggtta tgggtatact   51840
cattgcttta ttggggttgg gcatgctatt tgggaagcat ttgccgatta aaataggatc  51900
ttttcaagtc aagccaggga atggtctat ctattttac ggaatagcct atgccgtgac    51960
atcacttggt tgtaccttgc cagccttat gttggtggtc tctgcatcgc tgaatgacaa   52020
tagcgtaacg gccgtgatca tcaagttcat catctactcc cttggtatgg gaattgtggt   52080
gacagcgatc acgatggtct cattgatttc acgacaattg gtacagaagt ttctgcacaa   52140
ctatatgggt tctatccaaa aaatagcagc tgttgtgatt ttcctctccg gtttgtacat   52200
ggcttattac tggtatttcg gttctggtgg catttgtaca ttttaaaatc caaccgatca   52260
ggtgtaacaa aaaatagatg aaagatgtaa aaaagctaaa cgaacaaatt tcaagttagg   52320
ctataggcca tgtatgtacc ttaaccaaag aataaaattt ttttagaaag agtggtgaga  52380
atgatggatg agaatcgctc gaaaggtaac cgctggggtg tttgggcctt tttcggaata   52440
ttattggttc cttttactt tgttgcgcag gaccgattct ccttgttgca                52500
ttagggagca caggtattgg tgccctcttt gctggtgcga caggaaattg gtggttgacc   52560
ggcattttttg cagcattggc cattgttatg attgctctga tcctcagcaa gttgttgaag  52620
aacaaataca attctcctga aggcaatgga aaaacaaaaa ataaaacgga ttgctgtacg   52680
cctccagaga gcgtggatcg gaaacatgag acaagataaa tatgagataa atgtacagaa  52740
ctgtctatca aactttaaat agaaagaggg attcaaatga ctcaaaattc atataaaata  52800
cccattcaag gcatgacatg cacaggctgt gaagaacatg taaccgaagc attggaacaa  52860
gccggagcta aagatgtttc ggccgatttc cgacgcggtg aggccatttt tgaactcagc   52920
gatgatcaga tcgaaaaggc taagcaaaat atttcggcag ccggctatca acccggagag   52980
gaagaaagcc agccctctga aaacagtgta gatttcaatc gggatggcga ttacgatctt   53040
ctgattattg gttccggcgg tgcggcgttt tctgcagcta tcaaggccaa tgaaaacggg  53100
gcgaaagtgg ccatggtaga acggggaacc gtcgggggga cctgcgttaa catcggttgt  53160
gtaccgtcaa aaaccatgct tcgtgccggt gaaataaacg gtctcgccca aaacaatccg   53220
tttaccggac ttcaaacgag taccggtgct gcggaccttg cccaattgac cgaacaaaaa  53280
gatggattag tcagtcaaat gcgtcaagaa aaatatatag acttgatcga agaatatgga   53340
tttgatctca ttcgtggcga ggcctcgttt atcgacgata agacgataca agtgaatgga  53400
caaaacatca cgtctaaaag cttttttaatc gcaacggggg cttctccggc tgttccggaa   53460
atcccgggaa tgaatgaggt tgattattta acaagtacat ccgcactcga attaaaagag  53520
gttccacaac gattggcagt gatcggttct ggctatatcg cagcggaatt aggtcaaatg   53580
tttcacaacc tcggaacaga agtgactctc atgcaaagaa gcgagcgtct gtttaaaacc   53640
```

```
tacgatcctg aaatttccga agccatcgat gaatccttaa ctgagcaagg acttaacctg   53700
atcactgggg tcacttatca aaaggttgag caaaacggta agtcgacaag catttatatt   53760
gaagtgaacg gtcaagaaca agtcatcgaa gccgatcaag tcctcgtggc aacaggaaga   53820
aagccgaaca cagagacttt aaaccttgaa tcagcaggtg tgaaaacagg gaaaaaaggc   53880
gaagtgctga ccaatgaata tttgcaaacg tcgataacc gaatatatgc cgcgggcgat   53940
gtgaccctcg gtccgcaatt cgtttatgtt gcagcttatg aaggcgggat tgtggcaaat   54000
aatgcgttgg gtctagcgaa acgcaaaatc gatcttcgct tgttcccgg cgtaaccttc   54060 accaatccat cgatcgccac agtcggcttg actgaacaac aggcaaaaga aaaaggttac   54120
gatgtcaaaa catcggtcct tccgttggac gctgtaccgc gggccttagt caatcacgaa   54180
acaacagggg tctataaact tgtagtcaac gcccaaaccc agaaattgat cggggcgcac   54240
attgtgagtg aaaatgctgg agatgtgatt tatgcggcaa cgttagcggt tcaatttgga   54300
ttgaccattg aagaccttac ggatagcttt gcgccttatt taacgatggc tgaaggatta   54360
aagcttgcag ccttgacgtt tgataaagac gtatcgaaat tatcttgttg tgcaggctaa   54420
tggttccttt tgattctaat gctatgttgc aggaggcact taaaacaatg aagtggagaa   54480
aatataagga ggaataagct tatgaaaaat atttcagaat tctcagccca acttaatcaa   54540 actttgatc aaggggaagc cgtctctatg gagtggttat tccgtccgtt gctaaaaatg   54600
ctggcggagg gcgatccagt ccccgttgag gacatcgcgg cggagaccgg gaagcccgtc   54660
gaggaagtta agcaagtcct acagactcta cctagtgtgg aacttgatga gcagggccgt   54720
gtcgtcggtt atggcctcac actggtccct accccccatc gcttcgaggt tgatgggaag   54780
caactatatg catggtgcgc ccttgacaca cttatgttcc cagcactcat cggccggacg   54840
gtccacatcg cttcgccttg tcacggcacc ggtaagtccg tacggttgac ggtggaaccg   54900
gaccgcgttg taagcgtcga gccttcaaca gccgttgtct cgattgttac accagatgaa   54960
atggcctcgg ttcggtcggc cttctgtaac aacgttcact tttcagttc accgagtgca   55020 gcccaagact ggcttaacca acaccctgag tcgagcgttt tgcccgttga agatgccttt   55080
gaactgggtc gccatttggg agcgcgttat gaggagtcag gacctactaa tgggtcctgt   55140
tgtaacattt aatcttaggc aattacgcct gcgtcaatct tggccttacg atgatgtcct   55200
gtaaccgaag ctctatctag tgaaaccaat tttatgggaa accaaataaa taaaagatc   55260 aattgcttgt gcctatatcg gggagttaat aaagcgagaa agtggattct tgaatatagg   55320
agtaaataag gtgccaaaat ggcaccttat ttaaaatatg taacgccaag gtctgccgta   55380
ttatattgca ttggaaaaag aaaaccttct gtataaggag atgttatatg atatttggta   55440
aactgttcgg cagtttgggc gtagaaagct tttgctcctt gaacatcacg tttgccagtt   55500
acaatgtcat ttaacaagtt taaagataaa aaattcatcg cttcctcatg acactttgct   55560
gatgcctcac ctgtagttcg atctaagtag acacttccat caaaagcggc aatcgcatca   55620
tataagtgta cgggcacttt ataatcgatg gtctgcttaa ggaaatcaag gtgagggta   55680 gggaagttat gagggactgg atccttatat actatcgtgc gtttccatgg cccgctattg   55740
taccaaatta atcgtctcat tgttgcttcc tggggatatc catacttact aattatggtt   55800 tttgccccctt ccaacggtgg tccctgccaa taggacaaaa tgtgatttaa atgactatcc   55860
attgccatac ctcctaaaca tttgcctaaa agcattgtat gcccaataaa tgaattttag   55920
gtaaatgtat atttaatgat cggcagattg cagtaaaata cgaatgcctg caatgcaatt   55980
```
aacatgggat ttaacactgg acagtaattt ttttgctggg attttgctat cagatagctt 56040
ttcttagtga tgataggata tgttgaccaa attggccgtg agattggagg ggtggttttt 56100
atggttagtt gttgttcaat cgatccatac actgaattcg aagtcattat tattggtgcc 56160
ggggtgccgg aggtttctct tgcctttcat ttgacttcat acggcataag gacggcactt 56220
gcggatgaac agaacgtgga taacagatta aaggactttt taagaacttt tcaagaattg 56280
attgagcgcg attcgggtat gccgtgaacg ttacaggcaa taaaagaaga tatgcacctc 56340
atcctttttg acggtaccat tacccttgaa ggtgaacatg ctgtccgtat tgatgaacac 56400
aaaattcggg gggatcgtat ggtcgtacca tttgatacgt ttaaacaaat aggaaaacct 56460
agaaaccaaa acgacatcca ttttaaaaac gatccttttc aaagagttac gaatgattta 56520
tggatcacga atccctcatt gtcagaagtg gatcaagaac aaatatggca gactggagac 56580
tatttttcaa aacaccttca gaacattgaa taaatgaagg gttctgttgc aaagtaaaaa 56640
aatatagcta accactaatt tatcatgtca gtgttcgctt aacttgctag catgatgcta 56700
atttcgtggc atggcgaaaa tccgtagatc tgaagagacc tgcggttctt tttatataga 56760
gcgtaaatac attcaatacc ttttaaagta ttctttgctg tattgatact ttgatacctt 56820
gtctttctta ctttaatatg acggtgatct tgctcaatga ggttattcag atatttcgat 56880
gtacaatgac agtcaggttt aagtttaaaa gctttaatta ctttagccat tgctaccttc 56940
gttgaaggtg cctgatctgt aattaccttt tgaggtttac caaattgttt aatgagacgt 57000
ttgataaacg catatgctga atgattatct cgttgcttac gcaaccaaat atctaatgta 57060
tgtccctctg catcaatggc acgatataaa tagctccatt ttccttttat tttgatgtac 57120
gtctcatcaa tacgccattt gtaataagct tttttatgct ttttcttcca aattcgatat 57180
aaaattgggg catattcttg aacccaacgg tagaccgttg aatgatgaac gtttacacca 57240
cgttccctta atatttcaga tatatcacga taactcaatg catatcttag atagtagcca 57300
acggctacag tgataacatc cttgttaaat tgtttatatc tgaaatagtt catacagaag 57360
gctccttttt gttaaaatta tactataaat tcaactttgc aacagaacct tattgcatat 57420
ctttttagcc atatcactga tagggtgaag catatcataa atgatgcggt tttt 57474

<210> SEQ ID NO 89
<211> LENGTH: 3050
<212> TYPE: DNA
<213> ORGANISM: Staphylococcus aureus

<400> SEQUENCE: 89
tcgtgccatt gatgcagagg gacatacatt agatatttgg ttgcgtaagc aacgagataa 60
tcattcagca tatgcgttta tcaaacgtct cattaaacaa tttggtaaac ctcaaaaggt 120
aattacagat caggcacctt caacgaaggt agcaatggct aaagtaatta aagcttttaa 180
acttaaacct gactgtcatt gtacatcgaa atatctgaat aacctcattg agcaagatca 240
ccgtcatatt aaagtaagaa agacaaggta tcaaagtatc aatacagcaa agaatacttt 300
aaaaggtatt gaatgtattt acgctctata taaaaagaac cgcaggtctc ttcagatcta 360
cggattttcg ccatgccacg aaattagcat catgctagca agttaagcga acactgacat 420
gataaattag tggttagcta tattttttta ctttgcaaca gaaccgaaaa taatctcttc 480
aatttatttt tatatgaatc ctgtgactca atgattgtaa tatctaaaga tttcagttca 540
tcatagacaa tgttcttttc aacatttttt atagcaaatt gattaaataa attctctaat 600
ttctcccgtt tgatttcact accatagatt atattatcat tgatatagtc aatgaataat 660

```
gacaaattat cactcataac agtcccaacc cctttatttt gatagactaa ttatcttcat    720
cattgtaaaa caaattacac cctttaaatt taactcaact taaatatcga caaattaaaa    780
aacaataaaa ttacttgaat attattcata atatattaac aactttatta tactgctctt    840
tatatataaa atcattaata attaaacaag ccttaaaata tttaactttt ttgtgattat    900
tacacattat cttatctgct ctttatcacc ataaaaatag aaaaaacaag attcctaaag    960
aatataggaa tcttgtttca gactgtggac aaactgattt tttatcagtt agcttattta   1020
gaaagtttta tttaaattac agtttctatt tttattagat cacaatttta ttttagctct   1080
tgttcaagta atcattttc gccaaaaact ttatactgaa tagcttctac attaaatact   1140
ttgtcaatga gatcatctac atctttaaat tcagaataat ttgcatatgg atctataaaa   1200
taaaattgtg gttctttacc ggaaacatta aatattctta atattaaata tttctgctta   1260
tattctttca tagcaaacat ttcatttagc gacataaaaa atggttcctc aatactagaa   1320
gatgtagatg ttttaatttc aataaatttt tctacagctt tatctgtatt tgttggatca   1380
aaagctacta aatcatagcc atgaccgtgt tgagagcctg gattatcatt taaaatattc   1440
ctaaactgtt ctttcttatc ttcgtctatt ttattatcaa ttagctcatt aaagtaattt   1500
agcgctaatt tttctccaac tttaccggtt aatttattct ctttatttga tttttcaatt   1560
tctgaatcat ttttagtagt ctttgataca ccttttttat attttggaat tattcctta    1620 ggtgcttcca cttccttgag tgtcttatct ttttgtgctg ttctaatttc ttcaatttcg   1680
ctgtcttcct gtatttcgtc tatgctattg accaagctat cataggatgt ttttgtaact   1740
tttgaagcta attcattaaa tagttctaaa aatttcttta aatcctctag catatcttct   1800
tctgtgaatc cttcattcaa atcataaat ttgaatctta ttgatccatg agaatatcct    1860
gatggataat cattttttaa atcataagat gaatctttat tttctgcgta ataaaatctt   1920
ccagtattaa attcatttga tgtaatatat ttattgagtt cggaagataa agttaatgct   1980 cttttgttttg cagcattttt atcccgcgga aacatatcac ttatctttga ccatccttga   2040
ttcaaagata agtatatgcc ttctccttcc ggatgaaaaa gatataccaa ataatatcca   2100
tcctttgttt cttttgttat attctcatca tatattgaaa tccaaggaac tttactatag   2160
ttcccagtag caaccttccc tacaactgaa tatttatctt cttttatatg cacttttaac   2220
tgcttgggta acttatcatg gactaaagtt ttatatagat caccttatc ccaatcagat    2280 tttttaacta cattattggt acgtttctct ttaattaatt taaggacctg cataaagttg   2340
tctatcattt gaaattccct cctattataa aatatattat gtctcatttt cttcaatatg   2400
tacttattta tattttaccg taatttacta tatttagttg cagaaagaat tttctcaaag   2460
ctagaacttt gcttcactat aagtattcag tataaagaat atttcgctat tatttacttg   2520
aaatgaaaga ctgcggaggc taactatgtc aaaaatcatg aacctcatta cttatgataa   2580
gcttctcctc gcataatctt aaatgctctg tacacttgtt caattaacac aacccgcatc   2640
atttgatgtg ggaatgtcat tttgctgaat gatagtgcgt agttactgcg ttgtaagacg   2700
tccttgtgca ggccgtttga tccgccaatg acgaaaacaa agtcgctttg cccttgggtc   2760
atgcgttggt tcaattcttg ggccaatcct tcggaagata gcatctttcc ttgtatttct   2820
aatgtaatga ctgtggattg tggtttgatt ttggctagta ttcgttggcc ttcttttct    2880 tttacttgct caatttcttt gtcactcata ttttctggtg cttttcgtc tggaacttct    2940 atgatgtcta tcttggtgta tgggcctaaa cgttttttcat attctgctat ggcttgcttc  3000
```

| caatatttct cttttagttt ccctacagct aaaatggtga ttttcatgtc | 3050 |

<210> SEQ ID NO 90
<211> LENGTH: 3050
<212> TYPE: DNA
<213> ORGANISM: Staphylococcus aureus

<400> SEQUENCE: 90

| acctcattga gcaagatcac cgtcatatta aagtaagaaa gacaaggtat caaagtatca | 60 |
| atacagcaaa gaatacttta aaaggtattg aatgtattta cgctctatat aaaaagaacc | 120 |
| gcaggtctct tcagatctac ggattttcgc catgccacga aattagcatc atgctagcaa | 180 |
| gttaagcgaa cactgacatg ataaattagt ggttagctat attttttttac tttgcaacag | 240 |
| aaccgaaaat aatctcttca atttattttt atatgaatcc tgtgactcaa tgattgtaat | 300 |
| atctaaagat ttcagttcat catagacaat gttcttttca acatttttta tagcaaattg | 360 |
| attaaataaa ttctctaatt tctcccgttt gatttcacta ccatagatta tattatcatt | 420 |
| gatatagtca atgaataatg acaaattatc actcataaca gtcccaaccc ctttcttttg | 480 |
| atagactaat tatcttcatc attgtaaaac aaattacacc ctttaaattt aactcaactt | 540 |
| aaatatcgac aaattaaaaa acaataaaat tacttgaata ttattcataa tatattaaca | 600 |
| actttattat actgctcttt atatataaaa tcattaataa ttaaacaagc cttaaaatat | 660 |
| ttaacttttt tgtgattatt acacattatc ttatctgctc tttatcacca taaaaataga | 720 |
| aaaaacaaga ttcctaaaga atataggaat cttgtttcag actgtggaca aactgatttt | 780 |
| ttatcagtta gcttatttag aaagttttat ttaaattaca gtttctattt ttattagatc | 840 |
| acaattttat tttagctctt gttcaagtaa tcattttttcg ccaaaaactt tatactgaat | 900 |
| agcttctaca ttaaatactt tgtcaatgag atcatctaca tctttaaatt cagaataatt | 960 |
| tgcatatgga tctataaaat aaaattgtgg ttctttaccg gaaacattaa atattcttaa | 1020 |
| tattaaatat ttctgcttat attctttcat agcaaacatt tcatttagcg acataaaaaa | 1080 |
| tggttcctca atactagaag atgtagatgt tttaatttca ataaattttt ctacagcttt | 1140 |
| atctgtatt gttggatcaa aagctactaa atcatagcca tgaccgtgtt gagagcctgg | 1200 |
| attatcattt aaaatattcc taaactgttc tttcttatct tcgtctattt tattatcaat | 1260 |
| tagctcatta aagtaattta gcgctaattt ttctccaact ttaccggtta atttattctc | 1320 |
| tttatttgat ttttcaattt ctgaatcatt tttagtagtc tttgatacac cttttttata | 1380 |
| ttttggaatt attcctttag gtgcttccac ttccttgagt gtcttatctt tttgtgctgt | 1440 |
| tctaatttct tcaatttcgc tgtcttcctg tatttcgtct atgctattga ccaagctatc | 1500 |
| ataggatgtt tttgtaactt tgaagctaa ttcattaaat agttctaaaa atttctttaa | 1560 |
| atcctctagc atatcttctt ctgtgaatcc ttcattcaaa tcataatatt tgaatcttat | 1620 |
| tgatccatga gaatatcctg atggataatc atttttttaaa tcataagatg aatctttatt | 1680 |
| ttctgcgtaa taaatcttc cagtattaaa ttcatttgat gtaatatatt tattgagttc | 1740 |
| ggaagataaa gttaatgctc tttgttttgc agcatttttta tcccgcggaa acatatcact | 1800 |
| tatctttgac catccttgat tcaaagataa gtatatgcct tctccttccg gatgaaaaag | 1860 |
| ataccaaaa taatatccat cctttgtttc ttttgttata ttctcatcat atattgaaat | 1920 |
| ccaaggaact ttactatagt tcccagtagc aaccttccct acaactgaat atttatcttc | 1980 |
| ttttatatgc acttttaact gcttgggtaa cttatcatgg actaaagttt tatatagatc | 2040 |
| acctttatcc caatcagatt ttttaactac attattggta cgtttctctt taattaattt | 2100 |

```
aaggacctgc ataaagttgt ctatcatttg aaattccctc ctattataaa atatattatg    2160
tctcattttc ttcaatatgt acttattat attttaccgt aatttactat atttagttgc    2220
agaaagaatt ttctcaaagc tagaactttg cttcactata agtattcagt ataaagaata    2280
tttcgctatt atttacttga aatgaaagac tgcggaggct aactatgtca aaaatcatga    2340
acctcattac ttatgataag cttcttaaaa acataacagc aattcacata aacctcatat    2400
gttctgatac attcaaaatc cctttatgaa gcggctgaaa aaaccgcatc atttatgata    2460
tgcttctcca cgcataatct taaatgctct atacacttgc tcaattaaca caacccgcat    2520
catttgatgt gggaatgtca ttttgctgaa tgatagtgcg tagttactgc gttgtaagac    2580
gtccttgtgc aggccgtttg atccgccaat gacgaataca aagtcgcttt gcccttgggt    2640
catgcgttgg ttcaattctt gggccaatcc ttcggaagat agcatctttc cttgtatttc    2700
taatgtaatg actgtggatt gtggtttaat tttggctagt attcgttggc cttcttttc    2760 ttttacttgc tcaatttctt tgtcgctcat attttctggt gcttttcgt ctggaacttc    2820 tatgatgtct atcttggtgt atgggcctaa acgttttca tattctgcta tggcttgctt    2880
ccaatatttc tcttttagtt tccctacagc taaaatggtg attttcatgt cgtttggtcc    2940
tccaaattgt tatcaacttt ccagttatcc acaagttatt aacttgttca cactgttccc    3000
tcttattata ccaatatttt ttgcagtttt tgatattttc ctgacattta    3050
```

<210> SEQ ID NO 91
<211> LENGTH: 2996
<212> TYPE: DNA
<213> ORGANISM: Staphylococcus aureus

<400> SEQUENCE: 91

```
atgaaacgag ccattggtta tttgcgccaa agtacaacga acaacaatc actcccagct      60 caaaagcaag caatagaatt attagctcca aagcacaata ttcaaaatat ccaatacatt     120
agtgataagc aatcaggcag aacagataat cgaacaggct atcaacaagt caccgaacgc     180
atccaacaaa gacaatgtga cgtattatgt tgttatcgct tgaatcgact tcatcgcaac     240
ttgaaaaatg cattaaaact catgaaactc tgtcaaaaat atcatgttca tattctaagt     300
gttcatgatg ctatttga tatggataaa gcgtttgatc gcctaaaact caatatattc     360
atgagtctgg ctgaacttga atccgataat attggagaac aagtcaaaaa tggacttaga     420
gaaaaggcaa acaaggtaa actcataacg acccatgcgc ctttcggtta tcactatcaa     480
aatggtactt tcatcattaa taatgatgaa tcacctaccg tcaaagctgt attcaattat     540
tatcttcaag gatatggcta caagaagatt gcacaatatt tagaagacga taataaactt     600
attacccgca agcctatca ggtacgaaat ataattatga acccaaatta ttgtggtcgt     660
gtcatcaatc aatatggtca atataacaat atggtaccac ctattgtttc ggcaacgaaa     720
tatgaacatg ctcaagcaat ccgtaataag aagcaacttc actgtatacc ttcagagaat     780
cagctgaaac aaaagatcaa atgtccttgt tgtgactcaa cactgacaaa tatgacaata     840
agaaaaaaac atacattgcg atattatatt tgtcctaaaa atatgaatga atctcgcttt     900
gtctgttcat tcaaggaat aaatgcacaa aaattagaag ttcaagtctt agctacatgt     960
cagaacttct ttcaaaacca acagctctat tcaaaaatta ataatgcaat tcatcaacgc    1020
ctcaaaaaac aaagagtgat agaagctaaa agtacgctaa ctcaagaaca actgatagat    1080
aaacttgcca aaggtatgat tgatgctgaa tcattcagaa aacagactca tttgatgaat    1140
```

-continued

| | |
|---|---|
| caaaagcaca aaaccatatc ctccataagt gataatcagt tacaaacatc actacaaaag | 1200 |
| gttatacaga aaagtttcac gttaaacatg ctgcatccct atattgatga aattcgcatt | 1260 |
| acaaaaaata aagcccttgt tgggatctat ttcaaaaatg aaccattgaa cattgtgaac | 1320 |
| caaacctcgc aatcatcgat tgcttaatca gaaaggatga aaaaatcatg caacaactca | 1380 |
| aacaaaaacg tgtcggtatc tatgttcgtg tatcaacgga atccaaagt actgaaggct | 1440 |
| atagtatcga tggacaaatc aatcaaattc gagaatattg tgatttcaat aactttgttg | 1500 |
| ttgtagatgt atacgcggat agaggtatct ctggaaaatc tatgaaccga ccagaactac | 1560 |
| aacgtttgtt aaaagatgcg aacgaaggtc agattgattc tgttatggtc tacaaaacaa | 1620 |
| accgactagc acgtaacact tctgacttac tcaaaattgt tgaagacctt catcgtcaaa | 1680 |
| atgtcgaatt cttcagctta tctgagcgta tggaagtcaa tacaagcagt ggtaaattga | 1740 |
| tgctacaaat tctagcgagt ttttcagaat ttgaaagaaa taatattgtc gaaaatgtat | 1800 |
| tcatgggtca aacccgacgc gctcaagaag gctattatca aggcaatttg ccgctgggct | 1860 |
| atgacaaaat accggatagc aagcatgaac tcatgataaa ccaacatgaa gcgaatattg | 1920 |
| tcaaatatat atttgagtca tatgctaaag gccacggata tcgtaaaatt gcgaatgcac | 1980 |
| tcaatcacaa aggatacgtg actaaaaaag gaaagccttt cagtattggt tcagtgacct | 2040 |
| atatcttatc taatccattc tatgttggta aaattcaatt cgcaaagtac aaagattgga | 2100 |
| atgaaaagcg tcgtaaaggg ctgaatgata accaataat agctgaaggt aagcattccc | 2160 |
| ctattattat tcaagactta tgggataaag tccaattacg taaaaaacaa gtcagtcaaa | 2220 |
| aacctcaagt ccacggtaaa ggaactaatc tattaacagg tatcgttcat tgtccacaat | 2280 |
| gtggtgcacc aatggcagct agtaacacaa cgaacacatt gaaagatggt accaagaagc | 2340 |
| gaatacgtta ttattcttgc agtaacttcc gaaacaaagg ctcaaaagta tgttctgcga | 2400 |
| atagcgttag agctgatgtg attgagaaat acgtcatgga tcaaatactc gaaattgtca | 2460 |
| aaagtgataa agtcattaac caagtcttag aacgtgtcaa tcaagaaaat aaagtcgata | 2520 |
| ttggtgcatt gaaccacgat atcgcttata acaacaaca atacgatgaa gtcagcggga | 2580 |
| aactccataa tttagttaaa accattgaag ataatccgga cctaacatct gcattgaaag | 2640 |
| caactattca tcaatatgaa acacaactca atgacattac aaatcaaatg aatcaactca | 2700 |
| aacagcaaca aaatcaagag aaactatctt atgatacgaa acaaatcgct gccctattac | 2760 |
| aacgaatatt tcaaaatata gaatcaatgg ataaagcaca actcaaagca ttatatctta | 2820 |
| cagtcattga ccgtattgat attcgtaaag acggtaatca taaaaaacag ttctacgtta | 2880 |
| cactaaaact caataatgaa attattaaac aactttcaa taatacccct ctcgacgaag | 2940 |
| tgctcctcag cacttcgtct ttattttgc ctcaaacgct ctttcttcaa atctaa | 2996 |

<210> SEQ ID NO 92
<211> LENGTH: 2153
<212> TYPE: DNA
<213> ORGANISM: Staphylococcus aureus

<400> SEQUENCE: 92

| | |
|---|---|
| ctgtagggaa actaaaagag aaatactgga agcaagccat agcagaatat gaaaaacgtt | 60 |
| taggcccata caccaagata gacatcatag aagttccaga cgaaaaagca ccagaaaata | 120 |
| tgagcgacaa agaaatcgag caagtaaaag aaaagaagg ccaacgaata ctagccaaaa | 180 |
| tcaaaccaca atccacagtc attacattag aaatacaagg aaagatgcta tcttccgaag | 240 |
| gattggccca agaattgaac caacgcatga cccaagggca aagcgacttt gtattcgtca | 300 |

```
ttggcggatc aaacggcctg cacaaggacg tcttacaacg cagtaactac gcactatcat        360
tcagcaaaat gacattccca catcaaatga tgcgggttgt gttaattgaa caagtgtaca        420
gagcatttaa gattatgcgt ggagaagcgt accacaaatg atgcggtttt ttatccagtt        480
ttttgtttaa tgaacaaggt aaattacgag ataatatttg aagaaaacaa taaagtagag        540
atggatttcc atatcctctt tagtagcggt ttttatctgt aaggtttatt aataattaaa        600
taaataggcg ggatagttat atatagctta ttaatgaaag aatatgatta ttaatttagt        660
attatatttt aatattaaaa agaagatatg aaataattat tcataccttc caccttacaa        720
taattagttt tcaatcgaat attaagatta ttagtagtct taaaagttaa gacttcctta        780
tattaatgac ctaatttatt atttgcctca tgaattatct ttttatttct ttgatatgtc        840
ccaaaccaca tcgtgatata cactacaata aatattatga tgaaactaat aatattctca        900
aagttcagat ggaaccaacc tgctagaata gcgagtggga agaataggat tatcatcaat        960
ataaagtgaa ctacagtctg ttttgttata ctccaatcgg tatctgtaaa tatcaaatta       1020
ccataagtaa acaaaattcc aatcaatgcc catagtgcta cacatattag cataataacc       1080
gcttcattaa agttttcata ataaatttta cccataaaag aatctggata tagtggtaca       1140
tatttatccc ttgaaaaaaa taagtgaagt aatgacagaa atcataagac cagtgaacgc       1200 accttttga acagcgtgga ataatttttt catagtgaga tggaccattc catttgtttc       1260
taacttcaag tgatcaatgt aatttagatt gataatttct gattttgaaa tacgcacgaa       1320
tattgaaccg acaagctctt caatttggta aagtcgctga taaagttta aagctttatt       1380 attcattgtt atcgcatacc tgtttatctt ctactatgaa ctgtgcaatt tgttctagat       1440
caattgggta acatgatgg ttctgttgca aagtaaaaaa atatagctaa ccactaattt       1500
atcatgtcag tgttcgctta acttgctagc atgatgctaa tttcgtggca tggcgaaaat       1560
ccgtagatct gatgagacct gcggttcttt ttatatagag cgtaaataca ttcaatacct       1620
tttaaagtat tctttgctgt attgatactt tgataccttg tctttcttac tttaatatga       1680
cggtgatctt gctcaatgag gttattcaaa tatttcgatg tacaatgaca gtcaggttta       1740
agtttaaaag ctttaattac tttagccatt gctaccttcg ttgaaggtgc ctgatctgta       1800
attacctttt gaggtttacc aaattgttta atgagacgtt taataaacgc atatgctgaa       1860
tgattatctc gttgcttacg caaccaaata tctaatgtat gtccctctgc atcaatggca       1920
cgatataaat agctccattt tccttttatt ttgatgtacg tctcatcaat acgccatttg       1980
taataagctt ttttatgctt tttcttccaa atttgatata aaattggggc atattcttga       2040
acccaacggt agaccgttga atgatgaacg tttacaccac gtccccttaa tatttcagat       2100
atatcacgat aactcaatgc atatcttaga tagtagccaa cggctacagt gat             2153
```

<210> SEQ ID NO 93
<211> LENGTH: 1696
<212> TYPE: DNA
<213> ORGANISM: Staphylococcus aureus

<400> SEQUENCE: 93

```
aaagagaaat attggaagca agccatagca gaatatgaaa aacgtttagg cccatacacc         60
aagatagaca tcatagaagt tccagacgaa aaagcaccag aaaatatgag tgacaaagaa        120
attgagcaag taaagaaaaa agaaggccaa cgaatactag ccaaaatcaa accacaatcc        180
acagtcatta cattagaaat acaaggaaag atgctatctt ccgaaggatt ggcccaagaa        240
```

```
ttgaaccaac gcatgaccca agggcaaagc gactttgttt tcgtcattgg cggatcaaac    300
ggcctgcaca aggacgtctt acaacgcagt aactacgcac tatcattcag caaaatgaca    360
ttcccacatc aaatgatgcg ggttgtgtta attgaacaag tgtacagagc atttaagatt    420
atgcgaggag aagcatatca taaatgatgc ggttatttca gccgtaattt tataatataa    480
agcagagttt attaaatttt aatgattact ttttattaag aattaattct agttgatata    540
ttataatgtg aaacacaaaa taataatttg taattgttag tttataggca tctgtatttg    600
gaattttttg tagactattt aaaaaatagt gtatataagt attgagttca tgtattaact    660
gtcttttttc atcgttcatc aagtataagg atgtagagat ttgttggata atttcttcgg    720
atgttttaa aattatcatt aaattagatg gtatctgatc ttgagttttg tttttagtgt    780
atgtatattt taaaaaattt ttgattgttg ttatttgact ctcttttaat ttgacaccct    840
catcaataaa tgtgttaaat atatcttcat ttgtacttaa atcatcaaaa tttgccaaca    900
aatatttgaa cgtctctaaa tcattatgtt tgagttccgt tttgctattc cataattcca    960
aaccatttgg tagaaagccc aagctgtgat tttgatctcc ccatatagct gaatttaaat   1020
cagtgagttg attaattttt tcaacacaga aatgtaattt tggaatgagg aatcgaagtt   1080
gttcttctac ttgctgtact tttcttttgt tttcaataaa atttctacac catactgtta   1140
tcaaaccgcc aattattgtg cacaatcctc caatgattgt agataaaatt gacaatatat   1200
tacacacctt tcttagaggt ttattaacat ctatttttga atttaaaatt attactttgg   1260
tagcgttata acctatttaa cagattagag aaaaattgaa tgatcgattg aagaatttcc   1320
aaaataccgt cccatatgcg ttgaaggaga tttctatttt cttctgtatt caaatctttg   1380
gctttatcct ttgctttatt caataaatca tctgagtttt tttcaatatt ttttaataca   1440
tctttggcat tttgtttaaa tactttagga tcggaagtta gggcattaga gtttgccaca   1500
ttaatcatat tattattaat catttgaatt tgattatctg ataatatctc tgataaccta   1560
cgctcatcga ggactttatt aacagtgtct tcaacttgtt gttgtgtgat tgtttatct   1620
tgattttgtt taatatctgc aagttgttct ttaatatctg ctatagaagc atttaaagct   1680
tcatctgaat acccat                                                   1696
```

<210> SEQ ID NO 94
<211> LENGTH: 991
<212> TYPE: DNA
<213> ORGANISM: Staphylococcus aureus

<400> SEQUENCE: 94

```
accatttag ctgtagggaa actaaaagag aaatactgga agcaagccat agcagaatat     60
gaaaaacgtt taggcccata caccaagata gacatcatag aagttccaga cgaaaaagca    120
ccagaaaata tgaactacaa agaaattgag caagtaaaag aaaaagaagg ccaacgaata    180
ctagccaaaa tcaaaccaca atcaacagtc attacattag aaatacaagg aaagatgcta    240
tcttccgaag gattggccca agaattgaac caacgcatga cccaagggca aagcgacttt    300
gtattcgtca ttggcggatc aaacggcctg cacaaggacg tcttacaacg cagtaactac    360
gcactatcat tcagcaaaat gacattccca catcaaatga tgcgggttgt gttaattgaa    420
caagtgtaca gagcatttaa gattatgcga ggagaagcgt atcataagtg atggtaaaaa    480
atatgagtaa gtagatgaag agtgaaaatc agattaatta ataataatgt atcaaattta    540
aataaagggg ttttaagta tgaatttaag aggtcatgaa aatagactta aatttcatgc    600
gaaatatgat gtgacaccta tatcacattt aaaattatta gaaggtcaaa agaaagacgg    660
```

```
tgaaggcggc atactgacag atagctatta ctgtttttca tacagcttaa aaggtaattc    720
taaaaaagtt ttaggtacgt ttaattgtgg ttatcatatt gctgaagatt tactaaaatt    780
atcaaatcaa gataaattac ctttatttaa cccgtttaaa gtaattaatg aaggtaatca    840
attgcagggc gtaacgaata aaggtaattt aaatattaat aggcaaagaa acagtataa    900 tgaagtggct ttacagcttt caaatgctat taatttaatc ataatttgtt atgaggataa    960
tattaaagaa ccactttcaa cgataaaata c                                    991
```

<210> SEQ ID NO 95
<211> LENGTH: 1108
<212> TYPE: DNA
<213> ORGANISM: Staphylococcus aureus

<400> SEQUENCE: 95

```
accattttag ctgtagggaa actaaaagag aaatattgga agcaagccat agcagaatat     60
gaaaaacgtt taggcccata caccaagata gacatcatag aagttccaga cgaaaaagca    120
ccagaaaata tgagcgacaa agaaattgag caagtaaaag aaaagaagg ccaacgaata     180 ctagccaaaa tcaaaccaca atccacagtc attacattag aaatacaagg aaagatgcta    240
tcttccgaag gattggccca agaattgaac caacgcatga cccagggca aagcgacttt     300 gtattcgtca ttggcggatc aaacggcctg cacaaggacg tcttacaacg cagtaactat    360
gcactatcat ttagcaaaat gacattccca catcaaatga tgcgggttgt gttaattgaa    420
caagtgtata gagcatttaa gattatgcgt ggagaagcgt accacaaata aaactaaaaa    480
atatgagaaa attattaaat tagctcaaat ctttgaagaa taaaaagtga atattaagtt    540
tgataattta ggtacaagta aagattaaga atttccatta tttaatacat ggtgtgtaaa    600
tcgacttctt tttgtattag atgtttgcag taagcgatgt aaagaagatg ctaataaata    660
tgtgaggaat gattacgata ctagataagc ggctaatgaa atttttttaaa gtacatatat    720 agacatattt ttcatttagt aaaattttga atttcacttt gctaagacta gtgtctagaa    780
atttataatg atttattaac acctatttga aacttaagta taataaatga ttcggatttt    840
atttttaata aagacaaact tgaacgtagc aaagtagttt ttatgataaa taataagttt    900
taataatgtg acgcttttat ataagcacat tattatgaac aatgtgaatt gagcatctac    960
aattacatta ataaatatat aaatgatgat ttaaattcac atatatttat aatacacata   1020
ctatatgaaa gttttgatta tccgaataaa tgctaaaatt aataaaataa ttaaaggaat   1080
catacttatt atacgtatac gtttagct                                       1108
```

<210> SEQ ID NO 96
<211> LENGTH: 1530
<212> TYPE: DNA
<213> ORGANISM: Staphylococcus aureus

<400> SEQUENCE: 96

```
ttagctgtag ggaaactaaa agagaaatat tggaagcaag ccatagcaga atatgaaaaa     60
cgtttaggcc catacaccaa gatagacatc atagaagttc cagacgaaaa agcaccagaa    120
aatatgagcg acaaagaaat tgagcaagta aagaaaaag aaggccaacg aatactagcc    180
aaaatcaaac cacaatccac agtcattaca ttagaaatac aaggaaagat gctatcttcc    240
gaaggattgg cccaagaatt gaaccaacgc atgacccaag ggcaaagcga ctttgtattc    300
gtcattggcg gatcaaacgg cctgcacaag gacgtcttac aacgcagtaa ctatgcacta    360
```

```
tcatttagca aaatgacatt cccacatcaa atgatgcggg ttgtgttaat tgaacaagtg      420
tatagagcat ttaagattat gcgtggagaa gcatatcata aatgatgcgg tttttttcagc     480 cgcttcataa agggggtga tcatatcgga acgtatgagg tttatgagaa ttgctgctat       540
gtttttatga agcgtatcat aaatgatgca gttttgata atttttttctt tatcagagat      600 tttactaaaa atcccctcaa agtttgtttt tttcaacttc aactttgaag ggaataaata      660
aggaacttat ttatatttat cctttatctc attaatatct attttttat taataatatt       720 ataaatatta aattctttag aaaagtcact atcactctta ttcttcatac taaacgttat      780
taatctaata atatcagcta ctattttctt aaattctatt gcatcttctt ttttataagt      840
agcgcctgta tgaacaattt tatttctcat accatagtaa tctttcatat atttttttac     900
acaattttta atttcattag aattatccaa atctagatta tcaattgtct ttaataaatg      960
atcattaaca acattagcat acccacatcc aagcttcttt tttatctctt catcacttaa     1020
attttcatct aatttataat atctttctaa aaaatttgtg ataaaaactt ctaatgcagt     1080
ctgaatttgt acaattgcta aattatagtc agatttataa aaagaacgtt cacctttttct    1140 catagccaaa acataaatat tgctaggatg attattgaaa atattataat tttttttaat    1200
atttaataaa tcacttttttt tgatagatga atactgatct tcttctatct ttccaggcat    1260
gtcaatcatg aaaatactca tctctttttat atttccatct atagtatata ttatataata   1320
tggaatactt aatatatccc ctaatgatag ctggtatata ttatgatact gatatttaac    1380
gctaataatt ttaataagat tatttagaca attaaattgc ttattaaaaa ttttcgttag    1440
actattactt ttctttgatt ccctagaagt agaatttgat ttcaattttt taaactgatt    1500
gtgcttgatt attgaagtta tttcaacata                                      1530

<210> SEQ ID NO 97
<211> LENGTH: 1256
<212> TYPE: DNA
<213> ORGANISM: Staphylococcus aureus

<400> SEQUENCE: 97
gctgtaggga aactaaaaga gaaatattgg aagcaagcca tagcagaata tgaaaaacgt      60
ttaggcccat acaccaagat agacatcata gaagttccag acgaaaaagc accagaaaat    120
atgagcgaca aagaaattga gcaagtaaaa gaaaaagaag gccaacgaat actagccaaa    180
attaaaccac aatccacagt cattacatta gaaatacaag gaaagatgct atcttccgaa    240
ggattggccc aagaattgaa ccaacgcatg acccaagggc aaagcgactt tgtattcgtc    300
attggcggat caaacggcct gcacaaggac gtcttacaac gcagtaacta cgcactatca    360
ttcagcaaaa tgcattccc acatcaaatg atgcgggttg tgttaattga gcaagtgtat      420
agagcattta agattatgcg tggagaagca tatcataaat gatgcggttt tttcagccgc    480
ttcataaagg gatttgaat gtatcagaac atatgaggtt tatgtgaatt gctgttatgt    540
ttttaagaag catatcataa gtgatgcggt tttattaat tagttgctaa aaatgaagt      600 atgcaatatt aattattatt aaattttgat atatttaaag aaagattaag tttagggtga    660
atgaatggct tatcaaagtg aatatgcatt agaaaatgaa gtacttcaac aacttgagga    720
attgaactat gaaagagtaa atatacataa tattaaatta gaattaatg aatatctcaa      780 agaactagga gtgttgaaaa atgaataagc agacaaatac tccagaacta agatttccag    840
agtttgatga ggaatggaaa aaaaggaaat taggtgaagt agtaaattat aaaaatggtg    900
gttcatttga aagtttagtg aaaaaccatg gtgtatataa actcataact cttaaatctg    960
```

-continued

```
ttaatacaga aggaaagttg tgtaattctg gaaaatatat cgatgataaa tgtgttgaaa    1020
cattgtgtaa tgatacttta gtaatgatac tgagcgagca agcaccagga ctagttggaa    1080
tgactgcaat tatacctaat aataatgagt atgtactaaa tcaacgagta gcagcactag    1140
tgcctaaaca atttatagat agtcaatttc tatctaagtt aattaataga aaccagaaat    1200
atttcagtgt gagatctgct ggaacaaaag tgaaaaatat ttctaaagga catgta       1256
```

SEQUENCES FOR DETECTION AND IDENTIFICATION OF METHICILLIN-RESISTANT *STAPHYLOCOCCUS AUREUS* (MRSA) OF MREJ TYPES XI TO XX

CROSS-REFERENCE TO RELATED APPLICATIONS

This application is a continuation-in-part of application Ser. No. 11/248,438, filed Oct. 11, 2005.

REFERENCE TO SEQUENCE LISTING

The present application is being filed along with a Sequence Listing in electronic format. The Sequence Listing was updated by a file entitled 2012_10_12_GENOM.057CP1.txt, created Oct. 12, 2012, which is 193 KB in size. The information in the electronic format of the Sequence Listing is incorporated herein by reference in its entirety.

BACKGROUND OF THE INVENTION

Field of the Invention

The present invention relates to novel SCCmec right extremity junction sequences for the detection of methicillin-resistant *Staphylococcus aureus*, and uses thereof for diagnostic and/or epidemiological purposes.

Description of the Related Art

The coagulase-positive species *Staphylococcus aureus* is well documented as a human opportunistic pathogen (Murray et al. Eds, 1999, Manual of Clinical Microbiology, 7th Ed., ASM Press, Washington, D.C.). Nosocomial infections caused by *S. aureus* are a major cause of morbidity and mortality. Some of the most common infections caused by *S. aureus* involve the skin, and they include furuncles or boils, cellulitis, impetigo, and postoperative wound infections at various sites. Some of the more serious infections produced by *S. aureus* are bacteremia, pneumonia, osteomyelitis, acute endocarditis, myocarditis, pericarditis, cerebritis, meningitis, scalded skin syndrome, and various abcesses. Food poisoning mediated by staphylococcal enterotoxins is another important syndrome associated with *S. aureus*. Toxic shock syndrome, a community-acquired disease, has also been attributed to infection or colonization with toxigenic *S. aureus*.

Methicillin-resistant *S. aureus* (MRSA) emerged in the 1980s as a major clinical and epidemiologic problem in hospitals (Oliveira et al., 2002, Lancet Infect Dis. 2:180-9). MRSA are resistant to all β-lactams including penicillins, cephalosporins, carbapenems, and monobactams, which are the most commonly used antibiotics to cure *S. aureus* infections. MRSA infections can only be treated with more toxic and more costly antibiotics, which are normally used as the last line of defense. Since MRSA can spread easily from patient to patient via personnel, hospitals over the world are confronted with the problem to control MRSA. Consequently, there is a need to develop rapid and simple screening or diagnostic tests for detection and/or identification of MRSA to reduce its dissemination and improve the diagnosis and treatment of infected patients.

Methicillin resistance in *S. aureus* is unique in that it is due to acquisition of DNA from other coagulase-negative staphylococci (CNS), coding for a surnumerary β-lactam-resistant penicillin-binding protein (PBP), which takes over the biosynthetic functions of the normal PBPs when the cell is exposed to β-lactam antibiotics. *S. aureus* normally contains four PBPs, of which PBPs 1, 2 and 3 are essential. The low-affinity PBP in MRSA, termed PBP 2a (or PBP2'), is encoded by the choromosomal mecA gene and functions as a β-lactam-resistant transpeptidase. The mecA gene is absent from methicillin-sensitive *S. aureus* but is widely distributed among other species of staphylococci and is highly conserved (Ubukata et al., 1990, Antimicrob. Agents Chemother. 34:170-172).

Nucleotide sequence determination of the DNA region surrounding the mecA gene from *S. aureus* strain N315 (isolated in Japan in 1982), led to the discovery that the mecA gene is carried by a novel genetic element, designated staphylococcal cassette chromosome mec (SCCmec), which is inserted into the chromosome. SCCmec is a mobile genetic element characterized by the presence of terminal inverted and direct repeats, a set of site-specific recombinase genes (ccrA and ccrB), and the mecA gene complex (Ito et al., 1999, Antimicrob. Agents Chemother. 43:1449-1458; Katayama et al., 2000, Antimicrob. Agents Chemother. 44:1549-1555). SCCmec is precisely excised from the chromosome of *S. aureus* strain N315 and integrates into a specific *S. aureus* chromosomal site in the same orientation through the function of a unique set of recombinase genes comprising ccrA and ccrB. Cloning and sequence analysis of the DNA surrounding the mecA gene from MRSA strains NCTC 10442 (the first MRSA strain isolated in England in 1961) and 85/2082 (a strain from New Zealand isolated in 1985) led to the discovery of two novel genetic elements that shared similar structural features of SCCmec. The three SCCmec have been designated type I (NCTC 10442), type II (N315) and type III (85/2082) based on the year of isolation of the strains (Ito et al., 2001, Antimicrob. Agents Chemother. 45:1323-1336). Hiramatsu et al. have found that the SCCmec DNAs are integrated at a specific site in the chromosome of methicillin-sensitive *S. aureus* (MSSA). The nucleotide sequence of the regions surrounding the left and right boundaries of SCCmec DNA (i.e. attL and attR, respectively), as well as those of the regions around the SCCmec DNA integration site (i.e. attBscc which is the bacterial chromosome attachment site for SCCmec DNA), were analyzed. Sequence analysis of the attL, attR attBscc sites revealed that attBscc is located at the 3' end of a novel open reading frame (ORF), orfX. orfX encodes a putative 159-amino acid polypeptide that exhibits sequence homology with some previously identified polypeptides of unknown function (Ito et al., 1999, Antimicrob. Agents Chemother. 43:1449-1458). Two new types of SCCmec, designated type IV and type V were recently described (Ma et al., 2002, Antimicrob. Agents Chemother. 46:1147-1152, Ito et al., 2004, Antimicrob Agents Chemother. 48:2637-2651, Oliveira et al., 2001, Microb. Drug Resist. 7:349-360). Sequence analysis of the right extremity of the new SCCmec type IV from *S. aureus* strains CA05 and 8/6-3P revealed that the sequences were nearly identical over 2000 nucleotides to that of type II SCCmec of *S. aureus* strain N315 (Ma et al., 2002, Antimicrob. Agents Chemother. 46:1147-1152; Ito et al., 2001, Antimicrob. Agents Chemother. 45:1323-1336). To date, sequence data for the right extremity of the SCCmec type IV from *S. aureus* strains HDE288 and PL72 is not publicly available (Oliveira et al., 2001, Microb. Drug Resist. 7:349-360).

Methods to detect and identify MRSA based on the detection of the mecA gene and *S. aureus*-specific chromosomal sequences have been described. (Saito et al., 1995, J. Clin. Microbiol. 33:2498-2500; Ubukata et al., 1992, J. Clin. Microbiol. 30:1728-1733; Murakami et al., 1991, J. Clin. Microbiol. 29:2240-2244; Hiramatsu et al., 1992, Microbiol. Immunol. 36:445-453). However, because the mecA gene is widely distributed in both *S. aureus* and coagulase-negative staphylococci, these methods are not always capable of discriminating MRSA from methicillin-resistant CNS (Suzuki et al., 1992, Antimicrob. Agents. Chemother. 36:429-434). To address this problem, Hiramatsu et al. developed a PCR-based assay specific for MRSA that utilizes primers that hybridize to the right extremities of the 3 types of SCCmec DNAs in combination with primers specific to the *S. aureus* chromosome, which corresponds to the nucleotide sequence on the right side of the SCCmec integration site (U.S. Pat. No. 6,156,507, hereinafter the "507 patent"). Nucleotide sequences surrounding the SCCmec integration site in other staphylococcal species (e.g., *S. epidermidis* and *S. haemolyticus*) are different from those found in *S. aureus*. Therefore, this PCR assay is specific for the detection of MRSA.

The PCR assay described in the "507 patent" also led to the development of "MREP typing" (mec right extremity polymorphism) of SCCmec DNA (Ito et al., 2001, Antimicrob. Agents Chemother. 45:1323-1336; Hiramatsu et al., 1996, J. Infect. Chemother. 2:117-129). The MREP typing method takes advantage of the fact that the nucleotide sequences of the three MREJ types differ at the right extremity of SCCmec DNAs adjacent to the integration site among the three types of SCCmec. Compared to type I, type III has a unique nucleotide sequence while type II has an insertion of 102 nucleotides to the right terminus of SCCmec. The MREP typing method described by Hiramatsu et al. uses the following nomenclature: SCCmec type I is MREP type i, SCCmec type II is MREP type ii, and SCCmec type III is MREP type iii.

Because SCCmec types II and IV have the same nucleotide sequence to the right extremity, the MREP typing method described above cannot differentiate the new SCCmec type IV described by Hiramatsu et al. (Ma et al., 2002, Antimicrob. Agents Chemother. 46:1147-1152) from SCCmec type II.

The phrase MREJ refers to the mec right extremity junction «mec right extremity junction». MREJs are approximately 1 kilobase (kb) in length and include sequences from the SCCmec right extremity as well as bacterial chromosomal DNA to the right of the SCCmec integration site. Strains that were classified as MREP types i-iii correspond to MREJ types i-iii. MREJ types iv, v, vi, vii, viii, ix, and x have been previously characterized (Huletsky et al., 2004, J Clin. Microbiol. 42:1875-1884; International Patent Application PCT/CA02/00824).

The embodiments described herein relate to the generation of SCCmec right extremity junction sequence data that enables the detection of more MRSA strains in order to improve NAT assays for detection of MRSA. There is a need for developing more ubiquitous primers and probes for the detection of most MRSA strains around the world.

SUMMARY OF THE INVENTION

Provided herein are specific, ubiquitous and sensitive methods and compositions for determining the presence and/or amount of nucleic acids from all methicillin-resistant *Staphylococcus aureus* (MRSA) strains. Methods, compositions and kits are disclosed that enable the detection and quantification of novel MREJ types xi-xx.

Some aspects relate to a method to detect the presence of an MRSA bacterium in a sample comprising bacterial nucleic acids. MRSA strains have SCCmec nucleic acid insert comprising a mecA gene. The SCCmec insert renders the MRSA bacterium resistant to methicillin. The SCCmec is inserted into the bacterial DNA at the 3' end of the open reading frame orfX, creating a polymorphic right extremity junction (MREJ). At least one primer and/or probe specific for MRSA strains is provided, wherein the primer or probe hybridizes to a polymorphic MREJ nucleic acid of MREJ types xi to xx. The primer(s) and/or probe(s) are annealed with the nucleic acids of the sample. Annealed primer and/or probe indicates the presence of MREJ.

In preferred embodiments, more than one primer and/or probe is provided. The primers and/or probes can anneal to the MREJ nucleic acids under substantially the same annealing conditions. The primers and/or probes can be at least 10 nucleotides, 12 nucleotides, 14 nucleotides, 16 nucleotides, 18 nucleotides, 20 nucleotides, 25 nucleotides, or 30 nucleotides in length. The probes and primers can be used together in the same physical enclosure or in different physical enclosures.

In some embodiments, the primers and/or probes anneal with any one of the nucleic acids of SEQ ID NOs: 15, 16, 17, 18, 19, 20, 21, 25, 26, 39, 40, 41, 42, 55, and 56. In some embodiments, the primers and/or probes altogether can anneal with MREJ types xi to xx, such as SEQ ID NOs: 15, 16, 17, 18, 19, 20, 21, 25, 26, 39, 40, 41, 42, 55, and 56. For example, in some embodiments, the primers and/or probes listed in Table 4 are used to detect MRSA bacteria comprising the following MREJ nucleic acid:

TABLE 4

| Primer/Probe SEQ ID NOs: | To Identify MREJ type |
|---|---|
| 30, 31, 32, 33, 34, 44, 45, 76 | xi |
| 30, 31, 32, 33, 35, 44, 45, 62 | xii |
| 29, 30, 31, 32, 33, 44, 45, 76 | xiii |
| 29, 30, 31, 32, 33, 44, 45, 59 | xiv |
| 24, 30, 31, 32, 33, 4, 45, 62 | xv |
| 36, 44 | xvi |
| 4, 30, 31, 32, 33, 44, 45, 62 | xvii |
| 7, 30, 31, 32, 33, 44, 45, 59 | xviii |
| 9, 30, 31, 32, 33, 44, 45, 59 | xix |
| 8, 30, 31, 32, 33, 44, 45, 59 | xx |

In some embodiments, primers and/or probes are provided that anneal under stringent conditions to more than one MREJ type strain. For example, in preferred embodiments, SEQ ID NOs: 31, 32, 33 are provided for the detection of MREJ types xi to xv and xvii to xx.

In further embodiments primers and/or probes are provided in pairs for the detection of at least one MRSA having MREJ of types xi to xx. Accordingly, in some embodiments, at least one pair of oligonucleotides selected from the group consisting of SEQ ID NOs: 34/45, 34/30, 34/76, and 34/44 are provided for detection of MREJ type xi. In other embodiments, at least one pair of oligonucleotides selected from the group consisting of SEQ ID NOs: 35/45, 35/30, 35/62, and 35/44 are provided for detection of MREJ type xii. In yet other embodiments, at least one pair of oligonucleotides selected from the group consisting of SEQ ID NOs: 29/45, 29/30, 29/76, and 29/44 is provided for detection of MREJ type xiii. In still other embodiments, at least one pair of oligonucleotides selected from the group consisting of SEQ ID NOs: 29/45, 29/30, 29/59, and 29/44 is provided for detection of MREJ type xiv. In other embodiments, at least one pair of oligonucleotides selected from the group consisting of SEQ ID NOs: 24/45, 24/30, 24/62, and 24/44 is provided for detection of MREJ type xv. In yet other embodiments, the oligonucleotides of SEQ ID NOs: 36 and 44 are provided for detection of MREJ type xvi. In still other embodiments, at least one pair of oligonucleotides selected from the group consisting of SEQ ID NOs: 4/45, 4/30, 4/62, and 4/44 is provided for the detection of MREJ type xvii. In yet other embodiments, at least one pair of oligonucleotides selected from the group consisting of 7/45, 7/30, 7/59 and 7/44 is provided for the detection of MREJ type xviii. In other embodiments, at least one pair of oligonucleotides selected from the group consisting of 9/45, 9/30, 9/59 and 9/44 is provided for the detection of MREJ type xix. In yet other embodiments, at least one pair of oligonucleotides selected from the group consisting of SEQ ID NOs: 8/45, 8/30, 8/59, and 8/44 is provided for the detection of MREJ type xx.

In some embodiments, at least two pairs of primers are provided for the detection of more than one MREJ type.

In other preferred embodiments, the primers and/or probes listed in Table 5 are provided together to detect MRSA bacteria comprising the following MREJ nucleic acid:

TABLE 5

| Primer/Probe SEQ ID NOs: | To Identify MREJ type |
|---|---|
| 51, 30, 31, 32, 33 | xi |
| 52, 30, 31, 32, 33 | xii |
| 29, 30, 31, 32, 33 | xiii |
| 29, 30, 31, 32, 33 | xiv |
| 24, 30, 31, 32, 33 | xv |
| 36, 44 | xvi |
| 4, 30, 31, 32, 33 | xvii |
| 7, 30, 31, 32, 33 | xviii |
| 9, 30, 31, 32, 33 | xix |
| 8, 30, 31, 32, 33 | xx |

In further embodiments, the methods described above further comprise providing primers and/or probes specific for a determined MREJ type, and detecting an annealed probe or primer as an indication of the presence of a determined MREJ type.

In yet other embodiments, primers and/or probes specific for the SEQ ID NOs listed in Table 6 are provided to detect MRSA bacteria comprising the following MREJ nucleic acid:

TABLE 6

| Primer/Probe SEQ ID NOs: | To Identify MREJ type |
|---|---|
| 17, 18, 19 | xi |
| 20 | xii |
| 15, 25, 26 | xiii |
| 16 | xiv |
| 56 | xv |
| 21 | xvi |
| 55 | xvii |
| 39, 40 | xviii |
| 41 | xix |
| 42 | xx |

In some embodiments, the primers are used in an amplification reaction, such as polymerase chain reaction (PCR) and variants thereof such as nested PCR and multiplex PCR, ligase chain reaction (LCR), nucleic acid sequence-based amplification (NABSA), self-sustained sequence replication (3SR), strand displacement amplification (SDA), branched DNA signal amplification (bDNA), transcription-mediated amplification (TMA), cycling probe technology (CPT), solid-phase amplification (SPA), nuclease dependent signal amplification (NDSA), rolling circle amplification, anchored strand displacement amplification, solid phase (immobilized) rolling circle amplification, Q beta replicase amplification and other RNA polymerase medicated techniques.

In preferred embodiments, PCR is used to amplify nucleic acids in the sample.

In other embodiments, oligonucleotides of at least 10, 12, 14, 16, 18, 20, 25, or 30 nucleotides in length which hybridize under stringent conditions with any of nucleic acids of SEQ ID NOs: 15, 16, 17, 18, 19, 20, 21, 25, 26, 39, 40, 41, 42, 55, and 56, and which hybridize with one or more MREJ of types selected from xi to xx are also provided.

In other embodiments, primer and/or probe pairs are provided for the detection of MRSA of all of types xi to xx. For example, in certain embodiments, the primer pairs (or probes) listed in Table 7 are provided:

TABLE 7

| Primer/Probe SEQ ID NOs: | To Identify MREJ type: |
|---|---|
| 34/45, 34/30, 34/76, 34/44 | xi |
| 35/45, 35/30, 35/62, 35/44 | xii |
| 29/45, 29/30, 29/76, 29/44 | xiii |
| 29/45, 29/30, 29/59, 29/44 | xiv |
| 24/45, 24/30, 24/62, 24/44 | xv |
| 36/44 | xvi |
| 4/45, 4/30, 4/62, 4/44 | xvii |
| 7/45, 7/30, 7/59, 7/44 | xviii |
| 9/45, 9/30, 9/59, 9/44 | xix |
| 8/45, 8/30, 8/59, 8/44 | xx |

In further embodiments of the method described above, internal probes having nucleotide sequences defined in any one of SEQ ID NOs: 31, 32, and 33 are provided.

In still other embodiments, primers and/or probes used detection of MREJ types xi to xx are used in combination with primers and/or probes capable of detecting MRSA of MREJ types i to x, such as for example those primers and or probes disclosed in co-pending International Patent Application PCT/CA02/00824.

Other aspects of the invention relate to nucleotide sequences comprising at least one of the nucleic acids of SEQ ID NOs: 15, 16, 17, 18, 19, 20, 21, 25, 26, 39, 40, 41, 42, 55, and 56, or the complement thereof. Further embodiments relate to fragments of the nucleic acids of SEQ ID NOs: 15, 16, 17, 18, 19, 20, 21, 25, 26, 39, 40, 41, 42, 55, and 56, wherein the fragments comprise at least 30, 50, 100, 150, 200, 300, or 500 consecutive nucleotides of the nucleic acids of SEQ ID NOs: 15, 16, 17, 18, 19, 20, 21, 25, 26, 39, 40, 41, 42, 55, and 56, or the complements thereof. Further aspects relate to vectors comprising the nucleic acid sequences of SEQ ID NOs: 15, 16, 17, 18, 19, 20, 21, 25, 26, 39, 40, 41, 42, 55, and 56, as host cells, such as *E. coli* host cells, comprising vectors comprising the nucleic acid sequences of SEQ ID NOs: 15, 16, 17, 18, 19, 20, 21, 25, 26, 39, 40, 41, 42, 55, and 56.

Still other aspects relate to oligonucleotides that are at least 10, 12, 14, 16, 18, 20, 25 or 30 nucleotides in length that anneal to any one of SEQ ID NOs: 15, 16, 17, 18, 19, 20, 21, 25, 26, 39, 40, 41, 42, 55, and 56. For example, some embodiments are oligonucleotides that comprise the sequence of any one of SEQ ID NOs: 31, 32, or 33. Yet other embodiments relate to oligonucleotides that are at least 10, 12, 14, 16, 18, 20, 25 or 30 nucleotides in length that anneal to only one of SEQ ID NOs: 15, 16, 17, 18, 19, 20, 21, 25, 26, 39, 40, 41, 42, 55, and 56.

Yet other aspects relate to kits comprising primers and/or probes. The primers and/or probes can be at least 10, 12, 14, 16, 18, 20, 25, or 30 nucleotides in length and hybridize with any one of the nucleic acids of MREJ type xi to xx. Further embodiments relate to kits comprising primers and/or probes that are at least 10, 12, 14, 16, 18, 20, 25, or 30 nucleotides in length and hybridize with any one of the nucleic acids of SEQ ID NOs: 15, 16, 17, 18, 19, 20, 21, 25, 26, 39, 40, 41, 42, 55, and 56. Some embodiments relate to kits that comprise primer pairs. For example, in some embodiments, the kits comprise the following primer pairs:

| Primer/Probe SEQ ID NOs: | To Identify MREJ type: |
|---|---|
| 34/45, 34/30, 34/76, 34/44 | xi |
| 35/45, 35/30, 35/62, 35/44 | xii |
| 29/45, 29/30, 29/76, 29/44 | xiii |
| 29/45, 29/30, 29/59, 29/44 | xiv |
| 24/45, 24/30, 24/62, 24/44 | xv |
| 36/44 | xvi |
| 4/45, 4/30, 4/62, 4/44 | xvii |
| 7/45, 7/30, 7/59, 7/44 | xviii |
| 9/45, 9/30, 9/59, 9/44 | xix |
| 8/45, 8/30, 8/59, 8/44 | xx |

BRIEF DESCRIPTION OF THE DRAWINGS

FIGS. 3A-3Q illustrate a multiple sequence alignment of 19 representative MREJ types i to ix and xi to xx comprising the orfX, the integration site, and the first 535 nucleotides of the SSCmec right extremity. MREJ types i to ix sequences are from co-pending International Patent Application PCT/CA02/00824, and correspond to SEQ ID NO: 89 (mrej_i), SEQ ID NO: 90 (mrej_ii), SEQ ID NO. 91 (mrej_iii), SEQ ID NO: 92 (mrej_iv), SEQ ID NO: 93 (mrej_v), SEQ ID NO: 94 (mrej_vi), SEQ ID NO: 95 (mrej_vii), SEQ ID NO: 96 (mrej_viii), and SEQ ID NO: 97 (mrej_ix) respectively. SEQ ID NO: 18 corresponds to MREJ type xi, SEQ ID NO: 20 corresponds to MREJ type xii, SEQ ID NO: 15 corresponds to MREJ type xiii, SEQ ID NO: 16 corresponds to MREJ type xiv, SEQ ID NO: 56 corresponds to MREJ type xv, SEQ ID NO: 21 corresponds to MREJ type xvi, SEQ ID NO: 55 corresponds to MREJ type xvii, SEQ ID NO: 39 corresponds to MREJ type xviii, SEQ ID NO: 41 corresponds to MREJ type, and SEQ ID NO: 42 corresponds to MREJ type xx.

DETAILED DESCRIPTION OF THE INVENTION

Figure 1:
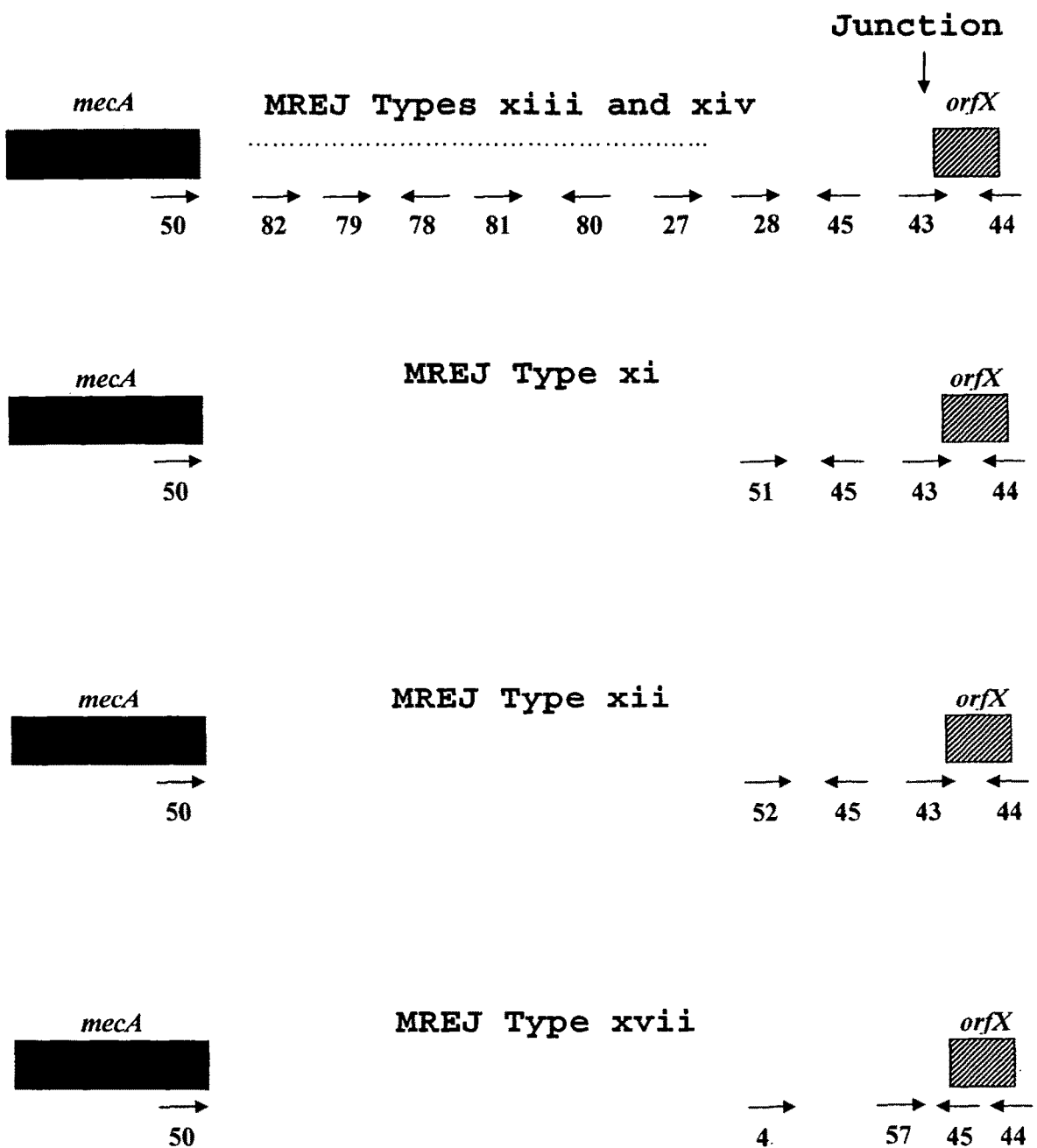
FIG. 1 depicts the SCCmec right extremity junctions. Shown are the positions and orientations of the primers used to sequence the novel MREJ types xi to xx. SEQ ID NOs.: 4, 24, 27-30, 36, 43-45, 50-57, 78-86 were used to sequence MREJ types xi, xii, xiii, xiv, xv, xvi, xvii, xviii, xix, and xx. Arrows and numbers below indicate the positions of primers and their respective SEQ ID NOs. Walk indicates the positions where the DNA Walking ACP (DW-ACP) primers from the DNA Walking SpeedUp Kit (Seegene, Del Mar, CA) have annealed on the SCCmec sequence.
Figure 1:
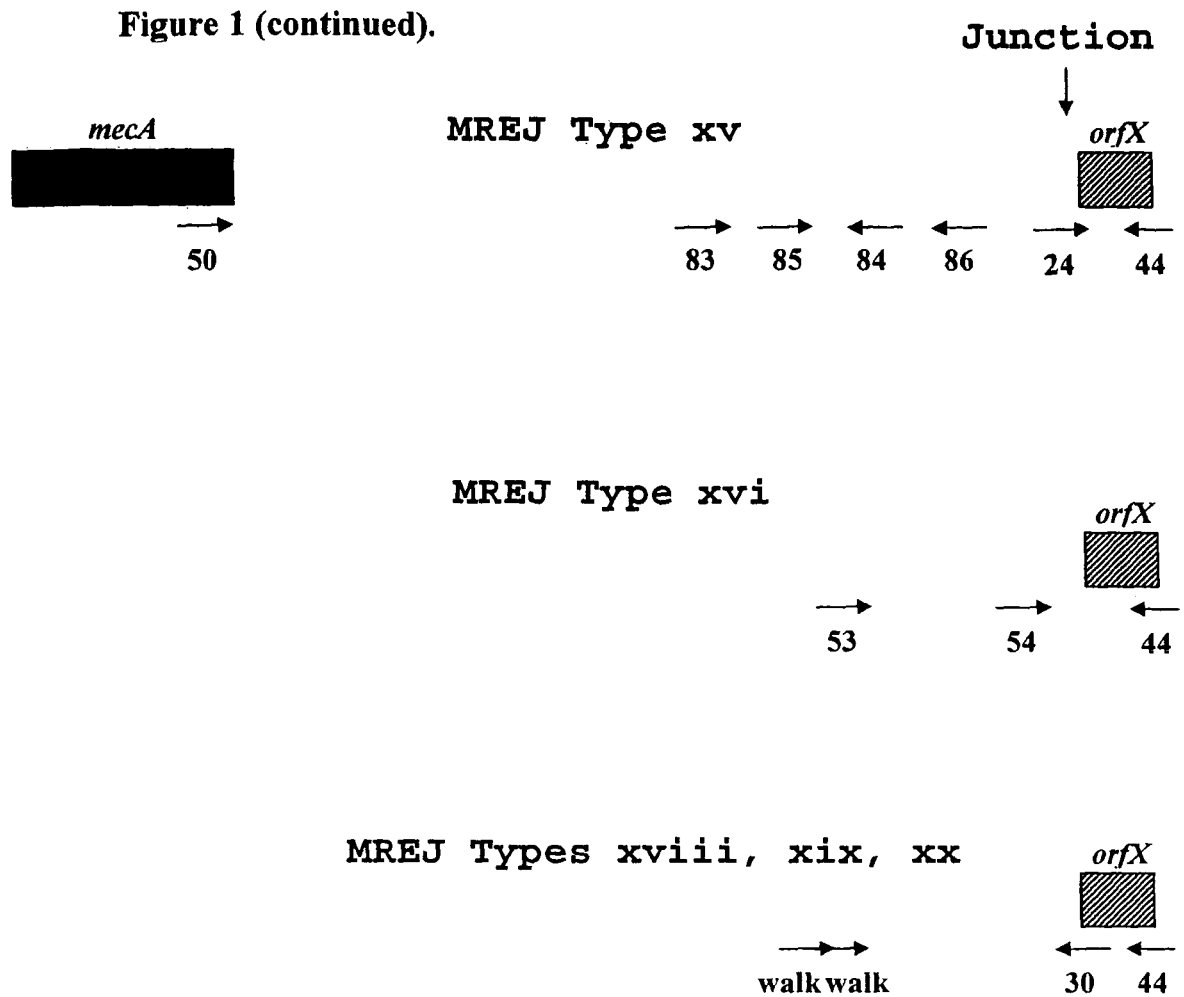

Methicillin-resistant *Staphylococcus aureus* (MRSA) pose a serious health threat to individuals and the need for rapid and simple methods for the detection, identification, and quantification of MRSA is readily apparent.

Disclosed herein are novel DNA sequences and DNA arrangements present in MRSA strains that allow for the detection of MRSA that were undetectable using previously available methods. The novel DNA sequences and DNA arrangements are present at the SCCmec region of MRSA DNA. MRSA strains comprise an SCCmec insert that comprises a mecA gene. The SCCmec is inserted into the bacterial DNA at the 3' end of the orfX open reading frame. The insertion of the SCCmec into the bacterial DNA creates a polymorphic right extremity junction, hereinafter referred to as MREJ standing for «mec right extremity junction». MREJ regions include sequences from the SCCmec right extremity, as well as chromosomal DNA adjacent to the right SCCmec integration site. Embodiments of the invention relate to the novel MREJ sequences and arrangements disclosed herein, which can be used as parental sequences from which primers and/or probes useful in the detection and identification of MRSA described below are derived. Other aspects of the invention relate to novel primers and/or probes derived from the novel MREJ sequences, as well as kits comprising primers and or probes that hybridize to MREJ types xi to xx, for the detection of MRSA.

Also disclosed herein are methods providing for the detection of the presence or absence of an MRSA strain in a sample that includes nucleic acids. At least one primer and/or probe that is specific for MRSA strains and that anneals to an MREJ nucleic acid of types xi to xx, disclosed herein, is provided. The primer(s) and/or probe(s) can be annealed to the nucleic acids of the sample. The detection of annealed primer(s) and/or probe(s) indicates the presence of an MRSA of the MREJ type that hybridizes to the primer(s) and/or probe(s).

Primers and Probes

As used herein, the terms "primer" and "probe" are not limited to oligonucleotides or nucleic acids, but rather encompass molecules that are analogs of nucleotides, as well as nucleotides. Nucleotides and polynucleotides, as used herein shall be generic to polydeoxyribonucleotides (containing 2-deoxy-D-ribose), to polyribonucleotides (containing D-ribose), to any other type of polynucleotide which is an N- or C-glycoside of a purine or pyrimidine base, and to other polymers containing nonnucleotidic backbones, for example, polyamide (e.g., peptide nucleic acids (PNAs) and polymorpholino (commercially available from the Anti-Virals, Inc., Corvallis, Oreg., as Neugene™ polymers), and other synthetic sequence-specific nucleic acid polymers providing that the polymers contain nucleobases in a configuration which allows for base pairing and base stacking, such as is found in DNA and RNA.

The terms nucleotide and polynucleotide include, for example, 3'-deoxy-2',5'-DNA, oligodeoxyribonucleotide N3'→P5' phosphoramidates, 2'-O-alkyl-substituted RNA, double- and single-stranded DNA, as well as double- and single-stranded RNA, DNA:RNA hybrids, and hybrids between PNAs and DNA or RNA. The terms also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with a halogen, an aliphatic group, or are functionalized as ethers, amines, or the like. Other modifications to nucleotides or polynucleotides involve rearranging, appending, substituting for, or otherwise altering functional groups on the purine or pyrimidine base which form hydrogen bonds to a respective complementary pyrimidine or purine. The resultant modified nucleotide or polynucleotide may form a base pair with other such modified nucleotidic units but not with A, T, C, G or U. For example, guanosine (2-amino-6-oxy-9-beta-D-ribofuranosyl-purine) may be modified to form isoguanosine (2-oxy-6-amino-9-beta-D-ribofuranosyl-purine). Such modification results in a nucleoside base which will no longer effectively form a standard base pair with cytosine. However, modification of cytosine (1-beta-D-ribofuranosyl-2-oxy-4-amino-pyrimidine) to form isocytosine (1-beta-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Mantsch et al. (1975) Biochem. 14:5593-5601, or by the method described U.S. Pat. No. 5,780,610 to Collins et al. The non-natural base pairs referred to as κ and π, may be synthesized by the method described in Piccirilli et al. (1990) Nature 343:33-37 for the synthesis of 2,6-diaminopyrimidine and its complement (1-methylpyrazolo[4,3]-pyrimidine-5,7-(4H,6H)-dione. Other such modified nucleotidic units which form unique base pairs have been described in Leach et al. (1992) J. Am. Chem. Soc. 114:3675-3683, or will be apparent to those of ordinary skill in the art.

Primers and/or probes can be provided in any suitable form, included bound to a solid support, liquid, and lyophilized, for example.

Specific binding or annealing of the primers and/or probes to nucleic acid sequences is accomplished through specific hybridization. It will be appreciated by one skilled in the art that specific hybridization is achieved by selecting sequences which are at least substantially complementary to the target or reference nucleic acid sequence. This includes base-pairing of the oligonucleotide target nucleic acid sequence over the entire length of the oligonucleotide sequence. Such sequences can be referred to as "fully complementary" with respect to each other. Where an oligonucleotide is referred to as "substantially complementary" with respect to a nucleic acid sequence herein, the two sequences can be fully complementary, or they may form mismatches upon hybridization, but retain the ability to hybridize under the conditions used to detect the presence of the MRSA nucleic acids.

A positive correlation exists between probe length and both the efficiency and accuracy with which a probe will anneal to a target sequence. In particular, longer sequences have a higher melting temperature ($T_m$) than do shorter ones, and are less likely to be repeated within a given target sequence, thereby minimizing promiscuous hybridization.

As used herein, "$T_m$" and "melting temperature" are interchangeable terms which refer to the temperature at which 50% of a population of double-stranded polynucleotide molecules becomes dissociated into single strands. Formulae for calculating the $T_m$ of polynucleotides are well known in the art. For example, the $T_m$ may be calculated by the following equation: $T_m=69.3+0.41\times.(G+C) \%-6-50/L$, wherein L is the length of the probe in nucleotides. The $T_m$ of a hybrid polynucleotide may also be estimated using a formula adopted from hybridization assays in 1 M salt, and commonly used for calculating $T_m$ for PCR primers: [(number of A+T)×2° C.+(number of G+C)×4° C.]. See, e.g., C. R. Newton et al. PCR, 2nd Ed., Springer-Verlag (New York: 1997), p. 24. Other more sophisticated computations exist in the art, which take structural as well as sequence characteristics into account for the calculation of $T_m$. A calculated $T_m$ is merely an estimate; the optimum temperature is commonly determined empirically.

Primer or probe sequences with a high G+C content or that comprise palindromic sequences tend to self-hybridize, as do their intended target sites, since unimolecular, rather than bimolecular, hybridization kinetics are generally favored in solution. However, it is also important to design a probe that contains sufficient numbers of G:C nucleotide pairings since each G:C pair is bound by three hydrogen bonds, rather than the two that are found when A and T (or A and U) bases pair to bind the target sequence, and therefore forms a tighter, stronger bond. Preferred G+C content is about 50%.

Hybridization temperature varies inversely with probe annealing efficiency, as does the concentration of organic solvents, e.g., formamide, which might be included in a hybridization mixture, while increases in salt concentration facilitate binding. Under stringent annealing conditions, longer hybridization probes, or synthesis primers, hybridize more efficiently than do shorter ones, which are sufficient under more permissive conditions. Preferably, stringent hybridization is performed in a suitable buffer under conditions that allow the reference or target nucleic acid sequence to hybridize to the probes. Stringent hybridization conditions can vary for example from salt concentrations of less than about 1 M, more usually less than about 500 mM and preferably less than about 200 mM) and hybridization temperatures can range (for example, from as low as 0° C. to greater than 22° C., greater than about 30° C. and (most often) in excess of about 37° C. depending upon the lengths and/or the nucleic acid composition of the probes. Longer fragments may require higher hybridization temperatures for specific hybridization. As several factors affect the stringency of hybridization, the combination of parameters is more important than the absolute measure of a single factor. "Stringent hybridization conditions" refers to either or both of the following: a) 6×SSC at about 45° C., followed by one or more washes in 0.2×SSC, 0.1% SDS at 65° C., and b) 400 mM NaCl, 40 mM PIPES pH 6.4, 1 mM EDTA, 50° C. or 70° C. for 12-16 hours, followed by washing.

In the methods described herein, detection of annealed primers and/or probes can be direct or indirect. For example, probes can be annealed to the sample being tested, and detected directly. On the other hand, primers can be annealed to the sample being tested, followed by an amplification step. The amplified products can be detected directly, or through detection of probes that anneal to the amplification products.

In some embodiments, more than one primer and/or probe is provided. For example, some embodiments relate to methods for detecting a plurality of MRSA strains comprising MREJ types xi to xx. A plurality of primers and/or probes may be used in reactions conducted in separate physical enclosures or in the same physical enclosure. Reactions testing for a variety of MRSA types can be conducted one at a time, or simultaneously. In embodiments where the plurality of primers is provided in the same physical enclosure, a multiplex PCR reaction can be conducted, with a plurality of oligonucleotides, most preferably that are all capable of annealing with a target region under common conditions.

In some embodiments, a plurality of primers and/or probes that are specific for different MREJ types are provided in a multiplex PCR reaction, such that the type of the MREJ can be determined. The primers and/or probes used for detection can have different labels, to enable to distinguish one MREJ type from another MREJ type. As used herein, the term "label" refers to entities capable of providing a detectable signal, either directly or indirectly. Exemplary labels include radioisotopes, fluorescent molecules, biotin and the like.

Although the sequences from orfX genes and some SCC-mec DNA fragments are available from public databases and have been used to develop DNA-based tests for detection of MRSA, the novel sequence data disclosed herein enable the detection of MRSA of MREJ types xi to xx, which heretofore were not detected using the assays known in the art. These novel sequences, which are listed in Table 8, could not have been predicted nor detected by PCR assays developed based on known MREJ sequences of MRSA (U.S. Pat. No. 6,156,507; International Patent Application PCT/CA02/00824; Ito et al., 2001, Antimicrob. Agents Chemother. 45:1323-1336; Huletsky et al., 2004, J Clin. Microbiol. 42:1875-1884; Ma et al, 2002, Antimicrob. Agents Chemother. 46:1147-1152; Ito et al, Antimicrob Agents Chemother. 2004. 48:2637-2651; Oliveira et al, 2001, Microb. Drug Resist. 7:349-360). Accordingly, the novel MREJ sequences improve current NAT assays for the diagnosis of MRSA as they enable the skilled artisan to design of primers and probes for the detection and/or identification of MRSA strains with MREJ types xi to xx.

Design and Synthesis of Oligonucleotide Primers and/or Probes

All oligonucleotides, including probes for hybridization and primers for DNA amplification, were evaluated for their suitability for hybridization or PCR amplification by computer analysis using publicly and commercially available computer software, such as the Genetics Computer Group GCG Wisconsin package programs, and the Oligo™ 6 and MFOLD 3.0 primer analysis software. The potential suitability of the PCR primer pairs was also evaluated prior to their synthesis by verifying the absence of unwanted features such as long stretches of one nucleotide and a high proportion of G or C residues at the 3' end (Persing et al., 1993, Diagnostic Molecular Microbiology: Principles and Applications, American Society for Microbiology, Washington, D.C.). Oligonucleotide amplification primers were synthesized using an automated DNA synthesizer (Applied Biosystems).

The oligonucleotide sequence of primers or probes may be derived from either strand of the duplex DNA. The primers or probes may consist of the bases A, G, C, or T or analogs and they may be degenerated at one or more chosen nucleotide position(s), using a nucleotide analog that pairs with any of the four naturally occurring nucleotides. (Nichols et al., 1994, Nature 369:492-493). Primers and probes may also contain nucleotide analogs such as Locked Nucleic Acids (LNA) (Koskin et al., 1998, Tetrahedron 54:3607-3630), and Peptide Nucleic Acids (PNA) (Egholm et al., 1993, Nature 365:566-568). Primers or probes may be of any suitable length, and may be selected anywhere within the DNA sequences from proprietary fragments, or from selected database sequences which are suitable for the detection of MRSA with MREJ types xi to xx. In preferred embodiments, the primers and/or probes are at least 10, 12, 14, 16, 18, 20, 25, or 30 nucleotides in length.

Variants for a given target microbial gene are naturally occurring and are attributable to sequence variation within that gene during evolution (Watson et al., 1987, Molecular Biology of the Gene, $4^{th}$ ed., The Benjamin/Cummings Publishing Company, Menlo Park, CA; Lewin, 1989, Genes IV, John Wiley & Sons, New York, NY). For example, different strains of the same microbial species may have a single or more nucleotide variation(s) at the oligonucleotide hybridization site. The skilled artisan readily appreciates the existence of variant nucleic acids and/or sequences for a specific gene and that the frequency of sequence variations depends on the selective pressure during evolution on a given gene product. Detection of a variant sequence for a region between two PCR primers may be achieved by sequencing the amplification product. On the other hand, to detect sequence variations that overlap with primer hybridization site, amplification and subsequent sequencing of a larger DNA target with PCR primers outside that hybridization site is required. Similar strategy may be used to detect variations at the hybridization site of a probe. Insofar as the divergence of the target nucleic acids and/or sequences or a part thereof does not affect significantly the sensitivity and/or specificity and/or ubiquity of the amplification primers or probes, variant MREJ sequences are contemplated, as are variant primer and/or probe sequences useful for amplification or hybridization to the variant MREJ.

Oligonucleotide sequences other than those explicitly described herein and which are appropriate for detection and/or identification of MRSA may also be derived from the novel MREJ sequences disclosed herein or selected public database sequences. For example, the oligonucleotide primers or probes may be shorter but of a length of at least 10 nucleotides or longer than the ones chosen; they may also be selected anywhere else in the MREJ sequences disclosed herein or in the sequences selected from public databases. Further, variants of the oligonucleotides disclosed herein can be designed. If the target DNA or a variant thereof hybridizes to a given oligonucleotide, or if the target DNA or a variant thereof can be amplified by a given oligonucleotide PCR primer pair, the converse is also true; a given target DNA may hybridize to a variant oligonucleotide probe or be amplified by a variant oligonucleotide PCR primer. Alternatively, the oligonucleotides may be designed from MREJ sequences for use in amplification methods other than PCR. The primers and/or probes disclosed herein were designed by targeting genomic DNA sequences which are used as a source of specific and ubiquitous oligonucleotide probes and/or amplification primers for MREJ types xi to xx. When a proprietary fragment or a public database sequence is selected for its specificity and ubiquity, it increases the probability that subsets thereof will also be specific and ubiquitous. Accordingly, although the selection and evaluation of oligonucleotides suitable for diagnostic purposes requires much effort, it is quite possible for the individual skilled in the art to derive, from the selected DNA fragments, oligonucleotides other than the ones listed in Tables 9, 10 and 11 which are suitable for diagnostic purposes.

The diagnostic kits, primers and probes disclosed herein can be used to detect and/or identify MRSA of MREJ types xi to xx, in both in vitro and/or in situ applications. For example, it is contemplated that the kits may be used in combination with previously described primers/probes detecting MRSA of MREJ types i to x. It is also contemplated that the diagnostic kits, primers and probes disclosed herein can be used alone or in combination with any other assay suitable to detect and/or identify microorganisms, including but not limited to: any assay based on nucleic acids detection, any immunoassay, any enzymatic assay, any biochemical assay, any lysotypic assay, any serological assay, any differential culture medium, any enrichment culture medium, any selective culture medium, any specific assay medium, any identification culture medium, any enumeration culture medium, any cellular stain, any culture on specific cell lines, and any infectivity assay on animals.

Samples may include but are not limited to: any clinical sample, any environmental sample, any microbial culture, any microbial colony, any tissue, and any cell line.

DNA Amplification

In some embodiments, an amplification and/or detection step follows the annealing step. Any type of nucleic acid amplification technology can be used in the methods described herein. Non-limiting examples of amplification reactions that can be used in the methods described herein include but are not restricted to: polymerase chain reaction (PCR) (See, PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y. (Innis)), ligase chain reaction (LCR) (See, Wu (1989) Genomics 4:560; Landegren (1988) Science 241:1077; Barringer (1990) Gene 89:117), nucleic acid sequence-based amplification (NASBA), self-sustained sequence replication (3SR) (See, Guatelli (1990) Proc. Natl. Acad. Sci. USA, 87:1874), strand displacement amplification (SDA), branched DNA signal amplification bDNA, transcription-mediated amplification (TMA) (See, Kwoh (1989) Proc. Natl. Acad. Sci. USA 86:1173), cycling probe technology (CPT), nested PCR, multiplex PCR, solid phase amplification (SPA), nuclease dependent signal amplification (NDSA), rolling circle amplification technology (RCA), Anchored strand displacement amplification, solid-phase (immobilized) rolling circle amplification, Q Beta replicase amplification and other RNA polymerase mediated techniques (e.g., NASBA, Cangene, Mississauga, Ontario). These and other techniques are also described in Berger (1987) Methods Enzymol. 152:307-316; Sambrook, Ausubel, Mullis (1987) U.S. Pat. Nos. 4,683,195 and 4,683,202; Amheim (1990) C & EN 36-47; Lomell J. Clin. Chem., 35:1826 (1989); Van Brunt, Biotechnology, 8:291-294 (1990); Wu (1989) Gene 4:560; Sooknanan (1995) Biotechnology 13:563-564.

In preferred embodiments, PCR is used to amplify nucleic acids in the sample. During DNA amplification by PCR, two oligonucleotide primers binding respectively to each strand of the heat-denatured target DNA from the microbial genome are used to amplify exponentially in vitro the target DNA by successive thermal cycles allowing denaturation of the DNA, annealing of the primers and synthesis of new targets at each cycle (Persing et al, 1993, Diagnostic Molecular Microbiology: Principles and Applications, American Society for Microbiology, Washington, D.C.).

Standard amplification protocols may be modified to improve nucleic acid amplification efficiency, including modifications to the reaction mixture. (Chakrabarti and Schutt, 2002, Biotechniques, 32:866-874; Al-Soud and Radstrom, 2002, J. Clin. Microbiol., 38:4463-4470; Al-Soud and Radstrom, 1998, Appl. Environ. Microbiol., 64:3748-3753; Wilson, 1997, Appl. Environ. Microbiol., 63:3741-3751). Such modifications of the amplification reaction mixture include but are not limited to the use of various polymerases or the addition of nucleic acid amplification facilitators such as betaine, BSA, sulfoxides, protein gp32, detergents, cations, and tetramethylamonium chloride.

Detection of Nucleic Acids

Detection of amplified nucleic acids may include any real-time or post-amplification technologies known to those skilled in the art. Classically, the detection of PCR amplification products is performed by standard ethidium bromide-stained agarose gel electrophoresis, however, the skilled artisan will readily appreciate that other methods for the detection of specific amplification products, which may be faster and more practical for routine diagnosis, may be used, such as those described in co-pending patent application WO01/23604 A2. Amplicon detection may also be performed by solid support or liquid hybridization using species-specific internal DNA probes hybridizing to an amplification product. Such probes may be generated from any sequence from the repertory of MREJ nucleic acids disclosed herein, and designed to specifically hybridize to DNA amplification. Alternatively, amplicons can be characterized by sequencing. See co-pending patent application WO01/23604 A2 for examples of detection and sequencing methods.

Other non-limiting examples of nucleic acid detection technologies that can be used in the embodiments disclosed herein include, but are not limited to the use of fluorescence resonance energy transfer (FRET)-based methods such as adjacent hybridization of probes (including probe-probe and probe-primer methods) (See, J. R. Lakowicz, "Principles of Fluorescence Spectroscopy," Kluwer Academic/Plenum Publishers, New York, 1999), TaqMan probe technology (See, European Patent EP 0 543 942), molecular beacon probe technology (See, Tyagi et al., (1996) Nat. Biotech. 14:303-308.), Scorpion probe technology (See, Thewell (2000), Nucl. Acids Res. 28:3752), nanoparticle probe technology (See, Elghanian, et al. (1997) Science 277:1078-1081.) and Amplifluor probe technology (See, U.S. Pat. Nos. 5,866,366; 6,090,592; 6,117,635; and 6,117,986).

In preferred embodiments, molecular beacons are used in post-amplification detection of the target nucleic acids. Molecular beacons are single stranded oligonucleotides that, unless bound to target, exist in a hairpin conformation. The 5' end of the oligonucleotide contains a fluorescent dye. A quencher dye is attached to the 3' end of the oligonucleotide. When the beacon is not bound to target, the hairpin structure positions the fluorophore and quencher in close proximity, such that no fluorescence can be observed. Once the beacon hybridizes with target, however, the hairpin structure is disrupted, thereby separating the fluorophore and quencher and enabling detection of flouorescence. (See, Kramer F R., 1996, Nat Biotechnol 3:303-8.). Other detection methods include target gene nucleic acids detection via immunological methods, solid phase hybridization methods on filters, chips or any other solid support. In these systems, the hybridization can be monitored by any suitable method known to those skilled in the art, including fluorescence, chemiluminescence, potentiometry, mass spectrometry, plasmon resonance, polarimetry, colorimetry, flow cytometry or scanometry. Nucleotide sequencing, including sequencing by dideoxy termination or sequencing by hybridization (e.g. sequencing using a DNA chip) represents another method to detect and characterize the nucleic acids of target genes.

MREJ Nucleic Acids

The MREJ fragments disclosed herein were obtained as a repertory of sequences created by amplifying MRSA nucleic acids with novel primers. The amplification and sequencing primers, the repertory of MREJ sequences, and the oligonucleotide sequences derived therefrom for diagnostic purposes, disclosed in Tables 8-11 are further objects of this invention.

Aspects of the invention relate to nucleic acids, in particular nucleic acid sequences from DNA fragments of SCCmec right extremity junction (MREJ), including sequences from SCCmec right extremity and chromosomal DNA to the right of the SCCmec integration site in MRSA types xi to xx. Some embodiments relate to the parental sequences of MREJ types xi to xx from which primers and/or probes specific for the MREJ type xi to xx strain are derived. Thus, some embodiments relate to the nucleotide sequence of SEQ ID NO:15, 16, 17, 18, 19, 20, 21, 25, 26, 39, 40, 41, 42, 55, or 56 or the complement thereof. Other embodiments relate to DNA fragments and oligonucleotides, such as primers and probes. For example, some embodiments relate to nucleic acids comprising at least 10, 20, 30, 40, 50, 75, 100, 150, 200, 250, 300, 350, 400, 450, 500, 600, 700, or 800 consecutive nucleotides of the nucleic acids of SEQ ID NO:15, 16, 17, 18, 19, 20, 21, 25, 26, 39, 40, 41, 42, 55, or 56.

The scope of this invention is not limited to the use of amplification by PCR, but rather includes the use of any nucleic acid amplification method or any other procedure which may be used to increase the sensitivity and/or the rapidity of nucleic acid-based diagnostic tests. The scope of the present invention also covers the use of any nucleic acids amplification and detection technology including real-time or post-amplification detection technologies, any amplification technology combined with detection, any hybridization nucleic acid chips or array technologies, any amplification chips or combination of amplification and hybridization chip technologies. Detection and identification by any nucleotide sequencing method is also under the scope of the present invention.

Example 1: Evaluation of Previously Described MRSA Diagnostic Amplification Assays Initially, the literature taught that five types of SCCmec right extremity sequences (SCCmec types I-V) are found among MRSA strains, based on DNA sequence homology (See, Ito et al., 1999, Antimicrob. Agents Chemother. 43:1449-1458; Katayama et al., 2000, Antimicrob. Agents Chemother. 44:1549-1555; Ito et al., 2001, Antimicrob. Agents Chemother. 45:1323-1336; Ma et al., 2002, Antimicrob. Agents Chemother. 46:1147-1152; Ito et al, 2004, Antimicrob. Agents Chemother. 48:2637-2651). SCCmec DNAs are integrated at a specific site of the chromosome of a methicillin-sensitive *Staphylococcus aureus* (MSSA), named orfX. Generally, each SCCmec type has a unique nucleotide sequence at the right extremity of the SCCmec cassette. The exception to this rule is seen with SCCmec types II and IV, which exhibit nearly identical sequence over 2000 nucleotides. However, SCCmec type II has an insertion of 102 nucleotides to the right terminus of SCCmec type I. Strains classified as SCCmec types I-III fall under the category of MREJ types i-iii.

Recently, we analyzed the MREJ regions of several MRSA strains. We described seven new sequences at the right extremity junction of SCCmec from MRSA that we named MREJ types iv, v, vi, vii, viii, ix, and x (Huletsky et al., 2004, J Clin. Microbiol. 42:1875-1884; International Patent Application PCT/CA02/00824).

We designed a real-time MRSA-specific multiplex PCR assay having primers that target the SCCmec portion of MREJ types i, ii, iii, iv, v, and vii with a primer targeting the *S. aureus* orfX. Three molecular beacon probes (MBPs) specific to the orfX sequence were used for detection of all sequence polymorphisms identified in this region of the orfX sequence (Huletsky et al., 2004, J. Clin. Microbiol. 42:1875-1884). The oligonucleotide of SEQ ID NO: 30, which hybridizes to the *S. aureus* orfX, and the oligonucleotides of SEQ ID NOs: 36, 70, 71, 72, and 74, which hybridize to the SCCmec portion of MREJ types i, ii, iii, iv, v, and vii were used in the PCR reaction. Oligonucleotides of SEQ ID NOs: 31, 32, and 33, which hybridize to *S. aureus* orfX were used as probes. The specificity and ubiquity (i.e., the ability to detect all or most MRSA strains) of the PCR assay was verified using a panel of 569 reference and clinical strains of methicillin-sensitive *S. aureus* (MSSA) and 1657 different MRSA strains from 32 different countries and which include well-known epidemic clones.

A list of the strains tested and used to build the repertories of MREJ nucleic acids and oligonucleotides derived therefrom disclosed herein is presented in Table 1. The *S. aureus* clinical isolates used in this invention are part of the SENTRY program collection and several supplier's collections. These *S. aureus* reference strains or clinical isolates originate from 32 countries: African countries (n=15), Albania (n=2), Argentina (n=50), Australia (n=71), Austria (n=2), Belgium (n=10), Brazil (n=78), Canada (n=607), Chile (n=42), China (n=70), Denmark (n=33), Egypt (n=1), Finland (n=12), France (n=50), Germany (n=47), Greece (n=7), Ireland (n=5), Israel (n=19), Italy (n=61), Japan (n=62), Mexico (n=1), The Netherlands (n=179), Poland (n=33), Portugal (n=24), Singapore (n=20), Slovenia (n=12), Spain (n=31), Sweden (n=10), Switzerland (n=13), Turkey (n=28), United Kingdom (n=22), and United States (n=528). Confirmation of the identification of the staphylococcal strains was performed by using the MicroScan WalkAway Panel type Positive Breakpoint Combo 13 when required (Dade Behring Canada Inc., Mississauga, Ontario, Canada). When needed, the identity was reconfirmed by PCR analysis using *S. aureus*-specific primers and mecA-specific primers (SEQ ID NOs.: 50, 60, 61, 63) (Martineau et al., 2000, Antimicrob. Agents Chemother. 44:231-238). The data from the assay is presented in Table 2.

Among the 569 MSSA strains tested, 26 strains were misidentified as MRSA based on the PCR assay. Of the 1657 MRSA strains tested, 1640 were specifically detected with the PCR assay whereas 23 of these MRSA strains, representing a broad variety of origins were not detected by the assay. Thus, the specificity and ubiquity (i.e. the ability to detect all or most MRSA strains) of this PCR assay was verified. Four of these 23 MRSA strains, CCRI-9208, CCRI-9770, CCRI-9681, and CCRI-9860, which were not detected in the above assay have previously been shown to harbor the MREJ types vi, viii, ix, and x, respectively (International Patent Application PCT/CA02/00824).

The 19 remaining MRSA strains that were not detected in the assay were analyzed further. PCR was performed on the genomic DNA from each strain, using a primer targeting the sequence at the SCCmec right extremity of MREJ types vi, viii, or ix in combination with a primer targeting the *S. aureus* orfX. Specifically, each PCR reaction contained the oligonucleotide of SEQ ID NO:65, which anneals to MREJ type vi, the oligonucleotide of SEQ ID NO:75, which anneals to MREJ type viii, or the oligonucleotide of SEQ ID NO:29, which anneals to MREJ type ix, in combination with the oligonucleotide of SEQ ID NO:30, which is a *S. aureus*-specific primer. MREJ type x was previously shown to have a deletion of the complete orfX and a portion at the right extremity of SCCmec type II (International Patent Application PCT/CA02/00824). Therefore, the oligonucleotide of SEQ ID NO:77, which anneals to orf22 in the *S. aureus* chromosome, and the oligonucleotide of SEQ ID NO:73, which anneals to orf27 located in SCCmec type II were used in a PCR reaction to detect MREJ type x. Two out of 19 strains, CCRI-11879 and CCRI-12036, were shown to harbor MREJ type ix with these PCR primers. However, 17 MRSA strains were not detected with primers targeting MREJ types vi, viii, ix, and x suggesting that these strains harbor new MREJ types (Tables 2 and 3).

Example 2: Sequencing of Novel MREJ Types from MRSA

To further characterize the MREJ region of the 17 MRSA strains from which DNA was not amplified with primers that allow the detection of MREJ types i to x, the nucleotide sequence of MREJ for 15 of these 17 MRSA strains was determined. First, a primer that anneals to mecA (SEQ ID NO.: 50) and a primer that anneals to the 5' end of orfX (SEQ ID NO.:44) were used together in a PCR reaction to amplify MREJ fragments of MRSA. The strategy used to select these primers is illustrated in FIG. 1. Four identical PCR reactions, each containing 100 ng of purified genomic DNA were performed. Each PCR reaction contained 1× HERCULASE™ DNA polymerase buffer (Stratagene, La Jolla, CA), 0.8 µM of each of the oligos of SEQ ID NOs.: 44 and 50, 0.56 mM of each of the four dNTPs and 5 units of HERCULASE™ DNA polymerase (Stratagene, La Jolla, CA) with 1 mM MgCl$_2$ in a final volume of 50 µl. PCR reactions were subjected to cycling using a standard thermal cycler (PTC-200 from MJ Research Inc.) as follows: 2 min at 92° C. followed by 35 or 40 cycles of 10 sec at 92° C. for the denaturation step, 30 sec at 55° C. for the annealing step and 15 min at 68° C. for the extension step.

The four PCR reactions were pooled. 10 µL of the PCR reaction was resolved by electrophoresis in a 0.7% agarose gel containing 0.25 µg/mL of ethidium bromide. The amplicons were then visualized with an Alpha-Imager (Alpha Innotech Corporation, San Leandro, CA) by exposing to UV light at 254 nm. The remaining PCR-amplified mixture (150-200 µl, total) was also resolved by electrophoresis in a 0.7% agarose gel and visualized by staining with methylene blue (Flores et al., 1992, Biotechniques, 13:203-205).

Of the 15 strains tested, the following eight yielded amplification products ranging from 12-20 kb in length with SEQ ID NOs.: 44 and 50 as primers: CCRI-11976, CCRI-11999, CCRI-12157, CCRI-12198, CCRI-12199, CCRI-12719, CCRI-9887, CCRI-9772. The amplification products were excised from the agarose gel and purified using the QIAquick™ gel extraction kit (QIAGEN Inc., Valencia, CA). The gel-purified DNA fragments were used directly in sequencing reactions. Both strands of the MREJ amplification products were sequenced by the dideoxynucleotide chain termination sequencing method using an Applied Biosystems automated DNA sequencer (model 377 or 3730xl) with their Big Dye™ Terminator Cycle Sequencing Ready Reaction Kit (Applied Biosystems, Foster City, CA). 425-495 ng of the gel-purified amplicons were used in sequencing reactions with SEQ ID NO.: 44, which was used for the amplification reaction. Based on the sequence information generated from the reactions with SEQ ID NO:44, internal sequencing primers were designed and used to obtain sequence data from both strands for a larger portion of each amplicon preparation. Specifically, the oligonucleotides of SEQ ID NOs.: 43 and 45 were used to sequence MRSA strains CCRI-11976 and CCRI-11999; SEQ ID NOs.: 43, 45, and 51 were used to sequence MRSA strains CCRI-12157, CCRI-12198, and CCRI-12199; SEQ ID NOs.: 43, 45, and 52 were used to sequence MRSA strain CCRI-12719; SEQ ID NO.: 24 was used to sequence MRSA strain CCRI-9887, and SEQ ID NOs.: 4, 45, and 57 were used to sequence MRSA strain CCRI-9772 (FIG. 1, Tables 9 and 11). The sequences of the 8 strains described in Table 3 are presented as SEQ ID NOs.: 15, 16, 17, 18, 19, 20, 55, and 56 (Table 8).

To ensure that the determined sequence did not contain errors attributable to the sequencing of PCR artifacts, two independent preparations of the gel-purified MREJ amplification products originating from two independent PCR amplifications were sequenced as described above. For most target fragments, the sequences determined for both amplicon preparations were identical. Furthermore, the sequences of both strands were 100% complementary thereby confirming the high accuracy of the determined sequence. The MREJ sequences determined using the above strategy are described in the Sequence Listing and in Table 8.

A different set of oligonucleotide primers (described in Oliviera et. al.) was used to further analyze the 17 MRSA strains that did not yield amplification products with primers for detection of MREJ types i-vii (Oliveira and de Lencastre. 2002, Antimicrob. Agents Chemother. 46:2155-2161). Two strains, (CCRI-12382 and CCRI-12383), harbored SCCmec type III and contained sequences specific to the ψccr complex. Another strain, (CCRI-12845), harbors SCCmec type II.

To determine the MREJ sequences of strains CCRI-12382 and CCRI-12383, a primer targeting the ψccr complex sequence located in SCCmec type III (SEQ ID NO.: 27) was used in combination with a primer targeting the 5'end of orfX (SEQ ID NO.: 44) to amplify MREJ fragments of these two MRSA strains (Table 10 and FIG. 1). Four identical PCR reactions, each containing 100 ng of purified genomic DNA were performed. Each PCR reaction contained 1× HERCULASE™ DNA polymerase buffer (Stratagene, La Jolla, CA), 0.8 µM of each of the 2 primers (SEQ ID NOs.: 27 and 44), 0.56 mM of each of the four dNTPs and 5 units of HERCULASE™ DNA polymerase (Stratagene, La Jolla, CA) with 1 mM MgCl$_2$ in a final volume of 50 µl. The PCR reactions were cycled using a standard thermal cycler (PTC-200 from MJ Research Inc., Watertown, MA) as follows: 2 min at 92° C. followed by 35 cycles of 10 sec at 92° C. for the denaturation step, 30 sec at 55° C. for the annealing step and 15 min at 68° C. for the extension step.

The PCR reactions were pooled and 10 µl of the PCR-amplified mixture was resolved by electrophoresis in a 0.7% agarose gel containing 0.25 µg/ml of ethidium bromide. The amplicons were then visualized with an Alpha-Imager (Alpha Innotech Corporation, San Leandro, CA) by exposing to UV light at 254 nm. The remaining PCR-amplified mixture (150-200 µl, total) was also resolved by electrophoresis in a 0.7% agarose gel and visualized by staining with methylene blue as described above. For these two MRSA strains, an amplification product of ~8 kb was obtained. The PCR amplification products were excised from the agarose gel and purified as described above. The gel-purified DNA fragment was then used directly in the sequencing protocol as described above. The sequencing reactions were performed by using SEQ ID NO.: 44 (also used in the amplification reaction) and 425-495 ng of the gel-purified amplicons for each reaction. Subsequently, different sets of internal sequencing primers were used to obtain sequence data from both strands and for a larger portion of the amplicon (SEQ ID NOs.: 28, 30, and 43) (FIG. 1, Tables 9 and 11). The sequence of the MRSA strains CCRI-12382 and CCRI-12383 described in Table 3 which were sequenced using this strategy are designated SEQ ID NOs.: 25 and 26, respectively (Table 8).

To sequence the MREJ fragment of strain CCRI-12845 (SCCmec type II) PCR amplification was performed using the oligonucleotide of SEQ ID NO:44, which anneals to the 5' end of orfX in combination with the oligonucleotide of SEQ ID NO:53, which anneals to the the SCCmec right extremity of MREJ type ii. 1 µL of a purified genomic DNA preparation was transferred directly into 4 tubes containing 39 µL of a PCR reaction mixture. Each PCR reaction contained 50 mM KCl, 10 mM Tris-HCl (pH 9.0), 0.1% Triton X-100, 2.5 mM $MgCl_2$, 0.4 µM of each of the oligonucleotides of SEQ ID NO.: 44 and 53, 200 µM of each of the four dNTPs, 3.3 µg/µl of BSA (Sigma-Aldrich Canada Ltd) and 0.5 unit of Taq DNA polymerase (Promega, Madison, WI) coupled with the TaqStart™ Antibody (BD Biosciences, San Jose, CA). PCR reactions were performed using a standard thermocycler (PTC-200 from MJ Research Inc., Watertown, MA) as follows: 3 min at 94° C. followed by 40 cycles of 5 sec at 95° C. for the denaturation step, 1 min at 58° C. for the annealing step and 1 min at 72° C. for the extension step. An amplification product of 4.5 kb was obtained with this primer set.

The amplification products were pooled and 10 µl of the mixture were resolved by electrophoresis in a 1.2% agarose gel containing 0.25 µg/ml of ethidium bromide. The amplicons were then visualized with the Alpha-Imager. Amplicon size was estimated by comparison with a 1 kb molecular weight ladder (Life Technologies, Bethesda, MD). The remaining PCR-amplified mixture (150 µl, total) was also resolved by electrophoresis in a 1.2% agarose gel and visualized by staining with methylene blue as described above. The PCR reaction yielded a 1.2 kb amplification product. The band corresponding to this specific amplification product was excised from the agarose gel and purified as described above. The gel-purified DNA fragment was then used directly in the sequencing protocol as described above. The sequencing reactions were performed using the oligonucleotides of SEQ ID NOs.: 44 and 53 as well as one internal primer (SEQ ID NO.: 54) and 10 ng/100 bp per reaction of the gel-purified amplicons (FIG. 1, Table 10). The MREJ sequence of strain CCRI-12845 is designated as SEQ ID NO.: 21 (Table 8).

To determine the MREJ sequences of the 4 last MRSA strains (CCRI-12524, CCRI-12535, CCRI-12810, and CCRI-12905), the oligonucleotide of SEQ ID NO: 44 was used in combination with each of the four DNA Walking ACP (DW-ACP) primers from the DNA WALKING SPEED UP™ Sequencing Kit (Seegene, Del Mar, CA) according to the manufacturer's instructions on a PTC-200 thermocycler. The DW-ACP primer system (DW ACP-PCR™ Technology) enables one to obtain genuine unknown target amplification products up to 2 kb. A first amplification product obtained with one of the DW-ACP primers was purified using the QIAQUIK™ PCR purification Kit (QIAGEN Inc., Valencia, CA). The purified PCR product was re-amplified using the DW-ACP-N primer in combination with the oligonucleotide of SEQ ID NO:30, which anneals to orfX under manufacturer recommended PCR conditions. The PCR-amplified mixture of 4 different 50-µL PCR reactions were pooled and resolved by electrophoresis in a 1.2% agarose gel. The amplicons were then visualized by staining with methylene blue as described above. Amplicon size was once again estimated by comparison with a 1 kb molecular weight ladder. An amplification product of 1.5 to 3 kb was obtained. The amplification product was excised from the agarose gel and purified as described above and the DNA was then used directly in the sequencing protocol as described above. 10 ng of purified DNA for every 100 bp of the amplicon was used in sequencing reactions using the oligonucleotides of SEQ ID NO.: 30 and DW-ACP-N. The MREJ sequences from MRSA strains strains CCRI-12524, CCRI-12535, CCRI-12810, and CCRI-12905 (described in Table 3) are designated SEQ ID NOs.: 39, 40, 41, and 42 (Table 8).

CCRI-12376 and CCRI-12593 described in Table 3 were not sequenced but rather characterized using PCR primers and shown to contain MREJ type xiii using specific amplification primers.

Example 3: Sequence Analysis of Novel MREJ Types xi-xx

The sequences obtained for 15 of the 17 strains non-amplifiable by the MRSA-specific primers detecting MREJ types i to x previously described were compared to the sequences available from public databases. In all cases except MRSA strain CCRI-12845, the orfX portion of the MREJ sequence had an identity close to 100% to publicly available sequences for orfX. CCRI-12845 has a deletion in orfX (SEQ ID NO.: 21) (described below). While the orfX portion of most MREJ fragments (SEQ ID NOs.: 15-20, 25-26, 39-42, 55-56) shared nearly 100% identity with publicly available *S. aureus* orfX sequences, with the exception of strain CCRI-12845, the DNA sequence within the right extremity of SCCmec itself was shown to be different from those of MREJ types i, ii, iii, iv, v, vi, vii, viii, ix, and x (International Patent Application PCT/CA02/00824; U.S. Pat. No. 6,156,507). The DNA sequence within the right extremity of SCCmec of CCRI-12845 was similar to that of MREJ type ii (see below). Thus, ten different novel MREJ sequence types are reported herein: MREJ types xi to xx.

The sequences within the right extremity of SCCmec obtained from strains CCRI-12157, CCRI-12198, and CCRI-12199 (SEQ ID NOs.: 17, 18, and 19) were nearly identical to each other, and different from those of MREJ types i, ii, iii, iv, v, vi, vii, viii, ix, and x (Ito et al., 2001, Antimicrob. Agents Chemother. 45:1323-1336; Ma et al., 2002, Antimicrob. Agents Chemother. 46:1147-1152, Huletsky et al., 2004, J. Clin. Microbiol. 42:1875-1884, International Patent Application PCT/CA02/00824, U.S. Pat. No. 6,156,507). These new sequences were designated as MREJ type xi (SEQ ID NOs.: 17-19). A BLAST™ search revealed that the first 86 bp of the SCCmec portion of MREJ type xi exhibited 87% identity with an unknown sequence of *Staphylococcus epidermidis* strain SR1 (GenBank accession number AF270046). The remainder of the MREJ sequence was shown to be unique, exhibiting no significant homology to any published sequence.

The sequence obtained at the right extremity of SCCmec from strain CCRI-12719 (SEQ ID NO.: 20) was different from MREJ types i to x as well as from MREJ type xi. The new MREJ type was designated as MREJ type xii. When compared with GenBank sequences using BLAST™, the sequence at the right extremity of SCCmec of MREJ type xii exhibited 100% identity with the sequence found at the right extremity of the SCCmec type V recently described (Ito et al., 2004, Antimicrob. Agents. Chemother. 48:2637-2651; GenBank accession number AB121219). The sequence also exhibited 85% identity with a 212-nucleotide region of the *Staphylococcus epidermidis* RP62a putative GTP-binding protein sequence.

The sequences within the right extremity of SCCmec obtained from strains CCRI-11976, CCRI-12382, and CCRI-12383 (SEQ ID NOs.: 15, 25, and 26) were 100% identical to each other, different from MREJ types i to x as well as from MREJ types xi and xii. The new MREJ sequences were designated as MREJ type xiii (SEQ ID NOs.: 15, 25, and 26).

The sequence within the right extremity of SCCmec obtained from strain CCRI-11999 (SEQ ID NO.: 16) was also different from MREJ types i to x as well as from MREJ types xi, xii, and xiii, and consequently, was designated as MREJ type xiv. A BLAST™ search of the MREJ types xiii and xiv sequences showed that a portion of the SCCmec of these two MREJ types was identical to that of MREJ type ix. Indeed, the SCCmec portions of MREJ types ix and xiv were preceded by one and two consecutive 102 bp insertions, respectively, when compared to MREJ type xiii. The rest of the MREJ types ix, xiii, and xiv sequences were 99.9% identical to each other. These sequences exhibited identities ranging from 97% to 100% (for the highest BLAST scores) with non-contiguous regions (in varying sizes of 1535 to 1880 nucleotides) of the SCC cassette without mecA harboring the chromosome recombinase genes of the methicillin-susceptible strain *S. epidermidis* ATCC 12228 (GenBank accession number BK001539). The sequence of the 102-pb insertion was 99-100% identical to that found in MREJ type ii.

The sequence obtained within the right extremity of SCCmec from strain CCRI-9887 was different from MREJ types i to x as well as from MREJ types xi to xiv and was therefore designated as MREJ type xv (SEQ ID NO.: 56). A BLAST search of the sequence obtained within the SCCmec portion of MREJ type xv revealed that this DNA fragment exhibited identities ranging from 92% to 96% (for the highest BLAST scores) with non-contiguous sequences (in varying sizes of 342 to 618 nucleotides) of the SCC cassette (which do not contain mecA) of the methicillin-susceptible *S. aureus* strain M (GenBank accession number U10927). Although the sequence of MREJ type xv has been described, the localization of this sequence downstream of orfX in a MRSA strain has heretofore not been described. The CCRI-9887 MREJ sequence also exhibited 94% identity with a 306-nucleotide region of strain *Staphylococcus haemolyticus* JCSC1435 located near the orfX sequence.

The sequence obtained for MREJ from strain CCRI-12845 (SEQ ID NO.: 21) revealed that the MREJ fragment of this strain has a deletion of nucleotides 165 to 434 of orfX (269-bp fragment), whereas the sequence at the right extremity of SCCmec (328 nucleotides) had identities ranging from 99.8 to 100% with that of MREJ type ii available in public databases. Although the MREJ sequence obtained from this strain exhibited a high level of identity with known MREJ sequences, the presence of a 269-bp deletion within orfX had heretofore never been described. As one of the oligonucleotides used in the initial PCR amplification assay described above falls within this 269 bp deletion, the deletion in orfX explains why this MRSA strain was not or could not have been detected with primers and probes previously described to detect MRSA (U.S. Pat. No. 6,156,507 and International Patent Application PCT/CA02/00824). The novel MREJ sequence of this strain was designated as MREJ type xvi.

The sequence obtained at the right extremity of SCCmec from strain CCRI-9772 was different from MREJ types i to x as well as from MREJ types xi to xvi. The new MREJ type was designated as MREJ type xvii (SEQ ID NO.:55). A BLAST™ search against the GenBank database revealed that the SCCmec portion of MREJ type xvii sequence exhibited 100% identity with the sequence at left of the SCCmec junction of *S. aureus* strain CA05 (JCSC 1968) (GenBank Accession number AB063172) harbouring SCCmec type IV (Ma et al., 2002. Antimicrob. Agents Chemother. 46:1147-1152). The genetic organization of MREJ type xvii is similar to the region downstream of orfx in MSSA. Although the sequence itself has been described previously, the localization of this sequence downstream of orfX in a MRSA strain has heretofore never been described.

The sequences obtained from the right extremity of SCCmec from strains CCRI-12524 and CCRI-12535 were nearly identical to each other but were different from MREJ types i to x as well as from MREJ types xi to xvii and were therefore designated as MREJ type xviii (SEQ ID NOs.:39 and 40). A BLAST search against GenBank sequences revealed a 100% identity with a 487-nucleotide region of the SCCmec cassette of *Staphylococcus haemolyticus* JCSC 1435. The remainder of the sequence was shown to be unique, exhibiting no significant homology to any published sequence.

The sequence obtained from strain CCRI-12810 was different from MREJ types i to x as well as from MREJ types xi to xviii and was designated as MREJ type xix (SEQ ID NO.:41). When compared with GenBank sequences using BLAST, the SCCmec portion of MREJ type xix sequence exhibited 100% identity with a 597-nucleotide region of unknown function of strain ATCC 25923 which is located at the left of SCCmec (GenBank accession number AB047239). This result has been observed with four other MRSA strains for which the SCCmec sequences have been published: MRSA252, 85/3907, 85/2082, and MR108 (GenBank accession numbers: BX571856, AB047088, AB037671 and AB096217, respectively). The genetic organization of MREJ type xix is similar to the region downstream of orfx in MSSA. Although the sequence itself had been described, the presence of this DNA fragment downstream of orfX had heretofore never been described.

The sequence obtained at the right extremity of SCCmec from strain CCRI-12905 was different from MREJ types i to x as well as from MREJ types xi to xix and was designated as MREJ type xx (SEQ ID NO.:42). When compared with Genbank sequences using BLAST, the SCCmec of MREJ type xx sequence exhibited 100% and 99% identities with two non-contiguous sequences (respectively 727 and 307 nucleotides long) downstream of orfX of the methicillin-susceptible S. aureus strain NCTC 8325 (GenBank accession number AB014440). The genetic organization of MREJ type xx is similar to the region downstream of orfx in MSSA. The localization of this sequence downstream of orfX in a MRSA strain has heretofore never been described. Identity levels ranging from 98% to 100% with non-contiguous fragments (in varying sizes of 91 to 727 nucleotides) was found with 11 MRSA strains for which the SCCmec sequences have been published: N315, NCTC 10442, COL, USA300, Mu50, 2314, 85/4231, 85/2235, JCSC 1978, PL72, HDE 288 (GenBank accession numbers: BA000018, AB033763, CP000046, CP000255, BA000017, AY271717, AB014428, AB014427, AB063173, AF411936, AF411935, respectively). These identical fragments are located downstream of the mecA gene towards (or even downstream) the left insertion point of SCCmec.

Example 4: Sequence Comparison of New MREJ Types xi to xx

Figure 3A:
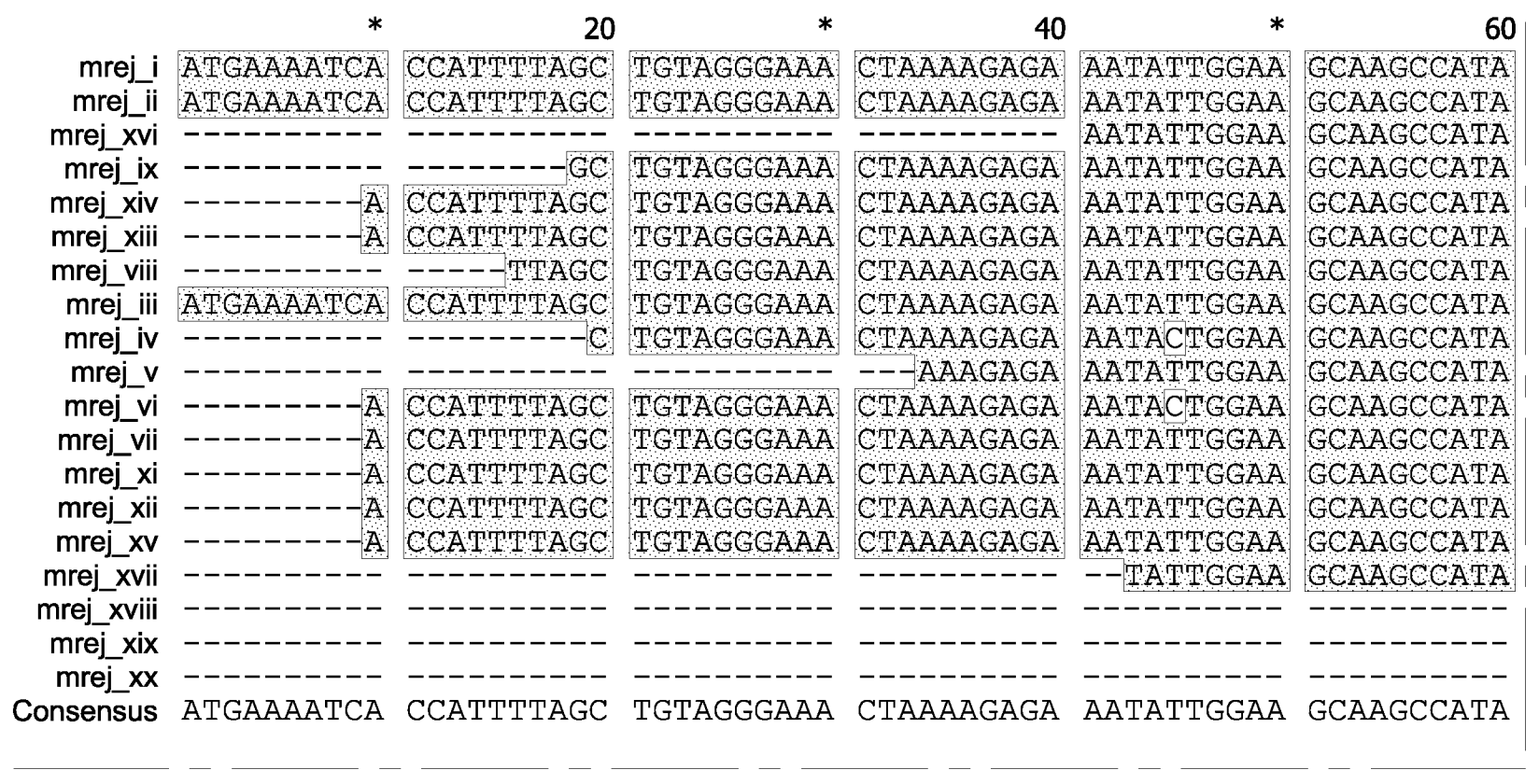
Figure 3B:
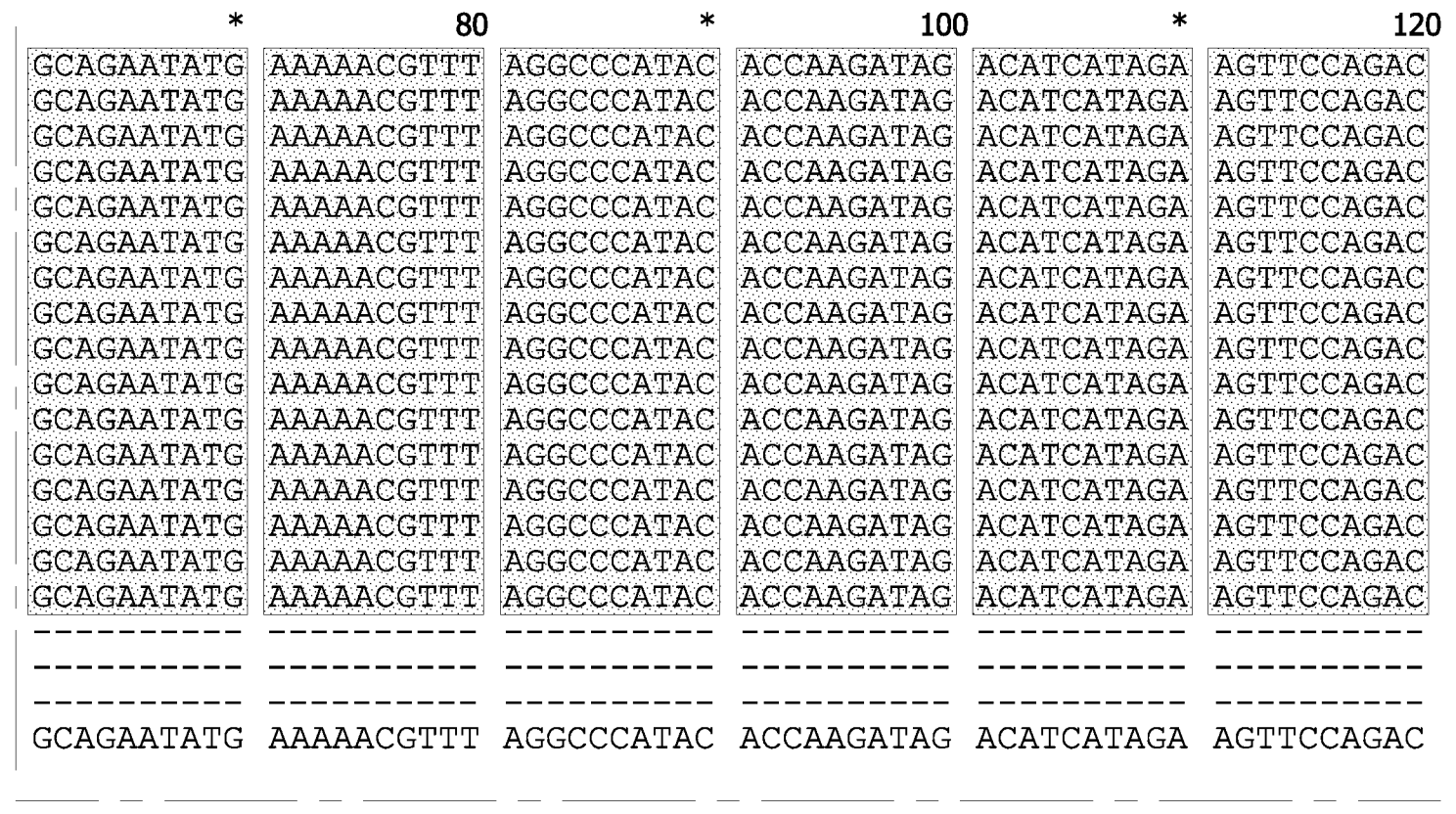
Figure 3C:
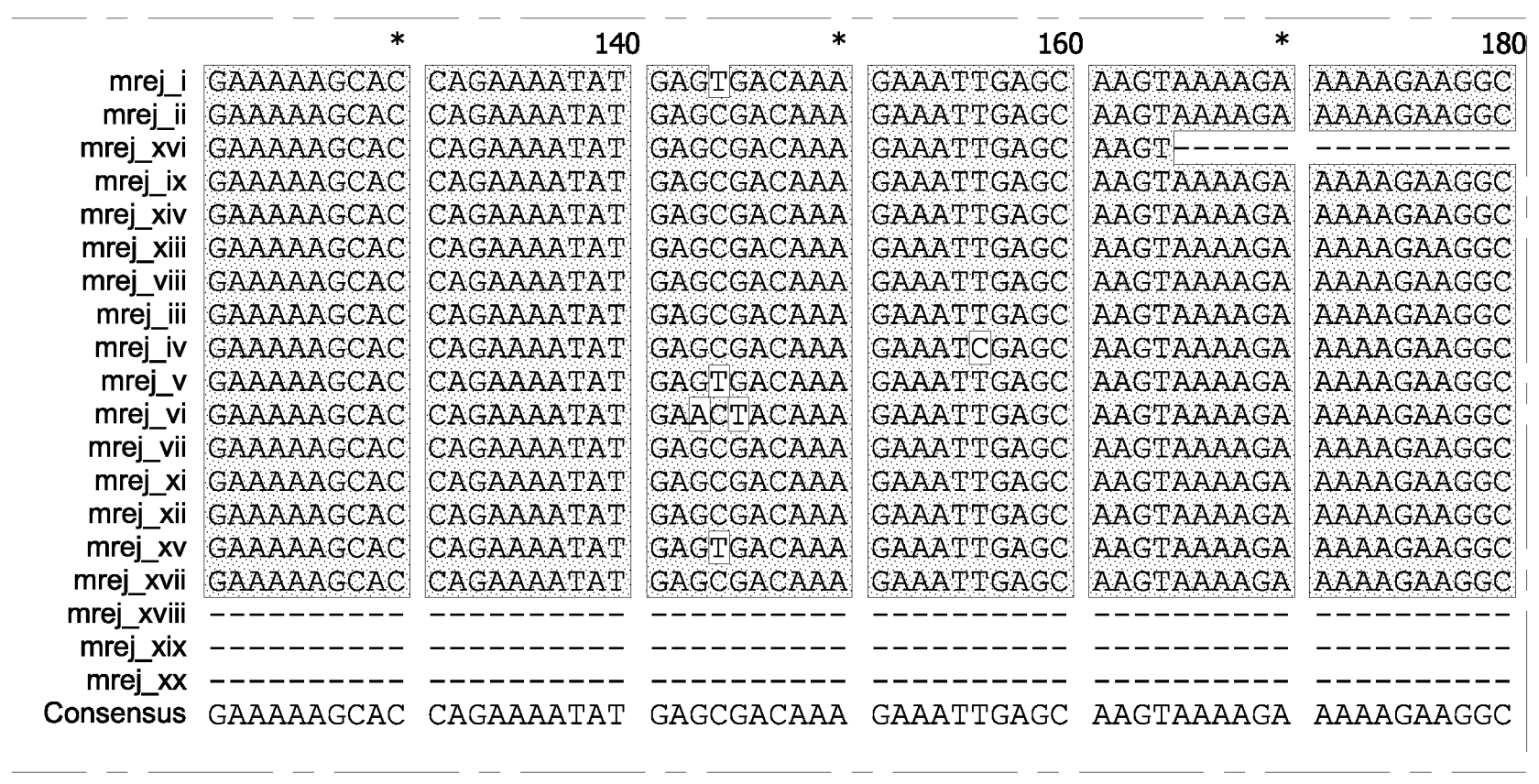
Figure 3D:
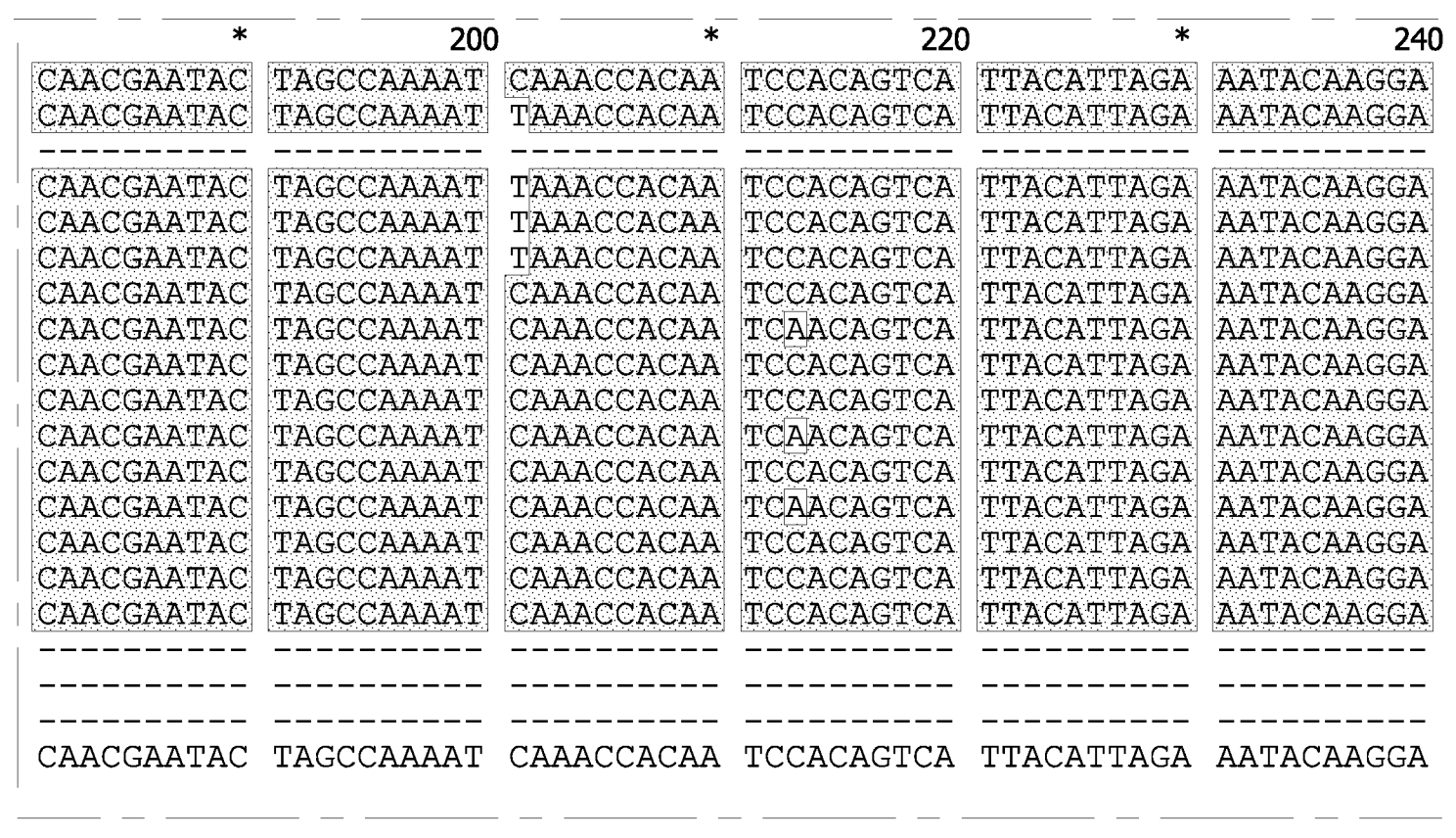
Figure 3F:
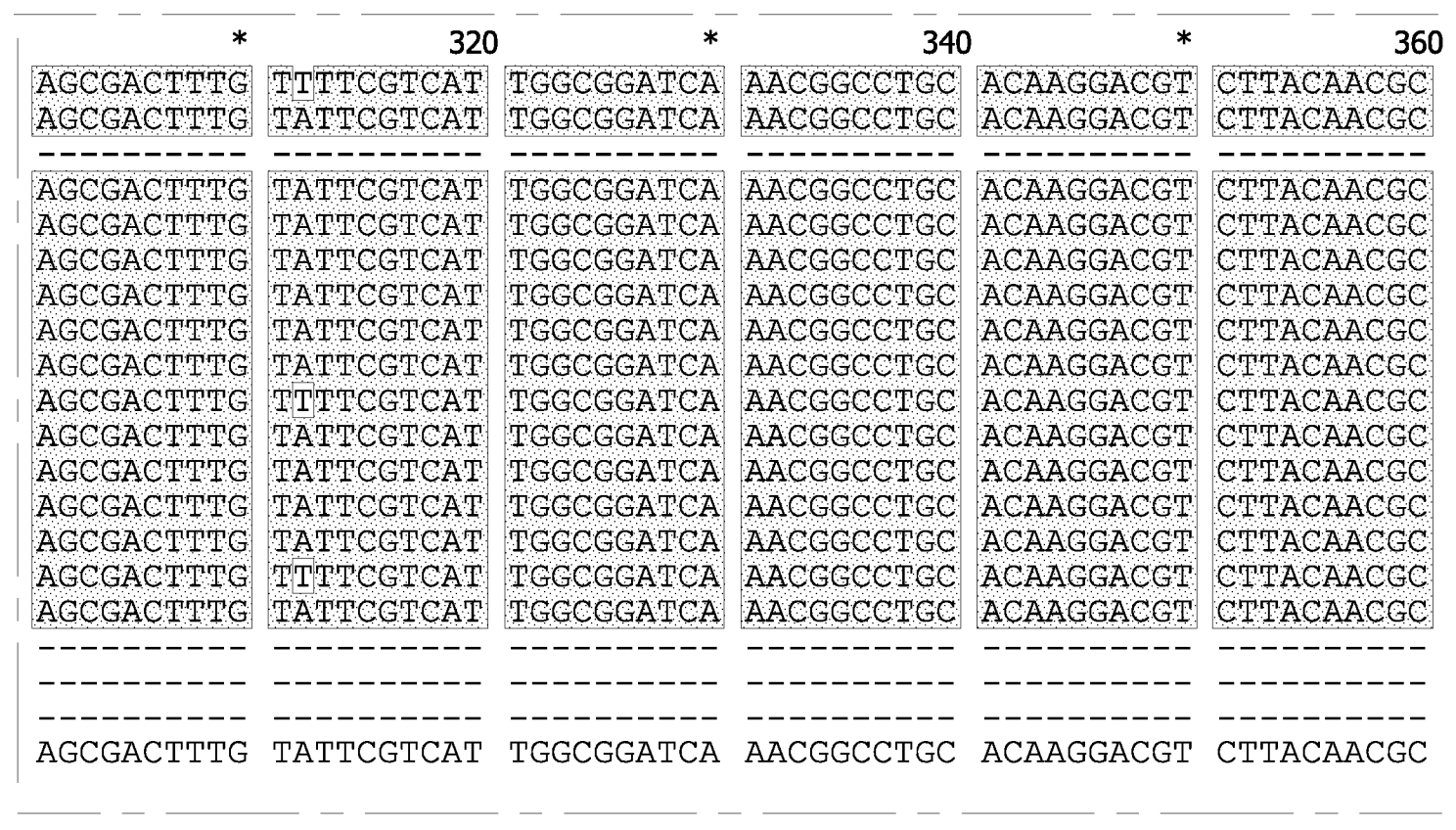
Figure 3G:
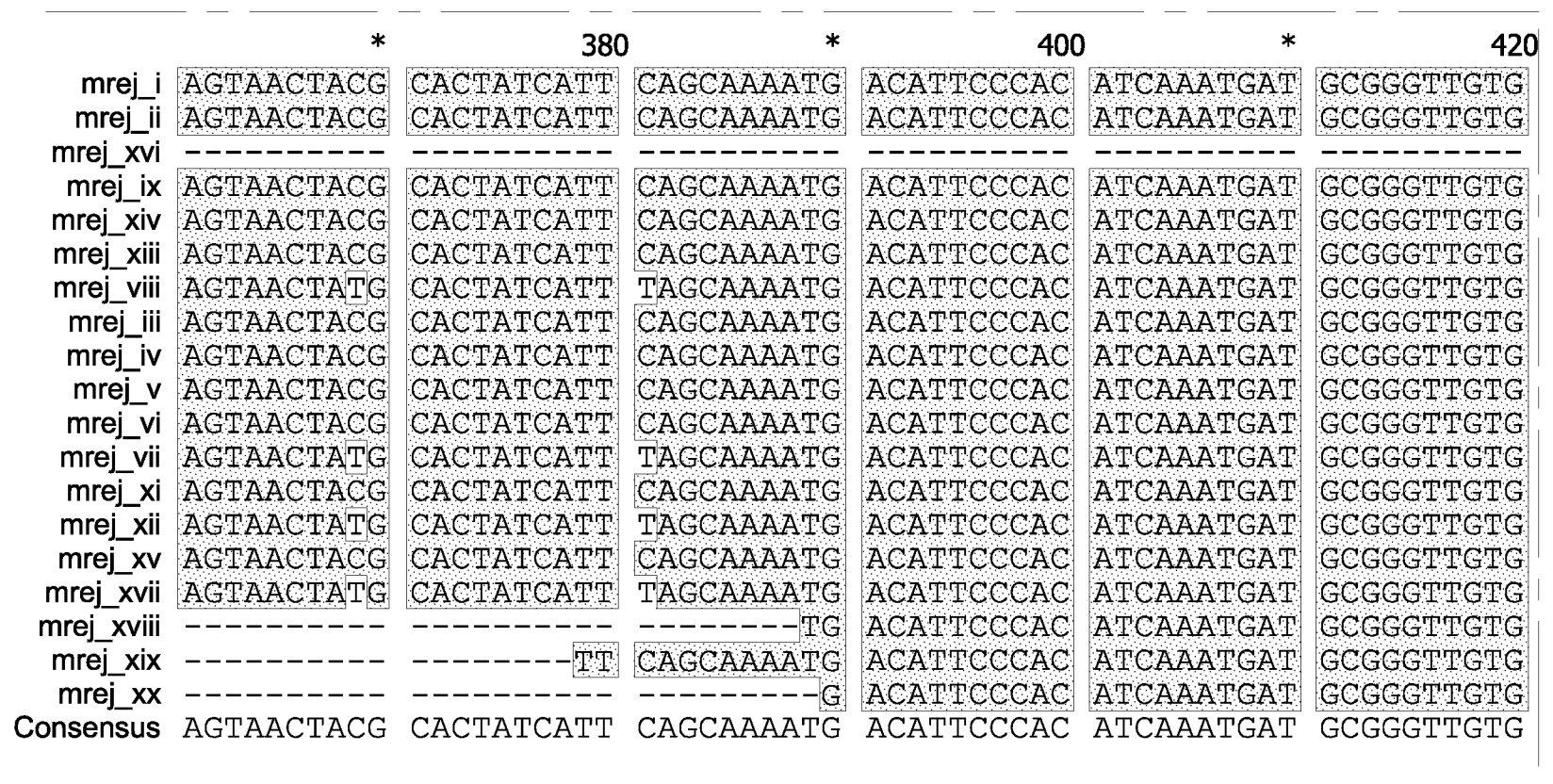
Figure 3H:
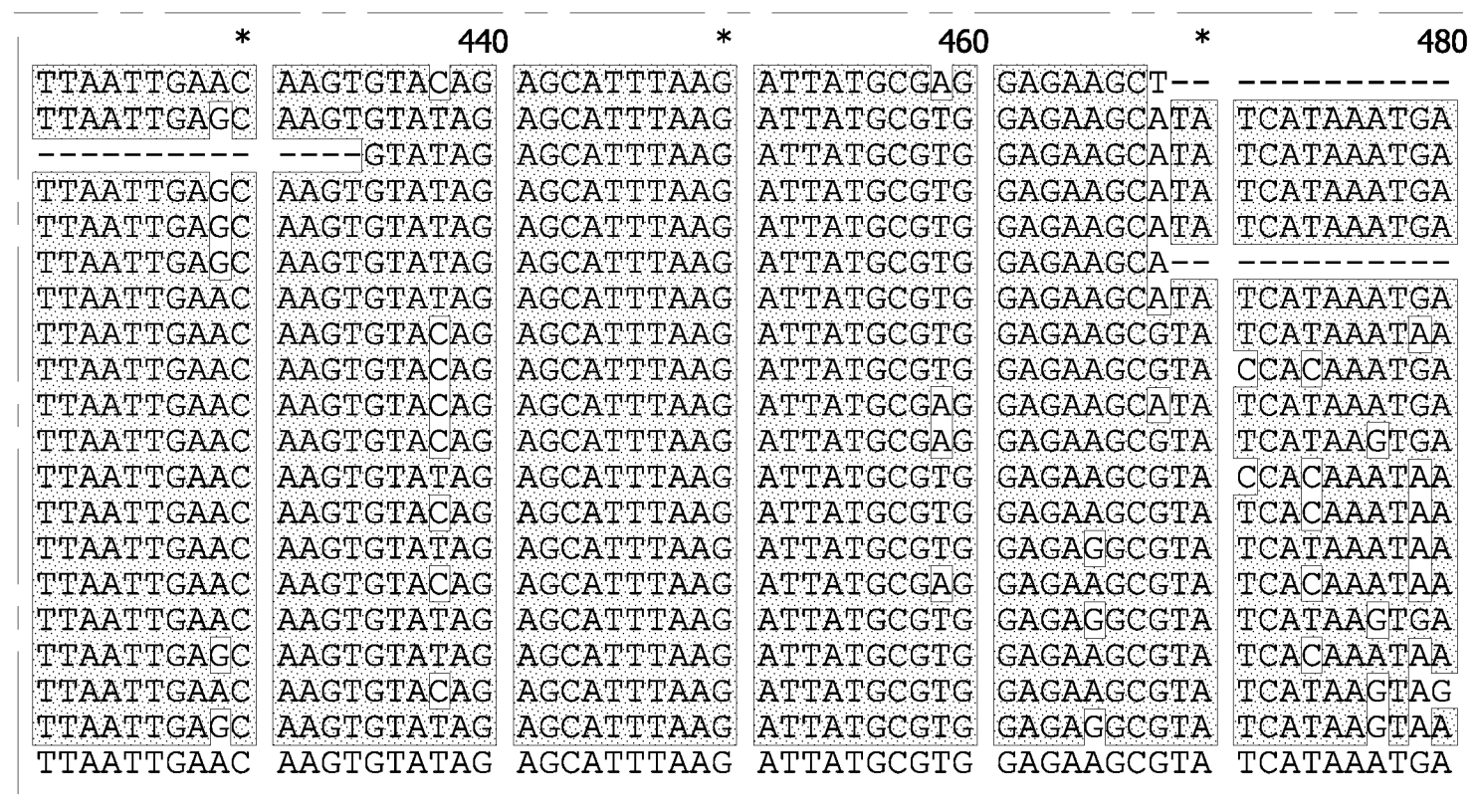
Figure 3I:
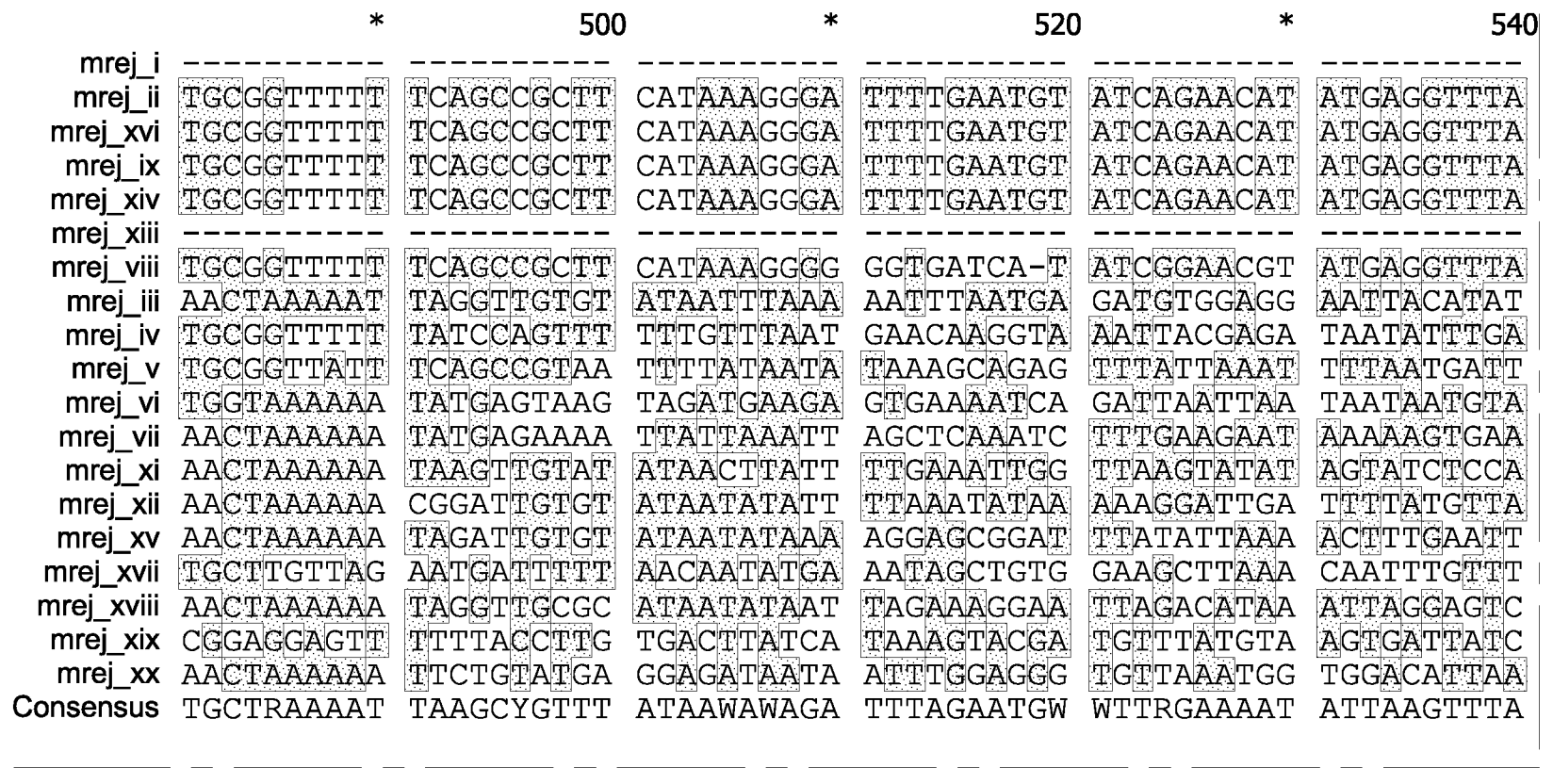
Figure 3K:
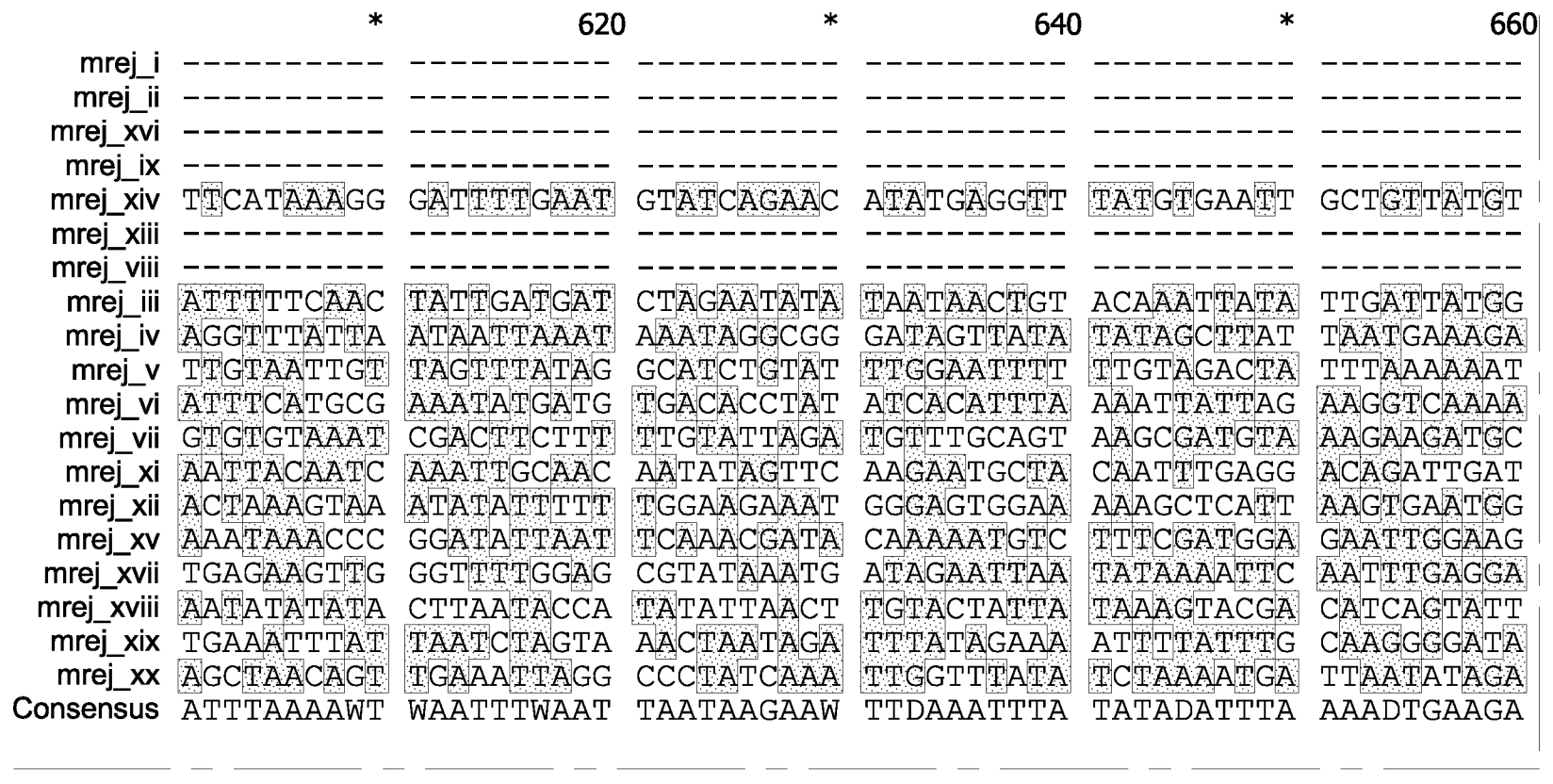
Figure 3L:
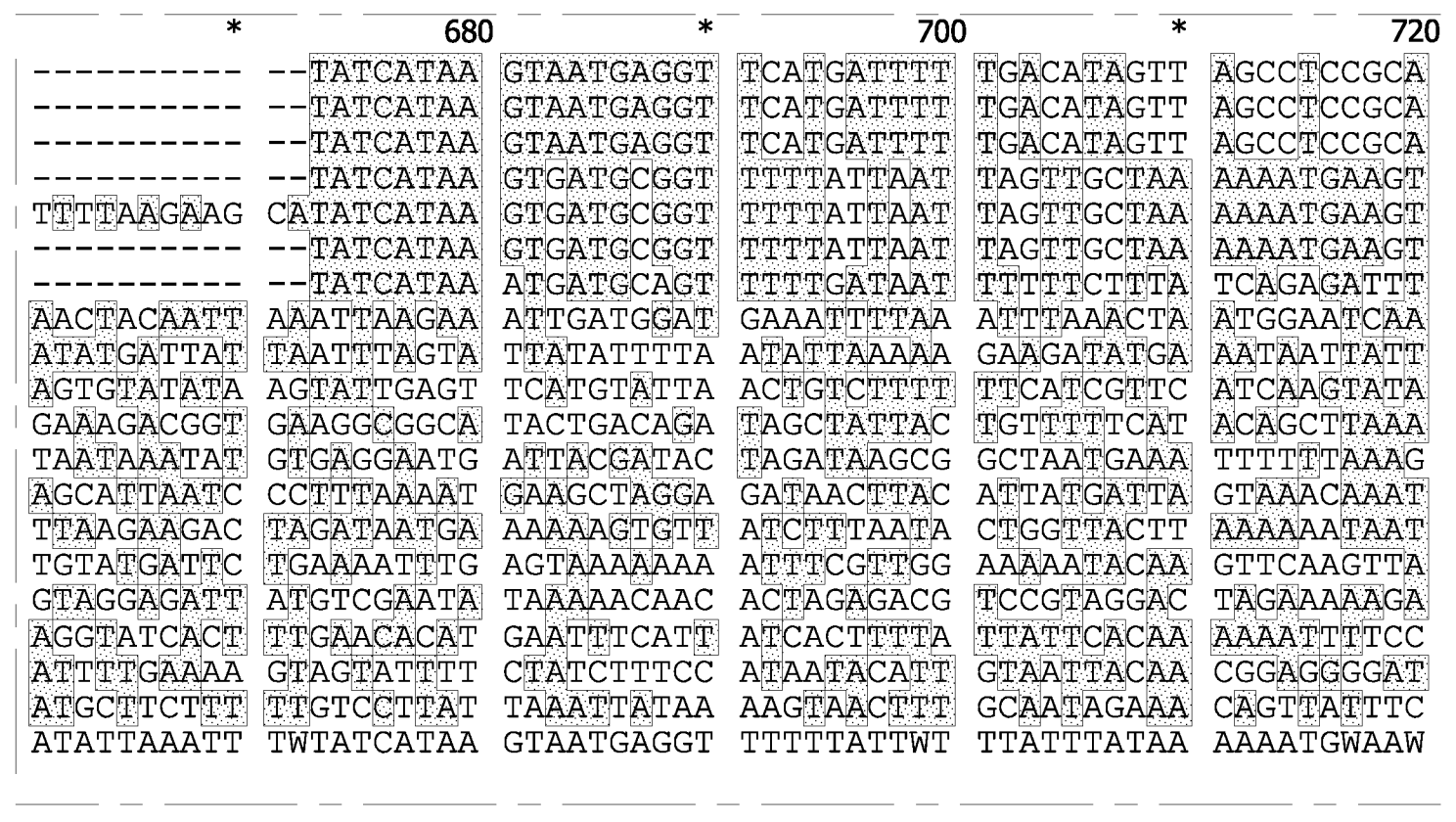
Figure 3M:
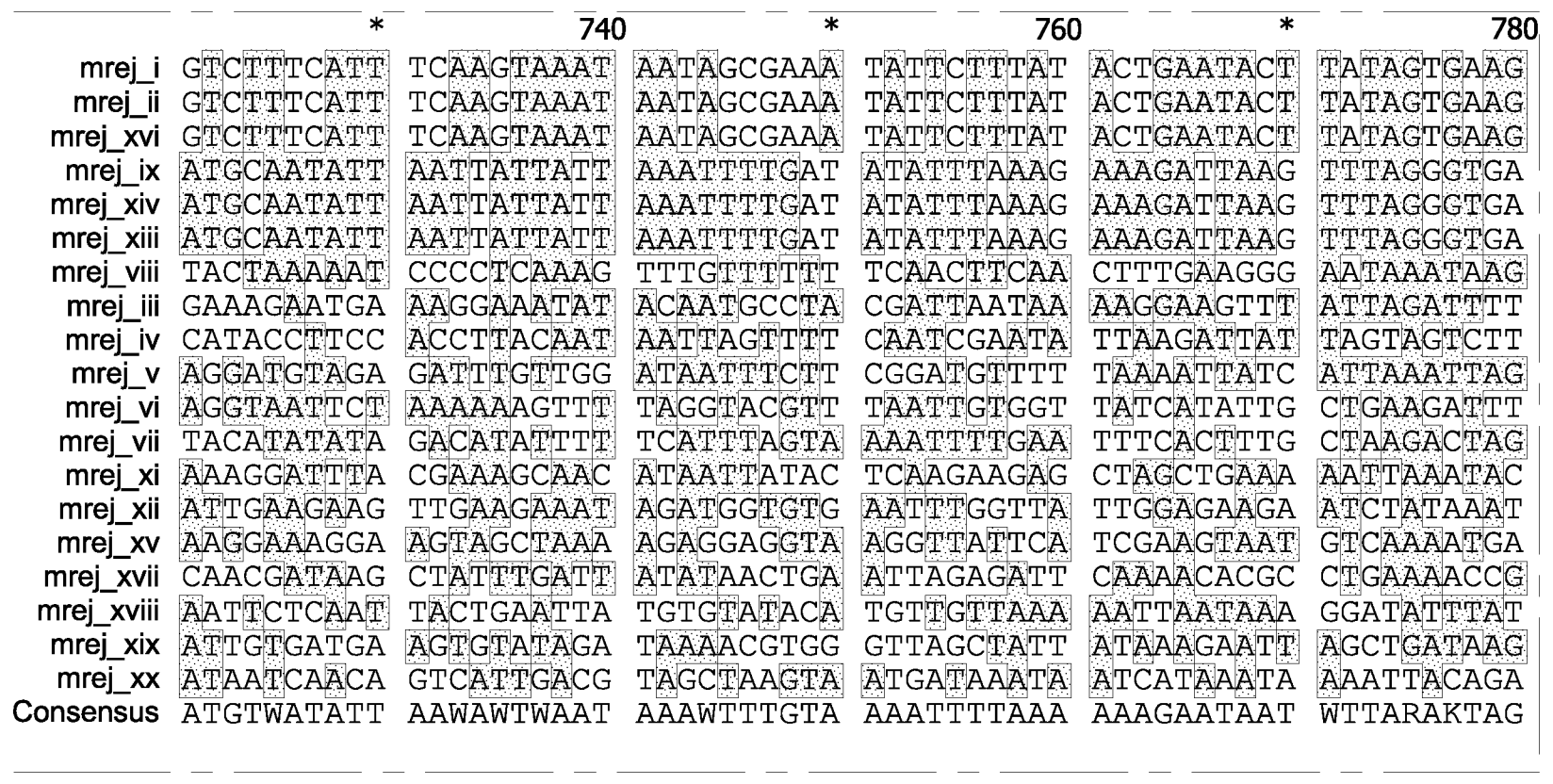
Figure 3N:
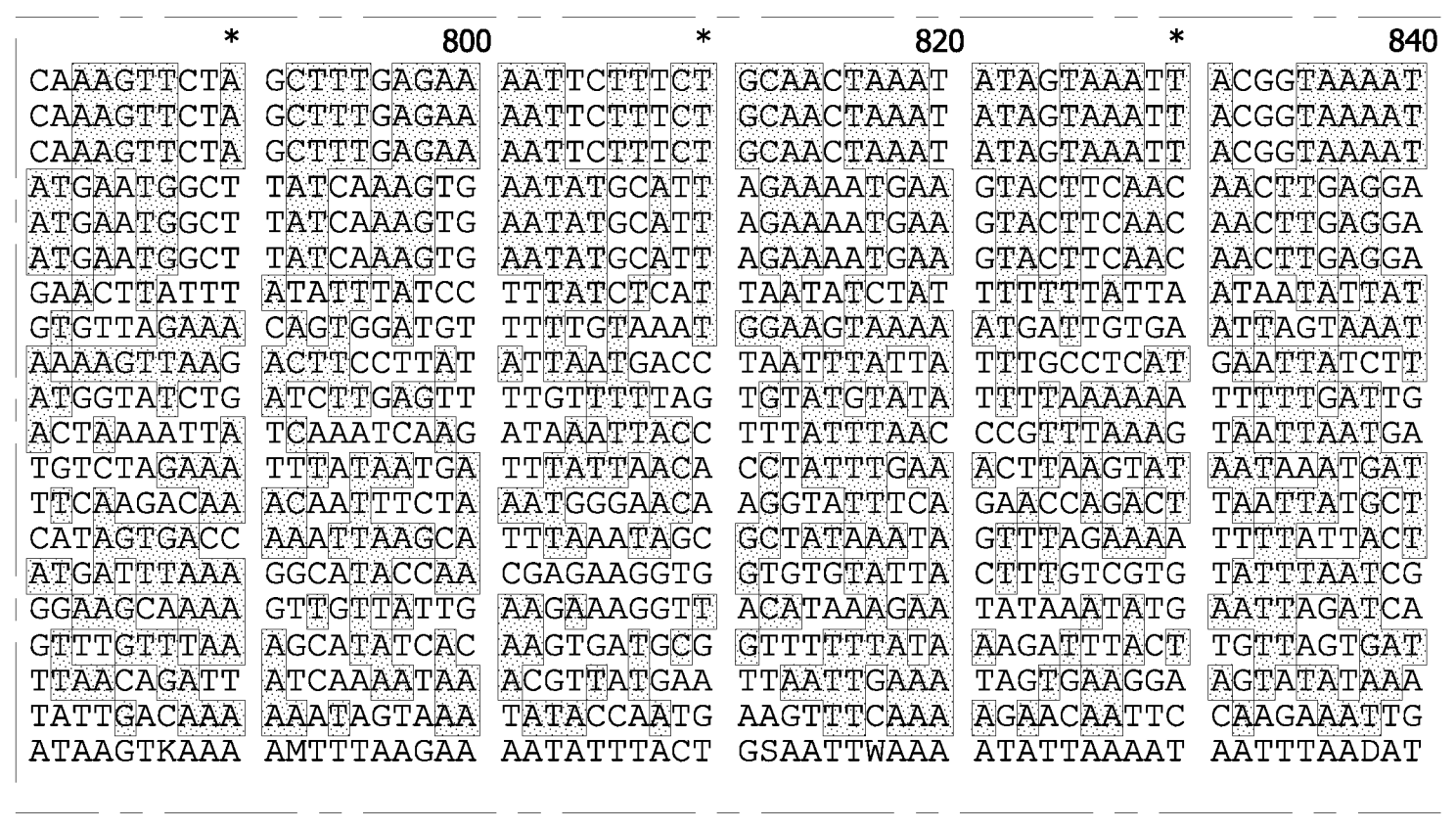
Figure 3P:
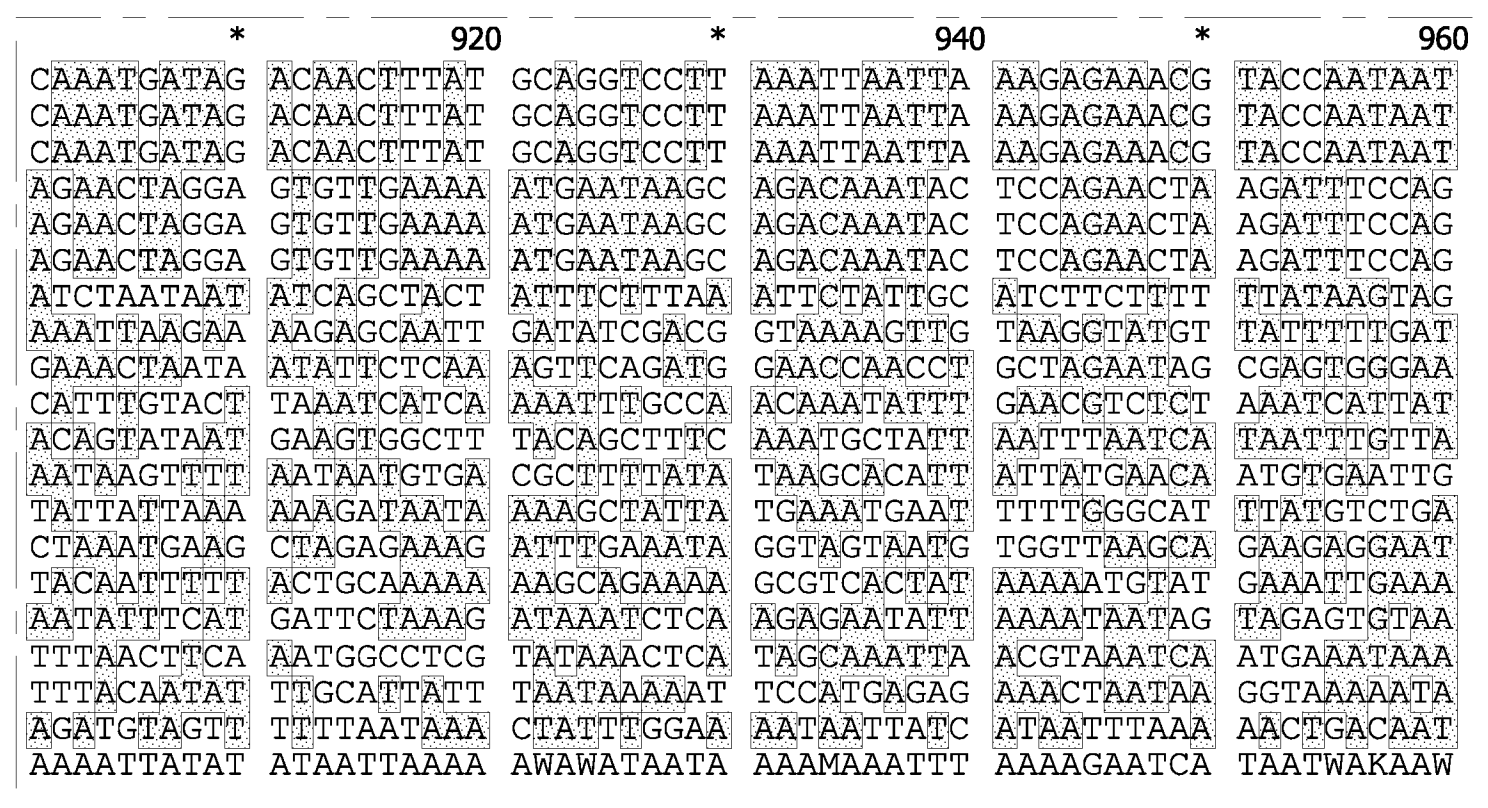

The sequences of the first 500-nucleotide portion of the SCCmec right extremity of all new MREJ types (xi to xx) were compared with each other and with those of the previously described MREJ types i to ix using GCG software programs Pileup and Gap (GCG, Wisconsin). Table 12 depicts the identities at the nucleotide level between the SCCmec right extremities of the 10 novel MREJ types (xi to xx) with those of the MREJ types previously described (i to ix) using the GCG program Gap. MREJ type x was excluded from this comparison since this MREJ sequence is deleted of the complete orfX and of the SCCmec integration site as well as ~4 kb at the right extremity of SCCmec when compared to the right extremity of SCCmec type II. The SCCmec right extremity of MREJ types ix, xiii, and xiv differed by only one and two 102-bp insertions present in MREJ types ix and xiv, respectively. However, the rest of these three sequences showed nearly 100% identity (FIGS. 3A-3Q). Although the SCCmec portion of MREJ type xvi is nearly 100% identical with that of MREJ type ii, the deletion of nucleotides 165 to 434 of orfX in MREJ type xvi has never been described previously. The SCCmec right extremities of all other new MREJ types showed identities ranging from 38.2 to 59.5% with each other or with MREJ types i to ix. The substantial variation between the novel MREJ sequences and the previously described sequences, from which the prior detection assays were based, explains why the right extremities of the novel MREJ types xi to xx disclosed in the present invention could not have been predicted nor detected with MREJ primers previously described (U.S. Pat. No. 6,156,507; International Patent Application PCT/CA02/00824; Ito et al., 2001, Antimicrob. Agents Chemother. 45:1323-1336; Huletsky et al., 2004, J Clin. Microbiol. 42:1875-1884; Ma et al, 2002, Antimicrob. Agents Chemother. 46:1147-1152; Ito et al, Antimicrob Agents Chemother. 2004. 48:2637-2651; Oliveira et al, 2001, Microb. Drug Resist. 7:349-360).

Figure 2:
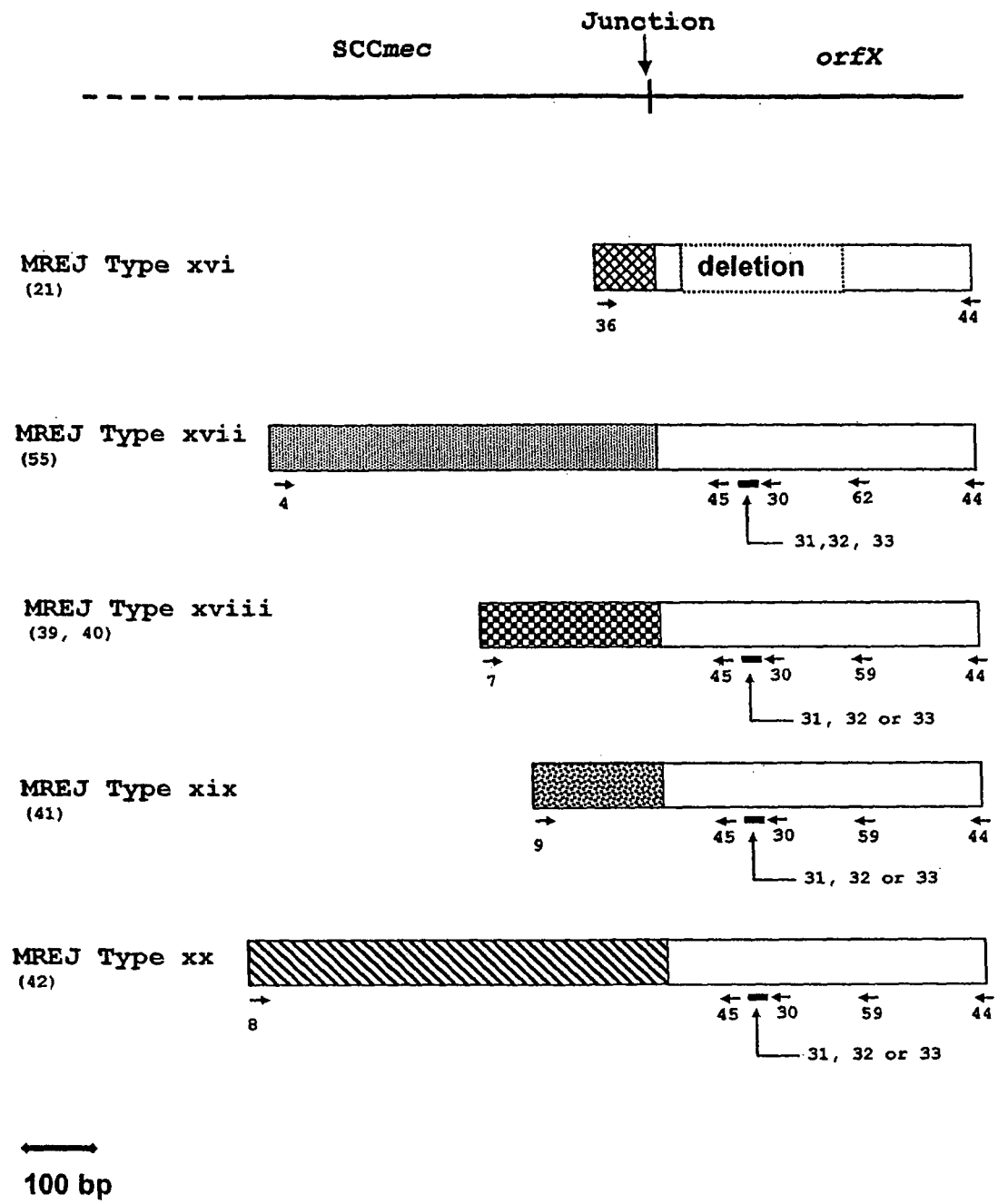
FIG. 2 depicts the SCCmec right extremity junction and the position of the primers (SEQ ID NOs.: 4, 7-9, 24, 29-36, 44, 45, 59, 62, 73) developed in the present invention for detection and identification of novel MREJ types xi, xii, xiii, xiv, xv, xvi, xvii, xviii, xix, and xx. Amplicon sizes are listed in Table 11. Numbers in parenthesis under MREJ types indicate MREJ SEQ ID NOs. Arrows indicate the positions of primers and the numbers below indicate their respective SEQ ID NOs. Dark bars and numbers below indicate the positions of probes and their respective SEQ ID NOs. Deletion in MREJ type xvi indicates the position of the 269-bp deletion in orfX.

Example 5: Selection of Amplification Primers from SCCmec/orfX Sequences of MRSA with MREJ Types xi to xx Upon analysis of the 10 new MREJ types xi to xx sequence data described above, primers specific to each new MREJ type sequence were designed (FIG. 2, Tables 9 and 11). Primers specific to MREJ type xi (SEQ ID NO.: 34), MREJ type xii (SEQ ID NO.: 35), MREJ types xiii and xiv (SEQ ID NO.: 29) (also detect MREJ type ix but each of MREJ types ix, xiii, and xiv has a different amplicon length), MREJ type xv (SEQ ID NO.: 24), MREJ type xvii (SEQ ID NO.: 4), MREJ type xviii (SEQ ID NO.: 7), MREJ type xix (SEQ ID NO.: 9), MREJ type xx (SEQ ID NO.: 8), were each used in combination with a primer specific to the S. aureus orfX (SEQ ID NO.: 30) and tested against their specific MREJ target. For the detection of MREJ type xvi, a primer targeting MREJ types i, ii, and xvi (Table 10) was used in combination with a primer targeting the S. aureus orfX (SEQ ID NO.: 44). MREJ types i, ii, and xvi can be distinguished from each other by their different amplicon length.

Oligonucleotides primers found to amplify specifically DNA from the target MRSA MREJ types were subsequently tested for their ubiquity by PCR amplification (i.e. ubiquitous primers amplified efficiently most or all isolates of MRSA of the target MREJ type). The specificity and ubiquity of the PCR assays were tested either directly with bacterial cultures or with purified bacterial genomic DNA. The specificity of the primers targeting MREJ types xi to xx was also verified by testing DNA from MRSA strains harboring all other MREJ types.

1 µl of a treated standardized bacterial suspension or of a genomic DNA preparation purified from bacteria were amplified in a 20 µl PCR reaction mixture. Each PCR reaction contained 50 mM KCl, 10 mM Tris-HCl (pH 9.0), 0.1% Triton X-100, 2.5 mM $MgCl_2$, 0.4 µM of each of MREJ type xi primer (SEQ ID NO.: 34), MREJ type xii primer (SEQ ID NO.: 35), MREJ types xiii and xiv primer (SEQ ID NO.: 29), MREJ type xv primer (SEQ ID NO.: 24), MREJ type xvi primer (SEQ ID NO.: 36), MREJ type xvii primer (SEQ ID NO.: 4), MREJ type xviii primer (SEQ ID NO.: 7), MREJ type xix primer (SEQ ID NO.: 9), or MREJ type xx primer (SEQ ID NO.: 8) which were each used in combination with 0.4 µM of a S. aureus-specific primer (SEQ ID NO.: 30 or SEQ ID NO.: 44 for MREJ type xvi), 200 µM of each of the four dNTPs (Pharmacia Biotech, Piscataway, NJ), 3.3 µg/µl of BSA (SIGMA, St. Louis, MO), and 0.5 U Taq polymerase (Promega, Madison, WI) coupled with TaqStart™ Antibody (BD Biosciences, San Jose, CA).

PCR reactions were then subjected to thermal cycling: 3 min at 94° C. followed by 40 cycles of 60 seconds at 95° C. for the denaturation step, 60 seconds at 55° C. for the annealing step, and 60 seconds at 72° C. for the extension step, then followed by a terminal extension of 7 minutes at 72° C. using a standard thermocycler (PTC-200 from MJ Research Inc., Watertown, MA). Detection of the PCR products was made by electrophoresis in agarose gels (1.2%) containing 0.25 µg/ml of ethidium bromide.

Each of the MRSA strains harbouring a specific MREJ target was specifically detected with their specific MREJ primers and there was no cross-detection with non targeted MREJ types.

This invention has been described herein above, and it is readily apparent that modifications can be made thereto without departing from the spirit of this invention. These modifications are under the scope of this invention, as defined in the appended claims.

TABLE 1

Reference *Staphylococcus aureus* strains used in the present invention[a]
Strain number Public collections (Type designation)

ATCC 6538[b]
ATCC 13301[b]
ATCC 23235[b]
ATCC 25923[b]
ATCC 27660[b]
ATCC 29737[b]
ATCC 29213[b]
ATCC 29247[b]
ATCC 33591
ATCC 33592
ATCC 33593
ATCC 43300
ATCC BAA-38 (Archaic)[c]
ATCC BAA-39 (Hungarian)[c]
ATCC BAA-40 (Portuguese)[c]
ATCC BAA-41 (New York)[c]
ATCC BAA-42 (Pediatric)[c]
ATCC BAA-43 (Brazilian)[c]
ATCC BAA-44 (Iberian)[c]
CCUG 41787 (Sa 501 V)[e]
CCUG 38266 (II)[e]
NCTC 8325[b]
NCTC 11939 (EMRSA-1)[e]
Canadian epidemic MRSA (Type designation)[d]

CMRSA-1
CMRSA-2
CMRSA-3
CMRSA-4
CMRSA-5
CMRSA-6
HARMONY collection of European epidemic MRSA (Type designation)[e]

96158 (B)
97117 (A)
97118 (A)
97120 (B)
97151 (B)
97392 (B)
97393 (A)
BM10827 (C)
3717 (EMRSA-GR1b)
97S97 (Belgian epidemic clone 1a)
359/96 (Berlin epidemic EMRSA IVc)
792/96 (Berlin epidemic EMRSA IVd)
844/96 (Berlin epidemic EMRSA IVb)
1966/97 (Hannover area EMRSA IIIc)
2594-2/97 (S. German EMRSA IIb)
131/98 (S. German EMRSA II d2)
406/98 (N. German EMRSA I c1)
408/98 (N. German EMRSA I c2)
872/98 (Hannover area EMRSA IIIb)
1155-1/98 (S. German EMRSA II c)
1163/98 (S. German EMRSA II d1)
1869/98 (N. German EMRSA I d)
HS 2 (I)
AO 17934/97 (II)
98/10618 (EMRSA-15/b2)
98/26821 (EMRSA-15/b3)
98/24344 (EMRSA-15/b7)
99/1139 (EMRSA-16/a2)
99/159 (EMRSA-16/a14)
6 (D)
13 (A')
14 (A')
18 (A)
25 (F')
30 (G)
33 (F)
54 (B)
60 (A")
80 (E)
98 (C)
162 (A)
920 (B)
95035 (A)
97121 (B)
BM10828 (C)
BM10882 (C)
37481 (Seinajoki E 14)
54511 (Turku I E6)
54518 (Turku II E7)
61974 (Helsinki I E1)
62176 (Kotka E10)
62305 (mecA-Tampere I E12)
62396 (Helsinki II E2)
75541 (Tampere II E13)
75916 (Helsinki V E5)
76167 (Kemi E17)
98442 (Helsinki VI E19)
98514 (Helsinki VII E20)
98541 (Lohja E24)
M307 (EMRSA-3)
90/10685 (EMRSA-15)
98/14719 (EMRSA-15/b4)
96/32010 (EMRSA-16)
99/579 (EMRSA-16/a3)
5 (E1)
3680 (EMRSA-GR1)
3713 (EMRSA-GR1a)
98S46 (Belgian epidemic clone 3b)
97S96 (Belgian epidemic clone 1a)
97S98 (Belgian epidemic clone 1b)
97S99 (Belgian epidemic clone 2a)
97S100 (Belgian epidemic clone 2b)
97S101 (Belgian epidemic clone 3a)
134/93 (N. German EMRSA I)
1000/93 (Hannover area EMRSA III)
1450/94 (N. German EMRSA Ia)
825/96 (Berlin epidemic EMRSA IV)
842/96 (Berlin epidemic EMRSA IVa)
2594-1/97 (S. German EMRSA II a)
1155-2/98 (S. German EMRSA II)
1442/98 (Hannover area EMRSA IIIa)
N8-890/99 (Sa 543 VI)
N8-3756/90 (Sa544 I)
9805-01937 (V)
AK 541 (IV)
ON 408/99 (VII)
AO 9973/97 (III)

[a]All *S. aureus* strains are resistant to methicillin except where otherwise indicated.
[b]These *S. aureus* strains are sensitive to oxacillin (MSSA).
[c]Informations on these strains and type designation based on pulse-field gel electrophoresis are from (6).
[d]Information on these strains and type designation based on pulse-field gel electrophoresis are from (47).
[e]Information on these strains and type designation based on pulse-field gel electrophoresis are available at http://www.phls.co.uk/inter/harmony/menu.htm.

TABLE 2

Evaluation of the MRSA-specific primers targeting MREJ types i to x using DNA from a variety of methicillin-sensitive and methicillin-resistant *Staphylococcus aureus* strains.

| *Staphylococcus aureus* strains[a] (number) | PCR results | |
| --- | --- | --- |
| | Positive (%) | Negative (%) |
| MRSA (1657) | 1640 (99) | 17 (1) |
| MSSA (569) | 26 (4.6) | 543 (95.4) |

[a]MRSA, methicillin-resistant *Staphylococcus aureus*; MSSA, methicillin-sensitive *Staphylococcus aureus*. Reference *S. aureus* strains used are listed in Table 1. The origin of the *S. aureus* clinical isolates is described in the text.

TABLE 3

Origin of 17 MRSA strains not amplifiable using primers targeting MREJ types i to x.

| Staphylococcus aureus strain designation: Original | CCRI[a] | Origin |
|---|---|---|
| 6-9637 | CCRI-12157 | Tempe, USA |
| 15-3967 | CCRI-12198 | New York, USA |
| 15-3972 | CCRI-12199 | New York, USA |
| 91 2290 | CCRI-12719 | Australia |
| SS1757 | CCRI-11976 | Houston, USA |
| 255 D | CCRI-12382 | Brazil |
| 106 I | CCRI-12383 | Brazil |
| 232 D | CCRI-12376 | Brazil |
| 6881 | CCRI-12593 | Spain |
| 5109 | CCRI-11999 | Wilmington, USA |
| BK793 | CCRI-9887 | Cairo, Egypt |
| 21 1 8424 | CCRI-12845 | Japan |
| SE46-1 | CCRI-9772 | Toronto, Canada |
| 1059 | CCRI-12524 | Italy |
| 1016 | CCRI-12535 | Italy |
| 816867 | CCRI-12905 | Rennes, France |
| 20 1 6060 | CCRI-12810 | Taiwan, China |

[a]CCRI stands for "Collection of the Centre de Recherche en Infectiologie".

TABLE 8

Novel *Staphylococcus aureus* MREJ[a] nucleotide sequences

| SEQ ID | S. aureus strain designation Original | CCRI[c] | Sequence[a,b] |
|---|---|---|---|
| 15 | SS1757 | CCRI-11976 | MREJ type xiii |
| 16 | 5109 | CCRI-11999 | MREJ type xiv |
| 17 | 6-9637 | CCRI-12157 | MREJ type xi |
| 18 | 15-3967 | CCRI-12198 | MREJ type xi |
| 19 | 15-3962 | CCRI-12199 | MREJ type xi |
| 20 | 91 2290 | CCRI-12719 | MREJ type xii |
| 21 | 21 1 8424 | CCRI-12845 | MREJ type xvi |
| 25 | 255 D | CCRI-12382 | MREJ type xiii |
| 26 | 106 I | CCRI-12383 | MREJ type xiii |
| 39 | 1059 | CCRI-12524 | MREJ type xviii |
| 40 | 1016 | CCRI-12535 | MREJ type xviii |
| 41 | 20 1 6060 | CCRI-12810 | MREJ type xix |
| 42 | 816867 | CCRI-12095 | MREJ type xx |
| 55 | SE46-1 | CCRI-9772 | MREJ type xvii |
| 56 | BK793 | CCRI-9887 | MREJ type xv |

[a]MREJ refers to mec right extremity junction and includes sequences from the SCCmec right extremity and chromosomal DNA to the right of the SCCmec integration site.
[b]Sequence refers to the target gene
[c]CCRI stands for "Collection for the Centre de Recherche en Infectiologie"

TABLE 9

Novel PCR amplification primers developed to detect MREJ types xi-xx

| Originating target DNA MREJ type | Originating target DNA SEQ ID NO | Oligo Position[a] | Oligo SEQ ID NO |
|---|---|---|---|
| MREJ type xvii | 55 | 954[b] | 4 |
| MREJ type xviii | 40 | 1080 | 7 |
| MREJ type xx | 42 | 987[b] | 8 |
| MREJ type xix | 41 | 581[b] | 9 |
| MREJ type xv | 38 | 624 | 23 |
| MREJ type xv | 56 | 566[b] | 24 |
| MREJ type ix, xiii, xiv | 15 | 756[b] | 28 |
| MREJ type xi | 17 | 615[b] | 34 |
| MREJ type xii | 20 | 612[b] | 35 |
| MREJ type xv | 56 | 457 | 48 |
| MREJ type xv | 56 | 564[b] | 49 |
| MREJ type xi | 17 | 956[b] | 51 |
| MREJ type xii | 20 | 1053[b] | 52 |
| MREJ type xvii | 55 | 415 | 57 |
| MREJ type xvii | 55 | 558 | 58 |

[a]Position refers to nucleotide position of 5' end of primer
[b]Primer is reverse-complement of target sequence

TABLE 10

Other amplification and/or sequencing primers and probes found in the sequence listing

| SEQ ID NO | Source | Target | Originating DNA Position[a] | Originating DNA SEQ ID NO |
|---|---|---|---|---|
| 27 | Oliveira and de Lencastre, 2002, Antimicrob. Agents Chemother. 46: 2155-2161 | SSCmec | — | — |
| 29 | SEQ ID NO.: 109[b] | MREJ types ix, xiii, and xiv | 652[c] | 29 |
| 30 | SEQ ID NO.: 64[b] | orfX | 325 | 18 |
| 31 | SEQ ID NO.: 84[b] | orfX | 346[c] | 18 |
| 32 | SEQ ID NO.: 163[b] | orfX | 346[c] | 20 |
| 33 | SEQ ID NO.: 164[b] | orfX | — | — |
| 36 | SEQ ID NO.: 66[b] | MREJ types i, ii, and xvi | 574[c] | 21 |
| 43 | SEQ ID NO.: 159[b] | orfX | 367[c] | 18 |
| 44 | SEQ ID NO.: 132[b] | orfX | 98 | 38 |
| 45 | SEQ ID NO.: 70[b] | orfX | 401 | 18 |
| 50 | SEQ ID NO.: 69[b] | mecA | 6945[c] | 22 |
| 53 | Oliveira and de Lencastre, 2002, Antimicrob. Agents Chemother. 46: 2155-2161 | SCCmec | — | — |
| 54 | SEQ ID NO.: 56[b] | MREJ types i and ii | — | — |
| 60 | SEQ ID NO.: 152[d] | putative membrane protein | | |
| 61 | SEQ ID NO.: 153[d] | putative membrane protein | | |

TABLE 10-continued

Other amplification and/or sequencing primers and probes found in the sequence listing

| SEQ ID NO | Source | Target | Originating DNA Position[a] | SEQ ID NO |
|---|---|---|---|---|
| 62 | This patent | orfX | 193 | 20 |
| 63 | SEQ ID NO.: 81[b] | mecA | 6798 | 22 |
| 65 | SEQ ID NO.: 204[b] | MREJ type vi | 642[c] | 191[b] |
| 66 | SEQ ID NO.: 115[b] | MREJ types ii, viii, ix, xiii, xiv | 514 | 167[b] |
| 73 | This patent | MREJ type x | 1913[c] | 69 |
| 74 | SEQ ID NO.: 112[b] | MREJ type vii | 503 | 189[b] |
| 75 | SEQ ID NO.: 116[b] | MREJ type viii | 601 | 167[b] |
| 76 | This patent | orfX | 193 | 17 |
| 77 | This patent | orf22 (MREJ type x) | 3257 | 69 |
| 78 | This patent | SCCmec | 22015 | 88 |
| 79 | This patent | SCCmec | 22100 | 88 |
| 80 | This patent | SCCmec | 21296 | 88 |
| 81 | This patent | SCCmec | 21401 | 88 |
| 82 | This patent | SCCmec | 22713 | 88 |
| 83 | This patent | SCCmec | 2062 | 87 |
| 84 | This patent | SCCmec | 1280 | 87 |
| 85 | This patent | SCCmec | 1364 | 87 |
| 86 | This patent | SCCmec | 718 | 87 |

[a]Position refers to nucleotide position of the 5' end of primer (on the target sequence).
[b]SEQ ID NOs from International Patent Application PCT/CA02/00824.
[c]Primer is reverse-complement of target sequence.
[d]SEQ ID NOs from WO96/08582.

TABLE 11

Length of amplicons obtained with primer pairs for MREJ types xi-xx

| Oligo Pair (SEQ ID NO) | Target DNA | Amplicon length[a] |
|---|---|---|
| 24/30 | MREJ type xv | 265 |
| 24/44 | MREJ type xv | 603 |
| 24/45 | MREJ type xv | 189 |
| 24/62 | MREJ type xv | 397 |
| 28/30 | MREJ type xiii, xiv | 464 (type xiii); 668 (type xiv) |
| 28/44 | MREJ type xiii, xiv | 802[b] (type xiii); 1006[b] (type xiv) |
| 28/45 | MREJ type xiii, xiv | 388 (type xiii); 592 (type xiv) |
| 28/76 | MREJ type xiii | 596 (type xiii) |
| 29/30 | MREJ type xiii, xiv | 267 (type xiii); 471 (type xiv) |
| 29/44 | MREJ type xiii, xiv | 605[b] (type xiii); 809[b] (type xiv) |
| 29/45 | MREJ type xiii, xiv | 191 (type xiii); 395 (type xiv) |
| 29/59 | MREJ type xiv | 605 |
| 29/76 | MREJ type xiii | 399 |
| 34/30 | MREJ type xi | 328 |
| 34/44 | MREJ type xi | 661[b] |
| 34/45 | MREJ type xi | 247 |
| 34/76 | MREJ type xi | 455 |
| 35/30 | MREJ type xii | 311 |
| 35/44 | MREJ type xii | 649[b] |
| 35/45 | MREJ type xii | 235 |
| 35/62 | MREJ type xii | 443 |
| 36/44 | MREJ type xvi | 348[b] |
| 4/30 | MREJ type xvii | 690 |
| 4/44 | MREJ type xvii | 968[b] |
| 4/45 | MREJ type xvii | 614 |
| 4/62 | MREJ type xvii | 822 |
| 7/30 | MREJ type xviii | 780[b] |
| 7/44 | MREJ type xviii | 1119[b] |
| 7/45 | MREJ type xviii | 704 |
| 7/59 | MREJ type xviii | 912[b] |
| 8/30 | MREJ type xx | 1076[b] |
| 8/44 | MREJ type xx | 1415[b] |
| 8/45 | MREJ type xx | 1000 |
| 8/59 | MREJ type xx | 1208[b] |
| 9/30 | MREJ type xix | 657[b] |
| 9/44 | MREJ type xix | 996[b] |
| 9/45 | MREJ type xix | 581 |
| 9/59 | MREJ type xix | 789[b] |

[a]Amplicon length is given in base pairs for MREJ types amplified by the set of primers
[b]Amplicon length is based on analysis by agarose gel electrophoresis

TABLE 12

Percentage of sequence identity for the first 500 nucleotides of SCCmec right extremities between 19 types of MREJ[a,b]

| | i | ii[d] | iii | iv | v | vi[c] | vii | viii | ix[f] | xi | xii | xiii | xiv[e] | xv | xvi | xvii | xviii | xix | xx |
|---|---|---|---|---|---|---|---|---|---|---|---|---|---|---|---|---|---|---|---|
| i | — | 100 | 44.4 | 39.1 | 40.4 | 42.9 | 43.2 | 41.5 | 42.4 | 41.1 | 40.2 | 42.4 | 42.4 | 42.1 | 100 | 42.1 | 44.1 | 42.5 | 40.4 |
| ii[d] | — | — | 44.4 | 39.1 | 40.4 | 42.9 | 43.2 | 41.5 | 42.4 | 41.1 | 40.2 | 42.4 | 42.4 | 42.1 | 100 | 42.1 | 44.1 | 42.5 | 40.4 |
| iii | — | — | — | 40.1 | 45.8 | 45.0 | 44.4 | 42.3 | 49.9 | 45.7 | 44.9 | 49.9 | 49.9 | 48.8 | 44.2 | 43.1 | 46.7 | 45.3 | 45.2 |
| iv | — | — | — | — | 45.2 | 45.0 | 44.4 | 42.1 | 42.7 | 42.7 | 38.2 | 42.7 | 42.7 | 39.0 | 42.1 | 39.6 | 40.3 | 37.2 | 41.4 |
| v | — | — | — | — | — | 45.0 | 41.3 | 46.5 | 43.8 | 41.2 | 43.6 | 43.8 | 43.8 | 41.7 | 43.3 | 42.3 | 49.8 | 43.8 | 39.8 |
| vi[c] | — | — | — | — | — | — | 45.1 | 40.8 | 43.2 | 43.8 | 42.0 | 43.2 | 43.2 | 44.2 | 42.9 | 39.4 | 43.4 | 42.2 | 45.8 |
| vii | — | — | — | — | — | — | — | 42.8 | 44.8 | 42.7 | 42.0 | 44.8 | 44.8 | 46.7 | 42.5 | 43.2 | 44.7 | 41.1 | 41.9 |
| viii | — | — | — | — | — | — | — | — | 41.1 | 41.1 | 41.9 | 41.1 | 41.1 | 37.6 | 52.2 | 40.9 | 41.2 | 42.4 | 39.1 |
| ix[f] | — | — | — | — | — | — | — | — | — | 46.0 | 42.5 | 100 | 100 | 43.4 | 44.1 | 40.9 | 45.0 | 40.6 | 42.9 |

TABLE 12-continued

Percentage of sequence identity for the first 500 nucleotides of SCCmec right extremities between 19 types of MREJ[a,b]

| | i | ii[d] | iii | iv | v | vi[e] | vii | viii | ix[f] | xi | xii | xiii | xiv[e] | xv | xvi | xvii | xviii | xix | xx |
|---|---|---|---|---|---|---|---|---|---|---|---|---|---|---|---|---|---|---|---|
| xi | — | — | — | — | — | — | — | — | — | — | 48.0 | 46.0 | 46.0 | 45.9 | 43.2 | 40.5 | 47.1 | 41.8 | 43.6 |
| xii | — | — | — | — | — | — | — | — | — | — | — | 42.5 | 42.5 | 47.6 | 39.2 | 43.3 | 43.7 | 44.7 | 45.6 |
| xiii | — | — | — | — | — | — | — | — | — | — | — | — | 100 | 43.4 | 44.1 | 40.9 | 45.0 | 40.6 | 42.9 |
| xiv[e] | — | — | — | — | — | — | — | — | — | — | — | — | — | 43.4 | 44.1 | 40.9 | 45.0 | 40.6 | 42.9 |
| xv | — | — | — | — | — | — | — | — | — | — | — | — | — | — | 43.6 | 41.5 | 47.5 | 42.5 | 43.8 |
| xvi | — | — | — | — | — | — | — | — | — | — | — | — | — | — | — | 41.9 | 45.4 | 45.1 | 45.7 |
| xvii | — | — | — | — | — | — | — | — | — | — | — | — | — | — | — | — | 40.0 | 43.3 | 42.5 |
| xviii | — | — | — | — | — | — | — | — | — | — | — | — | — | — | — | — | — | 43.4 | 45.7 |
| xix | — | — | — | — | — | — | — | — | — | — | — | — | — | — | — | — | — | — | 45.5 |
| xx | — | — | — | — | — | — | — | — | — | — | — | — | — | — | — | — | — | — | — |

[a]"First 500 nucleotides" refers to the 500 nucleotides within the SCCmec right extremity, starting from the integration site of SCCmec in the *Staphylococcus aureus* chromosome as shown on FIG. 3.

[b]Sequences were extracted from International patent application PCT/CA02/00824 (SEQ ID NOs.: 1, 2, 232, 46, 50, 171, 166, 167 and 168 for types i to ix, respectively). MREJ type x was excluded from the sequence comparison because it is deleted from the completed orfX, the integration site, and part of the SCCmec right extremity. Sequences for types xi to xx were extracted from SEQ ID NOs.: 18, 20, 25, 16, 56, 21, 55, 39, 41 and 42, respectively.

[c]Sequence from the SCCmec right extremity of MREJ type vi is limited to 371 nucleotides.

[d]The first 102 nucleotides from the SCCmec right extremity of MREJ type ii were excluded from the sequence comparison.

[e]The first 206 nucleotides from the SCCmec right extremity of MREJ type xiv were excluded from the sequence comparison.

[f]The first 102 nucleotides from the SCCmec right extremity of MREJ type ix were excluded from the sequence comparison.

What is claimed is:

1. A method of treating a methicillin resistant *Staphylococcus aureus* (MRSA) in a subject comprising:
contacting or having contacted under annealing conditions a plurality of primers comprising a first primer and a second primer with a sample from the subject to be analyzed for the presence of an MREJ type xv sequence, said MREJ type xv sequence from a MRSA strain including a SCCmec element containing a mecA gene inserted into chromosomal DNA, thereby generating a polymorphic MREJ type xv sequence that comprises sequences from both the SCCmec element right extremity and chromosomal DNA adjoining said right extremity, wherein said first and second primers are at least 16 nucleotides in length, wherein said first primer anneals to said SCCmec element right extremity of a MREJ type xv sequence consisting of SEQ ID NO: 56, and said second primer anneals to a chromosomal sequence of *S. aureus*, wherein said first primer and said second primer together generate a first amplicon of MREJ type xv specific sequence that spans the mec right extremity junction of the MREJ type xv sequence under amplification conditions only if said MREJ type xv sequence is present in the sample from the subject;
generating and detecting, or having generated and detected, the presence of said first amplicon of MREJ type xv specific sequence as indicative of the presence of MRSA in the sample from the subject; and
treating the MRSA in the subject by administering an antibiotic to the subject.

2. The method of claim 1, wherein said detecting said first amplicon comprises hybridization with at least one probe.

3. The method of claim 2, wherein said contacting of the plurality of primers and the hybridization with at least one probe occurs in the same physical enclosure.

4. The method of claim 2, wherein the plurality of primers and the at least one probe are each at least 16 nucleotides in length.

5. The method of claim 2, wherein the plurality of primers further comprises primers for the detection of additional MREJ type nucleic acid sequences that anneal to the SCCmec element right extremity of a MREJ sequence of each of SEQ ID NOs: 15, 16, 17, 18, 19, 20, 21, 25, 26, 39, 40, 41, 42, and 55.

6. The method of claim 2, wherein the plurality of primers and the at least one probe comprise at least one primer or probe selected from the group consisting of SEQ ID NOs: 44, 45, 76, 51, 30, 31, 32, and 33 for the detection of MREJ type xi.

7. The method of claim 2, wherein the plurality of primers and the at least one probe comprise at least one primer or probe selected from the group consisting of SEQ ID NOs: 35, 44, 45, 62, 52, 30, 31, 32, and 33, for the detection of MREJ type xii.

8. The method of claim 2, wherein the plurality of primers and the at least one probe comprise at least one primer or probe selected from the group consisting of SEQ ID NOs: 28, 44, 45, 59, 29, 30, 31, 32, and 33 for the detection of MREJ type xiii.

9. The method of claim 2, wherein the plurality of primers and the at least one probe comprise at least one primer or probe selected from the group consisting of SEQ ID NOs: 28, 44, 45, 59, 29, 30, 31, 32, and 33 for the detection of MREJ type xiv.

10. The method of claim 2, wherein the plurality of primers and the at least one probe comprise at least one primer or probe selected from the group consisting of SEQ ID NOs: 44, 45, 62, 24, 30, 31, 32, and 33 for the detection of MREJ type xv.

11. The method of claim 2, wherein the plurality of primers and the at least one probe comprise at least one primer or probe selected from the group consisting of SEQ ID NOs: 36 and 44 for the detection of MREJ type xvi.

12. The method of claim 2, wherein the plurality of primers and the at least one probe comprise at least one primer or probe selected from the group consisting of SEQ ID NOs: 44, 45, 57, 58, 62, 4, 30, 31, 32, and 33 for the detection of MREJ type xvii.

13. The method of claim 2, wherein the plurality of primers and the at least one probe comprise at least one primer or probe selected from the group consisting of SEQ ID NOs: 44, 45, 59, 7, 30, 31, 32, and 33 for the detection of MREJ type xviii.

14. The method of claim 2, wherein the plurality of primers and the at least one probe comprise at least one primer or probe selected from the group consisting of SEQ ID NOs: 44, 45, 59, 9, 30, 31, 32, and 33 for the detection of MREJ type xix.

15. The method of claim 2, wherein the plurality of primers and the at least one probe comprise at least one primer or probe selected from the group consisting of SEQ ID NOs: 44, 45, 59, 8, 30, 31, 32, and 33 for the detection of MREJ type xx.

16. The method of claim 5, wherein the plurality of primers and the at least one probe comprise a plurality of primers or probes selected from the group consisting of:
SEQ ID NOs: 51, 30, 31, 32, 33, 52, 29, 24, 36, 44, 4, 7, 9, and 8.

17. The method of claim 16, wherein the plurality of primers or probes further comprise at least one primer and/or probe selected from the group consisting of: SEQ ID NOs: 34, 35, 44, 45, 52, 59, 62, and 76.

18. The method of claim 1, wherein the plurality of primers comprise a primer pair, wherein the primer pair is selected from the group consisting of:
SEQ ID NOs: 34 and 45; SEQ ID NOs: 34 and 30; SEQ ID NOs: 34 and 76; and SEQ ID NOs: 34 and 44 for the detection of MREJ type xi.

19. The method of claim 1, wherein the plurality of primers comprise a primer pair, wherein a primer pair is selected from the group consisting of:

SEQ ID NOs: 35 and 45; SEQ ID NO's: 35 and 30; SEQ ID NOs: 35 and 62; and SEQ ID NOs: 35 and 44, for the detection of MREJ type xii.

20. The method of claim 1, wherein the plurality of primers comprise a primer pair, wherein the primer pair is selected from the group consisting of:

SEQ ID NOs: 29 and 45; SEQ ID NOs: 29 and 30; SEQ ID NOs: 29 and 76; and SEQ ID NOs: 29 and 44, for the detection of MREJ type xiii.

21. The method of claim 1, wherein the plurality of primers comprise a primer pair, wherein the primer pair is selected from the group consisting of:

SEQ ID NOs: 29 and 45; SEQ ID NOs: 29 and 30; SEQ ID NOs: 29 and 59; and SEQ ID NOs: 29 and 44, for the detection of MREJ type xiv.

22. The method of claim 1, wherein the plurality of primers comprise a primer pair, wherein the primer pair is selected from the group consisting of:

SEQ ID NOs: 24 and 45; SEQ ID NOs: 24 and 30; SEQ ID NOs: 24 and 62; and SEQ ID NOs: 24 and 44, for the detection of MREJ type xv.

23. The method of claim 1, wherein the plurality of primers comprise a primer pair, wherein the primer pair is selected from the group consisting of:

SEQ ID NOs: 4 and 45; SEQ ID NOs: 4 and 30; SEQ ID NOs: 4 and 62; and SEQ ID NOs: 4 and 44, for the detection of MREJ type xvii.

24. The method of claim 1, wherein the plurality of primers comprise a primer pair, wherein the primer pair is selected from the group consisting of:

SEQ ID NOs: 7 and 45; SEQ ID NOs: 7 and 30; SEQ ID NOs: 7 and 59; and SEQ ID NOs: 7 and 44, for the detection of MREJ type xviii.

25. The method of claim 1, wherein the plurality of primers comprise a primer pair, wherein the primer pair is selected from the group consisting of:

SEQ ID NOs: 9 and 45; SEQ ID NOs: 9 and 30; SEQ ID NOs: 9 and 59; and SEQ ID NOs: 9 and 44, for the detection of MREJ type xix.

26. The method of claim 1, wherein the plurality of primers comprise a primer pair, wherein the primer pair is selected from the group consisting of:

SEQ ID NOs: 8 and 45, SEQ ID NOs: 8 and 30; SEQ ID NOs: 8 and 59; and SEQ ID NOs: 8 and 44, for the detection of xx.

27. The method of claim 1, wherein the plurality of primers further comprise a primer pair for the detection of an additional MREJ type nucleic acid sequences, wherein the primer pair is selected from the group consisting of:

SEQ ID NOs: 34 and 45; SEQ ID NOs: 34 and 30; SEQ ID NOs: 34 and 76; SEQ ID NOs: 34 and 44; SEQ ID NOs: 35 and 45; SEQ ID NOs: 35 and 30; SEQ ID NOs: 35 and 62; SEQ ID NOs: 35 and 44; SEQ ID NOs: 29 and 45; SEQ ID NOs: 29 and 30; SEQ ID NOs: 29 and 76; SEQ ID NOs: 29 and 44; SEQ ID NOs: 29 and 45; SEQ ID NOs: 29 and 30; SEQ ID NOs: 29 and 59; SEQ ID NOs: 29 and 44; SEQ ID NOs: 36 and 44; SEQ ID NOs: 4 and 45; SEQ ID NOs: 4 and 30; SEQ ID NOs: 4 and 62, SEQ ID NOs: 4 and 44; SEQ ID NOs: 7 and 45; SEQ ID NOs: 7 and 30; SEQ ID NOs: 7 and 59; SEQ ID NOs: 7 and 44; SEQ ID NOs: 9 and 45; SEQ ID NOs: 9 and 30; SEQ ID NOs: 9 and 59; SEQ ID NOs: 9 and 44; SEQ ID NOs: 8 and 45; SEQ ID NOs: 8 and 30; SEQ ID NOs: 8 and 59; and SEQ ID NOs: 8 and 44.

28. The method of claim 27, further comprising probes having the following sequences:

SEQ ID NOs: 33, 31, and 32.

29. The method of claim 28, wherein said probes and primers are used together.

30. The method of claim 29, wherein said probes and/or primers are used together in the same physical enclosure.

31. The method of claim 1, wherein the detecting comprises detecting an annealed probe and/or primer as an indication of the presence of said MREJ type xv sequence in the sample.

32. The method of claim 1, wherein the detecting the presence of said first amplicon comprises a method selected from the group consisting of: agarose gel electrophoresis, fluorescence resonance energy transfer, chemiluminscense, potentiometry, mass spectrometry, plasmon resonance, polarimetry, colorimetry, flow cytometry, scanometry, and DNA sequencing, or any combination thereof.

33. The method of claim 1, wherein the plurality of primers comprise a primer pair, wherein the primer pair is SEQ ID NOs: 36 and 44, for detection of MREJ type xvi.

34. The method of claim 1, further comprising contacting the sample with at least one primer pair selected from the group consisting of: SEQ ID NOs: 30 and 36; SEQ ID NOs: 30 and 70; SEQ ID NOs: 30 and 71; SEQ ID NOs: 30 and 72; SEQ ID NOs: 30 and 65; SEQ ID NOs: 30 and 74; SEQ ID NOs: 30 and 29; and SEQ ID NOs: 73 and 77 under said amplifying conditions.

35. The method of claim 34, wherein said contacting further comprises providing at least one probe, wherein the probe comprises a nucleic acid sequence selected from the group consisting of: SEQ ID NO:31, SEQ ID NO:32, and SEQ ID NO:33.

36. The method of claim 1, wherein said detecting comprises sequencing said first amplicon.

37. The method of claim 1, wherein said detecting comprises determining the size of said first amplicon by gel electrophoresis.

38. The method of claim 1, further comprising detecting the presence of at least one further MREJ type nucleic acid sequence in said sample, said at least one further MREJ type nucleic acid sequence being an MREJ type xi, xii, xiv, xvi, xvii, xviii, xix, or xx MRSA strain, comprising:

contacting at least a third primer with the sample, said MREJ type xi, xii, xiv, xvi, xvii, xviii, xix, or xx type sequence from a MRSA strain including a Staphylococcal cassette chromosome mec (SCCmec) element containing a mecA gene inserted into chromosomal DNA, thereby generating a polymorphic MREJ type xi, xii, xiv, xvi, xvii, xviii, xix, or xx sequence that comprises sequences from both the SCCmec right extremity and chromosomal DNA adjoining said right extremity, wherein said third primer and a primer that anneals to a chromosomal sequence of *S. aureus* together generate a second amplicon that spans the mec right extremity junction of the MREJ type xi, xii, xiv, xvi, xvii, xviii, xix, or xx sequence under amplification conditions only if said MREJ type xi, xii, xiv, xvi, xvii, xviii, xix, or xx sequence, respectively, is present in the sample and wherein said contacting takes place under annealing conditions; and generating and detecting the presence of said second amplicon as indicative of the presence of said MREJ type xi, xii, xiv, xvi, xvii, xviii, xix, or xx sequence in the sample.

39. The method of claim 1, wherein said first and second primers are at least 18 nucleotides in length.

\* \* \* \* \*